(12) United States Patent
Gray et al.

(10) Patent No.: US 10,787,436 B2
(45) Date of Patent: Sep. 29, 2020

(54) INHIBITORS OF CYCLIN-DEPENDENT KINASE 7 (CDK7)

(71) Applicant: Dana-Farber Cancer Institute, Inc., Boston, MA (US)

(72) Inventors: Nathanael Gray, Boston, MA (US); Tinghu Zhang, Brookline, MA (US); Nicholas Paul Kwiatkowski, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/130,975

(22) Filed: Sep. 13, 2018

(65) Prior Publication Data
US 2019/0100511 A1 Apr. 4, 2019
US 2020/0017475 A9 Jan. 16, 2020

Related U.S. Application Data

(62) Division of application No. 14/436,496, filed as application No. PCT/US2013/065708 on Oct. 18, 2013, now Pat. No. 10,112,927.

(60) Provisional application No. 61/727,640, filed on Nov. 16, 2012, provisional application No. 61/715,574, filed on Oct. 18, 2012.

(51) Int. Cl.
| | |
|---|---|
| *C07D 403/04* | (2006.01) |
| *A61K 31/635* | (2006.01) |
| *A61K 31/506* | (2006.01) |
| *C07D 401/04* | (2006.01) |
| *C07D 471/04* | (2006.01) |
| *A61K 45/06* | (2006.01) |
| *A61K 31/4439* | (2006.01) |
| *C07D 417/04* | (2006.01) |
| *C07D 513/04* | (2006.01) |
| *G01N 33/50* | (2006.01) |

(52) U.S. Cl.
CPC ........ *C07D 403/04* (2013.01); *A61K 31/4439* (2013.01); *A61K 31/506* (2013.01); *A61K 31/635* (2013.01); *A61K 45/06* (2013.01); *C07D 401/04* (2013.01); *C07D 417/04* (2013.01); *C07D 471/04* (2013.01); *C07D 513/04* (2013.01); *A61K 2300/00* (2013.01); *G01N 33/5011* (2013.01)

(58) Field of Classification Search
None
See application file for complete search history.

(56) References Cited

U.S. PATENT DOCUMENTS

| | | | |
|---|---|---|---|
| 4,231,938 A | 11/1980 | Monaghan et al. | |
| 4,270,537 A | 6/1981 | Romaine et al. | |
| 4,596,556 A | 6/1986 | Morrow et al. | |
| 4,782,084 A | 11/1988 | Vyas et al. | |
| 4,790,824 A | 12/1988 | Morrow et al. | |
| 4,885,314 A | 12/1989 | Vyas et al. | |
| 4,886,499 A | 12/1989 | Cirelli et al. | |
| 4,940,460 A | 7/1990 | Casey et al. | |
| 4,941,880 A | 7/1990 | Burns et al. | |
| 5,015,235 A | 5/1991 | Crossman et al. | |

(Continued)

FOREIGN PATENT DOCUMENTS

| | | | |
|---|---|---|---|
| CA | 2486101 A1 | 11/2003 | |
| CA | 2503646 A1 | 5/2004 | |

(Continued)

OTHER PUBLICATIONS

International Search Report and Written Opinion for PCT/US2012/065618, dated Mar. 19, 2013.

(Continued)

*Primary Examiner* — Kortney L. Klinkel
*Assistant Examiner* — Tori Strong
(74) *Attorney, Agent, or Firm* — Wolf, Greenfield & Sacks, P.C.

(57) ABSTRACT

The present invention provides novel compounds of Formula (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating or preventing proliferative diseases (e.g., cancers (e.g., leukemia, lymphoma, melanoma, multiple myeloma, breast cancer, Ewing's sarcoma, osteosarcoma, brain cancer, neuroblastoma, lung cancer), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of a kinase, such as cyclin-dependent kinase (CDK) (e.g., cyclin-dependent kinase 7 (CDK7)), and therefore, induce cellular apoptosis and/or inhibit transcription in the subject.

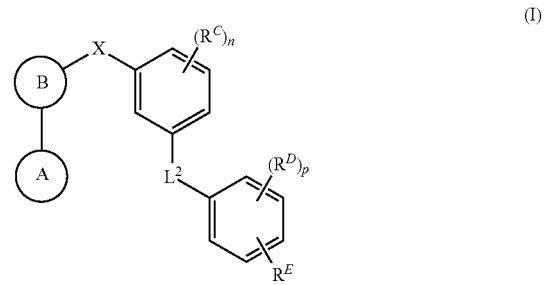

37 Claims, 30 Drawing Sheets
Specification includes a Sequence Listing.

(56) References Cited

U.S. PATENT DOCUMENTS

| | | |
|---|---|---|
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,273,765 B2 | 9/2012 | Fancelli et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,814,709 B2 | 11/2017 | Liu et al. |
| 9,862,688 B2 | 1/2018 | Gray et al. |
| 9,879,003 B2 | 1/2018 | Gray et al. |
| 10,000,483 B2 | 6/2018 | Gray et al. |
| 10,017,477 B2 | 7/2018 | Gray et al. |
| 10,112,927 B2 | 10/2018 | Gray et al. |
| 10,144,730 B2 | 12/2018 | Gray et al. |
| 2003/0139416 A1 | 7/2003 | Buchanan et al. |
| 2004/0106634 A1 | 6/2004 | Satoh et al. |
| 2004/0209878 A1 | 10/2004 | Guzi et al. |
| 2005/0026914 A1 | 2/2005 | Buchanan et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2013/0184287 A1 | 7/2013 | Gray et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2018/0093990 A1 | 4/2018 | Gray et al. |
| 2018/0169097 A1 | 6/2018 | Hammerman et al. |
| 2018/0319801 A1 | 11/2018 | Gray et al. |
| 2018/0362483 A1 | 12/2018 | Gray et al. |
| 2019/0015411 A9 | 1/2019 | Hammerman et al. |
| 2019/0055248 A1 | 2/2019 | Gray et al. |
| 2019/0112305 A1 | 4/2019 | Gray et al. |
| 2019/0248778 A1 | 8/2019 | Gray et al. |
| 2019/0315747 A9 | 10/2019 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| GB | 796524 A | 6/1958 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 A | 10/2016 |
| JP | 2017-504651 A | 2/2017 |

(56) References Cited

FOREIGN PATENT DOCUMENTS

| | | |
|---|---|---|
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 00/50032 A1 | 8/2000 |
| WO | WO 00/61186 A1 | 10/2000 |
| WO | WO 01/02369 A2 | 1/2001 |
| WO | WO 01/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 2002/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 2003/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/039796 A1 | 5/2004 |
| WO | WO 2004/074283 A1 | 9/2004 |
| WO | WO 2004/078757 A2 | 9/2004 |
| WO | WO 2004/087699 A2 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A1 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/008847 A2 | 1/2010 |
| WO | WO 2010/044885 A2 | 4/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/115725 A2 | 9/2011 |
| WO | WO 2013/014162 A1 | 1/2013 |
| WO | WO 2013/040436 A1 | 3/2013 |
| WO | WO 2013/074986 A1 | 5/2013 |
| WO | WO 2013/136070 A1 | 9/2013 |
| WO | WO 2013/154778 A1 | 10/2013 |
| WO | WO 2014/063061 A1 | 4/2014 |
| WO | WO 2014/063068 A1 | 4/2014 |
| WO | WO 2015/013635 A2 | 1/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/023014 A2 | 2/2016 |
| WO | WO 2016/105528 A2 | 6/2016 |
| WO | WO 2017/037576 A1 | 3/2017 |

OTHER PUBLICATIONS

International Preliminary Report on Patentability for PCT/US2012/065618, dated May 30, 2014.
International Search Report and Written Opinion for PCT/US2013/065708, dated Feb. 4, 2014.
International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.

(56) References Cited

OTHER PUBLICATIONS

International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
International Preliminary Report on Patentability for PCT/US/2016/037086, dated Dec. 21, 2017.
Partial European Search Report for EP 16773870.7, dated Jul. 12, 2018.
Extended European Search Report for EP 15773870.7, dated Oct. 17, 2018.
Invitation to Pay Additional Fees for PCT/US2016/024345, dated Aug. 9, 2016.
International Search Report and Written Opinion for PCT/US2016/024345, dated Oct. 6, 2016.
International Preliminary Report on Patentability for PCT/US2016/024345, dated Oct. 12, 2017.
Invitation to Pay Additional Fees for PCT/US2016/051118, dated Dec. 1, 2016.
International Search Report and Written Opinion for PCT/US2016/051118, dated Mar. 13, 2017.
International Preliminary Report on Patentability for PCT/US2016/051118, dated Mar. 22, 2018.
Invitation to Pay Additional Fees for PCT/US2011/025423, dated May 31, 2011.
International Search Report and Written Opinion from PCT/US2011/025423, dated Nov. 5, 2012.
International Preliminary Report on Patentability for PCT/US2011/025423, dated Nov. 29, 2012.
Akira et al., Toll-like receptor signalling. Nat Rev Immunol. Jul. 2004;4(7):499-511.
Attoub et al., The c-kit tyrosine kinase inhibitor STI571 for colorectal cancer therapy. Cancer Res. Sep. 1, 2002;62(17):4879-83.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Berge et al., Pharmaceutical salts. J. Pharmaceutical Sciences 1977 66:1-19.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bosken et al., The structure and substrate specificity of human Cdk12/Cyclin K. Nat Commun. Mar. 24, 2014;5:3505. doi: 10.1038/ncomms4505.
Brunton et al., eds., Chemotherapy of Neoplastic Diseases. In Goodman & Gilman's the Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Carvajal et al., KIT as a therapeutic target in metastatic melanoma. JAMA. Jun. 8, 2011;305(22):2327-34. doi: 10.1001/jama.2011.746.
CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christensen et al., Targeting transcriptional addictions in small cell lung cancer with a covalent CDK7 inhibitor. Cancer Cell. Dec. 8, 2014;26(6):909-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Davies et al., Mutations of the BRAF gene in human cancer Nature. Jun. 27, 2002;417(6892):949-54. Epub Jun. 9, 2002.
Desai et al., Effects of phosphorylation by CAK on cyclin binding by CDC2 and CDK2. Mol Cell Biol. Jan. 1995;15(1):345-50.

(56) References Cited

OTHER PUBLICATIONS

Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fan et al., Dual leucine zipper-bearing kinase (DLK) activates p46SAPK and p38mapk but not ERK2. J Biol Chem. Oct. 4, 1996;271(40):24788-93.
Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
GenBank Accession No. M80629. Lapidot-Lifson et al., Dec. 31, 1994. 2 pages.
GenBank Accession No. NP_001790. Yang et al., Oct. 6, 2016. 4 pages.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kanakaraj et al., Interleukin (IL-)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.

(56) References Cited

OTHER PUBLICATIONS

Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marelli et al., Tumor targeting via integrin ligands. Front. Oncol., Aug. 30, 2013. https://doi.org/10.3389/fonc.2013.00222.
Marques et al., A new subfamily of high molecular mass CDC2-related kinases with PITAI/VRE motifs. Biochem Biophys Res Commun. Dec. 29, 2000;279(3):832-7.
Matsuyama et al., Activation of Discoidin Domain Receptor 1 Isoform b with Collagen Up—Regulates Chemokine Production in Human Macrophages: Role of p38 Mitogen-Activated Protein Kinase and NF-κB. J Immunol Feb. 15, 2004, 172 (4) 2332-2340; DOI: https://doi.org/10.4049/jimmunol.172.4.2332.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Peifer et al., Small-molecule inhibitors of PDK1. ChemMedChem. Dec. 2008;3(12):1810-38. doi: 10.1002/cmdc.200800195.
Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.
PubChem-CID-68365059. Available at https://pubchem.ncbi.nlm.nih.gov/compound/68365059. Accessed Jun. 17, 2016.
Roberts et al., Antiangiogenic and antitumor activity of a selective PDGFR tyrosine kinase inhibitor, CP-673,451. Cancer Res. Feb. 1, 2005;65(3):957-66.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Rubin et al., KIT activation is a ubiquitous feature of gastrointestinal stromal tumors. Cancer Res. Nov. 15, 2001;61(22):8118-21.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Sengupta et al., DLK induces developmental neuronal degeneration via selective regulation of proapoptotic JNK activity. Journal of Cell Biology 2011;194(5):751-764. DOI https://doi.org/10.1083/jcb.201103153.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Shin et al., Dual leucine zipper kinase is required for retrograde injury signaling and axonal regeneration. Neuron. Jun. 21, 2012;74(6):1015-22. doi: 10.1016/j.neuron.2012.04.028.
Smith et al., Recent advances in the research and development of RAF kinase inhibitors. Curr. Top Med. Chem. 2006; 6(11):1071-89.
Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.
Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Takemori et al., Inactivation of HDACS by SIK1 in AICAR-treated C2C12 myoblasts. Endocr J. 2009;56(1):121-30. Epub Oct. 22, 2008.
Terai et al., Activation of the FGF2-FGFR1 autocrine pathway: a novel mechanism of acquired resistance to gefitinib in NSCLC. Mol Cancer Res. Jul. 2013;11(7):759-67.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Uniprot No. Q9NYV4. Last modified Mar. 15, 2017. 14 pages.
Wang et al., IRAK-4 inhibitors for inflammation. Curr Top Med Chem. 2009;9(8):724-37.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Wietek et al., IRAK-4: a new drug target in inflammation, sepsis, and autoimmunity. Mol Interv. Jul. 2002;2(4):212-5.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Yasuda et al., The stem cell factor/c-kit receptor pathway enhances proliferation and invasion of pancreatic cancer cells. Mol Cancer. Oct. 18, 2006;5:46.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zebisch et al., Back to the roots: the remarkable RAF oncogene story Cell Mol Life Sci. Jun. 2006;63(11):1314-30.
Zhang et al., Discovery of potent and selective covalent inhibitors of JNK. Chem Biol. Jan. 27, 2012;19(1):140-54. doi: 10.1016/j.chembiol.2011.11.010.

(56) References Cited

OTHER PUBLICATIONS

Zhou et al., Novel mutant-selective EGFR kinase inhibitors against EGFR T790M. Nature. Dec. 24, 2009;462(7276):1070-4.

Partial Supplementary Search Report for EP 16808476.2, dated Mar. 7, 2019.

Extended European Search Report for EP 16845194.6, dated Mar. 1, 2019.

Dent et al., Coding categorical and coordinate spatial relations in visual-spatial short-term memory. Q J Exp Psychol (Hove). Dec. 2009;62(12):2372-87. doi: 10.1080/17470210902853548. Epub May 11, 2009.

Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258.

Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.

Girotti et al., No longer an untreatable disease: How targeted and immunotherapies have changed the management of melanoma patients. Mol Oncol. Sep. 2014; 8(6): 1140-1158. Published online Aug. 15, 2014. doi: 10.1016/j.molonc.2014.07.027.

Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.

Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.

Extended European Search Report for EP 19168422.4, dated Aug. 13, 2019.

Extended European Search Report for EP 16808476.2, dated Jun. 14, 2019.

Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.

Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript.

Cayrol et al., THZ1 targeting CDK7 suppresses STAT transcriptional activity and sensitizes T-cell lymphomas to BCL2 inhibitors. Nat Commun. Jan. 30, 2017;8:14290. doi: 10.1038/ncomms14290.

Chipumuro et al., CDK7 inhibition suppresses super-enhancer-linked oncogenic transcription in MYCN-driven cancer. Cell. Nov. 20, 2014;159(5):1126-1139. doi: 10.1016/j.cell.2014.10.024. Epub Nov. 6, 2014.

Eliades et al., High MITF Expression is Associated with Super-Enhancers and Suppressed by CDK7 Inhibition in Melanoma. J Invest Dermatol. Jul. 2018;138(7):1582-1590. doi: 10.1016/j.jid.2017.09.056. Epub Feb. 8, 2018.

Fancelli et al., Potent and selective Aurora inhibitors identified by the expansion of a novel scaffold for protein kinase inhibition. J Med Chem. Apr. 21, 2005;48(8):3080-4.

Iniguez et al., EWS/FLI Confers Tumor Cell Synthetic Lethality to CDK12 Inhibition in Ewing Sarcoma. Cancer Cell. Feb. 12, 2018;33(2):202-216.e6. doi:10.1016/j.ccell.2017.12.009. Epub Jan. 18, 2018.

Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript.

McAuley et al., CARMA3 is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.

Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012.

Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.

Rusan et al., Suppression of Adaptive Responses to Targeted Cancer Therapy by Transcriptional Repression. Cancer Discov. Jan. 2018;8(1):59-73. doi: 10.1158/2159-8290.CD-17-0461. Epub Oct. 20, 2017.

Sidow et al., Concepts in solid tumor evolution. Trends Genet. Apr. 2015;31(4):208-14. doi: 10.1016/j.tig.2015.02.001. Epub Feb. 27, 2015. Author manuscript.

Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.001.

Wang et al., CDK7-dependent transcriptional addiction in triple-negative breast cancer. Cell. Sep. 24, 2015;163(1):174-86. doi: 10.1016/j.cell.2015.08.063.

Zeng et al., Targeting MYC dependency in ovarian cancer through inhibition of CDK7 and CDK12/13. Elife. Nov. 13, 2018;7. pii: e39030. doi: 10.7554/eLife.39030.

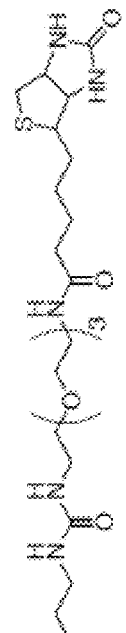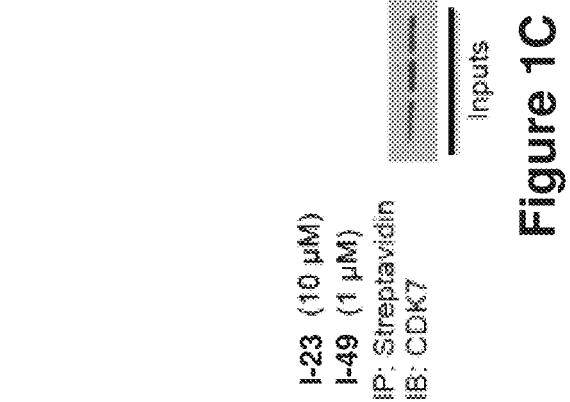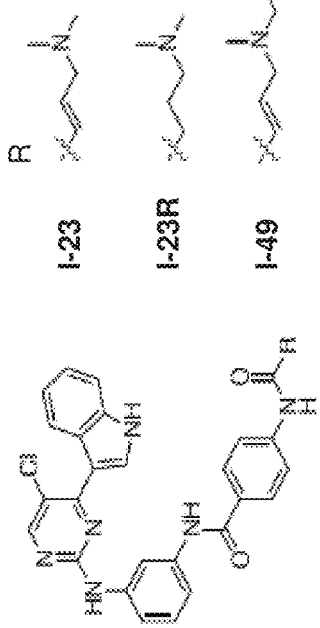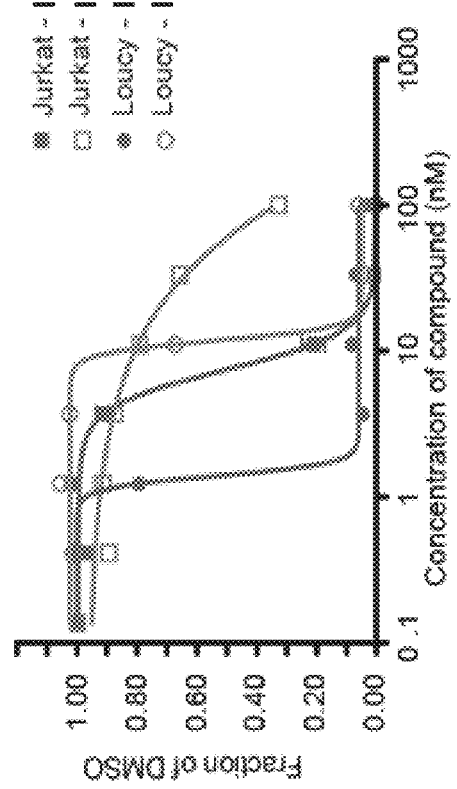
Figure 1A
Figure 1B
Figure 1C

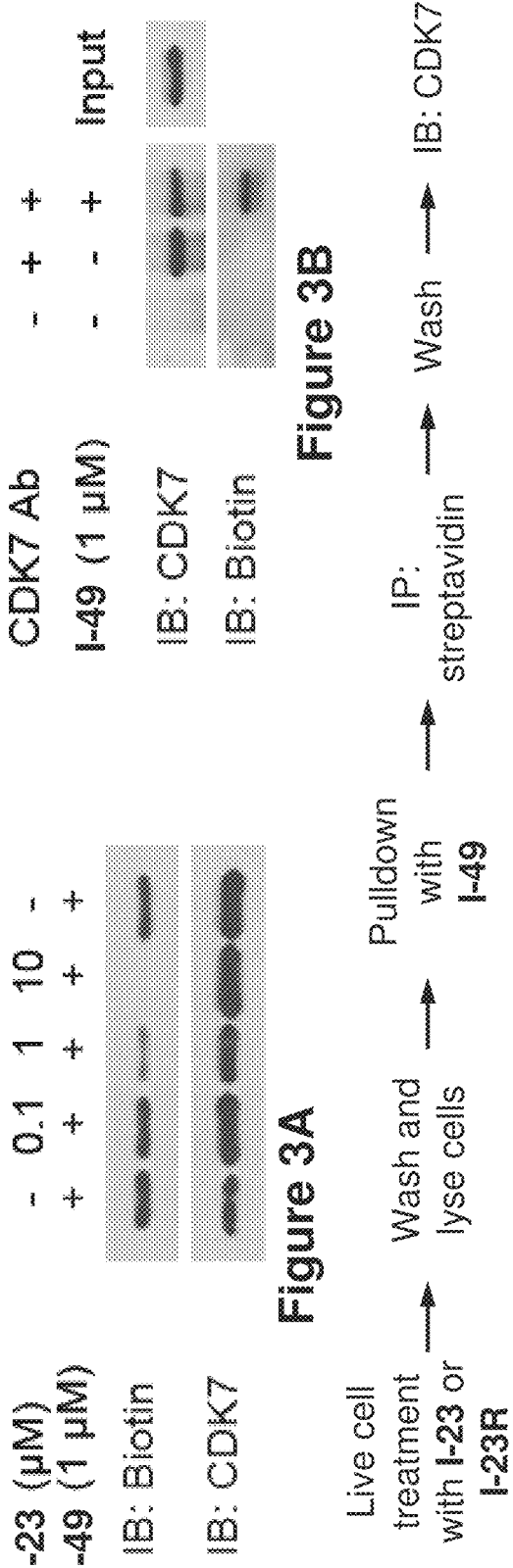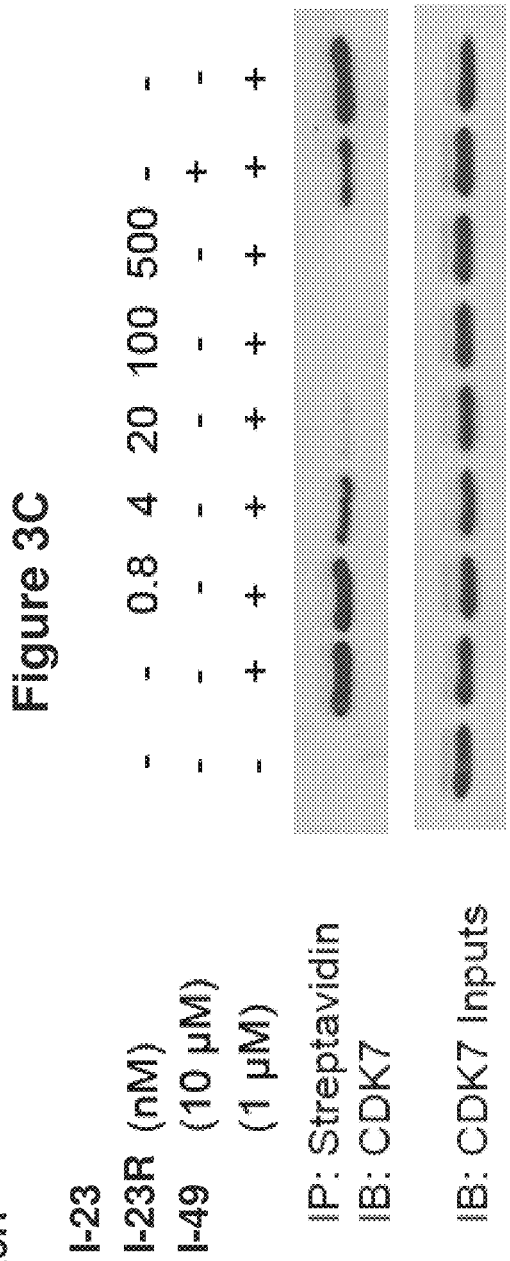

| Kinase/ CDK7 residue# | Pro308 | Arg309 | Pro310 | Asn311 | Cys312 | Pro313 | Val314 | Glu315 |
|---|---|---|---|---|---|---|---|---|
| CDK7 | P | R | P | N | C | P | V | E |
| mCDK7 | P | R | P | N | C | P | V | E |
| CDK1 | | | | | | | | |
| CDK2 | | | | | | | | |
| CDK4 | | | | | | | | |
| CDK5 | | | | | | | | |
| CDK6 | | | | | | | | |
| CDK8 | Q | - | P | Y | P | K | K | E |
| CDK9 | L | S | T | H | L | T | T | - |
| CDK11 | W | P | A | K | S | E | S | Q |
| CDK12 | L | N | - | H | S | N | P | E |
| CDK13 | L | N | - | H | S | N | P | E |
| CDK19 | Q | - | P | Y | P | K | R | E |

Figure 4B

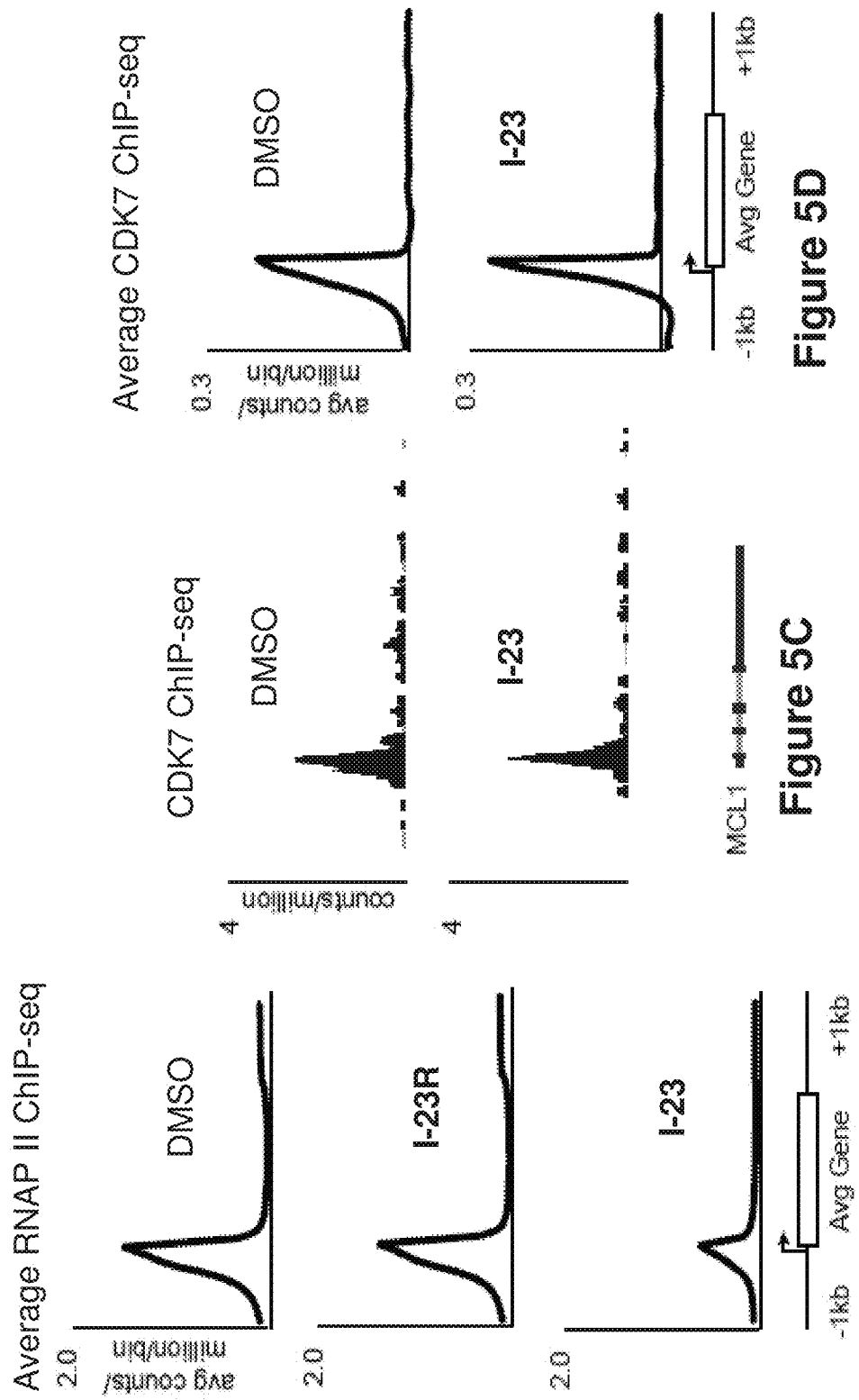

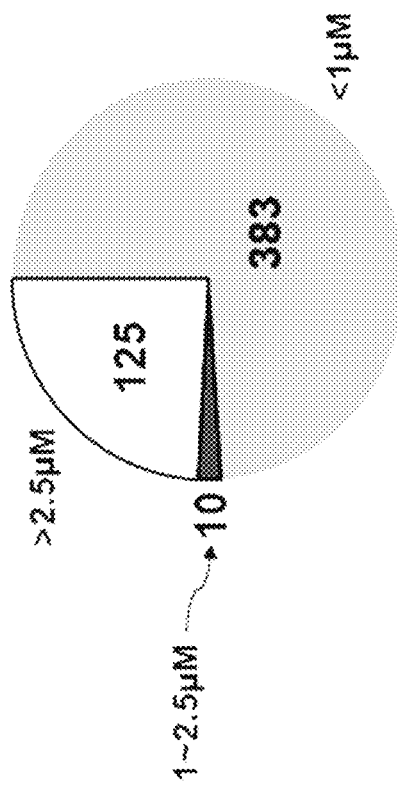
Figure 6C
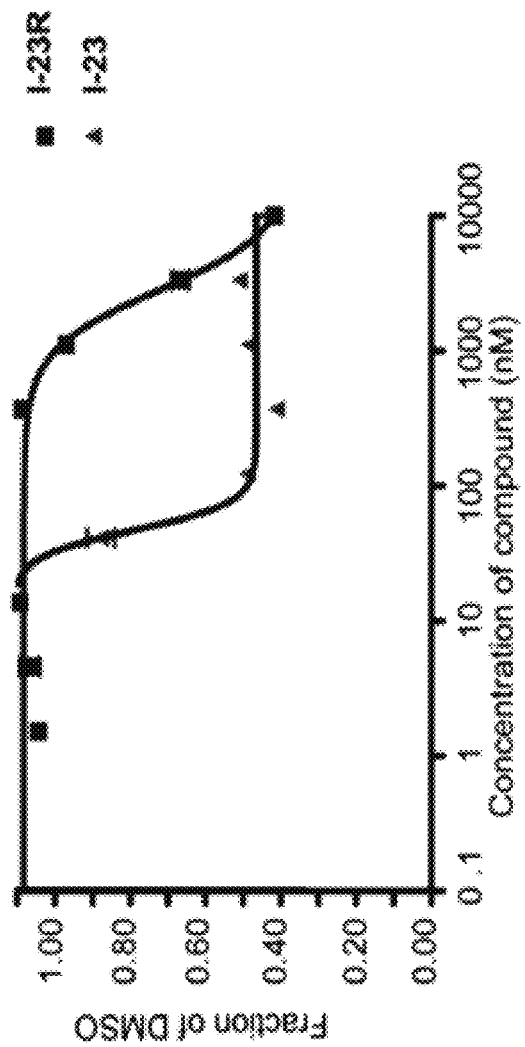
Figure 6D
Figure 6E

| Matrix | Route | Dose (mg/kg) | $T_{max}$ (hr) | $^{a}C_0, C_{max}$ (ng/mL) | $AUC_{last}$ (hr*ng/mL) | $AUC_{INF}$ (hr*ng/mL) | $T_{1/2}$ (hr) | CL (mL/min/kg) | $V_{ss}$ (L/kg) | $\%F^{b}$ |
|---|---|---|---|---|---|---|---|---|---|---|
| Plasma | i.v. | 1 | - | 1563.02 | 385.26 | 449.34 | 13.88 | 37.09 | 20.61 | |
| | p.o. | 10 | 0.50 | 9.01 | 63.93 | NR | - | - | - | 2 | a - $C_0$ back extrapolated conc. for i.v. group.
b - $AUC_{last}$ was considered for calculating bioavailability
NR – not reported since $AUC_{INF}$ is 20% greater than $AUC_{last}$

Figure 6F

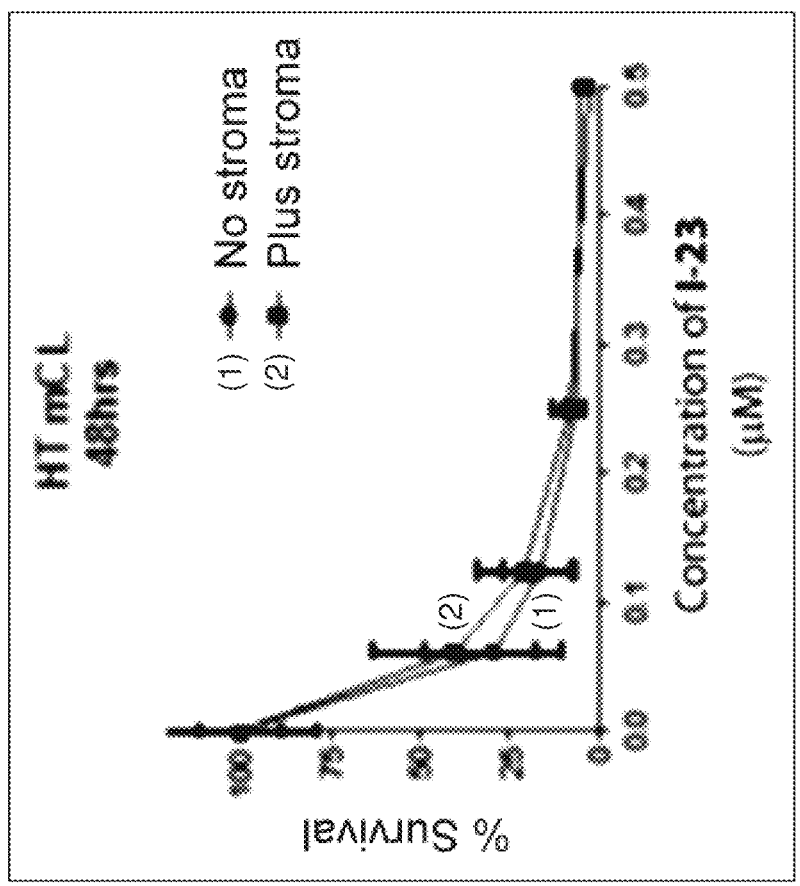
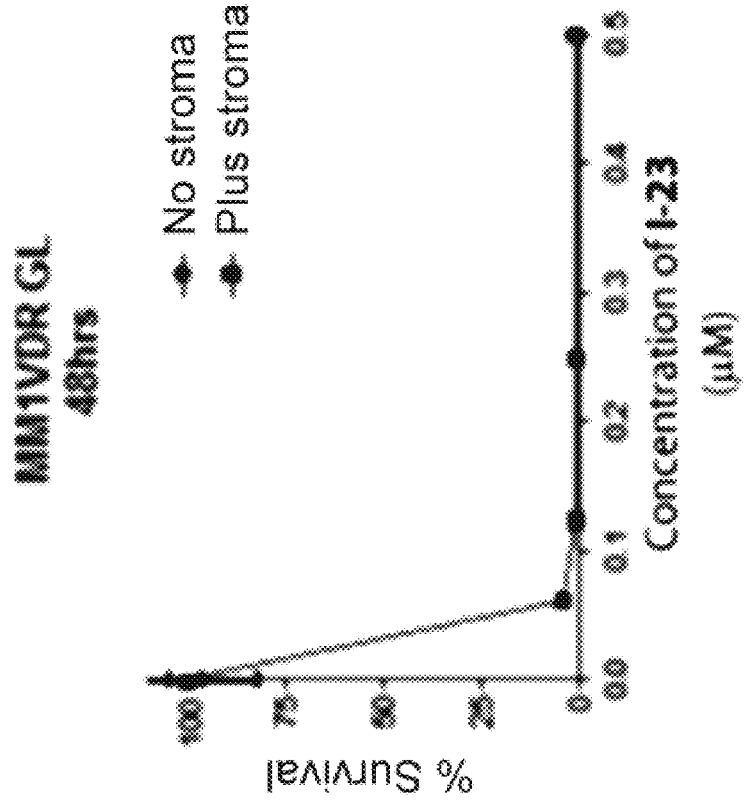
Figure 11C

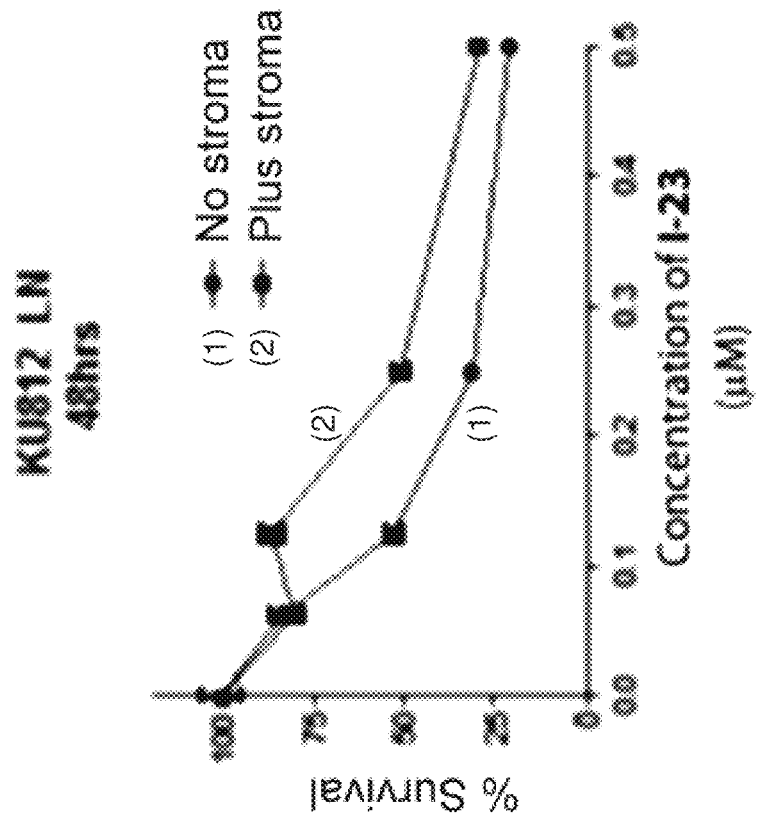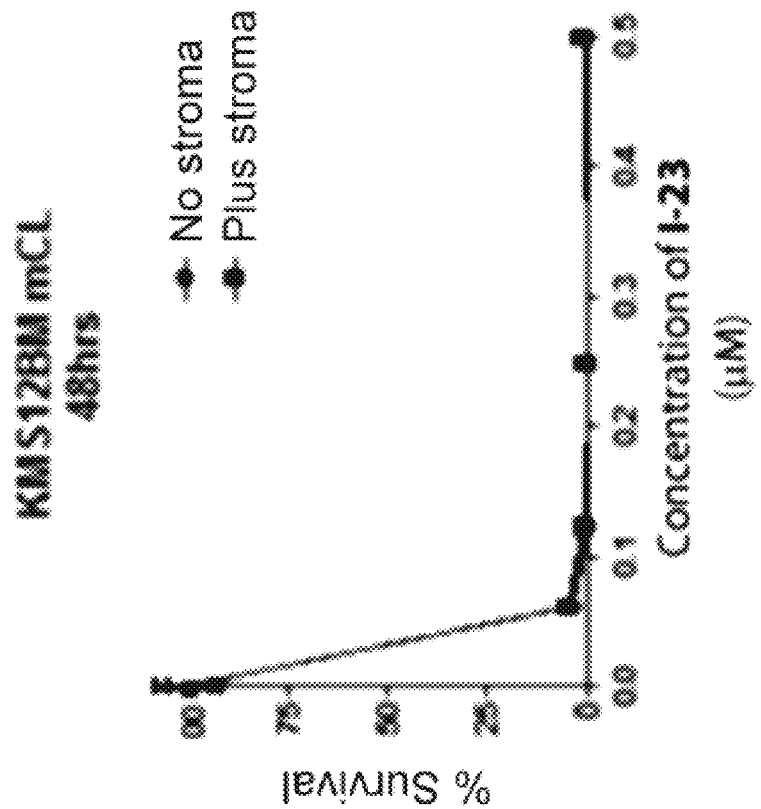
Figure 11D

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1

Val Pro Phe Leu Pro Gly Asp Ser Asp Leu Asp Gln Leu Thr Arg
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 2

Leu Asp Phe Leu Gly Glu Gly Gln Phe Ala Thr Val Tyr Lys
1               5                   10

<210> SEQ ID NO 3
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 3

Tyr Ser Phe Asn Arg Pro Gly Pro Thr Pro Gly Cys Ala Cys Gln Leu
1               5                   10                  15

Pro Arg Pro Asn Cys Ala Cys Pro Val Glu Thr Leu Lys
```

```
<210> SEQ ID NO 4
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 4

Tyr Phe Ser Asn Arg Pro Gly Pro Thr Pro Gly Cys Ala Cys Gln Leu
1               5                   10                  15

Pro Arg Pro Asn Cys Ala Cys Pro Val Glu Thr Leu Lys
            20                  25
```

INHIBITORS OF CYCLIN-DEPENDENT KINASE 7 (CDK7)

RELATED APPLICATIONS

The present application is a divisional of and claims priority under 35 U.S.C § 120 to U.S. Application, U.S. Ser. No. 14/436,496, filed Apr. 17, 2015, which is a national stage filing under 35 U.S.C. 371 of international PCT application, PCT/US2013/065708, filed Oct. 18, 2013, which claims priority under 35 U.S.C. § 119(e) to U.S. provisional patent applications, U.S. Ser. No. 61/715,574, filed Oct. 18, 2012, and U.S. Ser. No. 61/727,640, filed Nov. 16, 2012, each of which is incorporated herein by reference.

GOVERNMENT SUPPORT

This invention was made with U.S. government support under grant number 5 U54 HG006097-02 awarded by the National Institutes of Health (NIH). The U.S. government has certain rights in the invention.

BACKGROUND OF THE INVENTION

The members of the cyclin-dependent kinase (CDK) family play critical regulatory roles in proliferation. There are currently 20 known mammalian CDKs. While CDK7-13 have been linked to transcription, only CDK1, 2, 4, and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2." *Mol. Cell Biol.* 15, 345-350 (1995); Kaldis et al., "Analysis of CAK activities from human cells." *Eur. J. Biochem.* 267, 4213-4221 (2000); Larochelle et al., "Requirements for CDK7 in the assembly of CDK1/cyclin B and activation of CDK2 revealed by chemical genetics in human cells." *Mol. Cell* 25, 839-850 (2007)). In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa. et al., "Association of CDK-activating kinase subunits with transcription factor TFIIH." *Nature* 374, 280-282 (1995); Shiekhattar et al., "CDK-activating kinase complex is a component of human transcription factor TFIIH." *Nature* 374, 283-287 (1995); Drapkin et al., "Human cyclin-dependent kinase-activating kinase exists in three distinct complexes." *Proc. Natl. Acad. Sci. U.S.A* 93, 6488-6493 (1996); Liu. et al., "Two cyclin-dependent kinases promote RNA polymerase II transcription and formation of the scaffold complex." *Mol. Cell Biol.* 24, 1721-1735 (2004); Akhtar et al., "TFIIH kinase places bivalent marks on the carboxy-terminal domain of RNA polymerase II." *Mol. Cell* 34, 387-393 (2009); Glover-Cutter et al., "TFIIH-associated CDK7 kinase functions in phosphorylation of C-terminal domain Ser7 residues, promoter-proximal pausing, and termination by RNA polymerase II." *Mol. Cell Biol.* 29, 5455-5464 (2009)). Together, the two functions of CDK7, i.e., CAK and CTD phosphorylation, support critical facets of cellular proliferation, cell cycling, and transcription.

Disruption of RNAP II CTD phosphorylation has been shown to preferentially effect proteins with short half-lives, including those of the anti-apoptotic BCL-2 family (Konig et al., "The novel cyclin-dependent kinase inhibitor flavopiridol downregulates Bcl-2 and induces growth arrest and apoptosis in chronic B-cell leukemia lines." *Blood* 1, 4307-4312 (1997); Gojo et al., "The cyclin-dependent kinase inhibitor flavopiridol induces apoptosis in multiple myeloma cells through transcriptional repression and down-regulation of Mcl-1." *Clin. Cancer Res.* 8, 3527-3538 (2002)). Cancer cells have demonstrated ability to circumvent pro-cell death signaling through upregulation of BCL-2 family members (Llambi et al., "Apoptosis and oncogenesis: give and take in the BCL-2 family." *Curr. Opin. Genet. Dev.* 21, 12-20 (2011)). Therefore, inhibition of human CDK7 kinase activity is likely to result in anti-proliferative activity, and pharmacological inhibition could be used to treat proliferative disorders, including cancer. Indeed, flavopiridol, a non-selective pan-CDK inhibitor that targets CTD kinases, has demonstrated efficacy for the treatment of chronic lymphocytic leukemia (CLL), but suffers from a poor toxicity profile (Lin et al., "Phase II study of flavopiridol in relapsed chronic lymphocytic leukemia demonstrating high response rates in genetically high-risk disease." *J. Clin. Oncol.* 27, 6012-6018 (2009); Christian et al., "Flavopiridol in chronic lymphocytic leukemia: a concise review." Clin. Lymphoma Myeloma 9 Suppl. 3, S179-S185 (2009)). A selective CDK7 inhibitor may hold promise as a therapeutic agent for the treatment of CLL and other cancers.

SUMMARY OF THE INVENTION

Cyclin dependent kinases (CDKs), e.g., CDK7, are key regulators of the cell cycle. Their successive activation and inactivation drives the cycle forward. The activity of CDKs is regulated by multiple mechanisms such as positive and negative phosphorylation, binding of regulatory proteins like cyclins, and CDK inhibitors. Most CDKs require the phosphorylation of a threonine residue located in the T-loop to achieve full kinase activity. This threonine residue is conserved in all CDKs that function in cell cycle regulation. The enzyme responsible for this phosphorylation is therefore termed CDK-activating-kinase or CAK. CAK complexes have been found to be composed of CDK7, cyclin H, and MAT1. The CAK complex containing CDK7 appears to constitute the major CAK activity in the cell. Besides its CAK function, CDK7 also plays a role in transcription and possibly in DNA repair. The trimeric CAK complex CDK7/cyclin H/MAT1 is also a component of TFIIH, the general transcription/DNA repair factor IIH. As a TFIIH subunit, CDK7 phosphorylates the carboxy-terminal-domain (CTD) of the largest subunit of RNAP II. This suggests that the CDK7 enzyme complexes are involved in multiple functions in the cell, e.g., cell cycle control, apoptosis, transcription regulation, and DNA repair.

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of a kinase. In certain embodiments, the kinase is CDK. In certain embodiments, the kinase is CDK7. In certain embodiments, the compound of Formula (I) is selective for CDK7 compared to other kinases. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK7) and as therapeutics for the prevention and/or treatment of diseases associated with overexpression and/or aberrant activity of a kinase (e.g., CDK7). In certain embodiments, the inventive compounds are used for the prevention and/or treatment of proliferative diseases (e.g., cancers (e.g., leukemia, lymphoma, melanoma, multiple myeloma, breast cancer, Ewing's sarcoma, osteosarcoma, brain cancer, neuroblastoma, lung cancer), benign neoplasms, angiogenesis, inflammatory diseases, autoinflammatory diseases, and autoimmune diseases) in a subject.

The compounds of Formula (I) may selectively inhibit the activity of CDK7. Since the discovery of selective inhibitors of CDK7 has been hampered by the high sequence and structural similarities of the kinase domain of CDK family members, the development of selective inhibitors of the transcriptional cyclin-dependent kinases (tCDKs) will allow dissection of their individual contributions to the regulation of transcription and evaluation of their therapeutic potential. Without wishing to be bound by any particular theory, the inventive compounds' selectivity for CDK7 may be due to the compounds' ability to covalently modify the cysteine (Cys312) residue of CDK7, the Cys312 residue being largely unique among the CDKs and other kinases.

In one aspect, the present invention provides compounds of Formula (I):

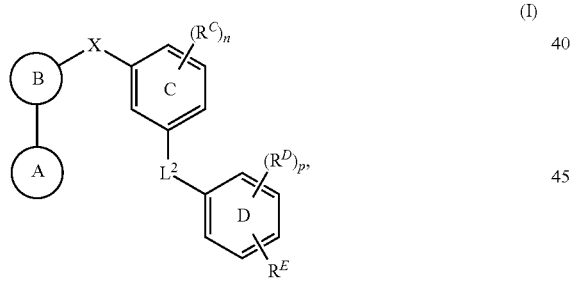

(I)

and pharmaceutically acceptable salts, solvates, hydrates, polymorphs, co-crystals, tautomers, stereoisomers, isotopically labeled derivatives, and prodrugs thereof, wherein Ring A, Ring B, X, $L^2$, $R^C$, $R^D$, $R^E$, n, and p are as defined herein.

In certain embodiments, a compound of Formula (I) is of the formula:

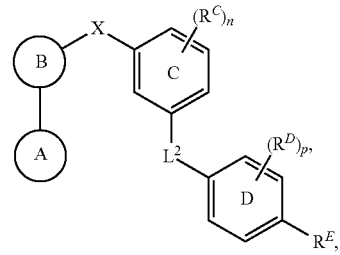

or a pharmaceutically acceptable salt, solvate, hydrate, polymorph, co-crystal, tautomer, stereoisomer, isotopically labeled derivative, or prodrug thereof In certain embodiments, a compound of Formula (I) is the formula:

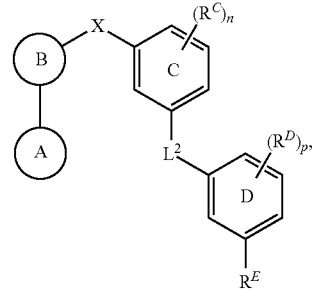

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to:

(I-17)

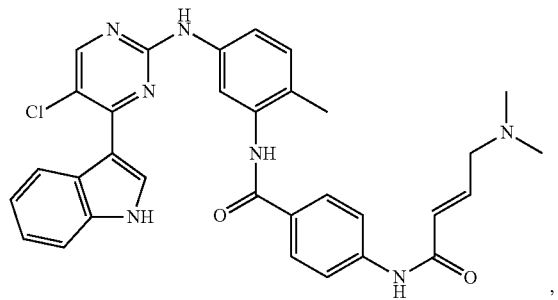

(I-18)

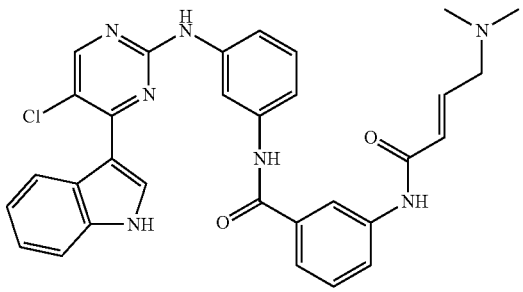

-continued
(I-19)
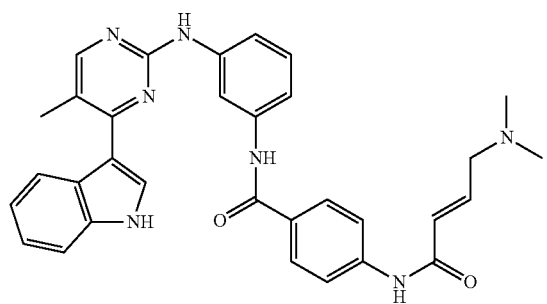
(I-20)
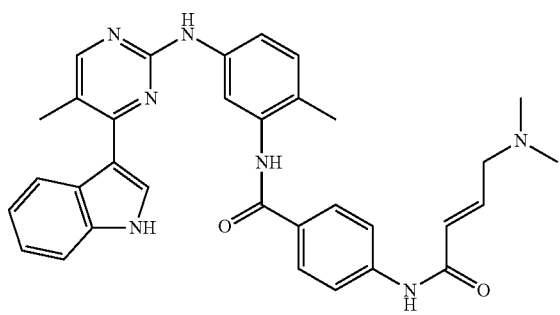
(I-21)
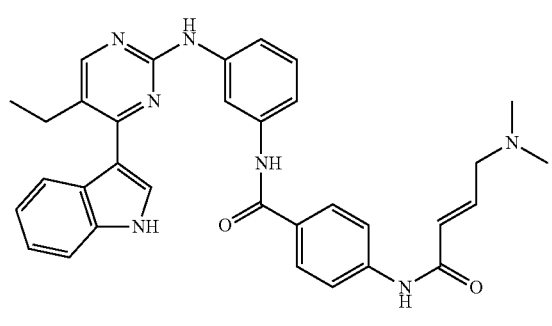
(I-22)
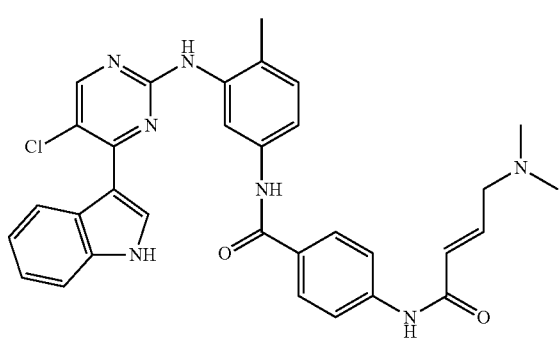
(I-23)
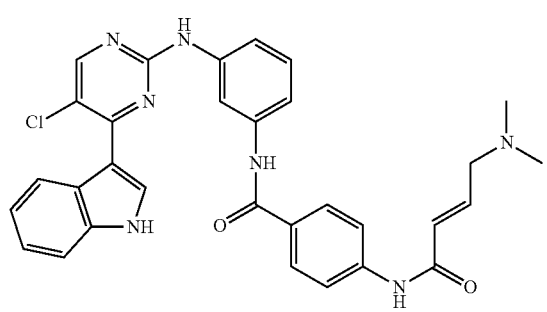
(I-24)
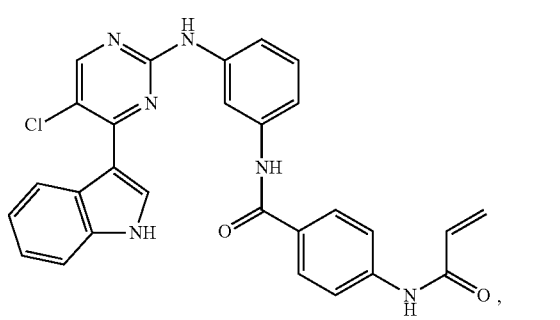
(I-25)
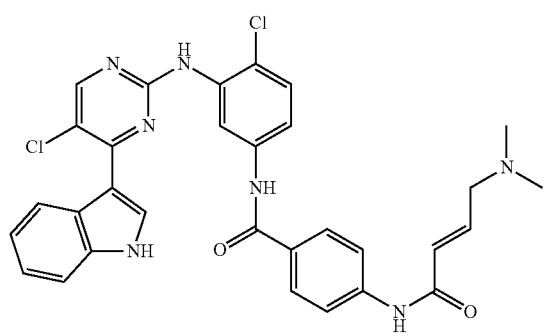
(I-26)
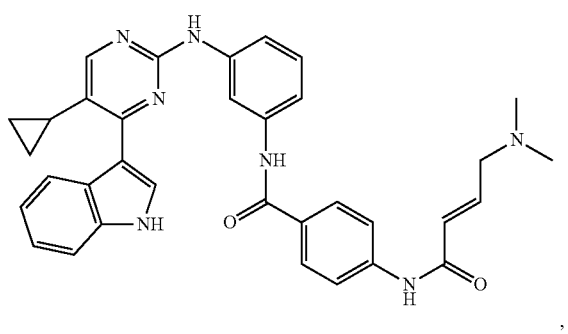

-continued
(I-27)
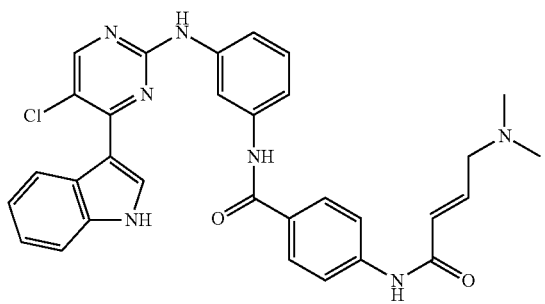
(I-28)
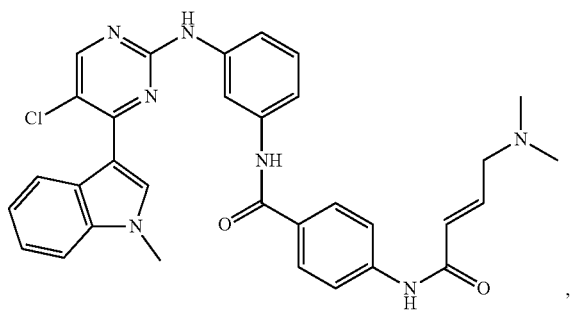
(I-29)
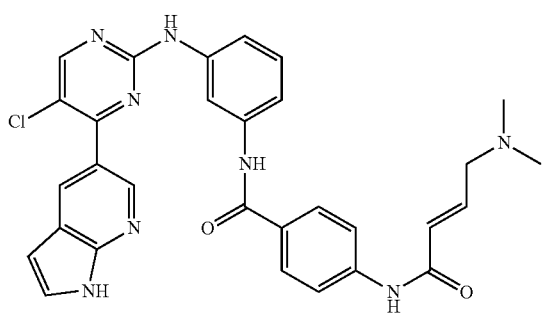
(I-30)
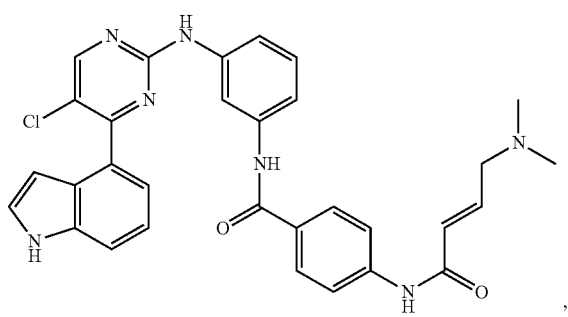
(I-31)
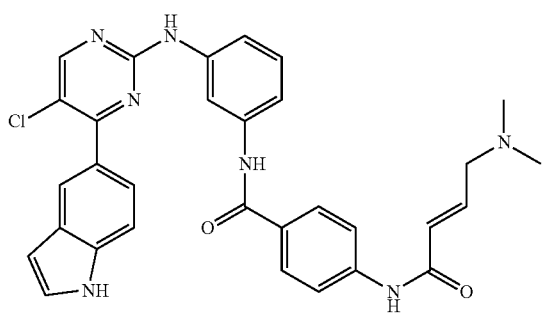
(I-32)
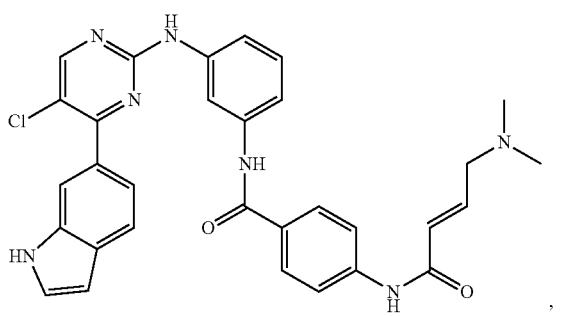
(I-33)
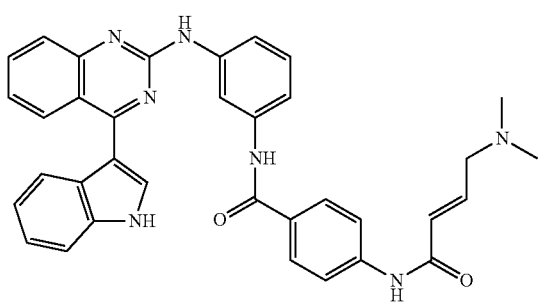
(I-34)
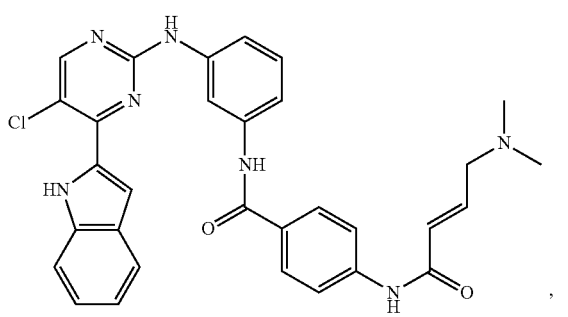

-continued
(I-35)
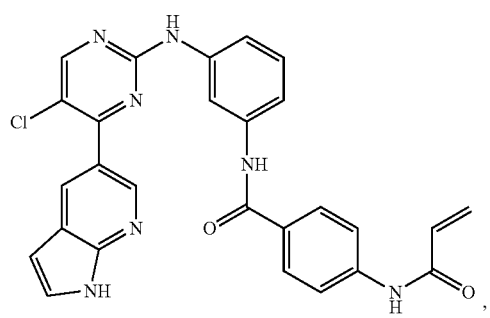
(I-36)
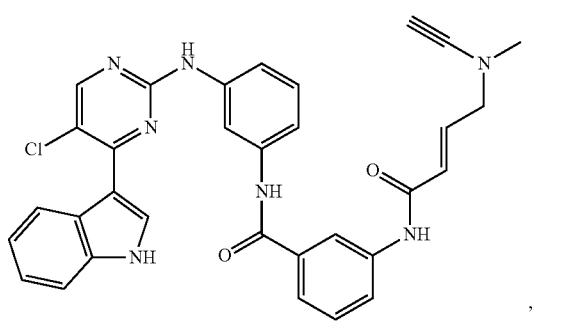
(I-37)
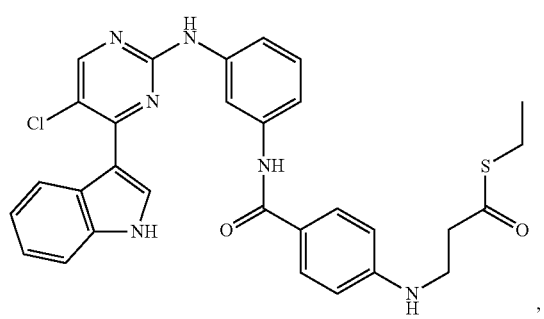
(I-38)
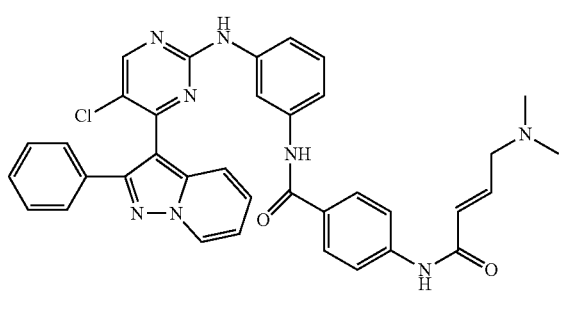
(I-39)
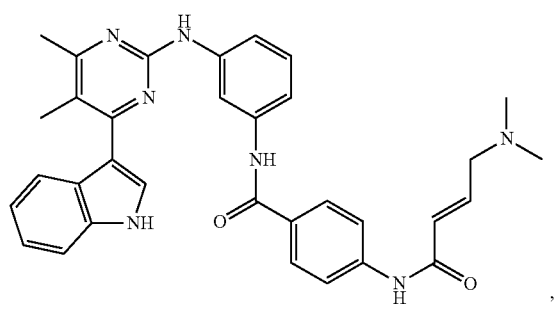
(I-40)
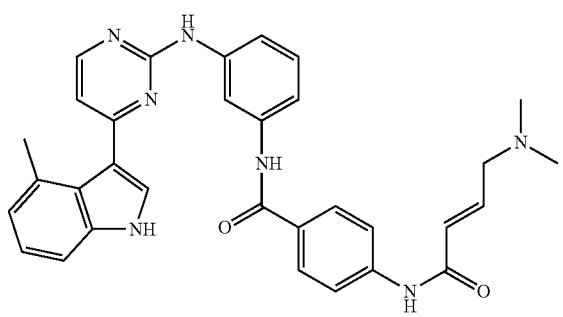
(I-41)
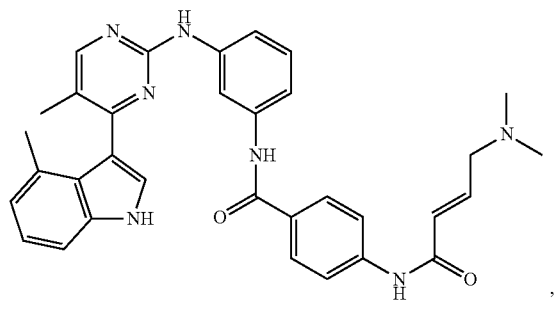
(I-42)
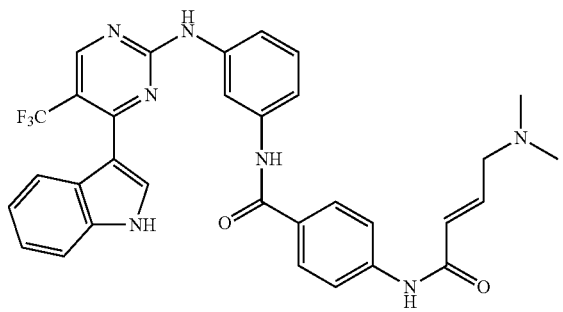

-continued
(I-43)
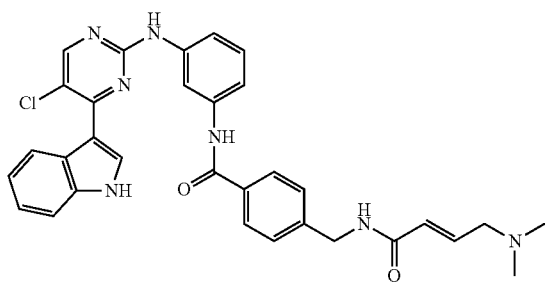
(I-44)
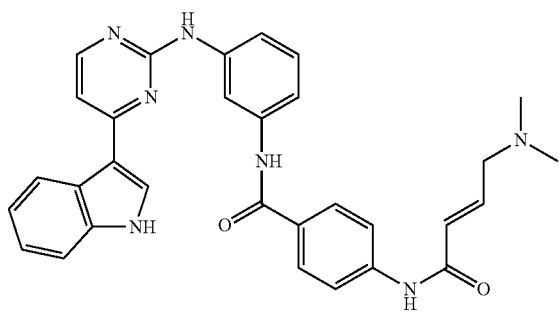
(I-45)
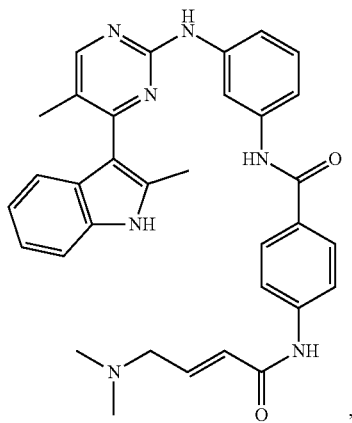
(I-46)
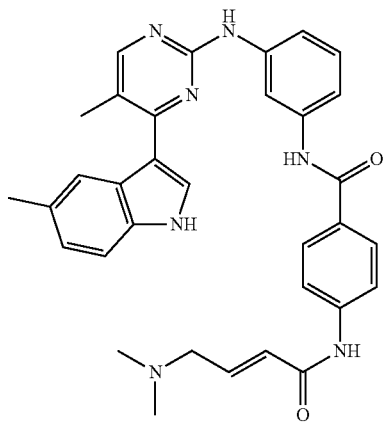
(I-47)
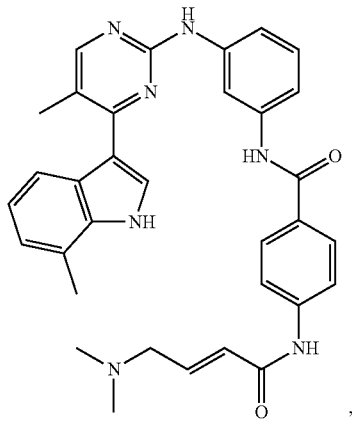
(I-48)
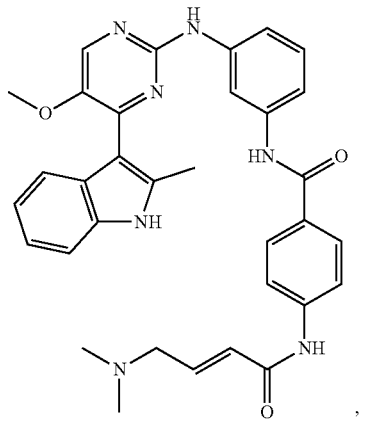
(I-49)
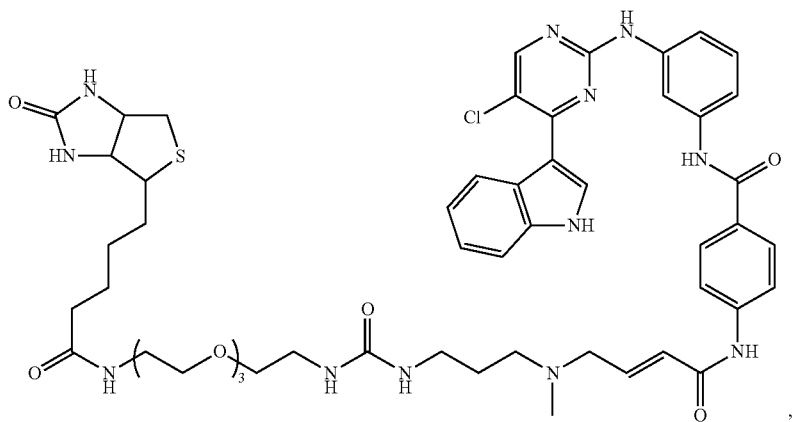

-continued
(I-50)
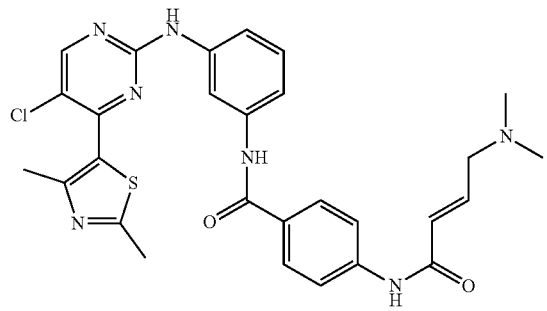
(I-51)
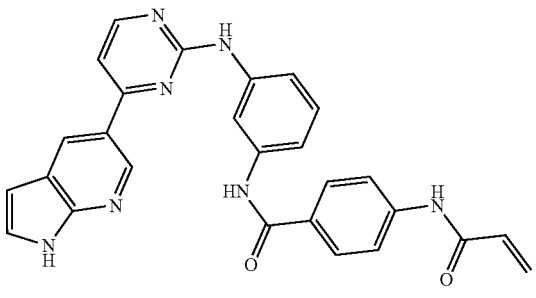
(I-52)
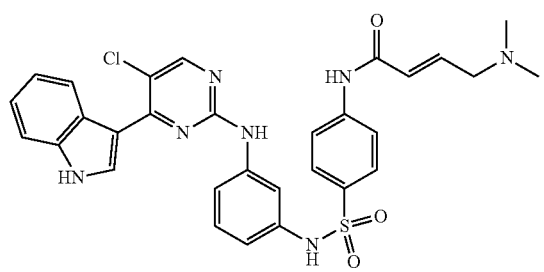
(I-53)
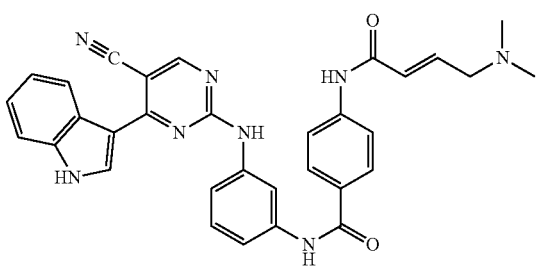
(I-54)
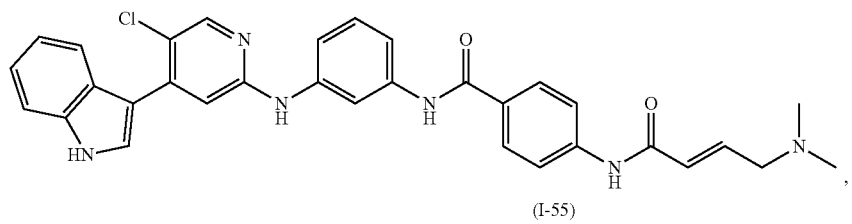
(I-55)
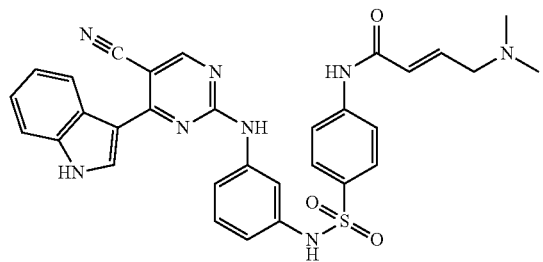
(I-56)
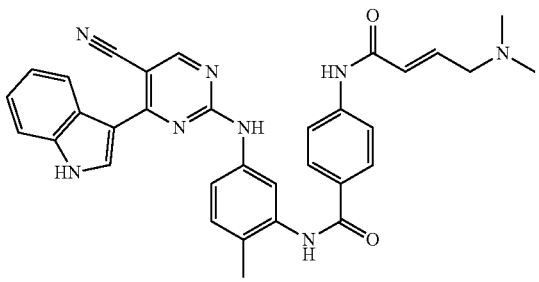
(I-57)
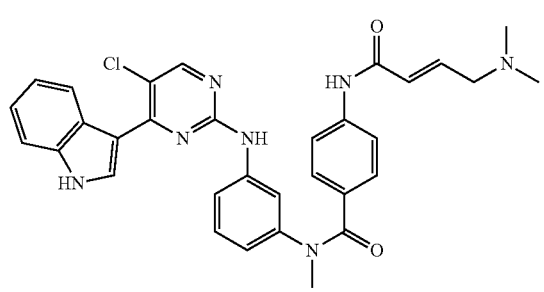
(I-58)
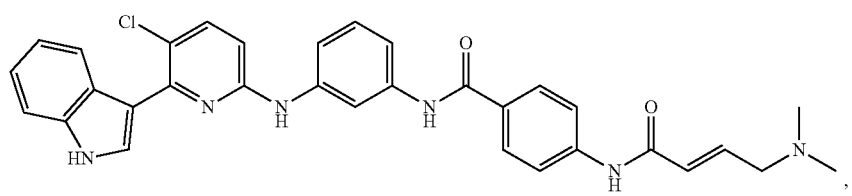

-continued
(I-60)
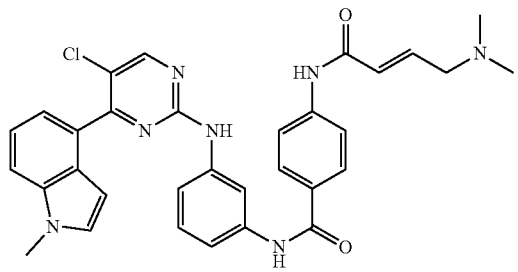
(I-61)
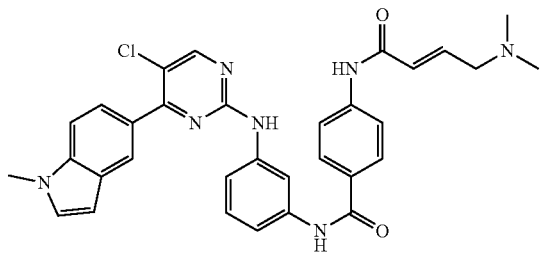
(I-62)
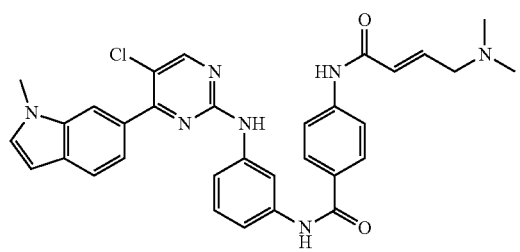
(I-63)
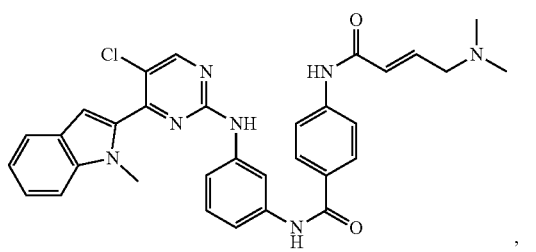
(I-64)
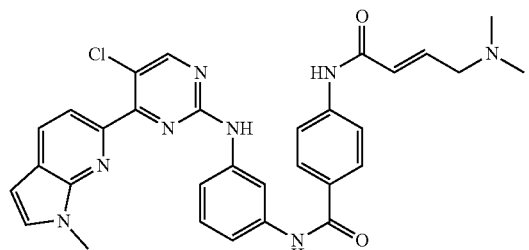
(I-65)
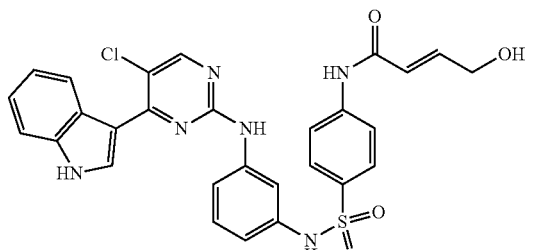
(I-66)
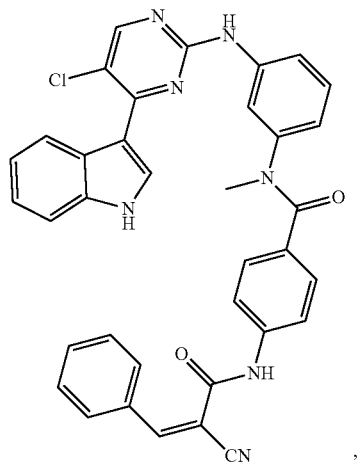
(I-67)
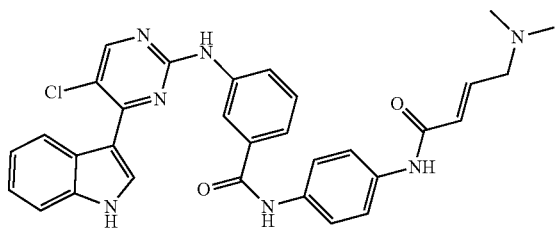
(I-68)
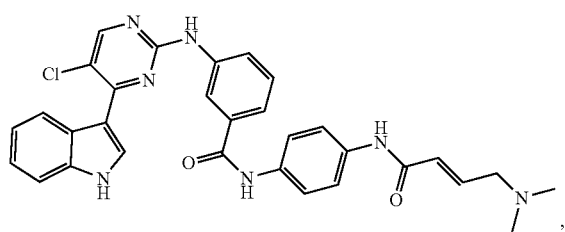

and pharmaceutically acceptable salts, solvates, hydrates, polymorphs, co-crystals, tautomers, stereoisomers, isotopically labeled derivatives, and prodrugs thereof.

Additional exemplary compounds include:

(I-69)

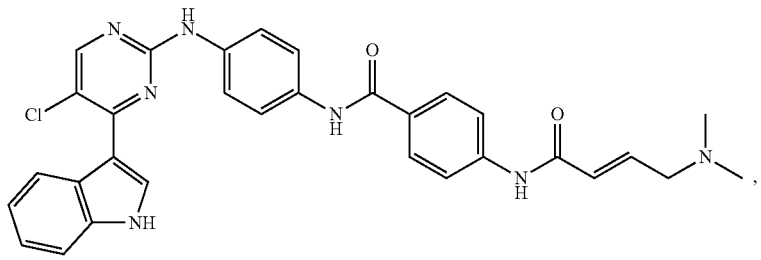

and pharmaceutically acceptable salts, solvates, hydrates, polymorphs, co-crystals, tautomers, stereoisomers, isotopically labeled derivatives, and prodrugs thereof.

Additional exemplary compounds include:

(I-70)

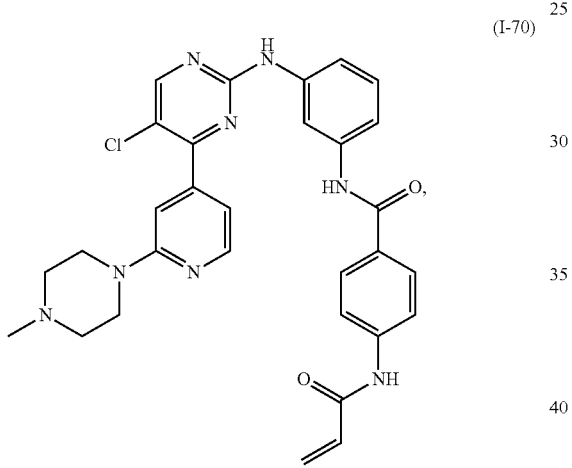

(I-71)

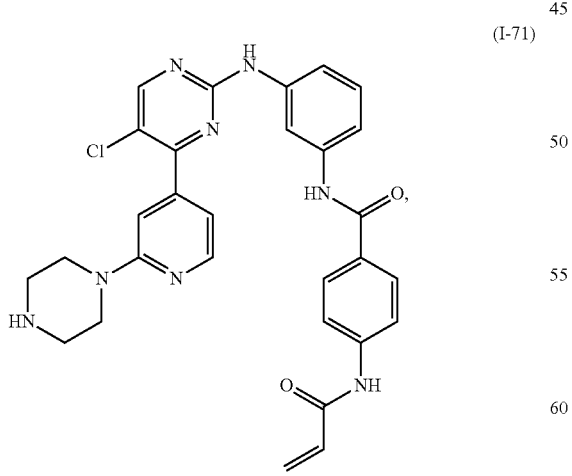

and pharmaceutically acceptable salts, solvates, hydrates, polymorphs, co-crystals, tautomers, stereoisomers, isotopically labeled derivatives, and prodrugs thereof.

In another aspect, the present invention provides novel classes of inhibitors of CDK7. These novel classes of CDK7 inhibitors are characterized by one or more the following structural and/or physicochemical features:

(a.) a pharmacophore generally of Formula (II):

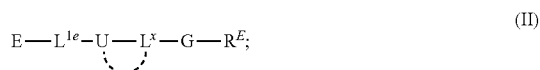

(II)

(b.) a G group that spans a total length between approximately 20 to approximately 30 Å, with a spatial arrangement provided in Formulae (III) and (IIIa) in certain embodiments:

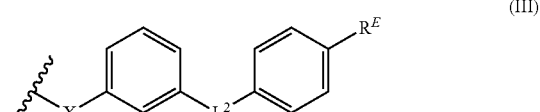

(III)

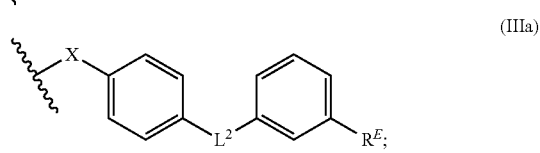

(IIIa)

(c.) an electrophilic group, $R^E$ that forms a covalent bond with the —SH group of Cys312 of CDK7 and is between approximately 12 to approximately 14 Å from the CDK7 inhibitor binding pocket;

(d.) a linker group $L^{1e}$ ranging between 0 to 3 atoms in length;

(e.) a linker group $L^x$ ranging between 0 to 5 atoms in length, which may contain at least one hydrogen bond donor moiety that forms a hydrogen bond to the backbone amide —CO— group of CDK7 residue methionine 94 (Met94);

(f.) an E group that is moderately hydrophobic with a fragment c Log P between 1.0 and 3.0, which associates with a hydrophobic pocket exposed by the inactive form of CDK7 characterized by a closed conformation of the activation loop (DFG "out"), and may optionally contain at least one hydrogen bond donor moiety that forms a hydrogen bond to the —N of CDK7 residue lysine 41 (Lys41);

(g.) a U group contain at least one hydrogen bond acceptor moiety that forms a hydrogen bond to the backbone amide —NH— of CDK7 residue methionine 94 (Met94);

(h.) binding of the compound within the binding pocket of CDK7 that is defined by amino acids: phenylalanine-93, aspartic acid-92, aspartic acid-97, asparagine-142, and leucine-144; and (i.) binding of the compound within the binding pocket of CDK7 that is defined by amino acids: methionine-94, lysine-41, and phenylalanine-91.

In another aspect, the present invention provides a method for the identification, design, or prediction of novel classes of inhibitors of CDK7 comprising the steps of:

(a) generating, on a computer, a three-dimensional representation of CDK7 having the coordinates of the solved X-ray structure, available publically as 1UA2 on PDB.org;

(b) identifying amino acid residues forming a binding pocket in the three-dimensional structure of CDK7 from step (a), in proximity to cysteine-312;

(c) generating a three-dimensional model of the active site;

(d) designing and/or selecting a compound that potentially binds to the active site using the three-dimensional model of the active site; and (e) synthesizing and/or choosing the potential binding compound.

In another aspect, the present invention discloses a method of identifying a drug candidate for the treatment of a disease, the method comprising:

(a) using the available atomic coordinates to form a three-dimensional structure of CDK7;

(b) selecting a test compound having the best fit with the structure of CDK7; and (c) assaying the ability of the test compound to modulate CDK7 activity, wherein a test compound that modulates CDK7 activity is considered a drug candidate for treating a disease.

In another aspect, the present invention discloses a CDK7 inhibitor having molecular dimensions compatible with the shape of the active site of CDK7 as defined by the atomic coordinates of phenylalanine-93, aspartic acid-92, aspartic acid-97, asparagine-142, and leucine-144, methionine-94, lysine-41, and phenylalanine-91, wherein a pendent electrophile covalently modifies cysteine-312, and preferably the compound has a biochemical $IC_{50}$ for CDK7 of less than approximately 100 nM.

In another aspect, the present invention discloses an inhibited Cyclin-dependent kinase comprising an irreversible CDK7 inhibitor having a covalent bond to the cysteine-312 residue of CDK7. In certain embodiments, based on an inhibitor of Formula (II) above such a modified CDK7 may have be of Formula (IV):

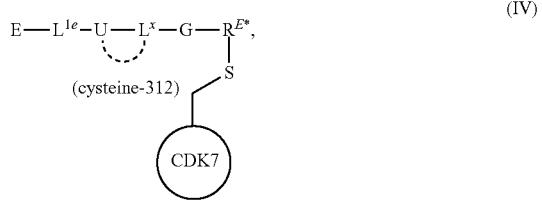

wherein $R^{E*}$ is an electrophilic moiety that has reacted with the nucleophilic —SH of cysteine-312, and E, $L^{1e}$, U, $L^x$, and G are defined herein.

In another aspect, the present invention discloses an inhibited Cyclin-dependent kinase comprising an irreversible CDK7 inhibitor having a covalent bond to the cysteine-312 residue of CDK7. In certain embodiments, based on an inhibitor of Formula (I) above such a modified CDK7 may have be of Formula (V):

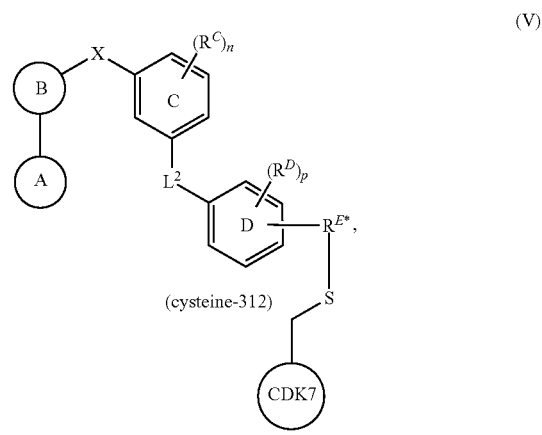

wherein $R^{E*}$ is an electrophilic moiety that has reacted with the nucleophilic —SH of cysteine-312 and A, B, X, C, D, $L^2$, $R^C$, $R^D$, p, and n are defined herein.

In another aspect, the present invention provides pharmaceutical compositions comprising a compound of Formula (I), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (I), or a pharmaceutically acceptable salt, solvate, hydrate, polymorph, co-crystal, tautomer, stereoisomer, isotopically labeled derivative, or prodrug thereof. The pharmaceutical composition may be useful for treating and/or preventing a proliferative disease (e.g., cancer) or an infectious disease.

In another aspect, the present invention provides methods for treating and/or preventing proliferative diseases. Exemplary proliferative diseases include cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases. In other embodiments, the present invention provides methods for treating and/or preventing an infectious disease (e.g., a viral infection).

In still another aspect, the present invention provides methods of down-regulating the expression of a kinase (e.g., CDK (e.g., CDK7)) in a biological sample or subject. In certain embodiments, the method involves the specific down-regulation of the expression of CDK7.

Another aspect of the invention relates to methods of inhibiting the activity of a kinase (e.g., CDK (e.g., CDK7)) in a biological sample or subject. In certain embodiments, the method involves the selective inhibition of CDK7.

Also provided by the present invention are methods of inhibiting transcription in a biological sample or subject. The transcription of genes affected by the activity of CDK7 may be inhibited by the compounds of the invention.

The present invention also provides methods of inhibiting cell growth in a biological sample or subject.

In still another aspect, the present invention provides methods of inducing apoptosis of a cell in a biological sample or a subject.

Another aspect of the invention relates to methods of screening a library of compounds (e.g., compounds of Formula (I)) to identify one or more compounds useful in the treatment of a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases) or an infectious disease (e.g., viral infection) in a subject, in inhibiting a kinase (e.g., CDK, such as CDK7), in inhibiting cell growth, in inducing apoptosis of a cell, and/or in inhibiting transcription.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease in a subject.

In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment or prevention of an infectious disease in a subject. In certain embodiments, the infectious disease is a viral infection.

Another aspect of the present invention relates to kits comprising a container with a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment and/or prevention of a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory diseases, autoinflammatory diseases, and autoimmune diseases) or an infectious disease in a subject. In certain embodiments, the kits described herein further include instructions for administering the compound of Formula (I), or the pharmaceutically acceptable salt, solvate, hydrate, polymorph, co-crystal, tautomer, stereoisomer, isotopically labeled derivative, or prodrug thereof, or the pharmaceutical composition thereof.

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

A "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —C$^A$H(C$^B$H$_2$C$^C$H$_3$)— includes only one carbon unit C$^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

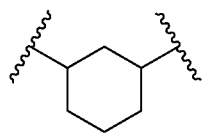 [SMILES: *C1CCCC(*)C1]

is a C$_3$ hydrocarbon chain. When a range of values is used, e.g., a C$_{1-6}$ hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

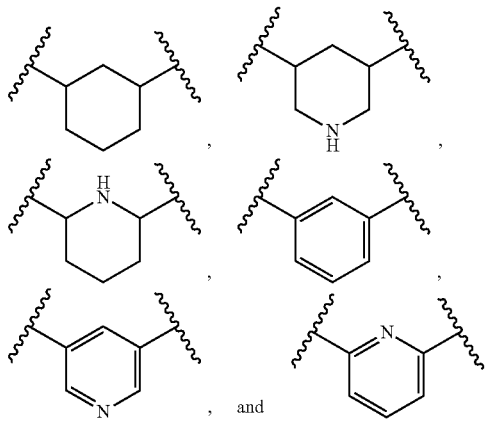

are all examples of a hydrocarbon chain. In contrast, in certain embodiments

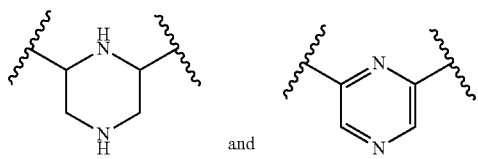 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("C$_{1-20}$ alkyl"). In some embodiments, an alkyl group has 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), and n-hexyl (C$_6$). Additional examples of alkyl groups include n-heptyl (C$_7$), n-octyl (C$_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted C$_{1-10}$ alkyl (e.g., —CH$_3$). In certain embodiments, the alkyl group is substituted C$_{1-10}$ alkyl.

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix-ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{a}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{C}$, —SO$_2$OR, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6, trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water.

Typically, the number of the water molecules contained in a hydrate of a compound is in a definite ratio to the number of the compound molecules in the hydrate. Therefore, a hydrate of a compound may be represented, for example, by the general formula R.xH$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2H$_2$O) and hexahydrates (R.6H$_2$O)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_1$ to $C_5$ alkyl, $C_2$-$C_5$ alkenyl, $C_2$-$C_5$ alkynyl, aryl, $C_7$-$C_{12}$ substituted aryl, and $C_7$-$C_{12}$ arylalkyl esters of the compounds of Formula (I) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration" refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemiallymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis);

muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multi-system inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of phosphate groups to an amino acid residue of a protein. For example, a serine kinase catalyzes the addition of a phosphate group to serine residue in a protein. In certain embodiments, the kinase is a protein kinase. Examples of kinases include, but are not limited to, a CMGC kinase (e.g., a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3α, GSK3β), or a CDC-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

The term "CDK" refers to a cyclin-dependent kinase. A CDK binds a cyclin (e.g., Cyclin H), which is a regulatory protein. CDKs phosphorylate their substrates at serines and threonines. The consensus sequence for the phosphorylation site in the amino acid sequence of a CDK substrate is [S/T*]PX[K/R], where S/T* is the phosphorylated serine or threonine, P is proline, X is any amino acid, K is lysine, and R is arginine. CDKs include CDK1, CDK2, CDK2, CDK4, CDK5, CDK7, CDK8, CDK9, CDK10, CDK11, CDK12, CDK14, CDK16, and CDK20. CDK7 is a CDK wherein the substrate is Cyclin H, MAT1 (e.g., MNAT1), or Cyclin H and MAT1.

The term "hydrophobic" refers to a moiety which tends not to dissolve in water and is fat-soluble. Hydrophobic moieties include, but are not limited to, hydrocarbons, such as alkanes, alkenes, alkynes, cycloalkanes, cycloalkenes, cycloalkynes, and aromatic compounds, such as aryls. Certain saturated and unsaturated heterocycles and moieties that are substantially similar to the side chains of hydrophobic natural and unnatural α-amino acids, including valine, leucine, isoleucine, methionine, phenylanine, α-amino isobutyric acid, alloisoleucine, tyrosine, and tryptophan.

The term "hydrogen bond" refers to a favorable interaction that occurs whenever a suitable donor atom, X, bearing a proton, H, and a suitable acceptor atom, Y, have a separation of between 2.5 Å and 3.5 Å and where the angle X—H - - - Y is greater than 90 degrees. Suitable donor and acceptor atoms are well understood in medicinal chemistry (G. C. Pimentel and A. L. McClellan, *The Hydrogen Bond*, Freeman, San Francisco, 1960; R. Taylor and O. Kennard, "Hydrogen Bond Geometry in Organic Crystals", *Accounts of Chemical Research*, 17, pp. 320-326 (1984)).

The term "c Log P" refers to a calculated partition coefficient which in the physical sciences, is the ratio of concentrations of a compound in a mixture of two immiscible phases at equilibrium. These coefficients are a measure of the difference in solubility of the compound in these two phases. In general, this is a measure of hydrophobicity of the compound as one phase is aqueous (traditionally water) and the other is hydrophobic (traditionally octanol). Higher values indicate greater partitioning of the compound into the hydrophobic phase, hence increased hydrophobicity.

BRIEF DESCRIPTION OF THE DRAWINGS

FIGS. 1A to 1C show that the kinome profiling and compound-based affinity chromatography identify phenylamino-pyrimidine scaffold as a potential CDK7 scaffold. FIG. 1A shows the structures of compounds I-23, I-23R, and I-49. FIG. 1B shows that compound I-23 potently inhibits proliferation of Jurkat and Loucy leukemia cell lines. The cell lines were treated with compound I-23 or I-23R for 72 hours, and the antiproliferative effect was determined by cell titer glo. FIG. 1C shows that compound I-49 pulls down CDK7 from cellular lysates. Loucy cellular lysates were treated with compound I-49 (1 µM) in the presence (10 µM) or absence of compound I-23 and incubated at 4° C. for 12 hours. Precipitated proteins were washed and probed for CDK7.

FIG. 2A shows that compound I-23 inhibits RNAP II CTD phosphorylation. Loucy cells were treated with compound I-23 or I-23R for 4 hours. Cellular lysates were then probed with antibodies recognizing the Ser-2, Ser-5, and Ser-7 CTD phospho-epitopes. FIG. 2B shows that compound I-23 exhibits time-dependent CDK7 inactivation. Loucy cells were treated with compound I-23 or I-23R for 0 to 4 hours. At each time point cells were lysed, and the cellular lysates were probed using antibodies as described herein. FIG. 2C shows that compound I-23, but not compound I-23R, shows irreversible inactivation of CDK7. Loucy cells were treated with compound I-23 or I-23R for 4 hours, followed by washout of inhibitor-containing medium. Cells were allowed to grow in medium without inhibitor for 0 to 6 hours. At each time point cells were lysed, and the cellular lysates were probed using antibodies as described herein. FIG. 2D shows that pre-incubation of compound I-23 increases its inhibitory activity against CDK7. Recombinant CAK complex was incubated with compound I-23 or I-23R in dose response format with and without pre-incubation prior to ATP (25 µM) addition. The kinase reaction was then allowed to proceed for 45 minutes at 30° C.

FIGS. 3A to 3D show that affinity chromatography result demonstrates compound I-23 binds irreversibly to CDK7. FIG. 3A shows that compound I-49 binds irreversibly to CDK7. Recombinant CAK complex containing His6-tagged CDK7, GST-tagged MAT1, and cyclin H, was incubated with compound I-49 and increasing concentrations of competing free compound I-23 at 37° C. for 4 hours. The samples were probed with streptavidin-HRP. FIG. 3B shows that compound I-49 labels CDK7 in lysates. Loucy cellular lysates were incubated with compound I-49 at 4° C. for 12 hours followed by immunoprecipitation of CDK7 at 4° C. for 3 hours. Precipitated proteins were washed and probed with streptavidin-HRP. FIG. 3C illustrates the workflow of a compound-I-49-pull-down competition experiment. FIG. 3D shows that a free intracellular compound I-23 competes with compound I-49 for binding to CDK7. Loucy cells were treated with increasing concentrations of compound I-23 for 4 hours. Cellular lysates were incubated with compound 1-49 and processed as in FIG. 1C.

FIGS. 4A to 4F show that CDK7 covalently binds a unique cysteine in a distal C-terminal region located outside the kinase domain. FIG. 4A depicts a docking model of compound I-23 in the ATP-binding pocket of CDK7 (PDB code 1UA2). Key residues are indicated. C312 has been modeled into the crystal structure. FIG. 4B shows that C312 is unique among CDKs. Independent sequence alignments of CDK C-terminal regions with CDK7 C312-containing region. FIGS. 4C to 4D show total ion chromatograms (TIC) and extracted ion chromatograms (XIC) for CDK7 peptides recorded during analysis of CAK complexes treated with DMSO or I-23, respectively. Efficiency of labeling was estimated from the reduction in signal of the triply and quadruply charged C312 containing peptide using signals from VPFLPGDSDLDQLTR (SEQ ID NO: 1) and LDFLGEGQFATVYK (SEQ ID NO: 2) for normalization. FIG. 4E shows high resolution Orbitrap HCD MS/MS spectrum of a quadruply charged CDK7 derived peptide labeled by I-23 at C312. FIG. 4F shows that the mutation of C312 to serine (C312S) rescues wild-type kinase activity in the presence of compound I-23. HCT116 cells stably expressing FLAG-tagged CDK7 (kinase dead (KD), wild-type (WT), and C312S mutant) were treated with compound I-23 or I-23R for 4 hours. Exogenous CDK7 was immuno-precipitated from cellular lysates using FLAG antibody. Precipitated proteins were washed and subjected to in vitro kinase assays at 30° C. for 30 minutes using the large subunit of RNAP II (RPB1) as substrate and 25 µM ATP.

FIGS. 5A to 5D show that compound I-23 decreases RNAP II processivity by disruption of CDK7 kinase activity. FIGS. 5A to 5B show that a treatment with 250 nM of compound I-23 for 6 hours dramatically altered the RNAP II occupancy where the RNAP II at the promoter proximal pause site is drastically diminished. RNAP II is largely depleted from the 3'-end of genes. FIGS. 5C to 5D show that treatment with compound I-23 did not disrupt CDK7 occupancy.

FIGS. 6A to 6F show that compound I-23 exhibits strong anti-proliferative activity against a wide range of cancer cell lines. FIG. 6A shows that a treatment with compound I-23 results in down-regulation of MCL-1 protein and induction of apoptosis. Loucy cells were treated with increasing amounts of compound I-23 or I-23R over a time course of 12 to 48 hours. At indicated time points, cellular lysates were harvested at the indicated times points and immunoblotted for the indicated proteins. Experiments were conducted in the presence or absence of compound I-23 or I-23R washout. FIG. 6B shows that the anti-proliferative effects of compound I-23 are impervious to inhibitor washout. Loucy cells were treated with compound I-23 or I-23R in a dose-response format for 48 hours. Anti-proliferative effects were determined using cell titer glo analysis. FIG. 6C shows that compound I-23 displays potent anti-proliferative activity in a human cancer cell line panel. Cells were treated with compound I-23 or I-23R in a dose-response format for 72 hours. Anti-proliferative effects were determined using alamarBlue® analysis. FIG. 6D shows select cell lines from distinct origins, which are sensitive to 1-23. FIG. 6E shows the results of anti-proliferative assays in human retinal pigment epithelial (RPE1) cells. Cells were treated with compound I-23 or I-23R in a dose-response format for 72 hours. Anti-proliferative effects were determined using cell titer glo analysis. RPE1 cells were largely resistant to both 1-23 and I-23R treatment. FIG. 6F shows the pharmacokinetic data for I-23 plasma following a single intravenous (i.v.) and oral (p.o.) administration in male Swiss Albino mice. Dose: i.v. 1 mg/kg and p.o. 10 mg/kg.

FIGS. 11A to 11H show that 1-23, but not I-23R, has potent anti-proliferative and anti-cancer activities in blood cancer cell lines. FIG. 11A shows that 1-23, but not I-23R, potently kills patient-derived chronic lymphocytic leukemia (CLL) isolates in vitro. Clinical isolates of CLL were cultured with compounds of Formula (I) or flavopiridol and assessed for cell death after a 24 hour time course by Annexin V staining. FIGS. 11B to 11H show that I-23, but not I-23R, displays potent anti-proliferative activity in multiple myeloma cell lines. Multiple myeloma cell lines were grown in the absence or presence of underlying stromal cells and assayed for anti-proliferative effect following a 48-hour treatment with I-23 and I-23R. Anti-proliferative effect was measured using cell titer glo analysis.

DETAILED DESCRIPTION OF CERTAIN EMBODIMENTS OF THE INVENTION

Figure 2A:
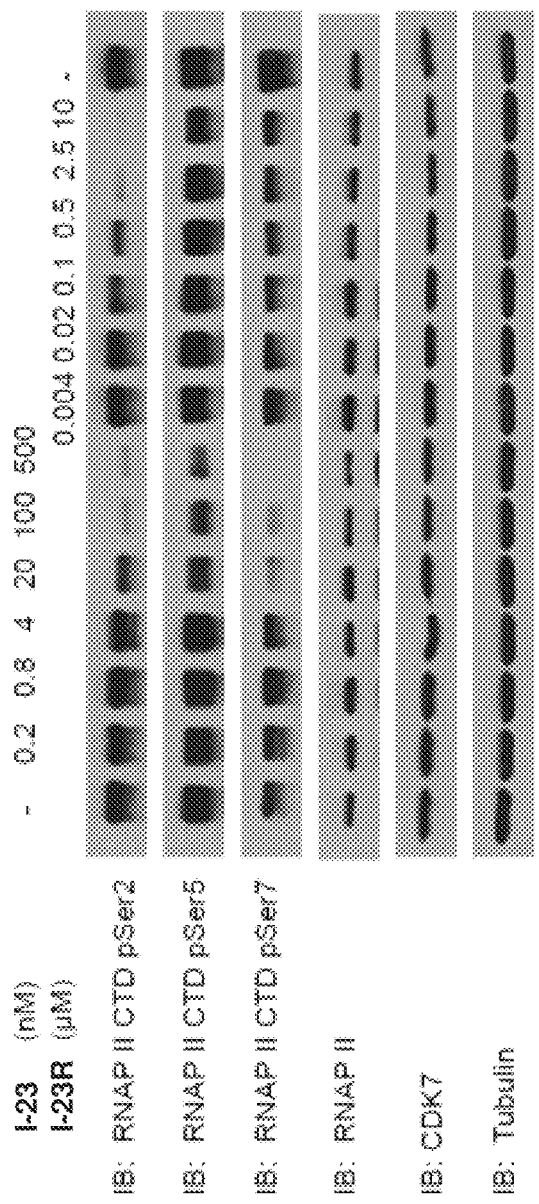
FIGS. 2A to 2D show that compound I-23 irreversibly inhibits RNAP II CTD phosphorylation.

The present invention provides compounds, which inhibit the activity of a kinase, for the prevention and/or treatment of a proliferative disease of a subject. In certain embodiments, the inventive compounds inhibit the activity of cyclin-dependent kinase (CDK). In certain embodiments, the inventive compounds inhibit the activity of cyclin-dependent kinase 7 (CDK7). The present invention further provides methods of using the compounds described herein, e.g., as biological probes to study the inhibition of the activity of a kinase (e.g., CDK (e.g., CDK7)), and as therapeutics, e.g., in the prevention and/or treatment of diseases associated with the overexpression and/or aberrant activity of the kinase (e.g., CDK (e.g., CDK7)). In certain embodiments, the diseases are proliferative diseases. The proliferative diseases include, but are not limited to, cancer (e.g., leukemia, melanoma, multiple myeloma), benign neoplasm, angiogenesis, inflammatory diseases, autoinflammatory diseases, and autoimmune diseases. In certain embodiments, the cancer is associated with the overexpression and/or aberrant activity of a kinase (e.g., CDK (e.g., CDK7)).

Compounds

In one aspect of the present invention, provided are compounds of Formula (I):

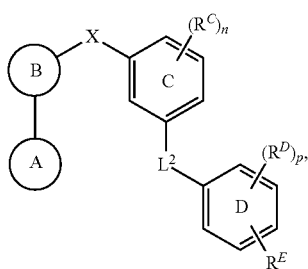
(I)

and pharmaceutically acceptable salts, solvates, hydrates, polymorphs, co-crystals, tautomers, stereoisomers, isotopically labeled derivatives, and prodrugs thereof; wherein:

Ring A is an optionally substituted heteroaryl ring of any one of the Formulae (i-1)-(i-5):

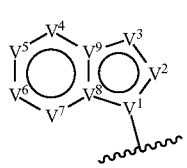
(i-1)

(i-2)

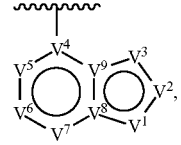
(i-3)

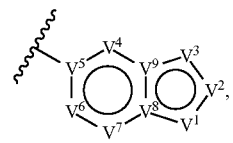
(i-4)

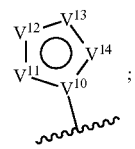
(i-5)

each instance of $V^1$, $V^2$, $V^3$, $V^4$, $V^5$, $V^6$, $V^7$, $V^8$, $V^9$, $V^{10}$, $V^{11}$, $V^{12}$, $V^{13}$, and $V^{14}$ is independently O, S, N, $NR^{41}$, C, or $CR^{42}$;

each instance of $R^{41}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of $R^{42}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{42a}$, —$N(R^{42a})_2$, and —$SR^{42a}$, wherein each occurrence of $R^{42a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{42a}$ groups are joined to form an optionally substituted heterocyclic ring;

optionally any two of $R^{41}$, $R^{42}$, and $R^{42a}$ groups are joined to form an optionally substituted carbocyclic, optionally substituted heterocyclic, optionally substituted aryl, or optionally substituted heteroaryl ring;

Ring B is of the formula:

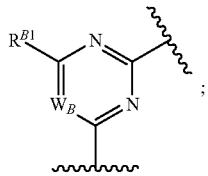

$R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B1a}$, —$N(R^{B1a})_2$, and —$SR^{B1a}$, wherein each occurrence of $R^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B1a}$ groups are joined to form an optionally substituted heterocyclic ring;

$W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{B2a}$, —$N(R^{B2a})_2$, and —$SR^{B2a}$, wherein each occurrence of $R^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{B2a}$ groups are joined to form an optionally substituted heterocyclic ring;

optionally $R^{B1}$ and $R^{B2}$ are joined to form an optionally substituted carbocyclyl, optionally substituted heterocyclyl, optionally substituted heteroaryl, or optionally substituted aryl ring;

X is an optionally substituted $C_{1-4}$ hydrocarbon chain, optionally wherein one or more carbon units of the hydrocarbon chain is replaced with —O—, —S—, or —$NR^X$—, wherein $R^X$ is hydrogen, $C_{1-6}$ alkyl, or a nitrogen protecting group;

$L^2$ is a bond, —O—, —S—, —$NR^{L2a}$—, —$NR^{L2a}C(=O)$—, —$C(=O)NR^{L2a}$—, —$SC(=O)$—, —$C(=O)S$—, —$OC(=O)$—, —$C(=O)O$—, —$NR^{L2a}C(=S)$—, —$C(=S)NR^{L2a}$—, trans-$CR^{L2b}=CR^{L2b}$—, cis-$CR^{L2b}=CR^{L2b}$—, —C≡C—, —$OC(R^{L2b})_2$—, —$C(R^{L2b})_2O$—, —$NR^{L2a}C(R^{L2b})_2$—, —$C(R^{L2b})_2NR^{L2a}$—, —$SC(R^{L2b})_2$—, —$C(R^{L2b})_2S$—, —$S(=O)_2O$—, —$OS(=O)_2$—, —$S(=O)_2NR^{L2a}$—, —$NR^{L2a}S(=O)_2$—, or an optionally substituted CA hydrocarbon chain, optionally wherein one or more carbon units of the hydrocarbon chain is replaced with —O—, —S—, —$NR^{L2a}$—, —$NR^{L2a}C(=O)$—, —$C(=O)NR^{L2a}$—, —$SC(=O)$—, —$C(=O)S$—, —$OC(=O)$—, —$C(=O)O$—, —$NR^{L2a}C(=S)$—, —$C(=S)NR^{L2a}$—, trans-$CR^{L2b}=CR^{L2b}$—, cis-$CR^{L2b}=CR^{L2b}$—, —C≡C—, —$S(=O)_2O$—, —$OS(=O)_2$—, —$S(=O)_2NR^{L2a}$—, or —$NR^{L2a}S(=O)_2$—, wherein $R^{L2a}$ is hydrogen, $C_{1-6}$ alkyl, or a nitrogen protecting group, and wherein each occurrence of $R^{L2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{L2b}$ groups are joined to form an optionally substituted carbocyclic or optionally substituted heterocyclic ring;

each instance of $R^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1})_2$, and —$SR^{C1}$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{C1}$ groups are joined to form an optionally substituted heterocyclic ring;

n is 0, 1, 2, 3, or 4;

each instance of $R^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{D1}$, —$N(R^{D1})_2$, and —$SR^{D1}$, wherein each occurrence of $R^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{D1}$ groups are joined to form an optionally substituted heterocyclic ring;

p is 0, 1, 2, 3, or 4;

$R^E$ is any one of the Formulae (ii-1)-(ii-17):

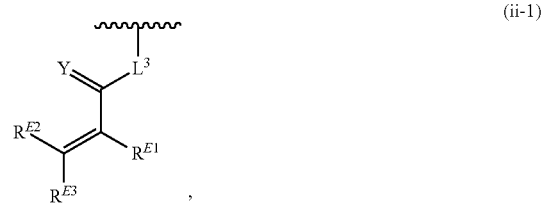

(ii-1)

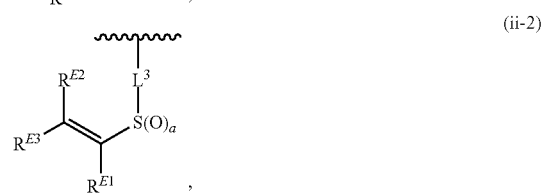

(ii-2)

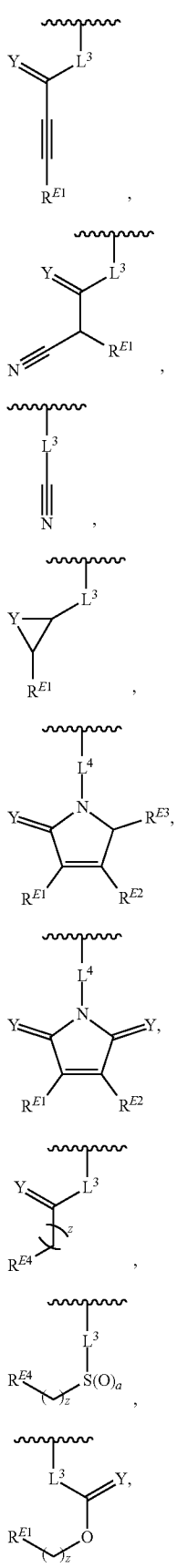

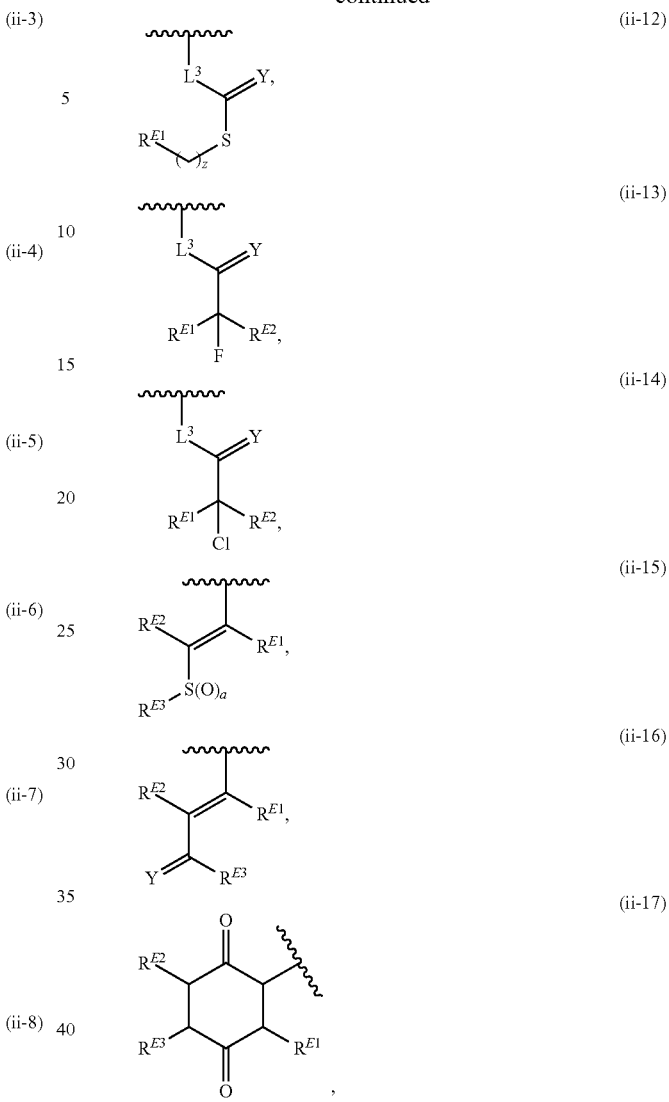

$R^E$ and $L^2$ are para or meta to each other;

$L^3$ is a bond, —O—, —S—, —NR$^{L3a}$—, or an optionally substituted $C_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted CA hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

optionally R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

Y is O, S, or NR$^{E5}$, wherein R$^{E5}$ is hydrogen, C$_{1-6}$ alkyl, or a nitrogen protecting group;

a is 1 or 2; and z is 0, 1, 2, 3, 4, 5, or 6.

In certain embodiments, the present invention provides compounds of Formula (I), and pharmaceutically acceptable salts, solvates, hydrates, polymorphs, co-crystals, tautomers, stereoisomers, isotopically labeled derivatives, and prodrugs thereof; wherein:

Ring A is an optionally substituted heteroaryl ring of any one of the Formulae (i-1)-(i-5);

each instance of V$^1$, V$^2$, V$^3$, V$^4$, V$^5$, V$^6$, V$^7$, V$^8$, V$^9$, V$^{10}$, V$^{11}$, V$^{12}$, V$^{13}$, and V$^{14}$ is independently O, S, N, NR$^{A1}$, C, or CR$^{A2}$;

each instance of R$^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group;

each instance of R$^{A2}$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A2a}$, —N(R$^{A2a}$)$_2$, and —SR$^{A2a}$, wherein each occurrence of R$^{A2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{A2a}$ groups are joined to form an optionally substituted heterocyclic ring;

optionally any two of R$^{A1}$, R$^{A2}$, and R$^{A2a}$ groups are joined to form an optionally substituted carbocyclic, optionally substituted heterocyclic, optionally substituted aryl, or optionally substituted heteroaryl ring;

Ring B is of the formula:

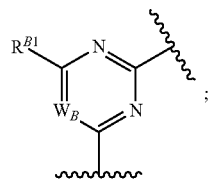

R$^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{B1a}$, —N(R$^{B1a}$)$_2$, and —SR$^{B1a}$, wherein each occurrence of R$^{B1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{B1a}$ groups are joined to form an optionally substituted heterocyclic ring;

W$_B$ is N or CR$^{B2}$, wherein R$^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{B2a}$, —N(R$^{B2a}$)$_2$, and —SR$^{B2a}$, wherein each occurrence of R$^{B2a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{B2a}$ groups are joined to form an optionally substituted heterocyclic ring;

optionally $R^{B1}$ and $R^{B2}$ are joined to form an optionally substituted carbocyclyl, optionally substituted heterocyclyl, optionally substituted heteroaryl, or optionally substituted aryl ring;

X is an optionally substituted $C_{1-4}$ hydrocarbon chain, optionally wherein one or more carbon units of the hydrocarbon chain is replaced with —O—, —S—, or —NR$^X$—, wherein R$^X$ is hydrogen, $C_{1-6}$ alkyl, or a nitrogen protecting group;

$L^2$ is a bond, —O—, —S—, —NR$^{L2a}$—, —NR$^{L2a}$C(=O)—, —C(=O)NR$^{L2a}$—, —SC(=O)—, —C(=O)S—, —OC(=O)—, —C(=O)O—, —NR$^{L2a}$C(=S)—, —C(=S)NR$^{L2a}$—, trans-CR$^{L2b}$=CR$^{L2b}$, cis-CR$^{L2b}$=CR$^{L2b}$—, —C≡C—, —OC(R$^{L2b}$)$_2$—, —C(R$^{L2b}$)$_2$O—, —NR$^{L2a}$C(R$^{L2b}$)$_2$—, —C(R$^{L2b}$)$_2$NR$^{L2a}$—, —SC(R$^{L2b}$)$_2$—, —C(R$^{L2b}$)$_2$S—, —S(=O)$_2$O—, —OS(=O)$_2$—, —S(=O)$_2$NR$^{L2a}$—, —NR$^{L2a}$S(=O)$_2$—, or an optionally substituted CA hydrocarbon chain, optionally wherein one or more carbon units of the hydrocarbon chain is replaced with —O—, —S—, —NR$^{L2a}$—, —NR$^{L2a}$C(=O)—, —C(=O)NR$^{L2a}$—, —SC(=O)—, —C(=O)S—, —OC(=O)—, —C(=O)O—, —NR$^{L2a}$C(=S)—, —C(=S)NR$^{L2a}$—, trans-CR$^{L2b}$CR$^{L2b}$ cis-CR$^{L2b}$=CR$^{L2b}$—, —C≡C—, —S(=O)$_2$O—, —OS(=O)$_2$—, —S(=O)$_2$NR$^{L2a}$—, or —NR$^{L2a}$S(=O)$_2$—, wherein R$^{L2a}$ is hydrogen, $C_{1-6}$ alkyl, or a nitrogen protecting group, and wherein each occurrence of R$^{L2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L2b}$ groups are joined to form an optionally substituted carbocyclic or optionally substituted heterocyclic ring;

each instance of R$^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1}$)$_2$, and —SR$^{C1}$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{C1}$ groups are joined to form an optionally substituted heterocyclic ring;

n is 0, 1, 2, 3, or 4;

each instance of R$^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$, wherein each occurrence of R$^{D1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{D1}$ groups are joined to form an optionally substituted heterocyclic ring;

p is 0, 1, 2, 3, or 4;

R$^E$ is any one of the Formulae (ii-1)-(ii-17);

R$^E$ and $L^2$ are para or meta to each other;

$L^3$ is a bond, —O—, —S—, —NR$^{L3a}$—, or an optionally substituted $C_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$, —C≡C—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted CA hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted aryl, optionally substituted heteroaryl, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two $R^{E3a}$ groups are joined to form an optionally substituted heterocyclic ring;

optionally $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring; $R^{E4}$ is a leaving group;

Y is O, S, or $NR^{E5}$, wherein $R^{E5}$ is hydrogen, $C_{1-6}$ alkyl, or a nitrogen protecting group;

a is 1 or 2; and z is 0, 1, 2, 3, 4, 5, or 6.

In certain embodiments, provided in the present invention are compounds of Formula (I), and pharmaceutically acceptable salts thereof.

Compounds of Formula (I) include Ring A attached to Ring B. Ring A may be an optionally substituted bicyclic heteroaryl ring. In certain embodiments, Ring A is an optionally substituted monocyclic heteroaryl ring fused with an optionally substituted monocyclic aryl ring. In certain embodiments, Ring A is an optionally substituted monocyclic heteroaryl ring fused with another optionally substituted monocyclic heteroaryl ring. Ring A may be an optionally substituted 6,5-membered heteroaryl ring or an optionally substituted 5,6-membered heteroaryl ring. In certain embodiments, Ring A is an optionally substituted monocyclic 5-membered heteroaryl ring fused with an optionally substituted monocyclic 6-membered aryl ring. In certain embodiments, Ring A is an optionally substituted monocyclic 5-membered heteroaryl ring fused with an optionally substituted monocyclic 6-membered heteroaryl ring. The point of attachment of Ring A to Ring B may be at any atom of Ring A, as valency permits. In certain embodiments, Ring A is of Formula (i-1):

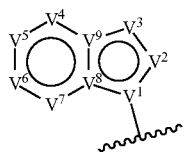

(i-1)

In certain embodiments, Ring A is of Formula (i-2):

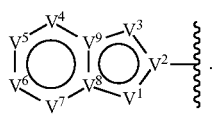

(i-2)

In certain embodiments, Ring A is of Formula (i-3):

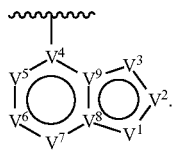

(i-3)

In certain embodiments, Ring A is of Formula (i-4):

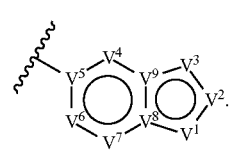

(i-4)

In compounds of Formula (I), $V^1$, $V^2$, $V^3$, $V^4$, $V^5$, $V^6$, $V^7$, $V^8$, and $V^9$ of Ring A may each independently be O, S, N, $NR^{41}$, C, or $CR^{42}$, as valency permits. In certain embodiments, $V^1$ is O, S, N or $NR^{41}$. In certain embodiments, $V^1$ is N or $NR^{41}$. In certain embodiments, Ring A is of the formula:

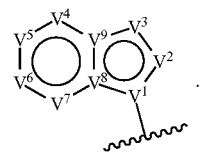

In certain embodiments, Ring A is of the formula:

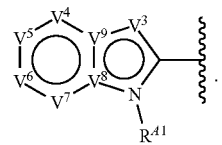

In certain embodiments, Ring A is of the formula:

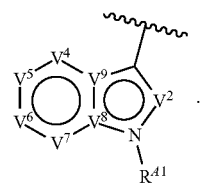

In certain embodiments, Ring A is of the formula:

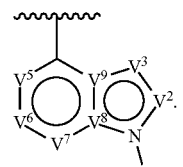

In certain embodiments, Ring A is of the formula:

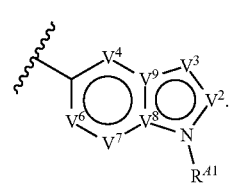

In certain embodiments, Ring A is of the formula:

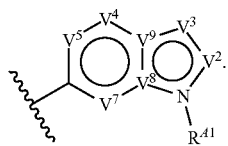

In certain embodiments, Ring A is of the formula:

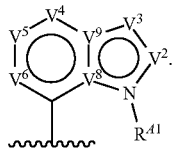

In certain embodiments, only one of $V^1$, $V^2$, $V^3$, $V^4$, $V^5$, $V^6$, $V^7$, $V^8$, and $V^9$ is selected from the group consisting of O, S, N, and $NR^{A1}$. In certain embodiments, only one of $V^1$, $V^2$, $V^3$, $V^4$, $V^5$, $V^6$, $V^7$, $V^8$, and $V^9$ is selected from the group consisting of N and $NR^{A1}$. In certain embodiments, $V^1$ is N or $NR^{A1}$; $V^2$, $V^3$, $V^4$, $V^5$, $V^6$, $V^7$, $V^8$, and $V^9$ are each independently C or $CR^{A2}$; and therefore, Ring A is an optionally substituted indole ring. In certain embodiments, Ring A is of Formula (iii-1):

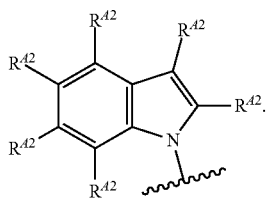

(iii-1)

In certain embodiments, Ring A is of Formula (iii-2):

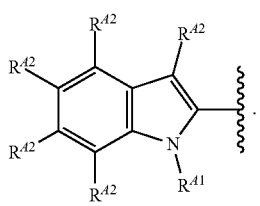

(iii-2)

In certain embodiments, Ring A is of Formula (iii-3):

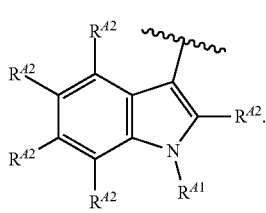

(iii-3)

In certain embodiments, Ring A is of Formula (iii-4):

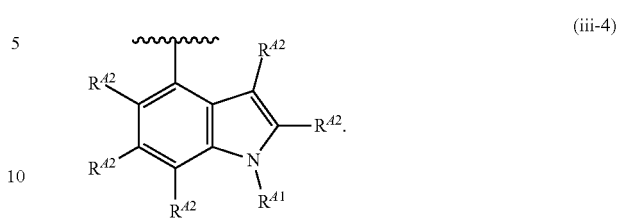

(iii-4)

In certain embodiments, Ring A is of Formula (iii-5):

(iii-5)

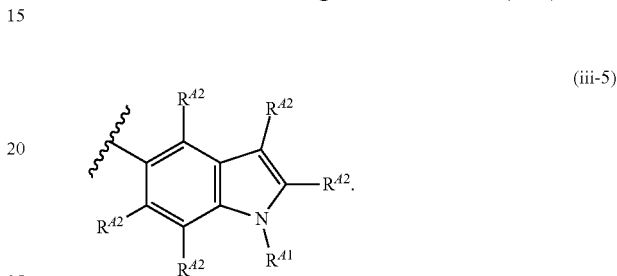

In certain embodiments, Ring A is of Formula (iii-6):

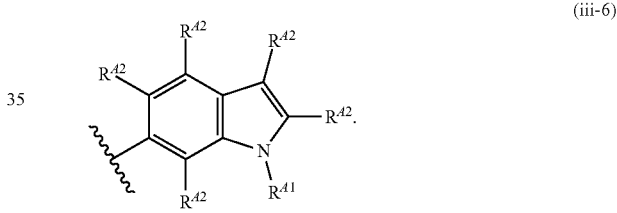

(iii-6)

In certain embodiments, Ring A is of Formula (iii-7):

(iii-7)

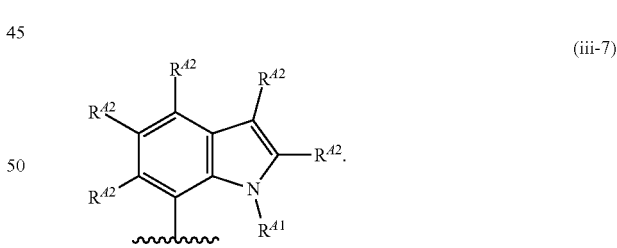

In certain embodiments, only two of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only two of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only one of $V^2$, $V^3$, $V^4$, $V^5$, $V^6$, $V^7$, $V^8$, and $V^9$ is N or $NR^{A1}$. In certain embodiments, $V^1$ and $V^2$ are each independently N or $NR^{A1}$; $V^3$, $V^4$, $V^5$, $V^6$, $V^7$, $V^8$, and $V^9$ are each independently C or $CR^{A2}$; and therefore, Ring A is an optionally substituted indazole ring. In certain embodiments, Ring A is of the formula:

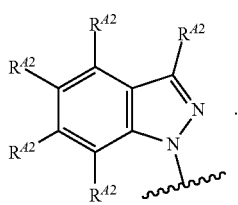

In certain embodiments, Ring A is of the formula:

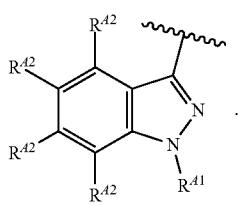

In certain embodiments, Ring A is of the formula:

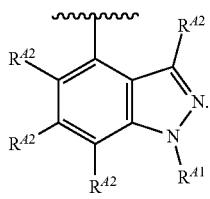

In certain embodiments, Ring A is of the formula:

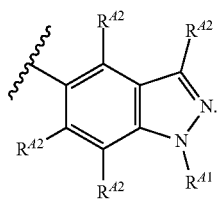

In certain embodiments, Ring A is of the formula:

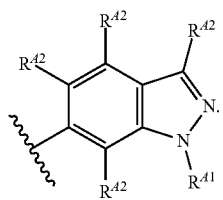

In certain embodiments, Ring A is of the formula:

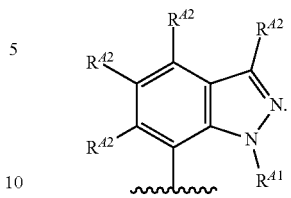

In certain embodiments, $V^1$ and $V^3$ are each independently N or $NR^{A1}$; $V^2$, $V^4$, $V^5$, $V^6$, $V^7$, $V^8$, and $V^9$ are each independently C or $CR^{A2}$; and therefore, Ring A is an optionally substituted benzimidazole ring. In certain embodiments, Ring A is of Formula (iv-1):

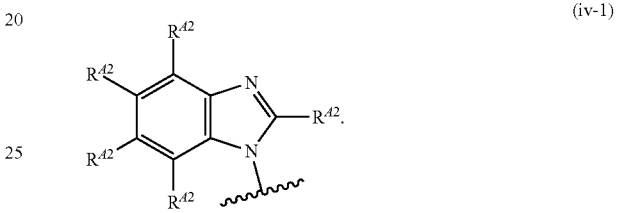

(iv-1)

In certain embodiments, Ring A is of Formula (iv-2):

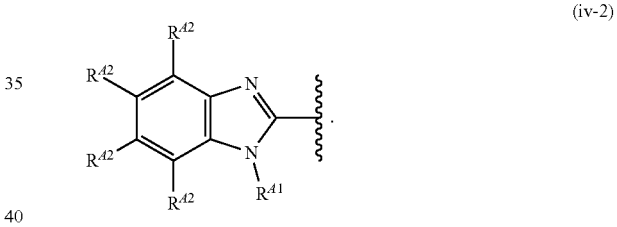

(iv-2)

In certain embodiments, Ring A is of Formula (iv-3):

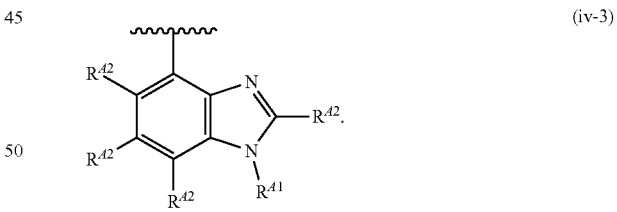

(iv-3)

In certain embodiments, Ring A is of Formula (iv-4):

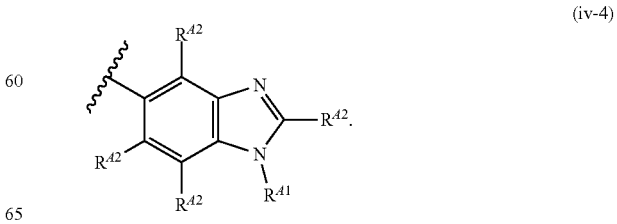

(iv-4)

In certain embodiments, Ring A is of Formula (iv-5):

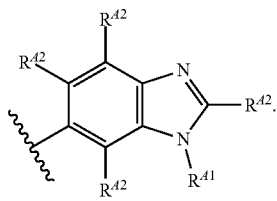

(iv-5)

In certain embodiments, Ring A is of Formula (iv-6):

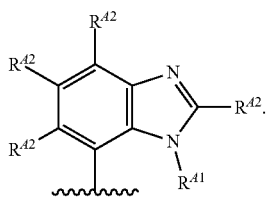

(iv-6)

In certain embodiments, $V^1$ and $V^4$ are each independently N or $NR^{A1}$; $V^2$, $V^3$, $V^5$, $V^6$, $V^7$, V, and $V^9$ are each independently C or $CR^{A2}$; and therefore, Ring A is an optionally substituted 4-azaindazole ring. In certain embodiments, Ring A is of the formula:

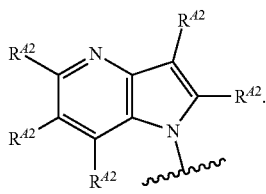

In certain embodiments, Ring A is of the formula:

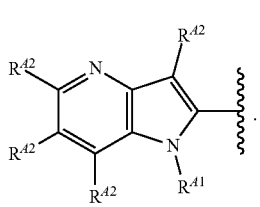

In certain embodiments, Ring A is of the formula:

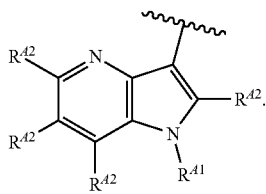

In certain embodiments, Ring A is of the formula:

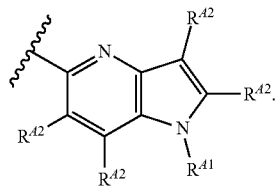

In certain embodiments, Ring A is of the formula:

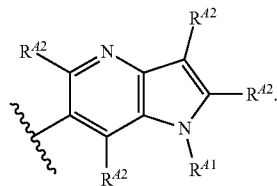

In certain embodiments, Ring A is of the formula:

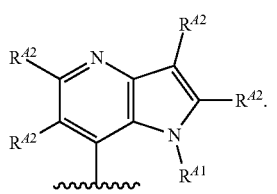

In certain embodiments, $V^1$ and $V^5$ are each independently N or $NR^{A1}$; $V^2$, $V^3$, $V^4$, $V^6$, $V^7$, $V^8$, and $V^9$ are each independently C or $CR^{A2}$; and therefore, Ring A is an optionally substituted 5-azaindazole ring. In certain embodiments, Ring A is of the formula:

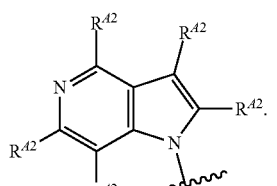

In certain embodiments, Ring A is of the formula:

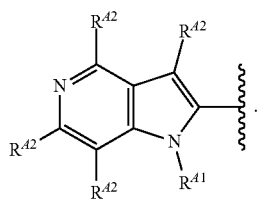

In certain embodiments, Ring A is of the formula:

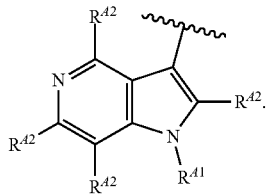

In certain embodiments, Ring A is of the formula:

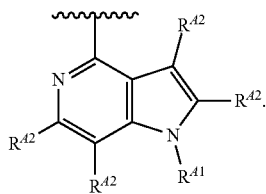

In certain embodiments, Ring A is of the formula:

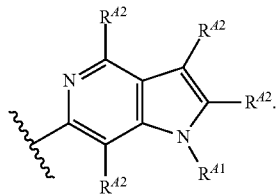

In certain embodiments, Ring A is of the formula:

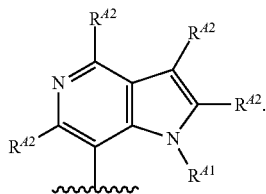

In certain embodiments, $V^1$ and $V^6$ are each independently N or $NR^{A1}$; $V^2$, $V^3$, $V^4$, $V^5$, $V^7$, $V^8$, and $V^9$ are each independently C or $CR^{A2}$; and therefore, Ring A is an optionally substituted 6-azaindole ring. In certain embodiments, Ring A is of the formula:

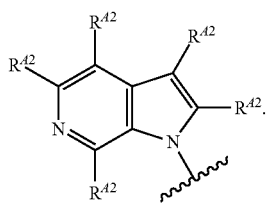

In certain embodiments, Ring A is of the formula:

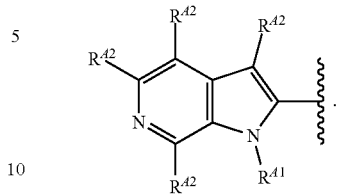

In certain embodiments, Ring A is of the formula:

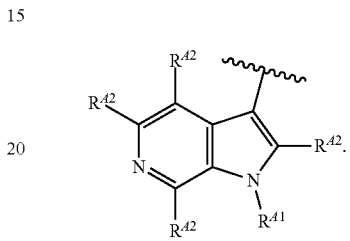

In certain embodiments, Ring A is of the formula:

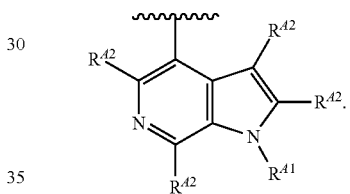

In certain embodiments, Ring A is of the formula:

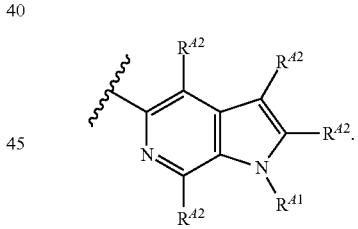

In certain embodiments, Ring A is of the formula:

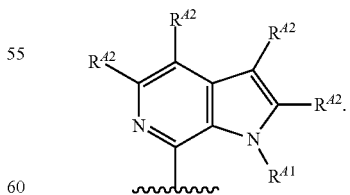

In certain embodiments, $V^1$ and $V^7$ are each independently N or $NR^{A1}$; $V^2$, $V^3$, $V^4$, $V^5$, $V^6$, V, and $V^9$ are each independently C or $CR^{A2}$; and therefore, Ring A is an optionally substituted 7-azaindole ring. In certain embodiments, Ring A is of Formula (v-1):

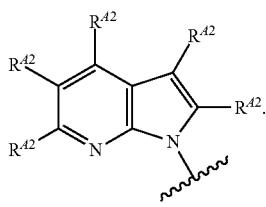
(v-1)

In certain embodiments, Ring A is of Formula (v-2):

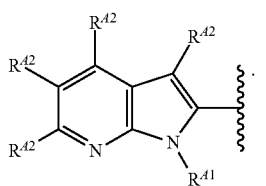
(v-2)

In certain embodiments, Ring A is of Formula (v-3):

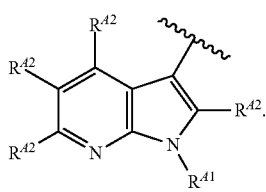
(v-3)

In certain embodiments, Ring A is of Formula (v-4):

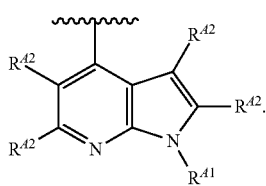
(v-4)

In certain embodiments, Ring A is of Formula (v-5):

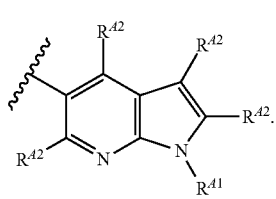
(v-5)

In certain embodiments, Ring A is of Formula (v-6):

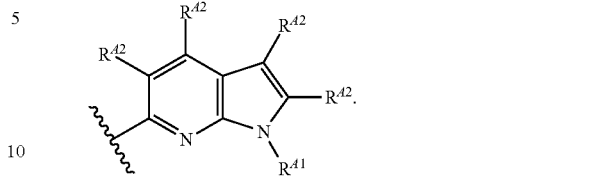
(v-6)

In certain embodiments, $V^1$ and $V^8$ are each independently N or $NR^{A1}$, $V^2$, $V^3$, $V^4$, $V^5$, $V^6$, $V^7$, and $V^9$ are each independently C or $CR^{A2}$; and therefore, Ring A is an optionally substituted 8-azaindole ring. In certain embodiments, Ring A is of Formula (vi-1):

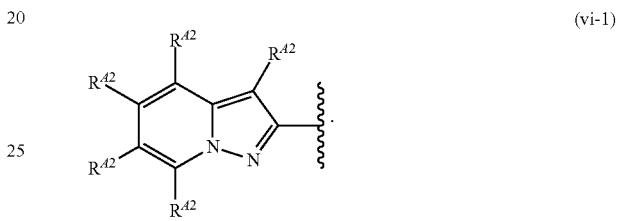
(vi-1)

In certain embodiments, Ring A is of Formula (vi-2):

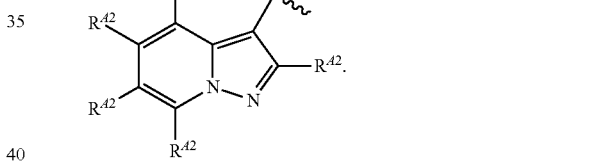
(vi-2)

In certain embodiments, Ring A is of Formula (vi-3):

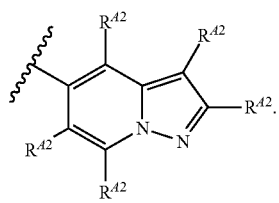
(vi-3)

In certain embodiments, Ring A is of Formula (vi-4):

(vi-4)

In certain embodiments, Ring A is of Formula (vi-5):

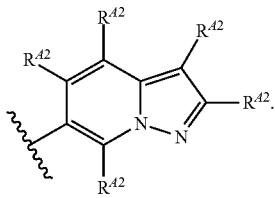

(vi-5)

In certain embodiments, Ring A is of Formula (vi-6):

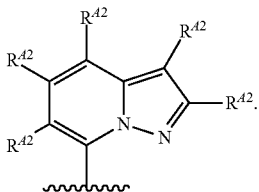

(vi-6)

In certain embodiments, $V^1$ and $V^9$ are each independently N or $NR^{A1}$; $V^2$, $V^3$, $V^4$, $V^5$, $V^6$, $V^7$, and $V^8$ are each independently C or $CR^{A2}$; and therefore, Ring A is an optionally substituted 9-azaindole ring. In certain embodiments, Ring A is of the formula:

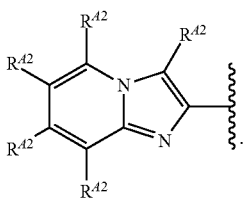

In certain embodiments, Ring A is of the formula:

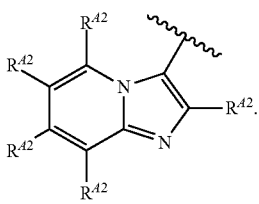

In certain embodiments, Ring A is of the formula:

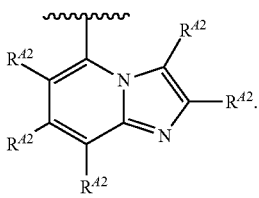

In certain embodiments, Ring A is of the formula:

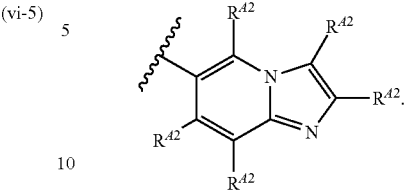

In certain embodiments, Ring A is of the formula:

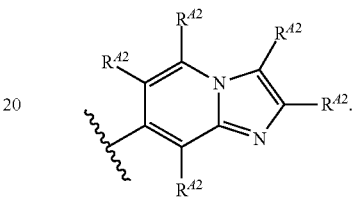

In certain embodiments, Ring A is of the formula:

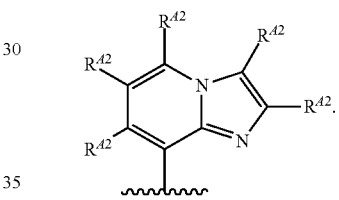

In certain embodiments, only three of $V^1$, $V^2$, $V^3$, $V^4$, $V^5$, $V^6$, $V^7$, $V^8$, and $V^9$ are each independently selected from the group consisting of O, S, N, and $NR^{A1}$. In certain embodiments, only three of $V^1$, $V^2$, $V^3$, $V^4$, $V^5$, $V^6$, $V^7$, $V^8$, and $V^9$ are each independently selected from the group consisting of N and $NR^{A1}$. In certain embodiments, $V^1$ is N or $NR^{A1}$; and only two of $V^2$, $V^3$, $V^4$, $V^5$, $V^6$, $V^7$, $V^8$, and $V^9$ are each independently N or $NR^{A1}$.

In compounds of Formula (I), Ring A may also be an optionally substituted 5-membered heteroaryl ring. In certain embodiments, Ring A is of Formula (i-5):

(i-5)

In compounds of Formula (I), $V^{10}$, $V^{11}$, $V^{12}$, $V^{13}$, and $V^{14}$ of Ring A may each independently be O, S, N, $NR^{A1}$, C, or $CR^{A2}$, as valency permits. In certain embodiments, only one of $V^{10}$, $V^{11}$, $V^{12}$, $V^{13}$, and $V^{14}$ is selected from the group consisting of O, S, N, and $NR^{A1}$. In certain embodiments, Ring A is of the formula:

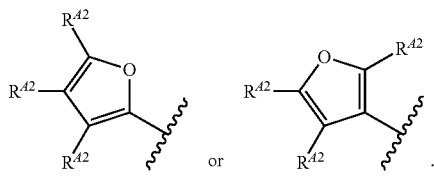

In certain embodiments, Ring A is of the formula:

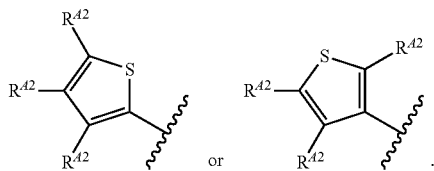

In certain embodiments, Ring A is of the formula:

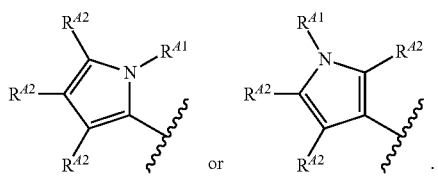

In certain embodiments, only two of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

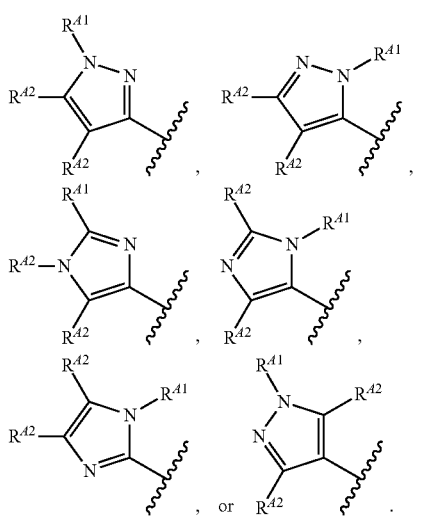

In certain embodiments, Ring A is of the formula:

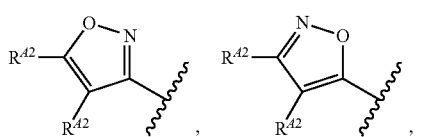

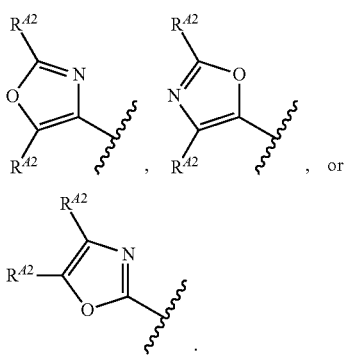

In certain embodiments, Ring A is of the formula:

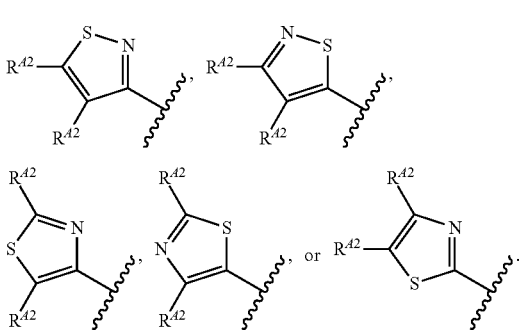

In certain embodiments, Ring A is of Formula (vii):

(vii)

In certain embodiments, Ring A is of the formula:

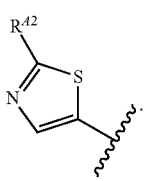

In certain embodiments, Ring A is of the formula:

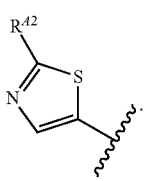

In certain embodiments, Ring A is of the formula:

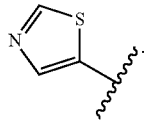

In certain embodiments, only three of $V^{10}$, $V^{11}$, $V^{12}$, $V^{13}$, and $V^{14}$ are each independently selected from the group consisting of O, S, N, and $NR^{A1}$. In certain embodiments, Ring A is of the formula:

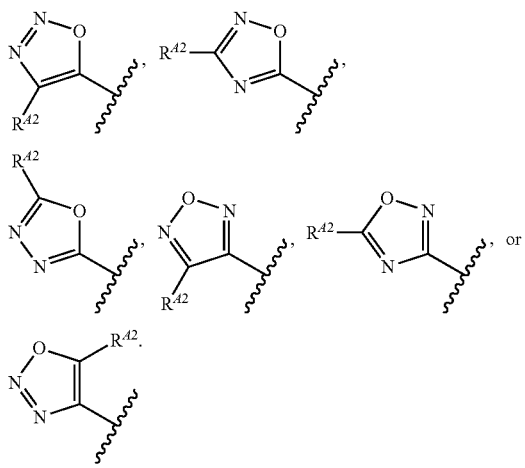

In certain embodiments, Ring A is of the formula:

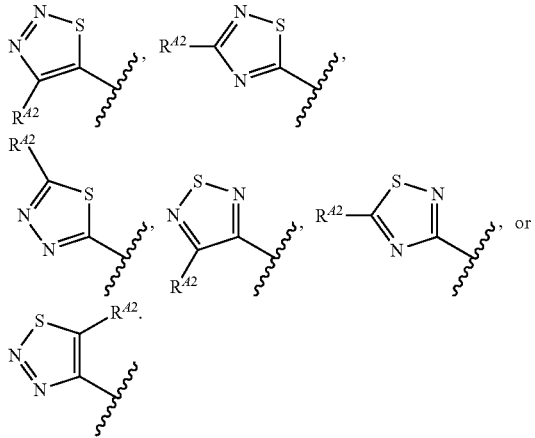

In certain embodiments, Ring A is of the formula:

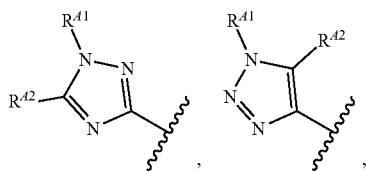

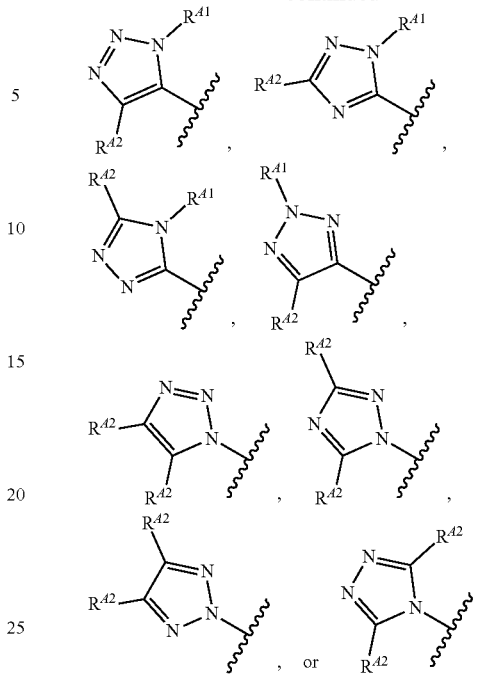

In certain embodiments, only four of $V^{10}$, $V^{11}$, $V^{12}$, $V^{13}$, and $V^{14}$ are each independently selected from the group consisting of N and $NR^{A1}$. In certain embodiments, Ring A is of the formula:

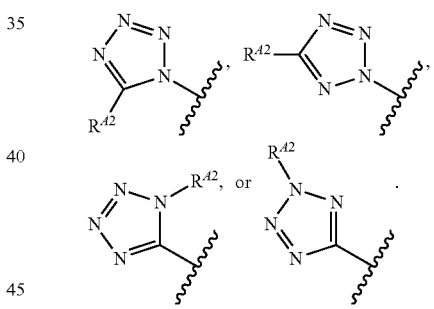

In compounds of Formula (I), Ring A may be substituted with one or more $R^{A1}$ groups when the $R^{A1}$ group is attached to a nitrogen atom. In certain embodiments, $R^{A1}$ is H (hydrogen). In certain embodiments, at least one instance of $R^{A1}$ is halogen. In certain embodiments, at least one instance of $R^{A1}$ is F (fluorine). In certain embodiments, at least one instance of $R^{A1}$ is Cl (chlorine). In certain embodiments, at least one instance of $R^{A1}$ is Br (bromine). In certain embodiments, at least one instance of $R^{A1}$ is I (iodine). In certain embodiments, at least one instance of $R^{A1}$ is substituted acyl. In certain embodiments, at least one instance of $R^{A1}$ is unsubstituted acyl. In certain embodiments, at least one instance of $R^{A1}$ is acetyl. In certain embodiments, at least one instance of $R^{A1}$ is substituted acetyl. In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl. In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl. In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is substituted heterocyclyl. In certain embodiments, at least one instance of $R^{A1}$ is unsubstituted heterocyclyl. In certain embodiments, at least one instance of $R^{A1}$ is substituted aryl. In certain embodiments, at least one instance of $R^{A1}$ is unsubstituted aryl. In certain embodiments, at least one instance of $R^{A1}$ is substituted phenyl. In certain embodiments, at least one instance of $R^{A1}$ is unsubstituted phenyl. In certain embodiments, at least one instance of $R^{A1}$ is substituted heteroaryl. In certain embodiments, at least one instance of $R^{A1}$ is unsubstituted heteroaryl. In certain embodiments, at least one instance of $R^{A1}$ is substituted pyridyl. In certain embodiments, at least one instance of $R^{A1}$ is unsubstituted pyridyl. In certain embodiments, at least one instance of $R^{A1}$ is a nitrogen protecting group. In certain embodiments, at least one instance of $R^{A1}$ is Bn, BOC, Cbz, Fmoc, trifluoroacetyl, triphenylmethyl, acetyl, acetyl, or Ts.

In certain embodiments, at least one $R^{A1}$ is hydrogen, $C_{1-6}$ alkyl, or a nitrogen protecting group. In certain embodiments, all instances of $R^{A1}$ are each independently hydrogen, $C_{1-6}$ alkyl, or a nitrogen protecting group. In certain embodiments, all instances of $R^{A1}$ are hydrogen.

In compounds of Formula (I), Ring A may be substituted with one or more $R^{A2}$ groups when the $R^{A2}$ group is attached to a carbon atom. In certain embodiments, at least one $R^{A2}$ is H. In certain embodiments, at least one $R^{A2}$ is halogen. In certain embodiments, at least one $R^{A2}$ is F. In certain embodiments, at least one $R^{A2}$ is Cl. In certain embodiments, at least one $R^{A2}$ is Br. In certain embodiments, at least one $R^{A2}$ is I (iodine). In certain embodiments, at least one $R^{A2}$ is substituted acyl. In certain embodiments, at least one $R^{A2}$ is unsubstituted acyl. In certain embodiments, at least one $R^{A2}$ is acetyl. In certain embodiments, at least one $R^{A2}$ is substituted acetyl. In certain embodiments, at least one $R^{A2}$ is substituted alkyl. In certain embodiments, at least one $R^{A2}$ is unsubstituted alkyl. In certain embodiments, at least one $R^{A2}$ is $C_{1-6}$ alkyl. In certain embodiments, at least one $R^{A2}$ is methyl. In certain embodiments, at least one $R^{A2}$ is ethyl. In certain embodiments, at least one $R^{A2}$ is propyl. In certain embodiments, at least one $R^{A2}$ is butyl. In certain embodiments, at least one $R^{A2}$ is substituted alkenyl. In certain embodiments, at least one $R^{A2}$ is unsubstituted alkenyl. In certain embodiments, at least one $R^{A2}$ is vinyl. In certain embodiments, at least one $R^{A2}$ is substituted alkynyl. In certain embodiments, at least one $R^{A2}$ is unsubstituted alkynyl. In certain embodiments, at least one $R^{A2}$ is ethynyl. In certain embodiments, at least one $R^{A2}$ is substituted carbocyclyl. In certain embodiments, at least one $R^{A2}$ is unsubstituted carbocyclyl. In certain embodiments, at least one $R^{A2}$ is substituted heterocyclyl. In certain embodiments, at least one $R^{A2}$ is unsubstituted heterocyclyl. In certain embodiments, at least one $R^{A2}$ is substituted aryl. In certain embodiments, at least one $R^{A2}$ is unsubstituted aryl. In certain embodiments, at least one $R^{A2}$ is substituted phenyl. In certain embodiments, at least one $R^{A2}$ is unsubstituted phenyl. In certain embodiments, at least one $R^{A2}$ is substituted heteroaryl. In certain embodiments, at least one $R^{A2}$ is unsubstituted heteroaryl. In certain embodiments, at least one $R^{A2}$ is substituted pyridyl. In certain embodiments, at least one $R^{A2}$ is unsubstituted pyridyl. In certain embodiments, at least one $R^{A2}$ is —$OR^{A2a}$. In certain embodiments, at least one $R^{A2}$ is —$N(R^{A2a})_2$. In certain embodiments, at least one $R^{A2}$ is —$SR^{A2a}$.

In certain embodiments, two $R^{A2}$ groups are each independently halogen, optionally substituted alkyl, or optionally substituted aryl; and all other instances of $R^{A2}$ are hydrogen. In certain embodiments, two $R^{A2}$ groups are each independently halogen or optionally substituted alkyl; and all other instances of $R^{A2}$ are hydrogen. In certain embodiments, two $R^{A2}$ groups are halogen; and all other instances of $R^{A2}$ are hydrogen. In certain embodiments, two $R^{A2}$ groups are optionally substituted alkyl; and all other instances of $R^{A2}$ are hydrogen. In certain embodiments, two $R^{A2}$ groups are $C_{1-6}$ alkyl; and all other instances of $R^{A2}$ are hydrogen. In certain embodiments, two $R^{A2}$ groups are methyl; and all other instances of $R^{A2}$ are hydrogen. In certain embodiments, two $R^{A2}$ groups are ethyl; and all other instances of $R^{A2}$ are hydrogen. In certain embodiments, two $R^{A2}$ groups are propyl; and all other instances of $R^{A2}$ are hydrogen. In certain embodiments, two $R^{A2}$ groups are butyl; and all other instances of $R^{A2}$ are hydrogen. In certain embodiments, two $R^{A2}$ groups are optionally substituted aryl; and all other instances of $R^{A2}$ are hydrogen. In certain embodiments, two $R^{A2}$ groups are optionally substituted phenyl; and all other instances of $R^{A2}$ are hydrogen.

In certain embodiments, one $R^{A2}$ groups is halogen, optionally substituted alkyl, or optionally substituted aryl; and all other instances of $R^{A2}$ are hydrogen. In certain embodiments, one $R^{A2}$ is halogen or optionally substituted alkyl; and all other instances of $R^{A2}$ are hydrogen. In certain embodiments, one $R^{A2}$ is halogen; and all other instances of $R^{A2}$ are hydrogen. In certain embodiments, one $R^{A2}$ is optionally substituted alkyl; and all other instances of $R^{A2}$ are hydrogen. In certain embodiments, one $R^{A2}$ is $C_{1-6}$ alkyl; and all other instances of $R^{A2}$ are hydrogen. In certain embodiments, one $R^{A2}$ is methyl; and all other instances of $R^{A2}$ are hydrogen. In certain embodiments, one $R^{A2}$ is ethyl; and all other instances of $R^{A2}$ are hydrogen. In certain embodiments, one $R^{A2}$ is propyl; and all other instances of $R^{A2}$ are hydrogen. In certain embodiments, one $R^{A2}$ is butyl; and all other instances of $R^{A2}$ are hydrogen. In certain embodiments, one $R^{A2}$ is optionally substituted aryl; and all other instances of $R^{A2}$ are hydrogen. In certain embodiments, one $R^{A2}$ is optionally substituted phenyl; and all other instances of $R^{A2}$ are hydrogen.

In certain embodiments, all instances of $R^{A2}$ are hydrogen.

In certain embodiments, when $R^{A2}$ is —$OR^{A2a}$, —$N(R^{A2a})_2$, or —$SR^{A2a}$, at least one $R^{A2a}$ is H. In certain embodiments, at least one $R^{A2a}$ is halogen. In certain embodiments, at least one $R^{A2a}$ is F. In certain embodiments, at least one $R^{A2a}$ is Cl. In certain embodiments, at least one $R^{A2a}$ is Br. In certain embodiments, at least one $R^{A2a}$ is I (iodine). In certain embodiments, at least one $R^{A2a}$ is substituted acyl. In certain embodiments, at least one $R^{A2a}$ is unsubstituted acyl. In certain embodiments, at least one $R^{A2a}$ is acetyl. In certain embodiments, at least one $R^{A2a}$ is substituted acetyl. In certain embodiments, at least one $R^{A2a}$ is substituted alkyl. In certain embodiments, at least one $R^{A2a}$ is unsubstituted alkyl. In certain embodiments, at least one $R^{A2a}$ is $C_{1-6}$ alkyl. In certain embodiments, at least one $R^{A2a}$ is methyl. In certain embodiments, at least one $R^{A2a}$ is ethyl. In certain embodiments, at least one $R^{A2a}$ is propyl. In certain embodiments, at least one $R^{A2a}$ is butyl. In certain embodiments, at least one $R^{A2a}$ is substituted alkenyl. In certain embodiments, at least one $R^{A2a}$ is unsubstituted alkenyl. In certain embodiments, at least one $R^{A2a}$ is vinyl. In certain embodiments, at least one $R^{A2a}$ is substituted alkynyl. In certain embodiments, at least one $R^{A2a}$ is unsubstituted alkynyl. In certain embodiments, at least one $R^{A2a}$ is ethynyl. In certain embodiments, at least one $R^{A2a}$ is substituted carbocyclyl. In certain embodiments, at least one $R^{A2a}$ is unsubstituted carbocyclyl. In certain embodiments, at least one $R^{A2a}$ is substituted heterocyclyl. In certain embodiments, at least one $R^{A2a}$ is unsubstituted heterocyclyl. In certain embodiments, at least one $R^{A2a}$ is substituted aryl. In certain embodiments, at least one $R^{A2a}$ is unsubstituted aryl. In certain embodiments, at least one $R^{A2a}$ is substituted phenyl. In certain embodiments, at least one $R^{A2a}$ is unsubstituted phenyl. In certain embodiments, at least one $R^{A2a}$ is substituted heteroaryl. In certain embodiments, at least one $R^{A2a}$ is unsubstituted heteroaryl. In certain embodiments, at least one $R^{A2a}$ is substituted pyridyl. In certain embodiments, at least one $R^{A2a}$ is unsubstituted pyridyl. In certain embodiments, at least one $R^{A2a}$ is a nitrogen protecting group when attached to a nitrogen atom. In certain embodiments, at least one $R^{A2a}$ is Bn, BOC, Cbz, Fmoc, trifluoroacetyl, triphenylmethyl, acetyl, acetyl, or Ts when attached to a nitrogen atom. In certain embodiments, at least one $R^{A2a}$ is an oxygen protecting group when attached to an oxygen atom. In certain embodiments, at least one $R^{A2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one $R^{A2a}$ is a sulfur protecting group when attached to a sulfur atom. In certain embodiments, at least one $R^{A2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{A2a}$ groups are joined to form a substituted heterocyclic ring. In certain embodiments, two $R^{A2a}$ groups are joined to form an unsubstituted heterocyclic ring.

In compounds of Formula (I), any two of $R^{A1}$, $R^{A2}$, and $R^{A2a}$ groups may be joined to form an optionally substituted carbocyclic, optionally substituted heterocyclic, optionally substituted aryl, or optionally substituted heteroaryl ring. In certain embodiments, one instance of $R^{A1}$ and one instance of $R^{A2}$ are joined to form a substituted carbocyclic ring. In certain embodiments, one instance of $R^{A1}$ and one instance of $R^{A2}$ are joined to form an unsubstituted carbocyclic ring. In certain embodiments, one instance of $R^{A1}$ and one instance of $R^{A2}$ are joined to form a substituted heterocyclic ring. In certain embodiments, one instance of $R^{A1}$ and one instance of $R^{A2}$ are joined to form an unsubstituted heterocyclic ring. In certain embodiments, one instance of $R^{A1}$ and one instance of $R^{A2}$ are joined to form a substituted aryl ring. In certain embodiments, one instance of $R^{A1}$ and one instance of $R^{A2}$ are joined to form an unsubstituted aryl ring. In certain embodiments, one instance of $R^{A1}$ and one instance of $R^{A2}$ are joined to form a substituted heteroaryl ring. In certain embodiments, one instance of $R^{A1}$ and one instance of $R^{A2}$ are joined to form an unsubstituted heteroaryl ring. In certain embodiments, one instance of $R^{A1}$ and one instance of $R^{A2a}$ are joined to form a substituted carbocyclic ring. In certain embodiments, one instance of $R^{A1}$ and one instance of $R^{A2a}$ are joined to form an unsubstituted carbocyclic ring. In certain embodiments, one instance of $R^{A1}$ and one instance of $R^{A2a}$ are joined to form a substituted heterocyclic ring. In certain embodiments, one instance of $R^{A1}$ and one instance of $R^{A2a}$ are joined to form an unsubstituted heterocyclic ring. In certain embodiments, one instance of $R^{A1}$ and one instance of $R^{A2a}$ are joined to form a substituted aryl ring. In certain embodiments, one instance of $R^{A1}$ and one instance of $R^{A2a}$ are joined to form an unsubstituted aryl ring. In certain embodiments, one instance of $R^{A1}$ and one instance of $R^{A2a}$ are joined to form a substituted heteroaryl ring. In certain embodiments, one instance of $R^{A1}$ and one instance of $R^{A2a}$ are joined to form an unsubstituted heteroaryl ring. In certain embodiments, one instance of $R^{A1}$ and one instance of $R^{A2}$ are joined to form an unsubstituted heteroaryl ring. In certain embodiments, one instance of $R^{A2a}$ and one instance of $R^{A2}$ are joined to form a substituted carbocyclic ring. In certain embodiments, one instance of $R^{A2a}$ and one instance of $R^{A2}$ are joined to form an unsubstituted carbocyclic ring. In certain embodiments, one instance of $R^{A2a}$ and one instance of $R^{A2}$ are joined to form a substituted heterocyclic ring. In certain embodiments, one instance of $R^{A2a}$ and one instance of $R^{A2}$ are joined to form an unsubstituted heterocyclic ring. In certain embodiments, one instance of $R^{A2a}$ and one instance of $R^{A2}$ are joined to form a substituted aryl ring. In certain embodiments, one instance of $R^{A2a}$ and one instance of $R^{A2}$ are joined to form an unsubstituted aryl ring. In certain embodiments, one instance of $R^{A2a}$ and one instance of $R^{A2}$ are joined to form a substituted heteroaryl ring. In certain embodiments, one instance of $R^{A2a}$ and one instance of $R^{A2}$ are joined to form an unsubstituted heteroaryl ring.

Compounds of Formula (I) include a substituted or unsubstituted heteroaryl ring of the formula:

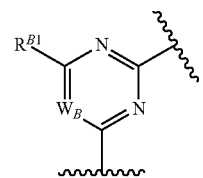

as Ring B. In certain embodiments, $W_B$ is N; and therefore, Ring B is of the formula:

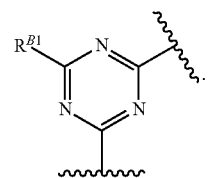

In certain embodiments, $W_B$ is $CR^{B2}$; and therefore, Ring B is of the formula:

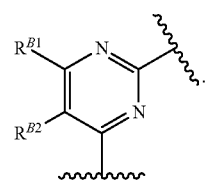

In certain embodiments, Ring B is of the formula:

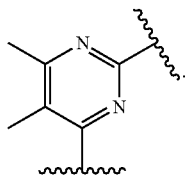 [SMILES: *c1nc(*)c(C)c(C)n1]

in certain embodiments, Ring B is of the formula:

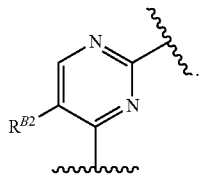

In certain embodiments, Ring B is of the formula:

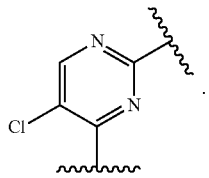 [SMILES: *c1ncc(Cl)c(*)n1]

In certain embodiments, Ring B is of the formula:

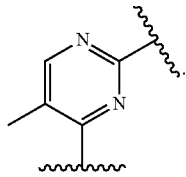 [SMILES: *c1ncc(C)c(*)n1]

In certain embodiments, Ring B is of the formula:

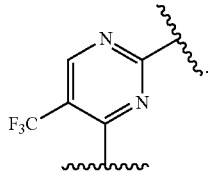 [SMILES: *c1ncc(C(F)(F)F)c(*)n1]

In certain embodiments, Ring B is of the formula:

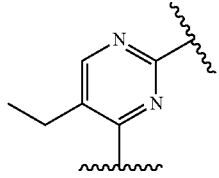

In certain embodiments, Ring B is of the formula:

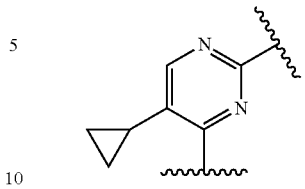

In certain embodiments, Ring B is of the formula:

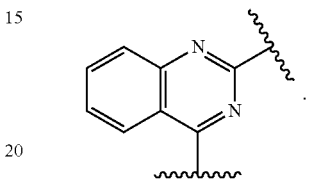

In compounds of Formula (I), Ring B includes a substituent $R^{B1}$. In certain embodiments, $R^{B1}$ is H. In certain embodiments, $R^{B1}$ is halogen. In certain embodiments, $R^{B1}$ is F. In certain embodiments, $R^{B1}$ is Cl. In certain embodiments, $R^{B1}$ is Br. In certain embodiments, $R^{B1}$ is I (iodine). In certain embodiments, $R^{B1}$ is substituted acyl. In certain embodiments, $R^{B1}$ is unsubstituted acyl. In certain embodiments, $R^{B1}$ is acetyl. In certain embodiments, $R^{B1}$ is substituted acetyl. In certain embodiments, $R^{B1}$ is substituted alkyl. In certain embodiments, $R^{B1}$ is unsubstituted alkyl. In certain embodiments, $R^{B1}$ is $C_{1-6}$ alkyl. In certain embodiments, $R^{B1}$ is methyl. In certain embodiments, $R^{B1}$ is ethyl. In certain embodiments, $R^{B1}$ is propyl. In certain embodiments, $R^{B1}$ is butyl. In certain embodiments, $R^{B1}$ is substituted alkenyl. In certain embodiments, $R^{B1}$ is unsubstituted alkenyl. In certain embodiments, $R^{B1}$ is vinyl. In certain embodiments, $R^{B1}$ is substituted alkynyl. In certain embodiments, $R^{B1}$ is unsubstituted alkynyl. In certain embodiments, $R^{B1}$ is ethynyl. In certain embodiments, $R^{B1}$ is substituted carbocyclyl. In certain embodiments, $R^{B1}$ is unsubstituted carbocyclyl. In certain embodiments, $R^{B1}$ is substituted heterocyclyl. In certain embodiments, $R^{B1}$ is unsubstituted heterocyclyl. In certain embodiments, $R^{B1}$ is substituted aryl. In certain embodiments, $R^{B1}$ is unsubstituted aryl. In certain embodiments, $R^{B1}$ is substituted phenyl. In certain embodiments, $R^{B1}$ is unsubstituted phenyl. In certain embodiments, $R^{B1}$ is substituted heteroaryl. In certain embodiments, $R^{B1}$ is unsubstituted heteroaryl. In certain embodiments, $R^{B1}$ is substituted pyridyl. In certain embodiments, $R^{B1}$ is unsubstituted pyridyl. In certain embodiments, $R^{B1}$ is $-OR^{B1a}$. In certain embodiments, $R^{B1}$ is $-N(R^{B1a})_2$. In certain embodiments, $R^{B1}$ is $-SR^{B1a}$.

In certain embodiments, when $R^{B1}$ is $-OR^{B1a}$, $-N(R^{B1a})_2$, or $-SR^{B1a}$, $R^{B1a}$ is H. In certain embodiments, $R^{B1a}$ is halogen. In certain embodiments, $R^{B1a}$ is F. In certain embodiments, $R^{B1a}$ is Cl. In certain embodiments, $R^{B1a}$ is Br. In certain embodiments, $R^{B1a}$ is I (iodine). In certain embodiments, $R^{B1a}$ is substituted acyl. In certain embodiments, $R^{B1a}$ is unsubstituted acyl. In certain embodiments, $R^{B1a}$ is acetyl. In certain embodiments, $R^{B1a}$ is substituted acetyl. In certain embodiments, $R^{B1a}$ is substituted alkyl. In certain embodiments, $R^{B1a}$ is unsubstituted alkyl. In certain embodiments, $R^{B1a}$ is $C_{1-6}$ alkyl. In certain embodiments, $R^{B1a}$ is methyl. In certain embodiments, $R^{B1a}$ is ethyl. In certain embodiments, $R^{B1a}$ is propyl. In certain embodiments, $R^{B1a}$ is butyl. In certain embodiments, $R^{B1a}$ is substituted alkenyl. In certain embodiments, $R^{B1a}$ is unsubstituted alkenyl. In certain embodiments, $R^{B1a}$ is vinyl. In certain embodiments, $R^{B1a}$ is substituted alkynyl. In certain embodiments, $R^{B1a}$ is unsubstituted alkynyl. In certain embodiments, $R^{B1a}$ is ethynyl. In certain embodiments, $R^{B1a}$ is substituted carbocyclyl. In certain embodiments, $R^{B1a}$ is unsubstituted carbocyclyl. In certain embodiments, $R^{B1a}$ is substituted heterocyclyl. In certain embodiments, $R^{B1a}$ is unsubstituted heterocyclyl. In certain embodiments, $R^{B1a}$ is substituted aryl. In certain embodiments, $R^{B1a}$ is unsubstituted aryl. In certain embodiments, $R^{B1a}$ is substituted phenyl. In certain embodiments, $R^{B1a}$ is unsubstituted phenyl. In certain embodiments, $R^{B1a}$ is substituted heteroaryl. In certain embodiments, $R^{B1a}$ is unsubstituted heteroaryl. In certain embodiments, $R^{B1a}$ is substituted pyridyl. In certain embodiments, $R^{B1a}$ is unsubstituted pyridyl. In certain embodiments, $R^{B1a}$ is a nitrogen protecting group when attached to a nitrogen atom. In certain embodiments, $R^{B1a}$ is Bn, BOC, Cbz, Fmoc, trifluoroacetyl, triphenylmethyl, acetyl, acetyl, or Ts when attached to a nitrogen atom. In certain embodiments, $R^{B1a}$ is an oxygen protecting group when attached to an oxygen atom. In certain embodiments, $R^{B1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1a}$ is a sulfur protecting group when attached to a sulfur atom. In certain embodiments, $R^{B1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{B1a}$ groups are joined to form a substituted heterocyclic ring. In certain embodiments, two $R^{B1a}$ groups are joined to form an unsubstituted heterocyclic ring.

In compounds of Formula (I), when $W_B$ is $CR^{B2}$, Ring B also includes a substituent $R^{B2}$. In certain embodiments, $R^{B2}$ is H. In certain embodiments, $R^{B2}$ is selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^{B2a}$, $—N(R^{B2a})_2$, and $—SR^{B2a}$. In certain embodiments, $R^{B2}$ is halogen. In certain embodiments, $R^{B2}$ is F. In certain embodiments, $R^{B2}$ is Cl. In certain embodiments, $R^{B2}$ is Br. In certain embodiments, $R^{B2}$ is I (iodine). In certain embodiments, $R^{B2}$ is substituted acyl. In certain embodiments, $R^{B2}$ is unsubstituted acyl. In certain embodiments, $R^{B2}$ is acetyl. In certain embodiments, $R^{B2}$ is substituted acetyl. In certain embodiments, $R^{B2}$ is substituted alkyl. In certain embodiments, $R^{B2}$ is unsubstituted alkyl. In certain embodiments, $R^{B2}$ is $C_{1-6}$ alkyl. In certain embodiments, $R^{B2}$ is partially fluorinated $C_{1-6}$ alkyl. In certain embodiments, $R^{B2}$ is perfluorinated $C_{1-6}$ alkyl. In certain embodiments, $R^{B2}$ is methyl. In certain embodiments, $R^{B2}$ is $—CH_2F$. In certain embodiments, $R^{B2}$ is $—CHF_2$. In certain embodiments, $R^{B2}$ is $—CF_3$. In certain embodiments, $R^{B2}$ is ethyl. In certain embodiments, $R^{B2}$ is $—C_2F_5$. In certain embodiments, $R^{B2}$ is propyl. In certain embodiments, $R^{B2}$ is butyl. In certain embodiments, $R^{B2}$ is substituted alkenyl. In certain embodiments, $R^{B2}$ is unsubstituted alkenyl. In certain embodiments, $R^{B2}$ is vinyl. In certain embodiments, $R^{B2}$ is substituted alkynyl. In certain embodiments, $R^{B2}$ is unsubstituted alkynyl. In certain embodiments, $R^{B2}$ is ethynyl. In certain embodiments, $R^{B2}$ is substituted carbocyclyl. In certain embodiments, $R^{B2}$ is unsubstituted carbocyclyl. In certain embodiments, $R^{B2}$ is cyclopropyl. In certain embodiments, $R^{B2}$ is cyclobutyl. In certain embodiments, $R^{B2}$ is cyclopentyl. In certain embodiments, $R^{B2}$ is cyclohexyl. In certain embodiments, $R^{B2}$ is cycloheptyl. In certain embodiments, $R^{B2}$ is substituted heterocyclyl. In certain embodiments, $R^{B2}$ is unsubstituted heterocyclyl. In certain embodiments, $R^{B2}$ is substituted aryl. In certain embodiments, $R^{B2}$ is unsubstituted aryl. In certain embodiments, $R^{B2}$ is substituted phenyl. In certain embodiments, $R^{B2}$ is unsubstituted phenyl. In certain embodiments, $R^{B2}$ is substituted heteroaryl. In certain embodiments, $R^{B2}$ is unsubstituted heteroaryl. In certain embodiments, $R^{B2}$ is substituted pyridyl. In certain embodiments, $R^{B2}$ is unsubstituted pyridyl. In certain embodiments, $R^{B2}$ is $—OR^{B2a}$. In certain embodiments, $R^{B2}$ is $—N(R^{B2a})_2$. In certain embodiments, $R^{B2}$ is $—SR^{B2a}$.

In certain embodiments, when $R^{B2}$ is $—OR^{B2a}$, $—N(R^{B2a})_2$, or $—SR^{B2a}$, $R^{B2a}$ is H. In certain embodiments, $R^{B2a}$ is halogen. In certain embodiments, $R^{B2a}$ is F. In certain embodiments, $R^{B2a}$ is Cl. In certain embodiments, $R^{B2a}$ is Br. In certain embodiments, $R^{B2a}$ is I (iodine). In certain embodiments, $R^{B2a}$ is substituted acyl. In certain embodiments, $R^{B2a}$ is unsubstituted acyl. In certain embodiments, $R^{B2a}$ is acetyl. In certain embodiments, $R^{B2a}$ is substituted acetyl. In certain embodiments, $R^{B2a}$ is substituted alkyl. In certain embodiments, $R^{B2a}$ is unsubstituted alkyl. In certain embodiments, $R^{B2a}$ is $C_{1-6}$ alkyl. In certain embodiments, $R^{B2a}$ is methyl. In certain embodiments, $R^{B2a}$ is ethyl. In certain embodiments, $R^{B2a}$ is propyl. In certain embodiments, $R^{B2a}$ is butyl. In certain embodiments, $R^{B2a}$ is substituted alkenyl. In certain embodiments, $R^{B2a}$ is unsubstituted alkenyl. In certain embodiments, $R^{B2a}$ is vinyl. In certain embodiments, $R^{B2a}$ is substituted alkynyl. In certain embodiments, $R^{B2a}$ is unsubstituted alkynyl. In certain embodiments, $R^{B2a}$ is ethynyl. In certain embodiments, $R^{B2a}$ is substituted carbocyclyl. In certain embodiments, $R^{B2a}$ is unsubstituted carbocyclyl. In certain embodiments, $R^{B2a}$ is substituted heterocyclyl. In certain embodiments, $R^{B2a}$ is unsubstituted heterocyclyl. In certain embodiments, $R^{B2a}$ is substituted aryl. In certain embodiments, $R^{B2a}$ is unsubstituted aryl. In certain embodiments, $R^{B2a}$ is substituted phenyl. In certain embodiments, $R^{B2a}$ is unsubstituted phenyl. In certain embodiments, $R^{B2a}$ is substituted heteroaryl. In certain embodiments, $R^{B2a}$ is unsubstituted heteroaryl. In certain embodiments, $R^{B2a}$ is substituted pyridyl. In certain embodiments, $R^{B2a}$ is unsubstituted pyridyl. In certain embodiments, $R^{B2a}$ is a nitrogen protecting group when attached to a nitrogen atom. In certain embodiments, $R^{B2a}$ is Bn, BOC, Cbz, Fmoc, trifluoroacetyl, triphenylmethyl, acetyl, acetyl, or Ts when attached to a nitrogen atom. In certain embodiments, $R^{B2a}$ is an oxygen protecting group when attached to an oxygen atom. In certain embodiments, $R^{B2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B2a}$ is a sulfur protecting group when attached to a sulfur atom. In certain embodiments, $R^{B2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{B2a}$ groups are joined to form a substituted heterocyclic ring. In certain embodiments, two $R^{B2a}$ groups are joined to form an unsubstituted heterocyclic ring.

In compounds of Formula (I), $R^{B1}$ and $R^{B2}$ groups may be joined to form a ring fused to Ring B. In certain embodiments, $R^{B1}$ and $R^{B2}$ are joined to form a substituted carbocyclic ring. In certain embodiments, $R^{B1}$ and $R^{B2}$ are joined to form an unsubstituted carbocyclic ring. In certain embodiments, $R^{B1}$ and $R^{B2}$ are joined to form a substituted heterocyclic ring. In certain embodiments, $R^{B1}$ and $R^{B2}$ are joined to form an unsubstituted heterocyclic ring. In certain embodiments, $R^{B1}$ and $R^{B2}$ are joined to form a substituted heteroaryl ring. In certain embodiments, $R^{B1}$ and $R^{B2}$ are joined to form an unsubstituted heteroaryl ring. In certain embodiments, $R^{B1}$ and $R^{B2}$ are joined to form a substituted pyridyl ring. In certain embodiments, $R^{B1}$ and $R^{B2}$ are joined to form an unsubstituted pyridyl ring. In certain embodiments, $R^{B1}$ and $R^{B2}$ are joined to form a substituted aryl ring. In certain embodiments, $R^{B1}$ and $R^{B2}$ are joined to form an unsubstituted aryl ring. In certain embodiments, $R^{B1}$ and $R^{B2}$ are joined to form a substituted phenyl ring. In certain embodiments, $R^{B1}$ and $R^{B2}$ are joined to form an unsubstituted phenyl ring.

In certain embodiments, Ring B is of the formula:

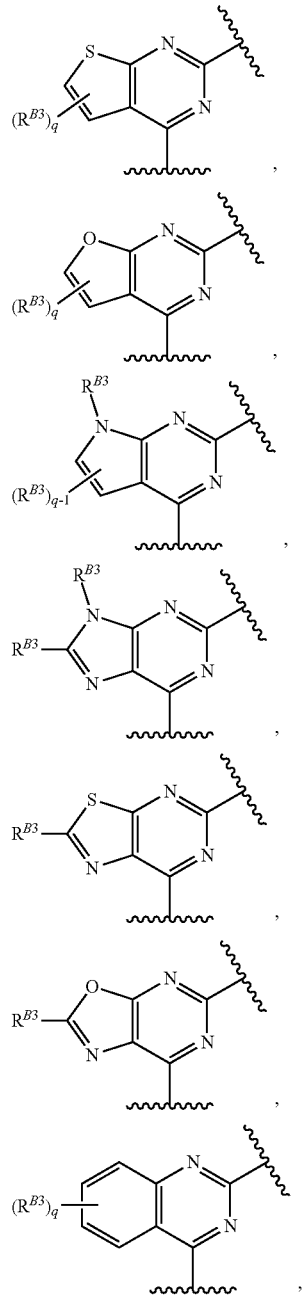

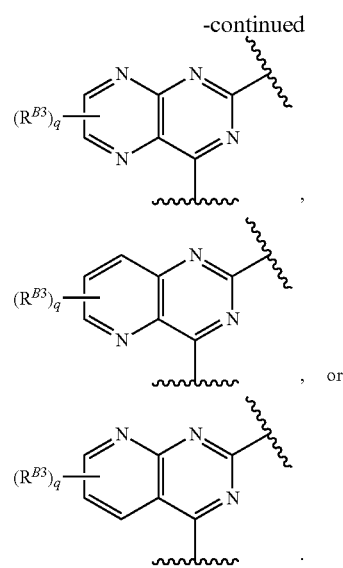

In certain embodiments, $R^{B3}$ is H. In certain embodiments, $R^{B3}$ is selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B3a}$, $-N(R^{B3a})_2$, and $-SR^{B3a}$. In certain embodiments, $R^{B3}$ is halogen. In certain embodiments, $R^{B3}$ is F. In certain embodiments, $R^{B3}$ is Cl. In certain embodiments, $R^{B3}$ is Br. In certain embodiments, $R^{B3}$ is I (iodine). In certain embodiments, $R^{B3}$ is substituted acyl. In certain embodiments, $R^{B3}$ is unsubstituted acyl. In certain embodiments, $R^{B3}$ is acetyl. In certain embodiments, $R^{B3}$ is substituted acetyl. In certain embodiments, $R^{B3}$ is substituted alkyl. In certain embodiments, $R^{B3}$ is unsubstituted alkyl. In certain embodiments, $R^{B3}$ is $C_{1-6}$ alkyl. In certain embodiments, $R^{B3}$ is methyl. In certain embodiments, $R^{B3}$ is ethyl. In certain embodiments, $R^{B3}$ is propyl. In certain embodiments, $R^{B3}$ is butyl. In certain embodiments, $R^{B3}$ is substituted alkenyl. In certain embodiments, $R^{B3}$ is unsubstituted alkenyl. In certain embodiments, $R^{B3}$ is vinyl. In certain embodiments, $R^{B3}$ is substituted alkynyl. In certain embodiments, $R^{B3}$ is unsubstituted alkynyl. In certain embodiments, $R^{B3}$ is ethynyl. In certain embodiments, $R^{B3}$ is substituted carbocyclyl. In certain embodiments, $R^{B3}$ is unsubstituted carbocyclyl. In certain embodiments, $R^{B3}$ is substituted heterocyclyl. In certain embodiments, $R^{B3}$ is unsubstituted heterocyclyl. In certain embodiments, $R^{B3}$ is substituted aryl. In certain embodiments, $R^{B3}$ is unsubstituted aryl. In certain embodiments, $R^{B3}$ is substituted phenyl. In certain embodiments, $R^{B3}$ is unsubstituted phenyl. In certain embodiments, $R^{B3}$ is substituted heteroaryl. In certain embodiments, $R^{B3}$ is unsubstituted heteroaryl. In certain embodiments, $R^{B3}$ is substituted pyridyl. In certain embodiments, $R^{B3}$ is unsubstituted pyridyl. In certain embodiments, $R^{B3}$ is $-OR^{B3a}$. In certain embodiments, $R^{B3}$ is $-N(R^{B3a})_2$. In certain embodiments, $R^{B3}$ is $-SR^{B3a}$.

In certain embodiments, when $R^{B3}$ is $-OR^{B3a}$, $-N(R^{B3a})_2$, or $-SR^{B3a}$, $R^{B3a}$ is H. In certain embodiments, $R^{B3a}$ is halogen. In certain embodiments, $R^{B3a}$ is F. In certain embodiments, $R^{B3a}$ is Cl. In certain embodiments, $R^{B3a}$ is Br. In certain embodiments, $R^{B3a}$ is I (iodine). In certain embodiments, $R^{B3a}$ is substituted acyl. In certain embodiments, $R^{B3a}$ is unsubstituted acyl. In certain embodiments, $R^{B3a}$ is acetyl. In certain embodiments, $R^{B3a}$ is substituted acetyl. In certain embodiments, $R^{B3a}$ is substituted alkyl. In certain embodiments, $R^{B3a}$ is unsubstituted alkyl. In certain embodiments, $R^{B3a}$ is $C_{1-6}$ alkyl. In certain embodiments, $R^{B3a}$ is methyl. In certain embodiments, $R^{B3a}$ is ethyl. In certain embodiments, $R^{B3a}$ is propyl. In certain embodiments, $R^{B3a}$ is butyl. In certain embodiments, $R^{B3a}$ is substituted alkenyl. In certain embodiments, $R^{B3a}$ is unsubstituted alkenyl. In certain embodiments, $R^{B3a}$ is vinyl. In certain embodiments, $R^{B3a}$ is substituted alkynyl. In certain embodiments, $R^{B3a}$ is unsubstituted alkynyl. In certain embodiments, $R^{B3a}$ is ethynyl. In certain embodiments, $R^{B3a}$ is substituted carbocyclyl. In certain embodiments, $R^{B3a}$ is unsubstituted carbocyclyl. In certain embodiments, $R^{B3a}$ is substituted heterocyclyl. In certain embodiments, $R^{B3a}$ is unsubstituted heterocyclyl. In certain embodiments, $R^{B3a}$ is substituted aryl. In certain embodiments, $R^{B3a}$ is unsubstituted aryl. In certain embodiments, $R^{B3a}$ is substituted phenyl. In certain embodiments, $R^{B3a}$ is unsubstituted phenyl. In certain embodiments, $R^{B3a}$ is substituted heteroaryl. In certain embodiments, $R^{B3a}$ is unsubstituted heteroaryl. In certain embodiments, $R^{B3a}$ is substituted pyridyl. In certain embodiments, $R^{B3a}$ is unsubstituted pyridyl. In certain embodiments, $R^{B3a}$ is a nitrogen protecting group when attached to a nitrogen atom. In certain embodiments, $R^{B3a}$ is Bn, BOC, Cbz, Fmoc, trifluoroacetyl, triphenylmethyl, acetyl, acetyl, or Ts when attached to a nitrogen atom. In certain embodiments, $R^{B3a}$ is an oxygen protecting group when attached to an oxygen atom. In certain embodiments, $R^{B3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B3a}$ is a sulfur protecting group when attached to a sulfur atom. In certain embodiments, $R^{B3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{B3a}$ groups are joined to form a substituted heterocyclic ring. In certain embodiments, two $R^{B3a}$ groups are joined to form an unsubstituted heterocyclic ring.

Ring B may be unsubstituted or may be substituted with one or more $R^{B3}$ groups. In certain embodiments, Ring B is unsubstituted, and thus q is 0. In certain embodiments, q is 1. In certain embodiments, q is 2. In certain embodiments, q is 3.

In compounds of Formula (I), X is a divalent linker moiety connecting Ring B and Ring C. X may be an optionally substituted $C_{1-4}$ hydrocarbon chain, optionally wherein one or more carbon units of the hydrocarbon chain is replaced with —O—, —S—, or —$NR^X$—. In certain embodiments, X is an optionally substituted $C_{1-2}$ hydrocarbon chain, optionally wherein one or more carbon units of the hydrocarbon chain is replaced with —O—, —S—, or —$NR^X$—. In certain embodiments, X is an optionally substituted $C_1$ hydrocarbon chain. In certain embodiments, X is —O—. In certain embodiments, X is —S—. In certain embodiments, X is —$NR^X$—. In certain embodiments, X is —NH—. In certain embodiments, X is —$C(R^X)_2$—. In certain embodiments, X is —$CH_2$—. In certain embodiments, X is an optionally substituted $C_3$ hydrocarbon chain, optionally wherein one or more carbon units of the hydrocarbon chain is replaced with —O—, —S—, or —$NR^X$—. In certain embodiments, X is an optionally substituted $C_4$ hydrocarbon chain, optionally wherein one or more carbon units of the hydrocarbon chain is replaced with —O—, —S—, or —$NR^X$—. In certain embodiments, when X is —$NR^X$— or —$C(R^X)_2$—, $R^X$ is H. In certain embodiments, $R^X$ is substituted alkyl. In certain embodiments, $R^X$ is unsubstituted alkyl. In certain embodiments, $R^X$ is $C_{1-6}$ alkyl. In certain embodiments, $R^X$ is methyl. In certain embodiments, $R^X$ is ethyl. In certain embodiments, $R^X$ is propyl. In certain embodiments, $R^X$ is butyl. In certain embodiments, when X is —$NR^X$—, $R^X$ is a nitrogen protecting group. In certain embodiments, $R^X$ is Bn, BOC, Cbz, Fmoc, trifluoroacetyl, triphenylmethyl, acetyl, acetyl, or Ts.

In compounds of Formula (I), $L^2$ is a divalent linker moiety connecting Ring C and Ring D. $L^2$ may contain 0-4 carbon or hetero atoms in the backbone of $L^2$. $L^2$ may be saturated or unsaturated. $L^2$ may be substituted or unsubstituted. $L^2$ may be branched or unbranched. In certain embodiments, $L^2$ is a bond. In certain embodiments, $L^2$ is —O—. In certain embodiments, $L^2$ is —S—. In certain embodiments, $L^2$ is —$NR^{L2a}$—. In certain embodiments, $L^2$ is —NH—. In certain embodiments, $L^2$ is —$NR^{L2a}C(=O)$—. In certain embodiments, $L^2$ is —NHC(=O)—. In certain embodiments, $L^2$ is —NH— or —NHC(=O)—. In certain embodiments, $L^2$ is —$C(=O)NR^{L2a}$—. In certain embodiments, $L^2$ is —C(=O)NH—. In certain embodiments, $L^2$ is —NH— or —C(=O)NH—. In certain embodiments, $L^2$ is —SC(=O)—. In certain embodiments, $L^2$ is —C(=O)S—. In certain embodiments, $L^2$ is —OC(=O)—. In certain embodiments, $L^2$ is —C(=O)O—. In certain embodiments, $L^2$ is —$NR^{L2a}C(=S)$—. In certain embodiments, $L^2$ is —NHC(=S)—. In certain embodiments, $L^2$ is —$C(=S)NR^{L2a}$—. In certain embodiments, $L^2$ is —C(=S)NH—. In certain embodiments, $L^2$ is trans-$CR^{L2b}=CR^{L2b}$—. In certain embodiments, $L^2$ is trans-CH=CH—. In certain embodiments, $L^2$ is cis-$CR^{L2b}=CR^{L2b}$—. In certain embodiments, $L^2$ is cis-CH=CH—. In certain embodiments, $L^2$ is —C≡C—. In certain embodiments, $L^2$ is —$OC(R^{L2b})_2$—. In certain embodiments, $L^2$ is —$OCH_2$—. In certain embodiments, $L^2$ is —$C(R^{L2b})_2O$—. In certain embodiments, $L^2$ is —$CH_2O$—. In certain embodiments, $L^2$ is —$NR^{L2a}C(R^{L2b})_2$—. In certain embodiments, $L^2$ is —$NR^{L2a}CH_2$—. In certain embodiments, $L^2$ is —$NHCH_2$—. In certain embodiments, $L^2$ is —$C(R^{L2b})_2NR^{L2a}$—. In certain embodiments, $L^2$ is —$CH_2NR^{L2a}$—. In certain embodiments, $L^2$ is —$CH_2NH$—. In certain embodiments, $L^2$ is —$SC(R^{L2b})_2$—. In certain embodiments, $L^2$ is —$SCH_2$—. In certain embodiments, $L^2$ is —$C(R^{L2b})_2S$—. In certain embodiments, $L^2$ is —$CH_2S$—. In certain embodiments, $L^2$ is —$S(=O)_2O$—. In certain embodiments, $L^2$ is —$OS(=O)_2$—. In certain embodiments, $L^2$ is —$S(=O)_2NR^{L2a}$—. In certain embodiments, $L^2$ is —$S(=O)_2NH$—. In certain embodiments, $L^2$ is —$NR^{L2a}S(=O)_2$—. In certain embodiments, $L^2$ is —$NHS(=O)_2$—. In certain embodiments, $L^2$ is a substituted $C_{1-4}$ hydrocarbon chain. In certain embodiments, $L^2$ is an unsubstituted $C_{1-4}$ hydrocarbon chain. In certain embodiments, $L^2$ is a substituted $C_2$ hydrocarbon chain. In certain embodiments, $L^2$ is an unsubstituted $C_2$ hydrocarbon chain. In certain embodiments, $L^2$ is a substituted $C_3$ hydrocarbon chain. In certain embodiments, $L^2$ is an unsubstituted $C_3$ hydrocarbon chain. In certain embodiments, $L^2$ is a substituted $C_4$ hydrocarbon chain. In certain embodiments, $L^2$ is an unsubstituted $C_4$ hydrocarbon chain. In certain embodiments, $L^2$ is an optionally substituted $C_{1-4}$ hydrocarbon chain, wherein one or more carbon units of the hydrocarbon chain is replaced with —O—, —S—, —$NR^{L2a}$—, —$NR^{L2a}C(=O)$—, —$C(=O)NR^{L2a}$—, —SC(=O)—, —C(=O)S—, —OC(=O)—, —C(=O)O—, —$NR^{L2a}C(=S)$—, —$C(=S)NR^{L2a}$—, trans-$CR^{L2b}=CR^{L2b}$—, cis-$CR^{L2b}=CR^{L2b}$—, —C≡C—, —$S(=O)_2O$—, —$OS(=O)_2$—, —$S(=O)_2NR^{L2a}$—, or —$NR^{L2a}S(=O)_2$—.

In certain embodiments, $R^{L2a}$ is H. In certain embodiments, $R^{L2a}$ is substituted alkyl. In certain embodiments, $R^{L2a}$ is unsubstituted alkyl. In certain embodiments, $R^{L2a}$ is $C_{1-6}$ alkyl. In certain embodiments, $R^{L2a}$ is methyl. In certain embodiments, $R^{L2a}$ is ethyl. In certain embodiments, $R^{L2a}$ is propyl. In certain embodiments, $R^{L2a}$ is butyl. In certain embodiments, $R^{L2a}$ is a nitrogen protecting group. In certain embodiments, $R^{L2a}$ is Bn, BOC, Cbz, Fmoc, trifluoroacetyl, triphenylmethyl, acetyl, acetyl, or Ts.

In certain embodiments, at least one $R^{L2b}$ is H. In certain embodiments, at least one $R^{L2b}$ is halogen. In certain embodiments, at least one $R^{L2b}$ is F. In certain embodiments, at least one $R^{L2b}$ is Cl. In certain embodiments, at least one $R^{L2b}$ is Br. In certain embodiments, at least one $R^{L2b}$ is I (iodine). In certain embodiments, at least one $R^{L2b}$ is substituted alkyl. In certain embodiments, at least one $R^{L2b}$ is unsubstituted alkyl. In certain embodiments, at least one $R^{L2b}$ is $C_{1-6}$ alkyl. In certain embodiments, at least one $R^{L2b}$ is methyl. In certain embodiments, at least one $R^{L2b}$ is ethyl. In certain embodiments, at least one $R^{L2b}$ is propyl. In certain embodiments, at least one $R^{L2b}$ is butyl. In certain embodiments, at least one $R^{L2b}$ is substituted alkenyl. In certain embodiments, at least one $R^{L2b}$ is unsubstituted alkenyl. In certain embodiments, at least one $R^{L2b}$ is vinyl. In certain embodiments, at least one $R^{L2b}$ is substituted alkynyl. In certain embodiments, at least one $R^{L2b}$ is unsubstituted alkynyl. In certain embodiments, at least one $R^{L2b}$ is ethynyl. In certain embodiments, at least one $R^{L2b}$ is substituted carbocyclyl. In certain embodiments, at least one $R^{L2b}$ is unsubstituted carbocyclyl. In certain embodiments, at least one $R^{L2b}$ is substituted heterocyclyl. In certain embodiments, at least one $R^{L2b}$ is unsubstituted heterocyclyl. In certain embodiments, at least one $R^{L2b}$ is substituted aryl. In certain embodiments, at least one $R^{L2b}$ is unsubstituted aryl. In certain embodiments, at least one $R^{L2b}$ is substituted phenyl. In certain embodiments, at least one $R^{L2b}$ is unsubstituted phenyl. In certain embodiments, at least one $R^{L2b}$ is substituted heteroaryl. In certain embodiments, at least one $R^{L2b}$ is unsubstituted heteroaryl. In certain embodiments, at least one $R^{L2b}$ is substituted pyridyl. In certain embodiments, at least one $R^{L2b}$ is unsubstituted pyridyl. In certain embodiments, two $R^{L2b}$ groups are joined to form a substituted carbocyclic ring. In certain embodiments, two $R^{L2b}$ groups are joined to form an unsubstituted carbocyclic ring. In certain embodiments, two $R^{L2b}$ groups are joined to form a substituted heterocyclic ring. In certain embodiments, two $R^{L2b}$ groups are joined to form an unsubstituted heterocyclic ring.

In compounds of Formula (I), Ring C is a meta-phenylene moiety. Ring C may be unsubstituted or may be substituted with one or more $R^C$ groups. In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is substituted acyl. In certain embodiments, at least one $R^C$ is unsubstituted acyl. In certain embodiments, at least one $R^C$ is acetyl. In certain embodiments, at least one $R^C$ is substituted acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is vinyl. In certain embodiments, at least one $R^C$ is substituted alkynyl. In certain embodiments, at least one $R^C$ is unsubstituted alkynyl. In certain embodiments, at least one $R^C$ is ethynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is $-OR^{C1}$. In certain embodiments, at least one $R^C$ is $-N(R^{C1})_2$. In certain embodiments, at least one $R^C$ is $-SR^{C1}$.

In certain embodiments, when $R^C$ is $-OR^{C1}$, $-N(R^{C1})_2$, or $-SR^{C1}$, at least one $R^{C1}$ is H. In certain embodiments, at least one $R^{C1}$ is halogen. In certain embodiments, at least one $R^{C1}$ is F. In certain embodiments, at least one $R^{C1}$ is Cl. In certain embodiments, at least one $R^{C1}$ is Br. In certain embodiments, at least one $R^{C1}$ is I (iodine). In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is vinyl. In certain embodiments, at least one $R^{C1}$ is substituted alkynyl. In certain embodiments, at least one $R^{C1}$ is unsubstituted alkynyl. In certain embodiments, at least one $R^{C1}$ is ethynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is Bn, BOC, Cbz, Fmoc, trifluoroacetyl, triphenylmethyl, acetyl, acetyl, or Ts when attached to a nitrogen atom. In certain embodiments, at least one $R^{C1}$ is an oxygen protecting group when attached to an oxygen atom. In certain embodiments, at least one $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, at least one $R^{C1}$ is a sulfur protecting group when attached to a sulfur atom. In certain embodiments, at least one $R^{C1}$ is acetamidomethyl, t-Bu, 3-nitro-2-pyridine sulfenyl, 2-pyridine-sulfenyl, or triphenylmethyl when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

Ring C may be unsubstituted or substituted with one or more $R^C$ groups. In certain embodiments, Ring C is unsubstituted, and thus n is 0.

In certain embodiments, n is 1. In certain embodiments, Ring C is of the formula:

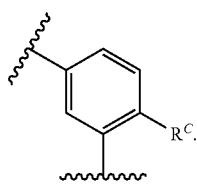

In certain embodiments, Ring C is of the formula:

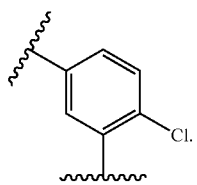 [SMILES: *c1ccc(Cl)c(*)c1]

In certain embodiments, Ring C is of the formula:

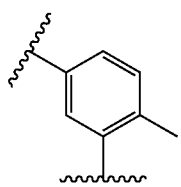

In certain embodiments, Ring C is of the formula:

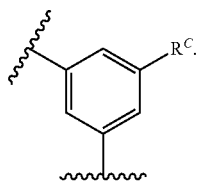

In certain embodiments, Ring C is of the formula:

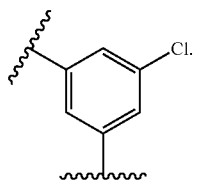 [SMILES: *c1cc(*)cc(Cl)c1]

In certain embodiments, Ring C is of the formula:

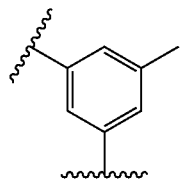

In certain embodiments, Ring C is of the formula:

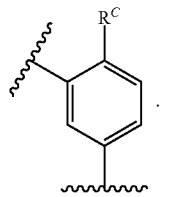

In certain embodiments, Ring C is of the formula:

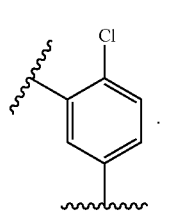 [SMILES: *c1ccc(Cl)c(*)c1]

In certain embodiments, Ring C is of the formula:

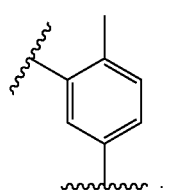 [SMILES: *c1ccc(C)c(*)c1]

In certain embodiments, Ring C is of the formula:

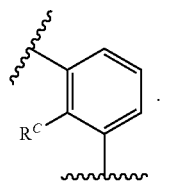

In certain embodiments, Ring C is of the formula:

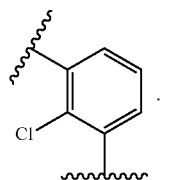 [SMILES: *c1cccc(*)c1Cl]

In certain embodiments, Ring C is of the formula:

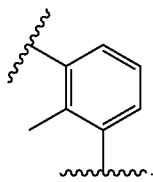 [SMILES: *c1cccc(*)c1C]

In certain embodiments, n is 2. In certain embodiments, Ring C is of the formula:

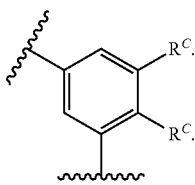

In certain embodiments, Ring C is of the formula:

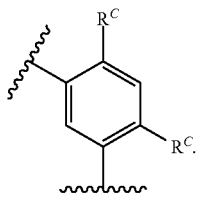

In certain embodiments, Ring C is of the formula:

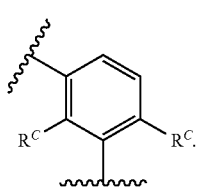

In certain embodiments, Ring C is of the formula:

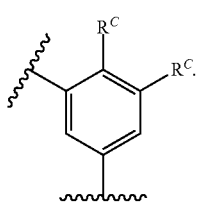

In certain embodiments, Ring C is of the formula:

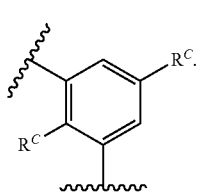

In certain embodiments, Ring C is of the formula:

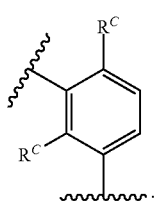

In certain embodiments, n is 3. In certain embodiments, Ring C is of the formula:

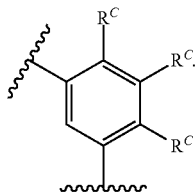

In certain embodiments, Ring C is of the formula:

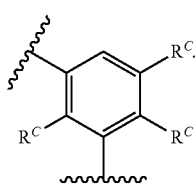

In certain embodiments, Ring C is of the formula:

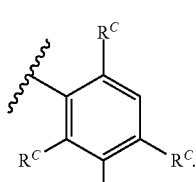

In certain embodiments, Ring C is of the formula:

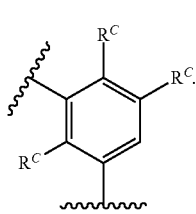

In certain embodiments, n is 4. In certain embodiments, Ring C is of the formula:

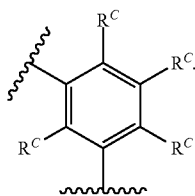

In certain embodiments, $R^C$ is halogen; and n is 1. In certain embodiments, $R^C$ is F; and n is 1. In certain embodiments, $R^C$ is Cl; and n is 1. In certain embodiments, $R^C$ is Br; and n is 1. In certain embodiments, $R^C$ is I (iodine); and n is 1. In certain embodiments, $R^C$ is substituted alkyl; and n is 1. In certain embodiments, $R^C$ is unsubstituted alkyl; and n is 1. In certain embodiments, $R^C$ is $C_{1-6}$ alkyl; and n is 1. In certain embodiments, $R^C$ is methyl; and n is 1. In certain embodiments, $R^C$ is ethyl; and n is 1. In certain embodiments, $R^C$ is propyl; and n is 1. In certain embodiments, $R^C$ is butyl; and n is 1.

In certain embodiments, each instance of $R^C$ is independently halogen or optionally substituted alkyl; and n is 2. In certain embodiments, each instance of $R^C$ is independently halogen or $C_{1-6}$ alkyl; and n is 2.

In compounds of Formula (I), Ring D is a phenyl ring. Ring D is substituted with RE and may also be substituted with one or more $R^D$ groups. In certain embodiments, at least one $R^D$ is H. In certain embodiments, at least one $R^D$ is halogen. In certain embodiments, at least one $R^D$ is F. In certain embodiments, at least one $R^D$ is Cl. In certain embodiments, at least one $R^D$ is Br. In certain embodiments, at least one $R^D$ is I (iodine). In certain embodiments, at least one $R^D$ is substituted acyl. In certain embodiments, at least one $R^D$ is unsubstituted acyl. In certain embodiments, at least one $R^D$ is acetyl. In certain embodiments, at least one $R^D$ is substituted acetyl. In certain embodiments, at least one $R^D$ is substituted alkyl. In certain embodiments, at least one $R^D$ is unsubstituted alkyl. In certain embodiments, at least one $R^D$ is $C_{1-6}$ alkyl. In certain embodiments, at least one $R^D$ is methyl. In certain embodiments, at least one $R^D$ is ethyl. In certain embodiments, at least one $R^D$ is propyl. In certain embodiments, at least one $R^D$ is butyl. In certain embodiments, at least one $R^D$ is substituted alkenyl. In certain embodiments, at least one $R^D$ is unsubstituted alkenyl. In certain embodiments, at least one $R^D$ is vinyl. In certain embodiments, at least one $R^D$ is substituted alkynyl. In certain embodiments, at least one $R^D$ is unsubstituted alkynyl. In certain embodiments, at least one $R^D$ is ethynyl. In certain embodiments, at least one $R^D$ is substituted carbocyclyl. In certain embodiments, at least one $R^D$ is unsubstituted carbocyclyl. In certain embodiments, at least one $R^D$ is substituted heterocyclyl. In certain embodiments, at least one $R^D$ is unsubstituted heterocyclyl. In certain embodiments, at least one $R^D$ is substituted aryl. In certain embodiments, at least one $R^D$ is unsubstituted aryl. In certain embodiments, at least one $R^D$ is substituted phenyl. In certain embodiments, at least one $R^D$ is unsubstituted phenyl. In certain embodiments, at least one $R^D$ is substituted heteroaryl. In certain embodiments, at least one $R^D$ is unsubstituted heteroaryl. In certain embodiments, at least one $R^D$ is substituted pyridyl. In certain embodiments, at least one $R^D$ is unsubstituted pyridyl. In certain embodiments, at least one $R^D$ is $-OR^{D1}$. In certain embodiments, at least one $R^D$ is $-N(R^{D1})_2$. In certain embodiments, at least one $R^D$ is $-SR^{D1}$.

In certain embodiments, when $R^D$ is $-OR^{D1}$, $-N(R^{D1})_2$, or $-SR^{D1}$, at least one $R^{D1}$ is H. In certain embodiments, at least one $R^{D1}$ is substituted acyl. In certain embodiments, at least one $R^{D1}$ is unsubstituted acyl. In certain embodiments, at least one $R^{D1}$ is acetyl. In certain embodiments, at least one $R^{D1}$ is substituted acetyl. In certain embodiments, at least one $R^{D1}$ is substituted alkyl. In certain embodiments, at least one $R^{D1}$ is unsubstituted alkyl. In certain embodiments, at least one $R^{D1}$ is $C_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is substituted alkenyl. In certain embodiments, at least one $R^{D1}$ is unsubstituted alkenyl. In certain embodiments, at least one $R^{D1}$ is vinyl. In certain embodiments, at least one $R^{D1}$ is substituted alkynyl. In certain embodiments, at least one $R^{D1}$ is unsubstituted alkynyl. In certain embodiments, at least one $R^{D1}$ is ethynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is a nitrogen protecting group when attached to a nitrogen atom. In certain embodiments, at least one $R^{D1}$ is Bn, BOC, Cbz, Fmoc, trifluoroacetyl, triphenylmethyl, acetyl, acetyl, or Ts when attached to a nitrogen atom. In certain embodiments, $R^{D1}$ is an oxygen protecting group when attached to an oxygen atom. In certain embodiments, $R^{D1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1}$ is a sulfur protecting group when attached to a sulfur atom. In certain embodiments, $R^{D1}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1}$ groups are joined to form a substituted heterocyclic ring. In certain embodiments, two $R^{D1}$ groups are joined to form an unsubstituted heterocyclic ring.

Ring D may be unsubstituted or substituted with one or more $R^D$ groups. In certain embodiments, Ring D is unsubstituted, and thus p is 0. In certain embodiments, p is 1. In certain embodiments, p is 2. In certain embodiments, p is 3. In certain embodiments, p is 4.

In certain embodiments, $R^D$ is halogen; and p is 1. In certain embodiments, $R^D$ is F; and p is 1. In certain embodiments, $R^D$ is Cl; and p is 1. In certain embodiments, $R^D$ is Br; and p is 1. In certain embodiments, $R^D$ is I (iodine); and p is 1. In certain embodiments, $R^D$ is substituted alkyl; and p is 1. In certain embodiments, $R^D$ is unsubstituted alkyl; and p is 1. In certain embodiments, $R^D$ is $C_{1-6}$ alkyl; and p is 1. In certain embodiments, $R^D$ is methyl; and p is 1. In certain embodiments, $R^D$ is ethyl; and p is 1. In certain embodiments, $R^D$ is propyl; and p is 1. In certain embodiments, $R^D$ is butyl; and p is 1.

In certain embodiments, each instance of $R^D$ is independently halogen or optionally substituted alkyl; and p is 2. In certain embodiments, each instance of $R^D$ is independently halogen or $C_{1-6}$ alkyl; and p is 2.

In compounds of Formula (I), Ring D also includes a substituent $R^E$. In certain embodiments, $R^E$ comprises a Michael acceptor moiety. This Michael acceptor moiety may react with a cysteine residue of a kinase (e.g., CDK (e.g., CDK7)) to allow covalent attachment of the compound to the kinase. In certain embodiments, the covalent attachment is irreversible. In other embodiments, the covalent attachment is reversible.

In certain embodiments, $R^E$ is of Formula (ii-1):

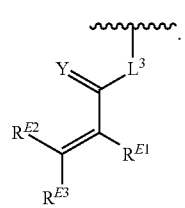

(ii-1)

In certain embodiments, RE is of Formula (ii-2):

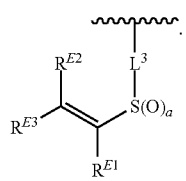

(ii-2)

In certain embodiments, $R^E$ is of Formula (ii-3):

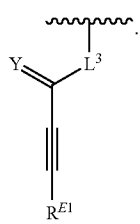

(ii-3)

In certain embodiments, $R^E$ is of Formula (ii-4):

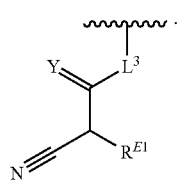

(ii-4)

In certain embodiments, $R^E$ is of Formula (ii-5):

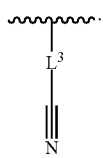

(ii-5)

In certain embodiments, $R^E$ is of Formula (ii-6):

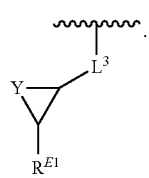

(ii-6)

In certain embodiments, $R^E$ is of Formula (ii-7):

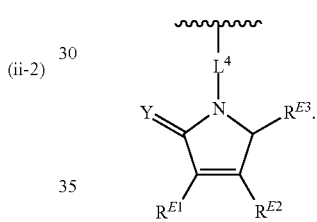

(ii-7)

In certain embodiments, $R^E$ is of Formula (ii-8):

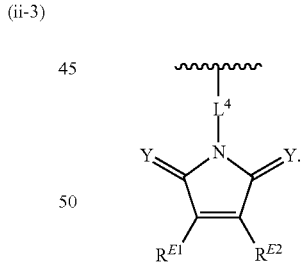

(ii-8)

In certain embodiments, $R^E$ is of Formula (ii-9):

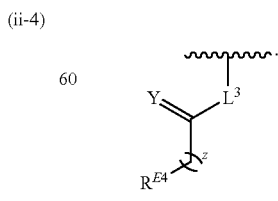

(ii-9)

In certain embodiments, $R^E$ is of Formula (ii-10):

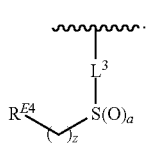

(ii-10)

In certain embodiments, $R^E$ is of Formula (ii-11):

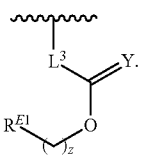

(ii-11)

In certain embodiments, $R^E$ is of Formula (ii-12):

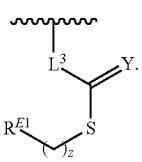

(ii-12)

In certain embodiments, $R^E$ is of Formula (ii-13):

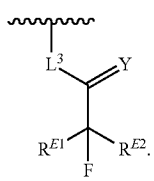

(ii-13)

In certain embodiments, $R^E$ is of Formula (ii-14):

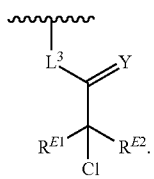

(ii-14)

In certain embodiments, $R^E$ is of Formula (ii-15):

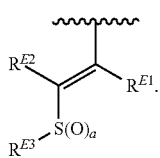

(ii-15)

In certain embodiments, $R^E$ is of Formula (ii-16):

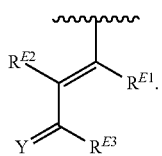

(ii-16)

In certain embodiments, $R^E$ is of Formula (ii-17):

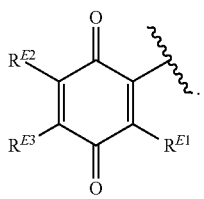

(ii-17)

In certain embodiments, $R^E$ and $L^2$ are meta to each other.

In certain embodiments, Ring D is of the formula:

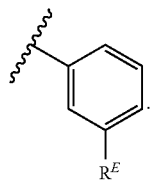

In certain embodiments, Ring D is of the formula:

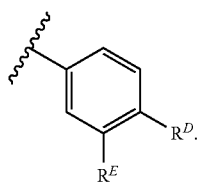

In certain embodiments, Ring D is of the formula:

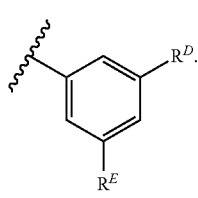

In certain embodiments, Ring D is of the formula:

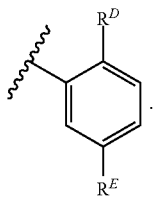

In certain embodiments, Ring D is of the formula:

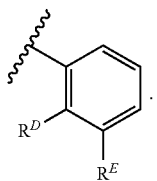

In certain embodiments, $R^E$ and $L^2$ are para to each other.
In certain embodiments, Ring D is of the formula:

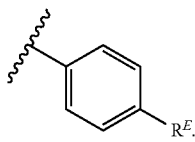

In certain embodiments, Ring D is of the formula:

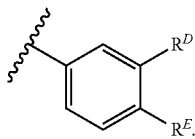

In certain embodiments, Ring D is of the formula:

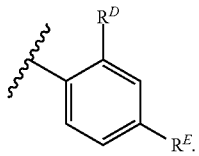

In compounds of Formula (I), $L^3$ is a divalent linker moiety. $L^3$ may contain 0-4 carbon or hetero atoms in the backbone of $L^3$. $L^3$ may be saturated or unsaturated. $L^3$ may be substituted or unsubstituted. $L^3$ may be branched or unbranched. In certain embodiments, $L^3$ is a bond. In certain embodiments, $L^3$ is —O—. In certain embodiments, $L^3$ is —S—. In certain embodiments, $L^3$ is —NR$^{L3a}$—. In certain embodiments, $L^3$ is —NH—. In certain embodiments, $L^3$ is a substituted $C_{1-4}$ hydrocarbon chain. In certain embodiments, $L^3$ is an unsubstituted $C_{1-4}$ hydrocarbon chain. In certain embodiments, $L^3$ is —C(R$^{L3b}$)$_2$—. In certain embodiments, $L^3$ is —CHR$^{L3b}$—. In certain embodiments, $L^3$ is —CH$_2$—. In certain embodiments, $L^3$ is a substituted $C_2$ hydrocarbon chain. In certain embodiments, $L^3$ is a unsubstituted $C_2$ hydrocarbon chain. In certain embodiments, $L^3$ is —C(R$^{L3b}$)$_2$C(R$^{L3b}$)$_2$—. In certain embodiments, $L^3$ is —CH$_2$CH$_2$—. In certain embodiments, $L^3$ is trans-CR$^{L3b}$=CR$^{L3b}$—. In certain embodiments, $L^3$ is trans-CH=CH—. In certain embodiments, $L^3$ is cis-CR$^{L3b}$=CR$^{L3b}$—. In certain embodiments, $L^3$ is cis-CH=CH—. In certain embodiments, $L^3$ is —C≡C—. In certain embodiments, $L^3$ is a substituted $C_3$ hydrocarbon chain. In certain embodiments, $L^3$ is an unsubstituted $C_3$ hydrocarbon chain. In certain embodiments, $L^3$ is —(CH$_2$)$_3$—. In certain embodiments, $L^3$ is —CH=CH—CH$_2$—, wherein CH=CH is trans or cis. In certain embodiments, $L^3$ is —CH$_2$—CH=CH—, wherein CH=CH is trans or cis. In certain embodiments, $L^3$ is —C≡C—CH$_2$—. In certain embodiments, $L^3$ is —CH$_2$—C≡C—. In certain embodiments, $L^3$ is a substituted $C_4$ hydrocarbon chain. In certain embodiments, $L^3$ is an unsubstituted $C_4$ hydrocarbon chain. In certain embodiments, $L^3$ is —(CH$_2$)$_4$—. In certain embodiments, $L^3$ is —CH=CH—CH=CH—, wherein each instance of CH=CH is independently trans or cis. In certain embodiments, $L^3$ is —CH=CH—C≡C—, wherein CH=CH is trans or cis. In certain embodiments, $L^3$ is —C≡C—CH=CH—, wherein CH=CH is trans or cis. In certain embodiments, $L^3$ is —C≡C—C≡C—. In certain embodiments, $L^3$ is an optionally substituted $C_{1-4}$ hydrocarbon chain, wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$NR$^{L3a}$—, or —NR$^{L3a}$S(=O)$_2$—.

In certain embodiments, $R^{L3a}$ is H. In certain embodiments, $R^{L3a}$ is substituted alkyl. In certain embodiments, $R^{L3a}$ is unsubstituted alkyl. In certain embodiments, $R^{L3a}$ is $C_{1-6}$ alkyl. In certain embodiments, $R^{L3a}$ is methyl. In certain embodiments, $R^{L3a}$ is ethyl. In certain embodiments, $R^{L3a}$ is propyl. In certain embodiments, $R^{L3a}$ is butyl. In certain embodiments, $R^{L3a}$ is a nitrogen protecting group. In certain embodiments, $R^{L3a}$ is Bn, BOC, Cbz, Fmoc, trifluoroacetyl, triphenylmethyl, acetyl, acetyl, or Ts.

In certain embodiments, at least one $R^{L3b}$ is H. In certain embodiments, at least one $R^{L3b}$ is halogen. In certain embodiments, at least one $R^{L3b}$ is F. In certain embodiments, at least one $R^{L3b}$ is Cl. In certain embodiments, at least one $R^{L3b}$ is Br. In certain embodiments, at least one $R^{L3b}$ is I (iodine). In certain embodiments, at least one $R^{L3b}$ is substituted alkyl. In certain embodiments, at least one $R^{L3b}$ is unsubstituted alkyl. In certain embodiments, at least one $R^{L3b}$ is $C_{1-6}$ alkyl. In certain embodiments, at least one $R^{L3b}$ is methyl. In certain embodiments, at least one $R^{L3b}$ is ethyl. In certain embodiments, at least one $R^{L3b}$ is propyl. In certain embodiments, at least one $R^{L3b}$ is butyl. In certain embodiments, at least one $R^{L3b}$ is substituted alkenyl. In certain embodiments, at least one $R^{L3b}$ is unsubstituted alkenyl. In certain embodiments, at least one $R^{L3b}$ is vinyl. In certain embodiments, at least one $R^{L3b}$ is substituted alkynyl. In certain embodiments, at least one $R^{L3b}$ is unsubstituted alkynyl. In certain embodiments, at least one $R^{L3b}$ is ethynyl. In certain embodiments, at least one $R^{L3b}$ is substituted carbocyclyl. In certain embodiments, at least one $R^{L3b}$ is unsubstituted carbocyclyl. In certain embodiments, at least one $R^{L3b}$ is substituted heterocyclyl. In certain embodiments, at least one $R^{L3b}$ is unsubstituted heterocyclyl. In certain embodiments, at least one $R^{L3b}$ is substituted aryl. In certain embodiments, at least one $R^{L3b}$ is unsubstituted aryl. In certain embodiments, at least one $R^{L3b}$ is substituted phenyl. In certain embodiments, at least one $R^{L3b}$ is unsubstituted phenyl. In certain embodiments, at least one $R^{L3b}$ is substituted heteroaryl. In certain embodiments, at least one $R^{L3b}$ is unsubstituted heteroaryl. In certain embodiments, at least one $R^{L3b}$ is substituted pyridyl. In certain embodiments, at least one $R^{L3b}$ is unsubstituted pyridyl. In certain embodiments, two $R^{L3b}$ groups are joined to form a substituted carbocyclic ring. In certain embodiments, two $R^{L3b}$ groups are joined to form an unsubstituted carbocyclic ring. In certain embodiments, two $R^{L3b}$ groups are joined to form a substituted heterocyclic ring. In certain embodiments, two $R^{L3b}$ groups are joined to form an unsubstituted heterocyclic ring.

In compounds of Formula (I), $L^4$ is a divalent linker moiety. $L^4$ may contain 0-4 carbon or hetero atoms in the backbone of $L^4$. $L^4$ may be saturated or unsaturated. $L^4$ may be substituted or unsubstituted. $L^4$ may be branched or unbranched. In certain embodiments, $L^4$ is a bond. In certain embodiments, $L^4$ is a substituted $C_{1-4}$ hydrocarbon chain. In certain embodiments, $L^4$ is an unsubstituted $C_{1-4}$ hydrocarbon chain. In certain embodiments, $L^4$ is —C($R^{L4b}$)$_2$—. In certain embodiments, $L^4$ is —CHR$^{L4b}$—. In certain embodiments, $L^4$ is —CH$_2$—. In certain embodiments, $L^4$ is a substituted $C_2$ hydrocarbon chain. In certain embodiments, $L^4$ is a unsubstituted $C_2$ hydrocarbon chain. In certain embodiments, $L^4$ is —C($R^{L4b}$)$_2$C($R^{L4b}$)$_2$—. In certain embodiments, $L^4$ is —CH$_2$CH$_2$—. In certain embodiments, $L^4$ is trans-CR$^{L4b}$=CR$^{L4b}$—. In certain embodiments, $L^4$ is trans-CH=CH—. In certain embodiments, $L^4$ is cis-CR$^{L4b}$=CR$^{L4b}$-. In certain embodiments, $L^4$ is cis-CH=CH—. In certain embodiments, $L^4$ is —C≡C—. In certain embodiments, $L^4$ is a substituted $C_3$ hydrocarbon chain. In certain embodiments, $L^4$ is an unsubstituted $C_3$ hydrocarbon chain. In certain embodiments, $L^4$ is —(CH$_2$)$_3$—. In certain embodiments, $L^4$ is —CH=CH—CH$_2$—, wherein CH=CH is trans or cis. In certain embodiments, $L^4$ is —CH$_2$—CH=CH—, wherein CH=CH is trans or cis. In certain embodiments, $L^4$ is —C≡C—CH$_2$—. In certain embodiments, $L^4$ is —CH$_2$—C≡C—. In certain embodiments, $L^4$ is a substituted $C_4$ hydrocarbon chain. In certain embodiments, $L^4$ is an unsubstituted $C_4$ hydrocarbon chain. In certain embodiments, $L^4$ is —(CH$_2$)$_4$—. In certain embodiments, $L^4$ is —CH=CH—CH=CH—, wherein each instance of CH=CH is independently trans or cis. In certain embodiments, $L^4$ is —CH=CH—C≡C—, wherein CH=CH is trans or cis. In certain embodiments, $L^4$ is —C≡C—CH=CH—, wherein CH=CH is trans or cis. In certain embodiments, $L^4$ is —C≡C—C≡C—.

In compounds of Formula (I), $R^E$ may include a substituent $R^{E1}$. In certain embodiments, $R^{E1}$ is H. In certain embodiments, $R^{E1}$ is halogen. In certain embodiments, $R^{E1}$ is F. In certain embodiments, $R^{E1}$ is Cl. In certain embodiments, $R^{E1}$ is Br. In certain embodiments, $R^{E1}$ is I (iodine). In certain embodiments, $R^{E1}$ is substituted acyl. In certain embodiments, $R^{E1}$ is unsubstituted acyl. In certain embodiments, $R^{E1}$ is acetyl. In certain embodiments, $R^{E1}$ is substituted acetyl. In certain embodiments, $R^{E1}$ is substituted alkyl. In certain embodiments, $R^{E1}$ is unsubstituted alkyl. In certain embodiments, $R^{E1}$ is $C_{1-6}$ alkyl. In certain embodiments, $R^{E1}$ is methyl. In certain embodiments, $R^{E1}$ is ethyl. In certain embodiments, $R^{E1}$ is propyl. In certain embodiments, $R^{E1}$ is butyl. In certain embodiments, $R^{E1}$ is substituted alkenyl. In certain embodiments, $R^{E1}$ is unsubstituted alkenyl. In certain embodiments, $R^{E1}$ is vinyl. In certain embodiments, $R^{E1}$ is substituted alkynyl. In certain embodiments, $R^{E1}$ is unsubstituted alkynyl. In certain embodiments, $R^{E1}$ is ethynyl. In certain embodiments, $R^{E1}$ is substituted carbocyclyl. In certain embodiments, $R^{E1}$ is unsubstituted carbocyclyl. In certain embodiments, $R^{E1}$ is substituted heterocyclyl. In certain embodiments, $R^{E1}$ is unsubstituted heterocyclyl. In certain embodiments, $R^{E1}$ is substituted aryl. In certain embodiments, $R^{E1}$ is unsubstituted aryl. In certain embodiments, $R^{E1}$ is substituted phenyl. In certain embodiments, $R^{E1}$ is unsubstituted phenyl. In certain embodiments, $R^{E1}$ is substituted heteroaryl. In certain embodiments, $R^{E1}$ is unsubstituted heteroaryl. In certain embodiments, $R^{E1}$ is substituted pyridyl. In certain embodiments, $R^{E1}$ is unsubstituted pyridyl. In certain embodiments, $R^{E1}$ is —CN. In certain embodiments, $R^{E1}$ is —OR$^{E1a}$. In certain embodiments, $R^{E1}$ is —N(R$^{E1a}$)$_2$. In certain embodiments, $R^{E1}$ is —SR$^{E1a}$. In certain embodiments, $R^{E1}$ is —CH$_2$OR$^{E1a}$. In certain embodiments, $R^{E1}$ is —CH$_2$N(R$^{E1a}$)$_2$. In certain embodiments, $R^{E1}$ is —CH$_2$SR$^{E1a}$.

In certain embodiments, when $R^{E1}$ is —OR$^{E1a}$, —N(R$^{E1a}$)$_2$, —SR$^{E1a}$, —CH$_2$OR$^{E1a}$, —CH$_2$N(R$^{E1a}$)$_2$, or —CH$_2$SR$^{E1a}$, $R^{E1a}$ is H. In certain embodiments, $R^{E1a}$ is substituted acyl. In certain embodiments, $R^{E1a}$ is unsubstituted acyl. In certain embodiments, $R^{E1a}$ is acetyl. In certain embodiments, $R^{E1a}$ is substituted acetyl. In certain embodiments, $R^{E1a}$ is substituted alkyl. In certain embodiments, $R^{E1a}$ is unsubstituted alkyl. In certain embodiments, $R^{E1a}$ is $C_{1-6}$ alkyl. In certain embodiments, $R^{E1a}$ is methyl. In certain embodiments, $R^{E1a}$ is ethyl. In certain embodiments, $R^{E1a}$ is propyl. In certain embodiments, $R^{E1a}$ is butyl. In certain embodiments, $R^{E1a}$ is substituted alkenyl. In certain embodiments, $R^{E1a}$ is unsubstituted alkenyl. In certain embodiments, $R^{E1a}$ is vinyl. In certain embodiments, $R^{E1a}$ is substituted alkynyl. In certain embodiments, $R^{E1a}$ is unsubstituted alkynyl. In certain embodiments, $R^{E1a}$ is ethynyl. In certain embodiments, $R^{E1a}$ is substituted carbocyclyl. In certain embodiments, $R^{E1a}$ is unsubstituted carbocyclyl. In certain embodiments, $R^{E1a}$ is substituted heterocyclyl. In certain embodiments, $R^{E1a}$ is unsubstituted heterocyclyl. In certain embodiments, $R^{E1a}$ is substituted aryl. In certain embodiments, $R^{E1a}$ is unsubstituted aryl. In certain embodiments, $R^{E1a}$ is substituted phenyl. In certain embodiments, $R^{E1a}$ is unsubstituted phenyl. In certain embodiments, $R^{E1a}$ is substituted heteroaryl. In certain embodiments, $R^{E1a}$ is unsubstituted heteroaryl. In certain embodiments, $R^{E1a}$ is substituted pyridyl. In certain embodiments, $R^{E1a}$ is unsubstituted pyridyl. In certain embodiments, $R^{E1a}$ is a nitrogen protecting group when attached to a nitrogen atom. In certain embodiments, $R^{E1a}$ is Bn, BOC, Cbz, Fmoc, trifluoroacetyl, triphenylmethyl, acetyl, acetyl, or Ts when attached to a nitrogen atom. In certain embodiments, $R^{E1a}$ is an oxygen protecting group when attached to an oxygen atom. In certain embodiments, $R^{E1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E1a}$ is a sulfur protecting group when attached to a sulfur atom. In certain embodiments, $R^{E1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E1a}$ groups are joined to form a substituted heterocyclic ring. In certain embodiments, two $R^{E1a}$ groups are joined to form an unsubstituted heterocyclic ring.

In compounds of Formula (I), $R^E$ may include a substituent $R^{E2}$. In certain embodiments, $R^{E2}$ is H. In certain embodiments, $R^{E2}$ is halogen. In certain embodiments, $R^{E2}$ is F. In certain embodiments, $R^{E2}$ is Cl. In certain embodiments, $R^{E2}$ is Br. In certain embodiments, $R^{E2}$ is I (iodine). In certain embodiments, $R^{E2}$ is substituted acyl. In certain embodiments, $R^{E2}$ is unsubstituted acyl. In certain embodiments, $R^{E2}$ is acetyl. In certain embodiments, $R^{E2}$ is substituted acetyl. In certain embodiments, $R^{E2}$ is substituted alkyl. In certain embodiments, $R^{E2}$ is unsubstituted alkyl. In certain embodiments, $R^{E2}$ is $C_{1-6}$ alkyl. In certain embodiments, $R^{E2}$ is methyl. In certain embodiments, $R^{E2}$ is ethyl. In certain embodiments, $R^{E2}$ is propyl. In certain embodiments, $R^{E2}$ is butyl. In certain embodiments, $R^{E2}$ is substituted alkenyl. In certain embodiments, $R^{E2}$ is unsubstituted alkenyl. In certain embodiments, $R^{E2}$ is vinyl. In certain embodiments, $R^{E2}$ is substituted alkynyl. In certain embodiments, $R^{E2}$ is unsubstituted alkynyl. In certain embodiments, $R^{E2}$ is ethynyl. In certain embodiments, $R^{E2}$ is substituted carbocyclyl. In certain embodiments, $R^{E2}$ is unsubstituted carbocyclyl. In certain embodiments, $R^{E2}$ is substituted heterocyclyl. In certain embodiments, $R^{E2}$ is unsubstituted heterocyclyl. In certain embodiments, $R^{E2}$ is substituted aryl. In certain embodiments, $R^{E2}$ is unsubstituted aryl. In certain embodiments, $R^{E2}$ is substituted phenyl. In certain embodiments, $R^{E2}$ is unsubstituted phenyl. In certain embodiments, $R^{E2}$ is substituted heteroaryl. In certain embodiments, $R^{E2}$ is unsubstituted heteroaryl. In certain embodiments, $R^{E2}$ is substituted pyridyl. In certain embodiments, $R^{E2}$ is unsubstituted pyridyl. In certain embodiments, $R^{E2}$ is —CN. In certain embodiments, $R^{E2}$ is —$OR^{E2a}$. In certain embodiments, $R^{E2}$ is —$N(R^{E2a})_2$. In certain embodiments, $R^{E2}$ is —$SR^{E2a}$. In certain embodiments, $R^{E2}$ is —$CH_2OR^{E2a}$. In certain embodiments, $R^{E2}$ is —$CH_2N(R^{E2a})_2$. In certain embodiments, $R^{E2}$ is —$CH_2SR^{E2a}$.

In certain embodiments, when $R^{E2}$ is —$OR^{E2a}$, —$N(R^{E2a})_2$, —$SR^{E2a}$, —$CH_2OR^{E2a}$, —$CH_2N(R^{E2a})_2$, or —$CH_2SR^{E2a}$, $R^{E2a}$ is H. In certain embodiments, $R^{E2a}$ is substituted acyl. In certain embodiments, $R^{E2a}$ is unsubstituted acyl. In certain embodiments, $R^{E2a}$ is acetyl. In certain embodiments, $R^{E2a}$ is substituted acetyl. In certain embodiments, $R^{E2a}$ is substituted alkyl. In certain embodiments, $R^{E2a}$ is unsubstituted alkyl. In certain embodiments, $R^{E2a}$ is $C_{1-6}$ alkyl. In certain embodiments, $R^{E2a}$ is methyl. In certain embodiments, $R^{E2a}$ is ethyl. In certain embodiments, $R^{E2a}$ is propyl. In certain embodiments, $R^{E2a}$ is butyl. In certain embodiments, $R^{E2a}$ is substituted alkenyl. In certain embodiments, $R^{E2a}$ is unsubstituted alkenyl. In certain embodiments, $R^{E2a}$ is vinyl. In certain embodiments, $R^{E2a}$ is substituted alkynyl. In certain embodiments, $R^{E2a}$ is unsubstituted alkynyl. In certain embodiments, $R^{E2a}$ is ethynyl. In certain embodiments, $R^{E2a}$ is substituted carbocyclyl. In certain embodiments, $R^{E2a}$ is unsubstituted carbocyclyl. In certain embodiments, $R^{E2a}$ is substituted heterocyclyl. In certain embodiments, $R^{E2a}$ is unsubstituted heterocyclyl. In certain embodiments, $R^{E2a}$ is substituted aryl. In certain embodiments, $R^{E2a}$ is unsubstituted aryl. In certain embodiments, $R^{E2a}$ is substituted phenyl. In certain embodiments, $R^{E2a}$ is unsubstituted phenyl. In certain embodiments, $R^{E2a}$ is substituted heteroaryl. In certain embodiments, $R^{E2a}$ is unsubstituted heteroaryl. In certain embodiments, $R^{E2a}$ is substituted pyridyl. In certain embodiments, $R^{E2a}$ is unsubstituted pyridyl. In certain embodiments, $R^{E2a}$ is a nitrogen protecting group when attached to a nitrogen atom. In certain embodiments, $R^{E2a}$ is Bn, BOC, Cbz, Fmoc, trifluoroacetyl, triphenylmethyl, acetyl, acetyl, or Ts when attached to a nitrogen atom. In certain embodiments, $R^{E2a}$ is an oxygen protecting group when attached to an oxygen atom. In certain embodiments, $R^{E2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E2a}$ is a sulfur protecting group when attached to a sulfur atom. In certain embodiments, $R^{E2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E2a}$ groups are joined to form a substituted heterocyclic ring. In certain embodiments, two $R^{E2a}$ groups are joined to form an unsubstituted heterocyclic ring.

In compounds of Formula (I), $R^E$ may include a substituent $R^{E3}$. In certain embodiments, $R^{E3}$ is H. In certain embodiments, $R^{E3}$ is halogen. In certain embodiments, $R^{E3}$ is F. In certain embodiments, $R^{E3}$ is Cl. In certain embodiments, $R^{E3}$ is Br. In certain embodiments, $R^{E3}$ is I (iodine). In certain embodiments, $R^{E3}$ is substituted acyl. In certain embodiments, $R^{E3}$ is unsubstituted acyl. In certain embodiments, $R^{E3}$ is acetyl. In certain embodiments, $R^{E3}$ is substituted acetyl. In certain embodiments, $R^{E3}$ is substituted alkyl. In certain embodiments, $R^{E3}$ is unsubstituted alkyl. In certain embodiments, $R^{E3}$ is $C_{1-6}$ alkyl. In certain embodiments, $R^{E3}$ is methyl. In certain embodiments, $R^{E3}$ is ethyl. In certain embodiments, $R^{E3}$ is propyl. In certain embodiments, $R^{E3}$ is butyl. In certain embodiments, $R^{E3}$ is substituted alkenyl. In certain embodiments, $R^{E3}$ is unsubstituted alkenyl. In certain embodiments, $R^{E3}$ is vinyl. In certain embodiments, $R^{E3}$ is substituted alkynyl. In certain embodiments, $R^{E3}$ is unsubstituted alkynyl. In certain embodiments, $R^{E3}$ is ethynyl. In certain embodiments, $R^{E3}$ is substituted carbocyclyl. In certain embodiments, $R^{E3}$ is unsubstituted carbocyclyl. In certain embodiments, $R^{E3}$ is substituted heterocyclyl. In certain embodiments, $R^{E3}$ is unsubstituted heterocyclyl. In certain embodiments, $R^{E3}$ is substituted aryl. In certain embodiments, $R^{E3}$ is unsubstituted aryl. In certain embodiments, $R^{E3}$ is substituted phenyl. In certain embodiments, $R^{E3}$ is unsubstituted phenyl. In certain embodiments, $R^{E3}$ is substituted heteroaryl. In certain embodiments, $R^{E3}$ is unsubstituted heteroaryl. In certain embodiments, $R^{E3}$ is substituted pyridyl. In certain embodiments, $R^{E3}$ is unsubstituted pyridyl. In certain embodiments, $R^{E3}$ is —CN. In certain embodiments, $R^{E3}$ is —$OR^{E3a}$. In certain embodiments, $R^{E3}$ is —$N(R^{E3a})_2$. In certain embodiments, $R^{E3}$ is —$SR^{E3a}$. In certain embodiments, $R^{E3}$ is —$CH_2OR^{E3a}$. In certain embodiments, $R^{E3}$ is —$CH_2N(R^{E3a})_2$. In certain embodiments, $R^{E3}$ is —$CH_2SR^{E3a}$.

In certain embodiments, when $R^{E3}$ is —$OR^{E3a}$, —$N(R^{E3a})_2$, —$SR^{E3a}$, —$CH_2OR^{E3a}$, —$CH_2N(R^{E3a})_2$, or —$CH_2SR^{E3a}$, $R^{E3a}$ is H. In certain embodiments, $R^{E3a}$ is substituted acyl. In certain embodiments, $R^{E3a}$ is unsubstituted acyl. In certain embodiments, $R^{E3a}$ is acetyl. In certain embodiments, $R^{E3a}$ is substituted acetyl. In certain embodiments, $R^{E3a}$ is substituted alkyl. In certain embodiments, $R^{E3a}$ is unsubstituted alkyl. In certain embodiments, $R^{E3a}$ is $C_{1-6}$ alkyl. In certain embodiments, $R^{E3a}$ is methyl. In certain embodiments, $R^{E3a}$ is ethyl. In certain embodiments, $R^{E3a}$ is propyl. In certain embodiments, $R^{E3a}$ is butyl. In certain embodiments, $R^{E3a}$ is substituted alkenyl. In certain embodiments, $R^{E3a}$ is unsubstituted alkenyl. In certain embodiments, $R^{E3a}$ is vinyl. In certain embodiments, $R^{E3a}$ is substituted alkynyl. In certain embodiments, $R^{E3a}$ is unsubstituted alkynyl. In certain embodiments, $R^{E3a}$ is ethynyl. In certain embodiments, $R^{E3a}$ is substituted carbocyclyl. In certain embodiments, $R^{E3a}$ is unsubstituted carbocyclyl. In certain embodiments, $R^{E3a}$ is substituted heterocyclyl. In certain embodiments, $R^{E3a}$ is unsubstituted heterocyclyl. In certain embodiments, $R^{E3a}$ is substituted aryl. In certain embodiments, $R^{E3a}$ is unsubstituted aryl. In certain embodiments, $R^{E3a}$ is substituted phenyl. In certain embodiments, $R^{E3a}$ is unsubstituted phenyl. In certain embodiments, $R^{E3a}$ is substituted heteroaryl. In certain embodiments, $R^{E3a}$ is unsubstituted heteroaryl. In certain embodiments, $R^{E3a}$ is substituted pyridyl. In certain embodiments, $R^{E3a}$ is unsubstituted pyridyl. In certain embodiments, $R^{E3a}$ is a nitrogen protecting group when attached to a nitrogen atom. In certain embodiments, $R^{E3a}$ is Bn, BOC, Cbz, Fmoc, trifluoroacetyl, triphenylmethyl, acetyl, acetyl, or Ts when attached to a nitrogen atom. In certain embodiments, $R^{E3a}$ is an oxygen protecting group when attached to an oxygen atom. In certain embodiments, $R^{E3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{E3a}$ is a sulfur protecting group when attached to a sulfur atom. In certain embodiments, $R^{E3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{E3a}$ groups are joined to form a substituted heterocyclic ring. In certain embodiments, two $R^{E3a}$ groups are joined to form an unsubstituted heterocyclic ring.

In compounds of Formula (I), $R^E$ may include a substituent $R^{E4}$. In certain embodiments, $R^{E4}$ is a leaving group. In certain embodiments, $R^{E4}$ is halogen. In certain embodiments, $R^{E4}$ is F. In certain embodiments, $R^{E4}$ is Cl. In certain embodiments, $R^{E4}$ is Br. In certain embodiments, $R^{E4}$ is I (iodine). In certain embodiments, $R^{E4}$ is $-OS(=O)_wR^{E4a}$. In certain embodiments, w is 1. In certain embodiments, w is 2. In certain embodiments, $R^Ea$ is —OMs. In certain embodiments, $R^{E4}$ is —OTf. In certain embodiments, $R^{E4}$ is —OTs. In certain embodiments, $R^{E4}$ is —OBs. In certain embodiments, $R^{E4}$ is 2-nitrobenzenesulfonyloxy. In certain embodiments, $R^{E4}$ is —$OR^{E4a}$. In certain embodiments, $R^{E4}$ is —OMe. In certain embodiments, $R^{E4}$ is —OCF$_3$. In certain embodiments, $R^{E4}$ is —OPh. In certain embodiments, $R^{E4}$ is —OC(=O)$R^{E4a}$. In certain embodiments, $R^{E4}$ is —OC(=O)Me. In certain embodiments, $R^{E4}$ is —OC(=O)CF$_3$. In certain embodiments, $R^{E4}$ is —OC(=O)Ph. In certain embodiments, $R^{E4}$ is —OC(=O)Cl. In certain embodiments, $R^{E4}$ is —OC(=O)O$R^{E4a}$. In certain embodiments, $R^E$ is —OC(=O)OMe. In certain embodiments, $R^{E4}$ is —OC(=O)O(t-Bu).

In certain embodiments, $R^{E4a}$ is substituted alkyl. In certain embodiments, $R^{E4a}$ is unsubstituted alkyl. In certain embodiments, $R^{E4a}$ is $C_{1-6}$ alkyl. In certain embodiments, $R^{E4a}$ is methyl. In certain embodiments, $R^{E4a}$ is ethyl. In certain embodiments, $R^{E4a}$ is propyl. In certain embodiments, $R^{E4a}$ is butyl. In certain embodiments, $R^{E4a}$ is substituted alkenyl. In certain embodiments, $R^{E4a}$ is unsubstituted alkenyl. In certain embodiments, $R^{E4a}$ is vinyl. In certain embodiments, $R^{E4a}$ is substituted alkynyl. In certain embodiments, $R^{E4a}$ is unsubstituted alkynyl. In certain embodiments, $R^{E4a}$ is ethynyl. In certain embodiments, $R^{E4a}$ is substituted carbocyclyl. In certain embodiments, $R^{E4a}$ is unsubstituted carbocyclyl. In certain embodiments, $R^{E4a}$ is substituted heterocyclyl. In certain embodiments, $R^{E4a}$ is unsubstituted heterocyclyl. In certain embodiments, $R^{E4a}$ is substituted aryl. In certain embodiments, $R^{E4a}$ is unsubstituted aryl. In certain embodiments, $R^{E4a}$ is substituted phenyl. In certain embodiments, $R^{E4a}$ is unsubstituted phenyl. In certain embodiments, $R^{E4a}$ is substituted heteroaryl. In certain embodiments, $R^{E4a}$ is unsubstituted heteroaryl. In certain embodiments, $R^{E4a}$ is substituted pyridyl. In certain embodiments, $R^{E4a}$ is unsubstituted pyridyl.

In compounds of Formula (I), $R^E$ may include a Y group. In certain embodiments, Y is =O. In certain embodiments, Y is —O—. In certain embodiments, Y is =S. In certain embodiments, Y is —S—. In certain embodiments, Y is =$NR^{E5}$. In certain embodiments, Y is —$NR^{E5}$—. In certain embodiments, Y is =NH. In certain embodiments, Y is —NH—.

In certain embodiments, $R^{E5}$ is H. In certain embodiments, $R^{E5}$ is substituted alkyl. In certain embodiments, $R^{E5}$ is unsubstituted alkyl. In certain embodiments, $R^{E5}$ is $C_{1-6}$ alkyl. In certain embodiments, $R^{E5}$ is methyl. In certain embodiments, $R^{E5}$ is ethyl. In certain embodiments, $R^{E5}$ is propyl. In certain embodiments, $R^{E5}$ is butyl. In certain embodiments, $R^{E5}$ is a nitrogen protecting group. In certain embodiments, $R^{E5}$ is Bn, BOC, Cbz, Fmoc, trifluoroacetyl, triphenylmethyl, acetyl, acetyl, or Ts.

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, $R^E$ is of Formula (ii-1); and $R^{E1}$ is hydrogen. In certain embodiments, $R^E$ is of Formula (ii-1); and $R^{E2}$ is hydrogen. In certain embodiments, $R^E$ is of Formula (ii-1); and $R^{E3}$ is hydrogen. In certain embodiments, $R^E$ is of Formula (ii-1); and $R^{E2}$ and $R^{E3}$ are each hydrogen. In certain embodiments, $R^E$ is of Formula (ii-1); and $R^{E1}$, $R^{E2}$ and $R^{E3}$ are each hydrogen. In certain embodiments, $R^E$ is of Formula (ii-1); and $R^{E1}$ is —$CH_2N(R^{E1a})$. In certain embodiments, $R^E$ is of Formula (ii-1); $R^{E1}$ is —$CH_2N(R^{E1a})$; and $R^{E1a}$ is $C_{1-6}$ alkyl. In certain embodiments, $R^E$ is of Formula (ii-1); $R^{E1}$ is —$CH_2N(R^{E1a})$; and $R^{E1a}$ is methyl. In certain embodiments, $R^E$ is of Formula (ii-1); and $R^{E2}$ is —$CH_2N(R^{E2a})$. In certain embodiments, $R^E$ is of Formula (ii-1); $R^{E2}$ is —$CH_2N(R^{E2a})$; and $R^{E2a}$ is $C_{1-6}$ alkyl. In certain embodiments, $R^E$ is of Formula (ii-1); $R^{E2}$ is —$CH_2N(R^{E2a})$; and $R^{E2a}$ is methyl. In certain embodiments, $R^E$ is of Formula (ii-1); and $R^{E3}$ is —$CH_2N(R^{E3a})$. In certain embodiments, $R^E$ is of Formula (ii-1); $R^{E3}$ is —$CH_2N(R^{E3a})$; and $R^{E3a}$ is $C_{1-6}$ alkyl. In certain embodiments, $R^E$ is of Formula (ii-1); $R^{E3}$ is —$CH_2N(R^{E3a})$; and $R^{E3a}$ is methyl. In certain embodiments, $R^E$ is of Formula (ii-1); and Y is =O. In certain embodiments, $R^E$ is of Formula (ii-1); and $L^3$ is —$NR^{L3a}$—. In certain embodiments, $R^E$ is of Formula (ii-1); and $L^3$ is —NH—.

In certain embodiments, $R^E$ is of Formula (ii-3); and $R^{E1}$ is hydrogen. In certain embodiments, $R^E$ is of Formula (ii-3); and $R^{E1}$ is —$CH_2N(R^{E1a})$. In certain embodiments, $R^E$ is of Formula (ii-3); $R^{E1}$ is —$CH_2N(R^{E1a})$; and $R^{E1a}$ is $C_{1-6}$ alkyl. In certain embodiments, $R^E$ is of Formula (ii-3); $R^{E1}$ is —$CH_2N(R^{E1a})$; and $R^{E1a}$ is methyl. In certain embodiments, $R^E$ is of Formula (ii-3); and Y is =O. In certain embodiments, $R^E$ is of Formula (ii-3); and $L^3$ is —$NR^{L3a}$—. In certain embodiments, $R^E$ is of Formula (ii-3); and $L^3$ is —NH—.

In certain embodiments, a compound of Formula (I) is of the formula:

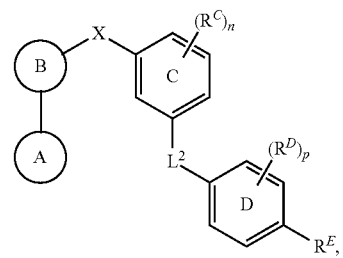

or a pharmaceutically acceptable salt, solvate, hydrate, polymorph, co-crystal, tautomer, stereoisomer, isotopically labeled derivative, or prodrug thereof In certain embodiments, a compound of Formula (I) is the formula:

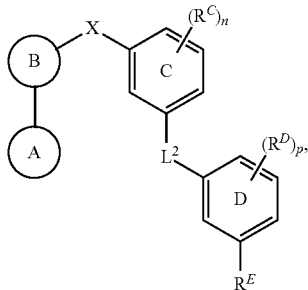

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (I-1):

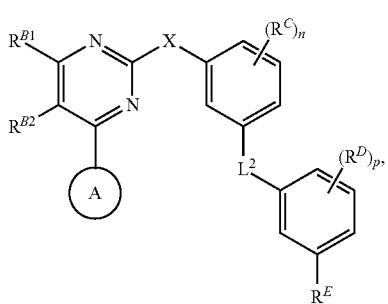

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (I-2):

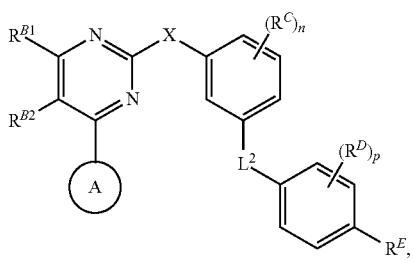

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (I-3):

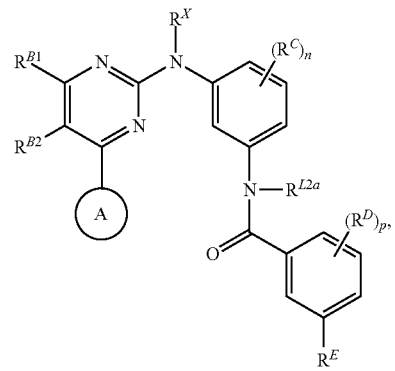

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-3); and Ring A is of any one of the Formulae (i-1)-(i-4). In certain embodiments, the compound of Formula (I) is of Formula (I-3); and Ring A is of any one of the Formulae (iii-1)-(iii-7). In certain embodiments, the compound of Formula (I) is of Formula (I-3); and Ring A is of any one of the Formulae (iv-1)-(iv-6). In certain embodiments, the compound of Formula (I) is of Formula (I-3); and Ring A is of any one of the Formulae (v-1)-(v-6). In certain embodiments, the compound of Formula (I) is of Formula (I-3); and Ring A is of any one of the Formulae (vi-1)-(vi-6). In certain embodiments, the compound of Formula (I) is of Formula (I-3); and Ring A is of Formula (i-5). In certain embodiments, the compound of Formula (I) is of Formula (I-3); and Ring A is of Formula (vii).

In certain embodiments, the compound of Formula (I) is of Formula (I-3); and $R^X$ and $R^{L2a}$ are each hydrogen.

In certain embodiments, the compound of Formula (I) is of Formula (I-3); and $R^E$ is of Formula (ii-1). In certain embodiments, the compound of Formula (I) is of Formula (I-3); and $R^E$ is of Formula (ii-3).

In certain embodiments, the compound of Formula (I) is of Formula (I-4):

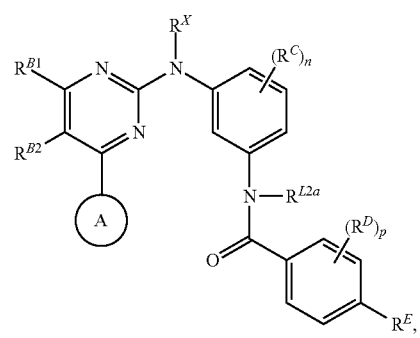

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-4); and Ring A is of any one of the Formulae (i-1)-(i-4). In certain embodiments, the compound of Formula (I) is of Formula (I-4); and Ring A is of any one of the Formulae (iii-1)-(iii-7). In certain embodiments, the compound of Formula (I) is of Formula (I-4); and Ring A is of any one of the Formulae (iv-1)-(iv-6). In certain embodiments, the compound of Formula (I) is of Formula (I-4); and Ring A is of any one of the Formulae (v-1)-(v-6). In certain embodiments, the compound of Formula (I) is of Formula (I-4); and Ring A is of any one of the Formulae (vi-1)-(vi-6). In certain embodiments, the compound of Formula (I) is of Formula (I-4); and Ring A is of Formula (i-5). In certain embodiments, the compound of Formula (I) is of Formula (I-4); and Ring A is of Formula (vii).

In certain embodiments, the compound of Formula (I) is of Formula (I-4); and $R^X$ and $R^{L2a}$ are each hydrogen.

In certain embodiments, the compound of Formula (I) is of Formula (I-4); and $R^E$ is of Formula (ii-1). In certain embodiments, the compound of Formula (I) is of Formula (I-4); and $R^E$ is of Formula (ii-3).

In certain embodiments, the compound of Formula (I) is of Formula (I-5):

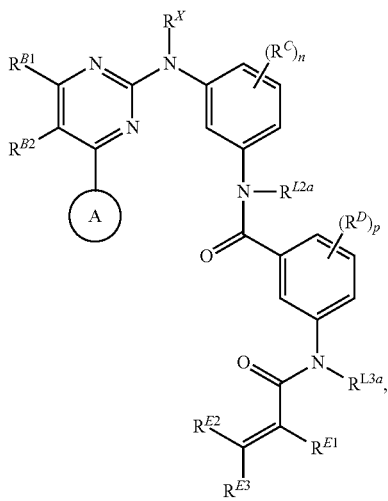

(I-5)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-5); and Ring A is of any one of the Formulae (i-1)-(i-4). In certain embodiments, the compound of Formula (I) is of Formula (I-5); and Ring A is of any one of the Formulae (iii-1)-(iii-7). In certain embodiments, the compound of Formula (I) is of Formula (I-5); and Ring A is of any one of the Formulae (iv-1)-(iv-6). In certain embodiments, the compound of Formula (I) is of Formula (I-5); and Ring A is of any one of the Formulae (v-1)-(v-6). In certain embodiments, the compound of Formula (I) is of Formula (I-5); and Ring A is of any one of the Formulae (vi-1)-(vi-6). In certain embodiments, the compound of Formula (I) is of Formula (I-5); and Ring A is of Formula (i-5). In certain embodiments, the compound of Formula (I) is of Formula (I-5); and Ring A is of Formula (vii).

In certain embodiments, the compound of Formula (I) is of Formula (I-5); and $R^X$, $R^{L2a}$, and $R^{L3a}$ are each hydrogen. In certain embodiments, the compound of Formula (I) is of Formula (I-5); and $R^{E1}$, $R^{E2}$, and $R^{E3}$ are each hydrogen. In certain embodiments, the compound of Formula (I) is of Formula (I-5); and $R^X$, $R^{L2a}$, $R^{L3a}$, $R^{E1}$, $R^{E2}$, and $R^{E3}$ are each hydrogen.

In certain embodiments, the compound of Formula (I) is of Formula (I-6):

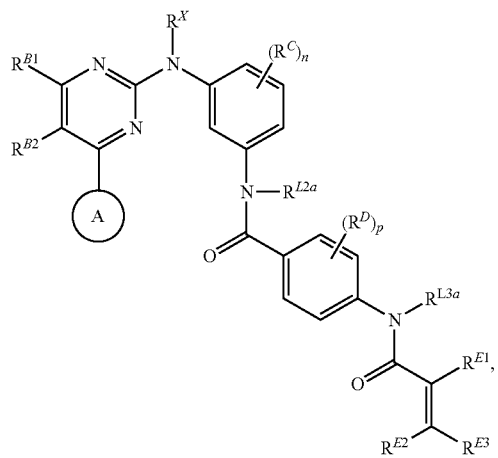

(I-6)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-6); and Ring A is of any one of the Formulae (i-1)-(i-4). In certain embodiments, the compound of Formula (I) is of Formula (I-6); and Ring A is of any one of the Formulae (iii-1)-(iii-7). In certain embodiments, the compound of Formula (I) is of Formula (I-6); and Ring A is of any one of the Formulae (iv-1)-(iv-6). In certain embodiments, the compound of Formula (I) is of Formula (I-6); and Ring A is of any one of the Formulae (v-1)-(v-6). In certain embodiments, the compound of Formula (I) is of Formula (I-6); and Ring A is of any one of the Formulae (vi-1)-(vi-6). In certain embodiments, the compound of Formula (I) is of Formula (I-6); and Ring A is of Formula (i-5). In certain embodiments, the compound of Formula (I) is of Formula (I-6); and Ring A is of Formula (vii).

In certain embodiments, the compound of Formula (I) is of Formula (I-6); and $R^X$, $R^{L2a}$, and $R^{L3a}$ are each hydrogen. In certain embodiments, the compound of Formula (I) is of Formula (I-6); and $R^{E1}$, $R^{E2}$, and $R^{E3}$ are each hydrogen. In certain embodiments, the compound of Formula (I) is of Formula (I-6); and $R^X$, $R^{L2a}$, $R^{L3a}$, $R^{E1}$, $R^{E2}$, and $R^{E3}$ are each hydrogen.

In certain embodiments, the compound of Formula (I) is of Formula (I-7):

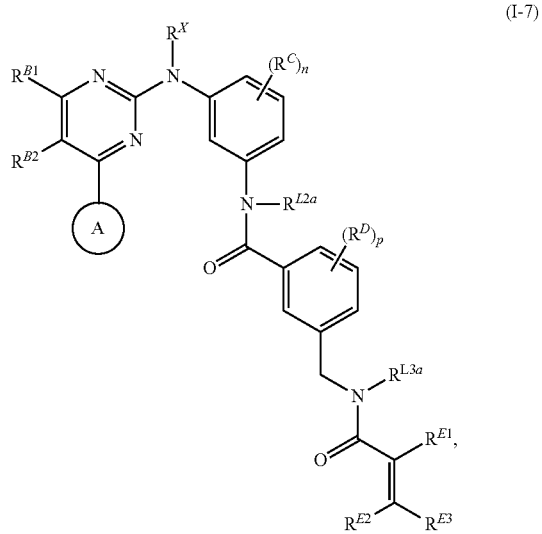

(I-7)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-7); and Ring A is of any one of the Formulae (i-1)-(i-4). In certain embodiments, the compound of Formula (I) is of Formula (I-7); and Ring A is of any one of the Formulae (iii-1)-(iii-7). In certain embodiments, the compound of Formula (I) is of Formula (I-7); and Ring A is of any one of the Formulae (iv-1)-(iv-6). In certain embodiments, the compound of Formula (I) is of Formula (I-7); and Ring A is of any one of the Formulae (v-1)-(v-6). In certain embodiments, the compound of Formula (I) is of Formula (I-7); and Ring A is of any one of the Formulae (vi-1)-(vi-6). In certain embodiments, the compound of Formula (I) is of Formula (I-7); and Ring A is of Formula (i-5). In certain embodiments, the compound of Formula (I) is of Formula (I-7); and Ring A is of Formula (vii).

In certain embodiments, the compound of Formula (I) is of Formula (I-7); and $R^X$, $R^{L2a}$, and $R^{L3a}$ are each hydrogen. In certain embodiments, the compound of Formula (I) is of Formula (I-7); and $R^{E1}$, $R^{E2}$, and $R^{E3}$ are each hydrogen. In certain embodiments, the compound of Formula (I) is of Formula (I-7); and $R^X$, $R^{L2a}$, $R^{L3a}$, $R^{E1}$, $R^{E2}$, and $R^{E3}$ are each hydrogen.

In certain embodiments, the compound of Formula (I) is of Formula (I-8):

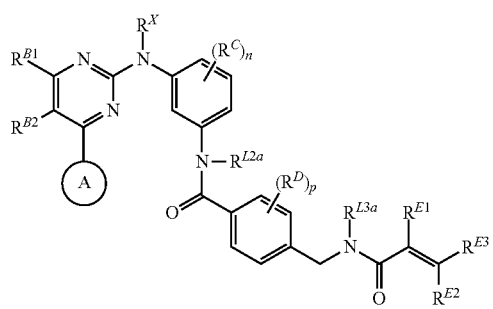

(I-8)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-8); and Ring A is of any one of the Formulae (i-1)-(i-4). In certain embodiments, the compound of Formula (I) is of Formula (I-8); and Ring A is of any one of the Formulae (iii-1)-(iii-7). In certain embodiments, the compound of Formula (I) is of Formula (I-8); and Ring A is of any one of the Formulae (iv-1)-(iv-6). In certain embodiments, the compound of Formula (I) is of Formula (I-8); and Ring A is of any one of the Formulae (v-1)-(v-6). In certain embodiments, the compound of Formula (I) is of Formula (I-8); and Ring A is of any one of the Formulae (vi-1)-(vi-6). In certain embodiments, the compound of Formula (I) is of Formula (I-8); and Ring A is of Formula (i-5). In certain embodiments, the compound of Formula (I) is of Formula (I-8); and Ring A is of Formula (vii).

In certain embodiments, the compound of Formula (I) is of Formula (I-8); and $R^X$, $R^{L2a}$, and $R^{L3a}$ are each hydrogen. In certain embodiments, the compound of Formula (I) is of Formula (I-8); and $R^{E1}$, $R^{E2}$, and $R^{E3}$ are each hydrogen. In certain embodiments, the compound of Formula (I) is of Formula (I-8); and $R^X$, $R^{L2a}$, $R^{L3a}$, $R^{E1}$, $R^{E2}$, and $R^{E3}$ are each hydrogen.

In certain embodiments, the compound of Formula (I) is of Formula (I-9):

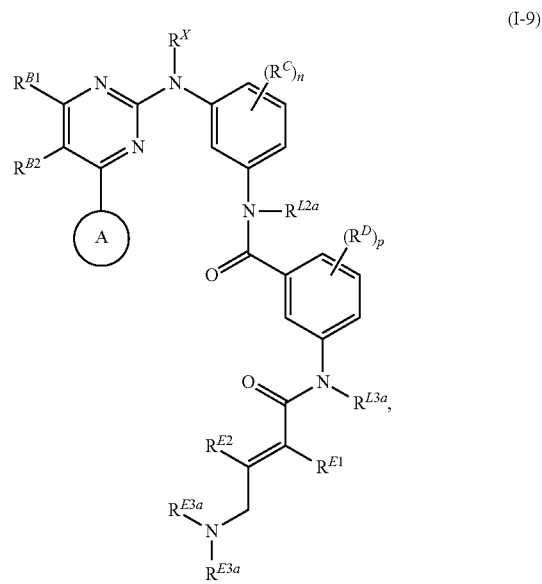

(I-9)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-9); and Ring A is of any one of the Formulae (i-1)-(i-4). In certain embodiments, the compound of Formula (I) is of Formula (I-9); and Ring A is of any one of the Formulae (iii-1)-(iii-7). In certain embodiments, the compound of Formula (I) is of Formula (I-9); and Ring A is of any one of the Formulae (iv-1)-(iv-6). In certain embodiments, the compound of Formula (I) is of Formula (I-9); and Ring A is of any one of the Formulae (v-1)-(v-6). In certain embodiments, the compound of Formula (I) is of Formula (I-9); and Ring A is of any one of the Formulae (vi-1)-(vi-6). In certain embodiments, the compound of Formula (I) is of Formula (I-9); and Ring A is of Formula (i-5). In certain embodiments, the compound of Formula (I) is of Formula (I-9); and Ring A is of Formula (vii).

In certain embodiments, the compound of Formula (I) is of Formula (I-9); and $R^X$, $R^{L2a}$, and $R^{L3a}$ are each hydrogen. In certain embodiments, the compound of Formula (I) is of Formula (I-9); and $R^{E1}$ and $R^{E2}$ are each hydrogen. In certain embodiments, the compound of Formula (I) is of Formula (I-9); and $R^X$, $R^{L2a}$, $R^{L3a}$, $R^{E1}$, and $R^{E2}$ are each hydrogen. In certain embodiments, the compound of Formula (I) is of Formula (I-9); and each instance of $R^{E3a}$ is independently optionally substituted alkyl. In certain embodiments, the compound of Formula (I) is of Formula (I-9); and each instance of $R^{E3a}$ is independently $C_{1-6}$ alkyl.

In certain embodiments, the compound of Formula (I) is of Formula (I-10):

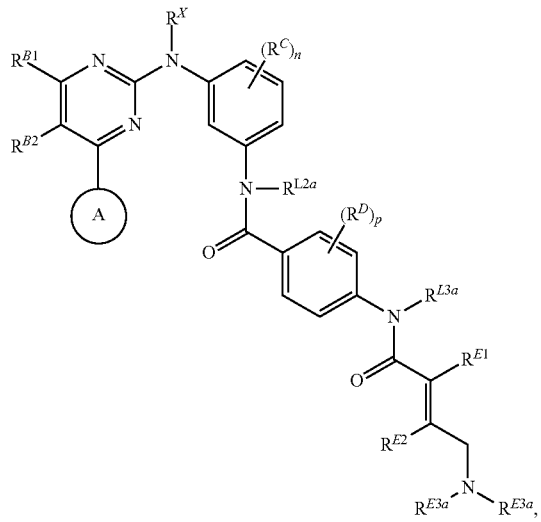

(I-10)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-10); and Ring A is of any one of the Formulae (i-1)-(i-4). In certain embodiments, the compound of Formula (I) is of Formula (I-10); and Ring A is of any one of the Formulae (iii-1)-(iii-7). In certain embodiments, the compound of Formula (I) is of Formula (I-10); and Ring A is of any one of the Formulae (iv-1)-(iv-6). In certain embodiments, the compound of Formula (I) is of Formula (I-10); and Ring A is of any one of the Formulae (v-1)-(v-6). In certain embodiments, the compound of Formula (I) is of Formula (I-10); and Ring A is of any one of the Formulae (vi-1)-(vi-6). In certain embodiments, the compound of Formula (I) is of Formula (I-10); and Ring A is of Formula (i-5). In certain embodiments, the compound of Formula (I) is of Formula (I-10); and Ring A is of Formula (vii).

In certain embodiments, the compound of Formula (I) is of Formula (I-10); and $R^X$, $R^{L2a}$, and $R^{L3a}$ are each hydrogen. In certain embodiments, the compound of Formula (I) is of Formula (I-10); and $R^{E1}$ and $R^{E2}$ are each hydrogen. In certain embodiments, the compound of Formula (I) is of Formula (I-10); and $R^X$, $R^{L2a}$, $R^{L3a}$, $R^{E1}$, and $R^{E2}$ are each hydrogen. In certain embodiments, the compound of Formula (I) is of Formula (I-10); and each instance of $R^{E3a}$ is independently optionally substituted alkyl. In certain embodiments, the compound of Formula (I) is of Formula (I-10); and each instance of $R^{E3a}$ is independently $C_{1-6}$ alkyl.

In certain embodiments, the compound of Formula (I) is of Formula (I-11):

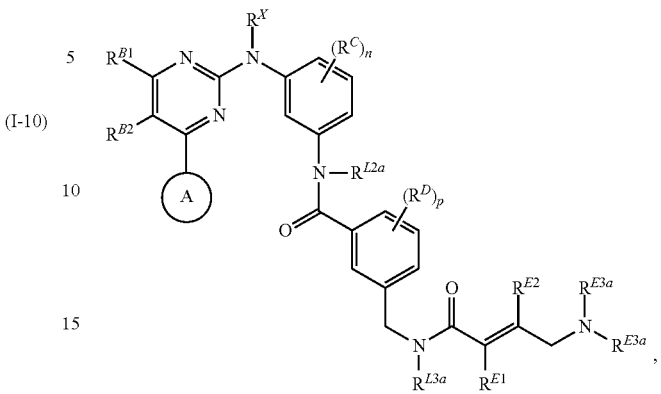

(I-11)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-11); and Ring A is of any one of the Formulae (i-1)-(i-4). In certain embodiments, the compound of Formula (I) is of Formula (I-11); and Ring A is of any one of the Formulae (iii-1)-(iii-7). In certain embodiments, the compound of Formula (I) is of Formula (I-11); and Ring A is of any one of the Formulae (iv-1)-(iv-6). In certain embodiments, the compound of Formula (I) is of Formula (I-11); and Ring A is of any one of the Formulae (v-1)-(v-6). In certain embodiments, the compound of Formula (I) is of Formula (I-11); and Ring A is of any one of the Formulae (vi-1)-(vi-6). In certain embodiments, the compound of Formula (I) is of Formula (I-11); and Ring A is of Formula (i-5). In certain embodiments, the compound of Formula (I) is of Formula (I-11); and Ring A is of Formula (vii).

In certain embodiments, the compound of Formula (I) is of Formula (I-11); and $R^X$, $R^{L2a}$, and $R^{L3a}$ are each hydrogen. In certain embodiments, the compound of Formula (I) is of Formula (I-11); and $R^{E1}$ and $R^{E2}$ are each hydrogen. In certain embodiments, the compound of Formula (I) is of Formula (I-11); and $R^X$, $R^{L2a}$, $R^{L3a}$, $R^{E1}$, and $R^{E2}$ are each hydrogen. In certain embodiments, the compound of Formula (I) is of Formula (I-11); and each instance of $R^{E3a}$ is independently optionally substituted alkyl. In certain embodiments, the compound of Formula (I) is of Formula (I-11); and each instance of $R^{E3a}$ is independently $C_{1-6}$ alkyl.

In certain embodiments, the compound of Formula (I) is of Formula (I-12):

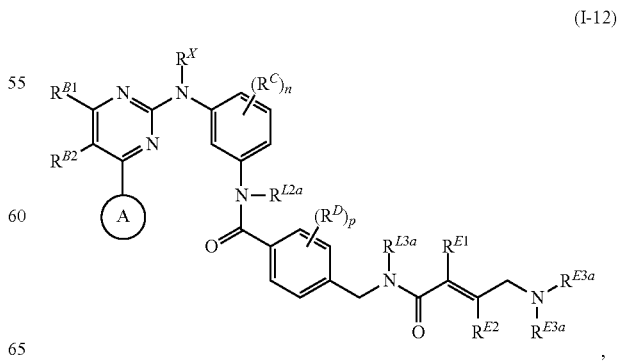

(I-12)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-12); and Ring A is of any one of the Formulae (i-1)-(i-4). In certain embodiments, the compound of Formula (I) is of Formula (I-12); and Ring A is of any one of the Formulae (iii-1)-(iii-7). In certain embodiments, the compound of Formula (I) is of Formula (I-12); and Ring A is of any one of the Formulae (iv-1)-(iv-6). In certain embodiments, the compound of Formula (I) is of Formula (I-12); and Ring A is of any one of the Formulae (v-1)-(v-6). In certain embodiments, the compound of Formula (I) is of Formula (I-12); and Ring A is of any one of the Formulae (vi-1)-(vi-6). In certain embodiments, the compound of Formula (I) is of Formula (I-12); and Ring A is of Formula (i-5). In certain embodiments, the compound of Formula (I) is of Formula (I-12); and Ring A is of Formula (vii).

In certain embodiments, the compound of Formula (I) is of Formula (I-12); and $R^X$, $R^{L2a}$, and $R^{L3a}$ are each hydrogen. In certain embodiments, the compound of Formula (I) is of Formula (I-12); and $R^{E1}$ and $R^{E2}$ are each hydrogen. In certain embodiments, the compound of Formula (I) is of Formula (I-12); and $R^X$, $R^{L2a}$, $R^{L3a}$, $R^{E1}$ and $R^{E2}$ are each hydrogen. In certain embodiments, the compound of Formula (I) is of Formula (I-12); and each instance of $R^{E3a}$ is independently optionally substituted alkyl. In certain embodiments, the compound of Formula (I) is of Formula (I-12); and each instance of $R^{E3a}$ is independently $C_{1-6}$ alkyl.

In certain embodiments, the compound of Formula (I) is of Formula (I-13):

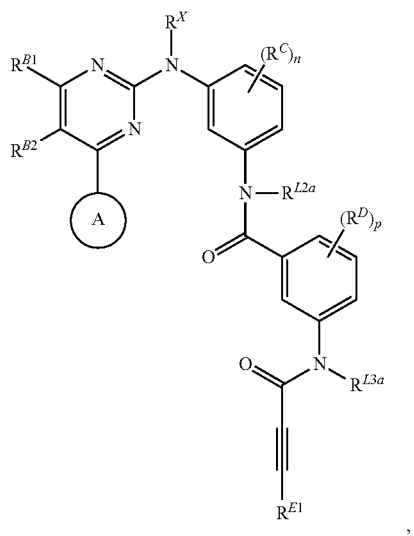

(I-13)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-13); and Ring A is of any one of the Formulae (i-1)-(i-4). In certain embodiments, the compound of Formula (I) is of Formula (I-13); and Ring A is of any one of the Formulae (iii-1)-(iii-7). In certain embodiments, the compound of Formula (I) is of Formula (I-13); and Ring A is of any one of the Formulae (iv-1)-(iv-6). In certain embodiments, the compound of Formula (I) is of Formula (I-13); and Ring A is of any one of the Formulae (v-1)-(v-6). In certain embodiments, the compound of Formula (I) is of Formula (I-13); and Ring A is of any one of the Formulae (vi-1)-(vi-6). In certain embodiments, the compound of Formula (I) is of Formula (I-13); and Ring A is of Formula (i-5). In certain embodiments, the compound of Formula (I) is of Formula (I-13); and Ring A is of Formula (vii).

In certain embodiments, the compound of Formula (I) is of Formula (I-13); and $R^X$, $R^{L2a}$, and $R^{L3a}$ are each hydrogen. In certain embodiments, the compound of Formula (I) is of Formula (I-13); and $R^{E1}$ is hydrogen. In certain embodiments, the compound of Formula (I) is of Formula (I-13); and $R^X$, $R^{L2a}$, $R^{L3a}$, and $R^{E1}$ are each hydrogen.

In certain embodiments, the compound of Formula (I) is of Formula (I-14):

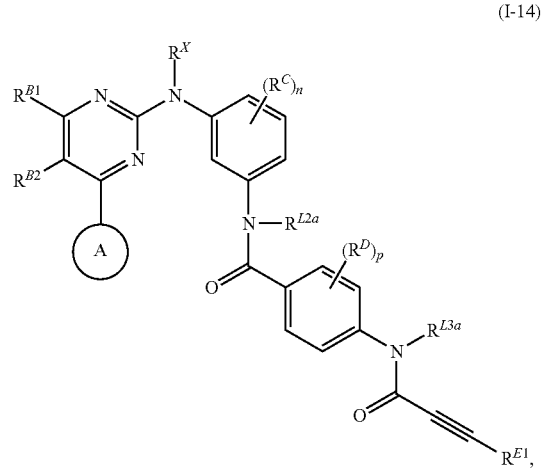

(I-14)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-14); and Ring A is of any one of the Formulae (i-1)-(i-4). In certain embodiments, the compound of Formula (I) is of Formula (I-14); and Ring A is of any one of the Formulae (iii-1)-(iii-7). In certain embodiments, the compound of Formula (I) is of Formula (I-14); and Ring A is of any one of the Formulae (iv-1)-(iv-6). In certain embodiments, the compound of Formula (I) is of Formula (I-14); and Ring A is of any one of the Formulae (v-1)-(v-6). In certain embodiments, the compound of Formula (I) is of Formula (I-14); and Ring A is of any one of the Formulae (vi-1)-(vi-6). In certain embodiments, the compound of Formula (I) is of Formula (I-14); and Ring A is of Formula (i-5). In certain embodiments, the compound of Formula (I) is of Formula (I-14); and Ring A is of Formula (vii).

In certain embodiments, the compound of Formula (I) is of Formula (I-14); and $R^X$, $R^{L2a}$, and $R^{L3a}$ are each hydrogen. In certain embodiments, the compound of Formula (I) is of Formula (I-14); and $R^{E1}$ is hydrogen. In certain embodiments, the compound of Formula (I) is of Formula (I-14); and $R^X$, $R^{L2a}$, $R^{L3a}$, and $R^{E1}$ are each hydrogen.

In certain embodiments, the compound of Formula (I) is of Formula (I-15):

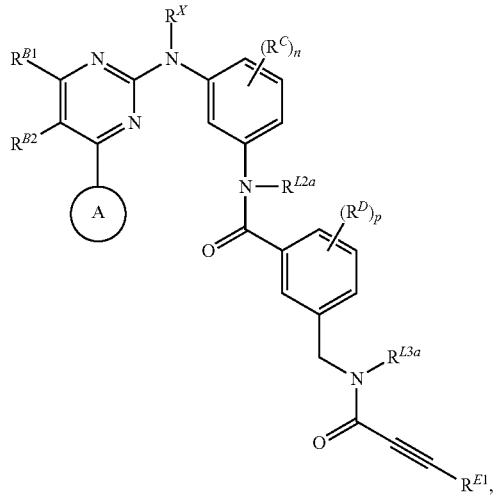

(I-15)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-15); and Ring A is of any one of the Formulae (i-1)-(i-4). In certain embodiments, the compound of Formula (I) is of Formula (I-15); and Ring A is of any one of the Formulae (iii-1)-(iii-7). In certain embodiments, the compound of Formula (I) is of Formula (I-15); and Ring A is of any one of the Formulae (iv-1)-(iv-6). In certain embodiments, the compound of Formula (I) is of Formula (I-15); and Ring A is of any one of the Formulae (v-1)-(v-6). In certain embodiments, the compound of Formula (I) is of Formula (I-15); and Ring A is of any one of the Formulae (vi-1)-(vi-6). In certain embodiments, the compound of Formula (I) is of Formula (I-15); and Ring A is of Formula (i-5). In certain embodiments, the compound of Formula (I) is of Formula (I-15); and Ring A is of Formula (vii).

In certain embodiments, the compound of Formula (I) is of Formula (I-15); and $R^X$, $R^{L2a}$, and $R^{L3a}$ are each hydrogen. In certain embodiments, the compound of Formula (I) is of Formula (I-15); and $R^{E1}$ is hydrogen. In certain embodiments, the compound of Formula (I) is of Formula (I-15); and $R^X$, $R^{L2a}$, $R^{L3a}$, and $R^{E1}$ are each hydrogen.

In certain embodiments, the compound of Formula (I) is of Formula (I-16):

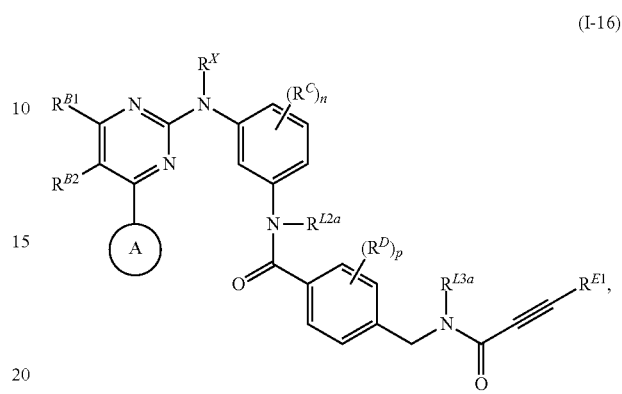

(I-16)

or a pharmaceutically acceptable salt, solvate, hydrate, polymorph, co-crystal, tautomer, stereoisomer, isotopically labeled derivative, or prodrug thereof. In certain embodiments, the compound of Formula (I) is of Formula (I-16); and Ring A is of any one of the Formulae (i-1)-(i-4). In certain embodiments, the compound of Formula (I) is of Formula (I-16); and Ring A is of any one of the Formulae (iii-1)-(iii-7). In certain embodiments, the compound of Formula (I) is of Formula (I-16); and Ring A is of any one of the Formulae (iv-1)-(iv-6). In certain embodiments, the compound of Formula (I) is of Formula (I-16); and Ring A is of any one of the Formulae (v-1)-(v-6). In certain embodiments, the compound of Formula (I) is of Formula (I-16); and Ring A is of any one of the Formulae (vi-1)-(vi-6). In certain embodiments, the compound of Formula (I) is of Formula (I-16); and Ring A is of Formula (i-5). In certain embodiments, the compound of Formula (I) is of Formula (I-16); and Ring A is of Formula (vii).

In certain embodiments, the compound of Formula (I) is of Formula (I-16); and $R^X$, $R^{L2a}$, and $R^{L3a}$ are each hydrogen. In certain embodiments, the compound of Formula (I) is of Formula (I-16); and $R^{E1}$ is hydrogen. In certain embodiments, the compound of Formula (I) is of Formula (I-16); and $R^X$, $R^{L2a}$, $R^{L3a}$, and $R^{E1}$ are each hydrogen.

In certain embodiments, the compound of Formula (I) is selected from the group consisting of:

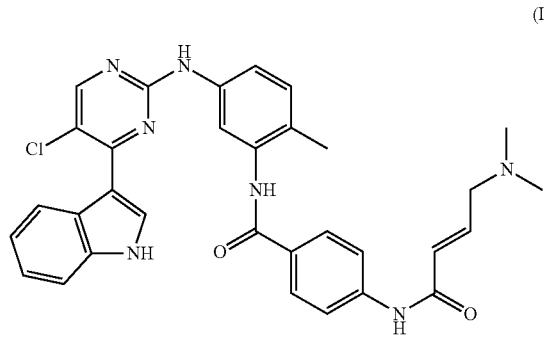

(I-17)

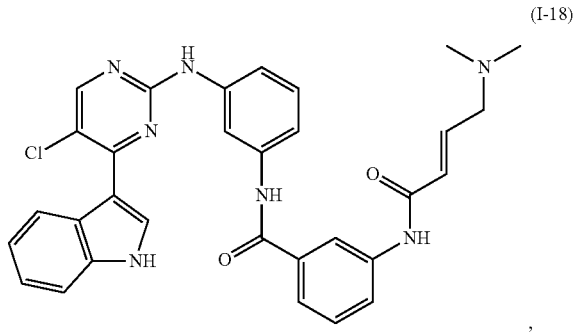

(I-18)

(I-19)
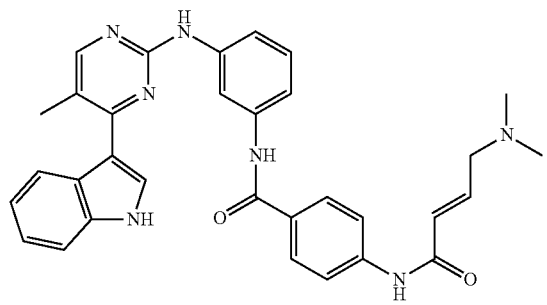
(I-20)
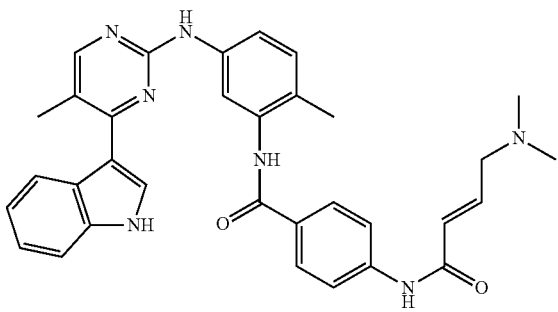
(I-21)
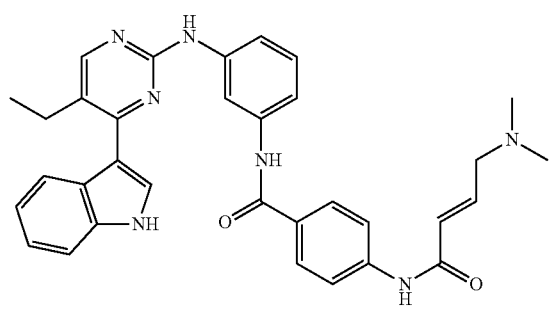
(I-22)
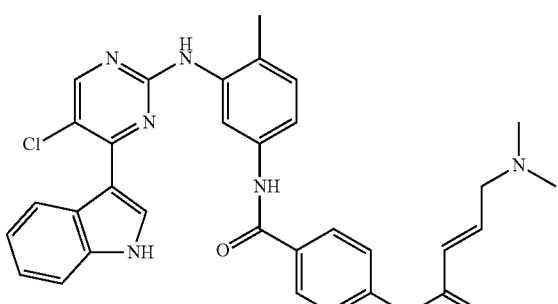
(I-23)
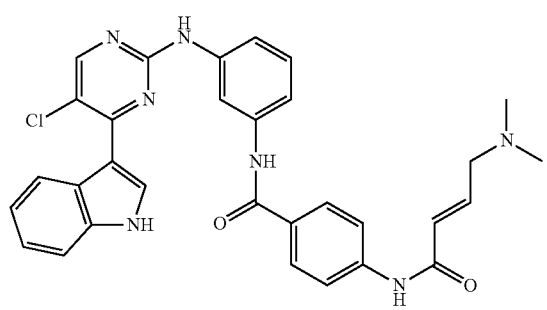
(I-24)
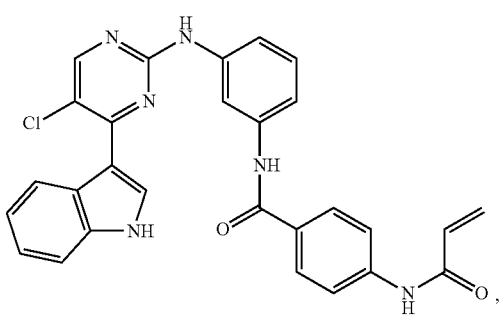
(I-25)
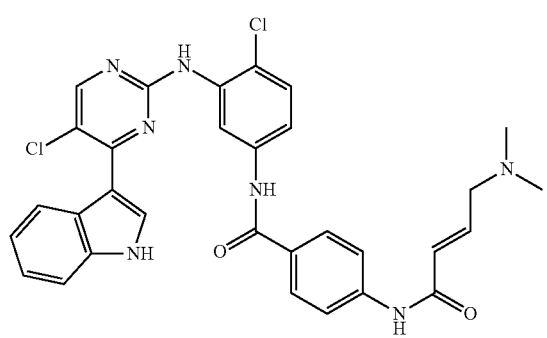
(I-26)
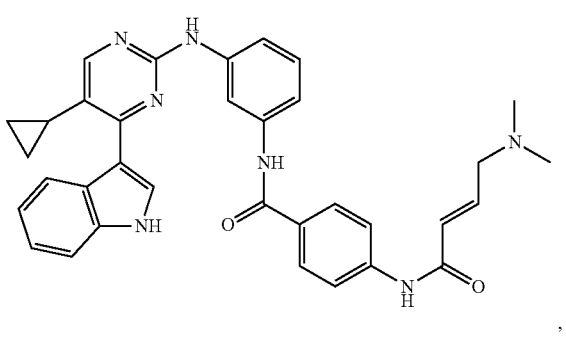

-continued
(I-27)
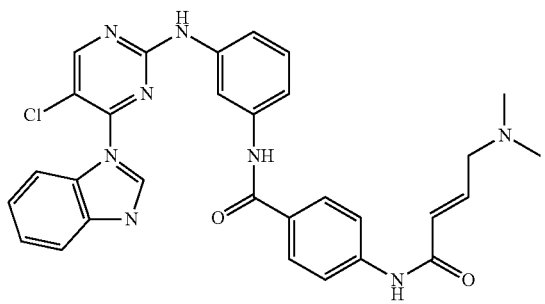
(I-28)
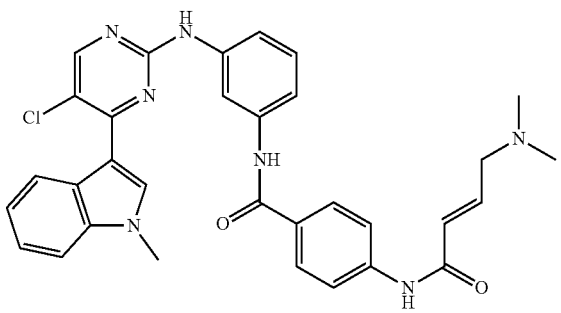
(I-29)
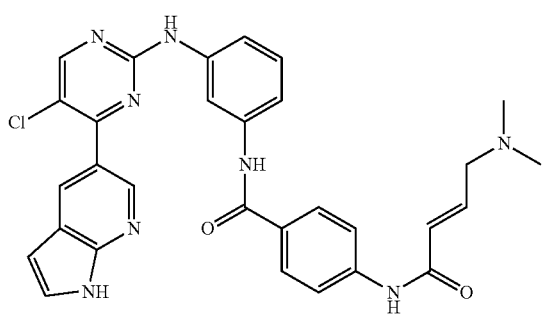
(I-30)
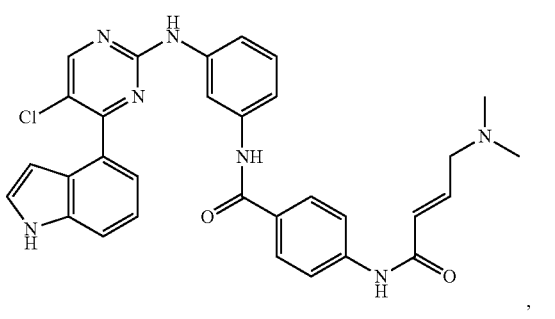
(I-31)
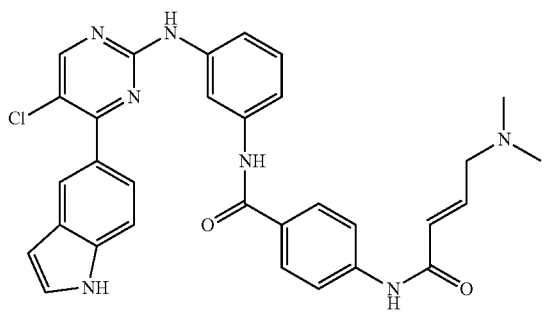
(I-32)
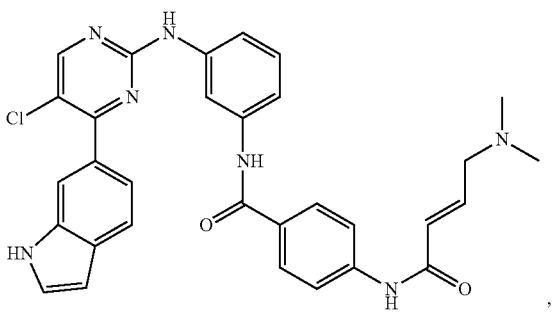
(I-33)
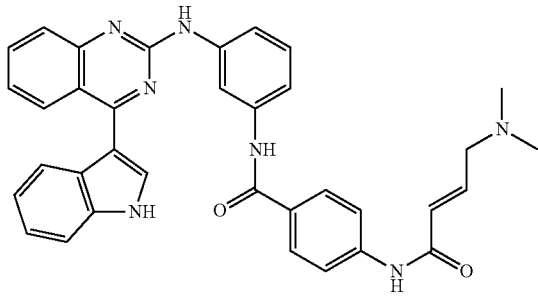
(I-34)
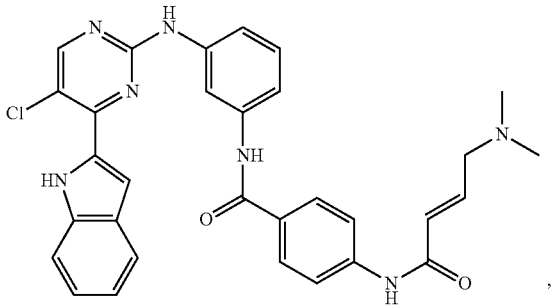

-continued
(I-35)
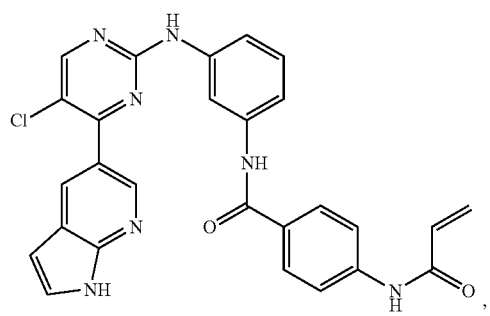
(I-36)
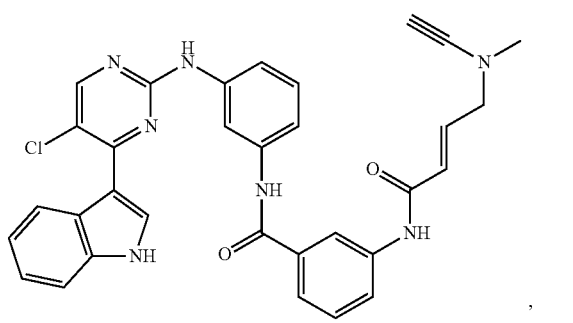
(I-37)
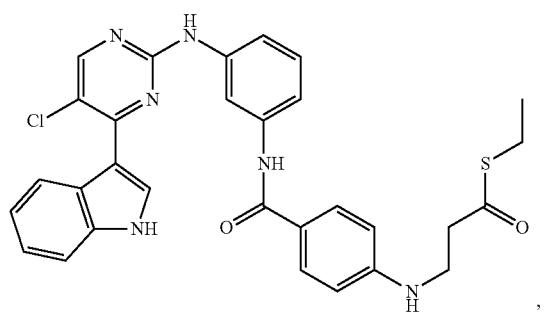
(I-38)
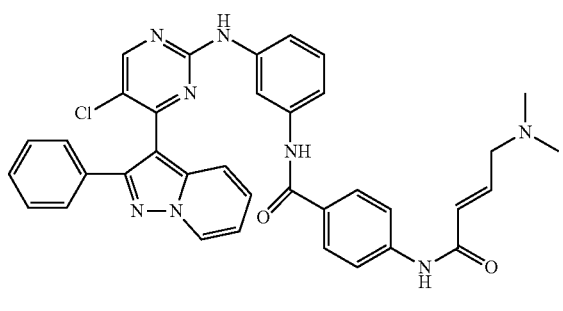
(I-39)
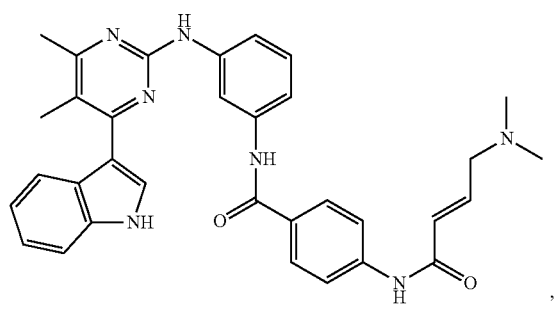
(I-40)
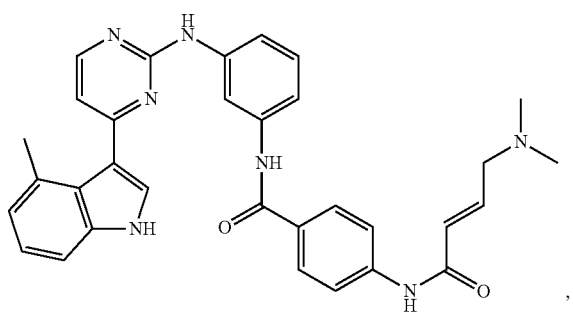
(I-41)
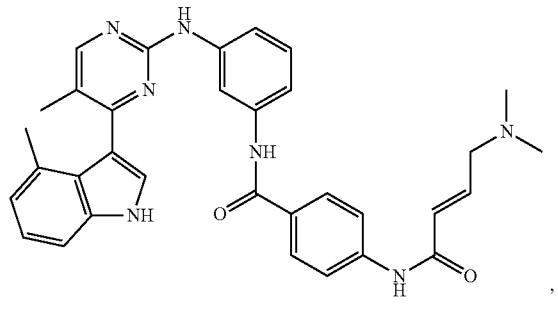
(I-42)
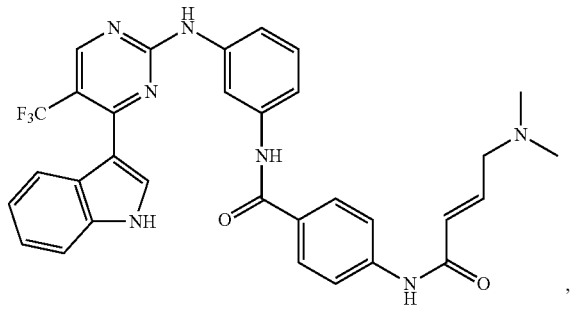

(I-43)
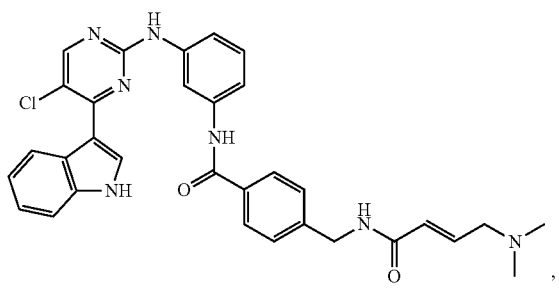
(I-44)
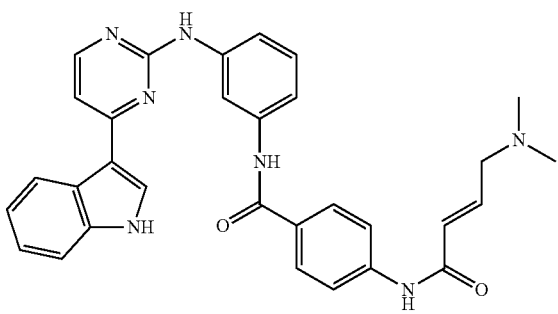
(I-45)
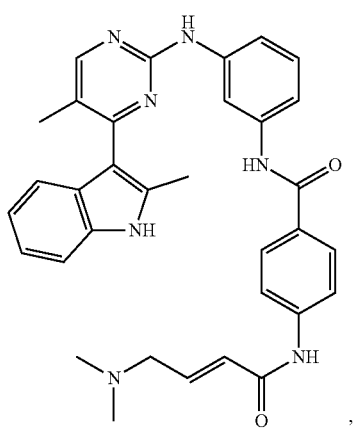
(I-46)
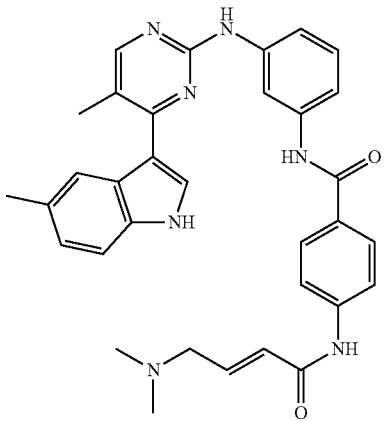
(I-47)
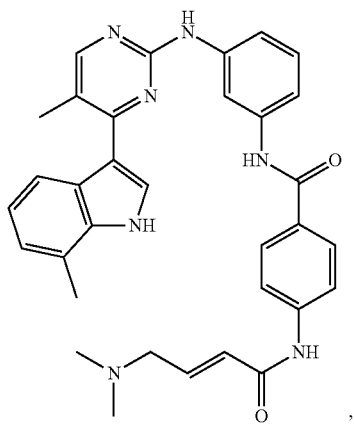
(I-48)
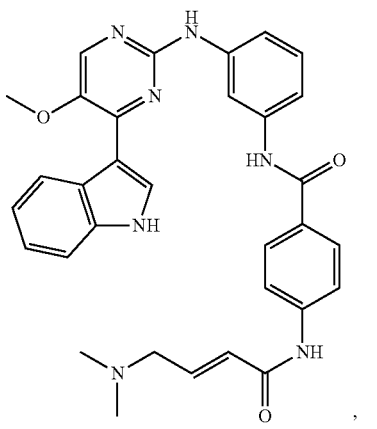
(I-51)
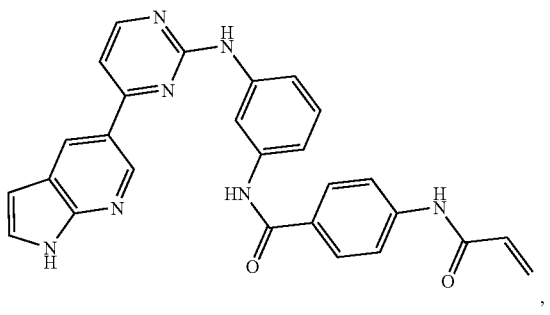
(I-52)
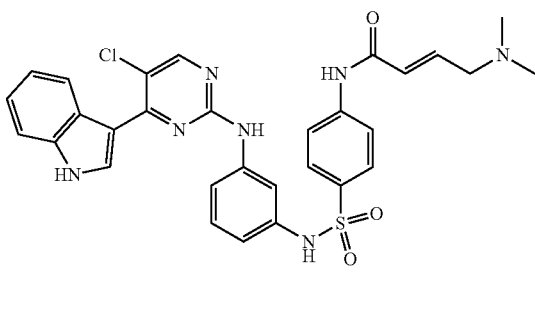

-continued
(I-53)
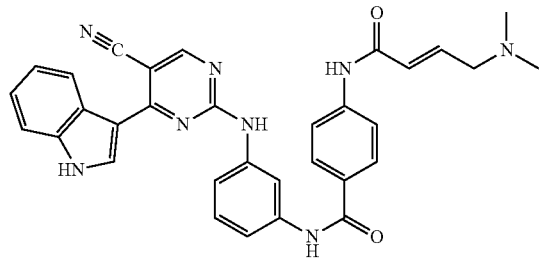
(I-54)
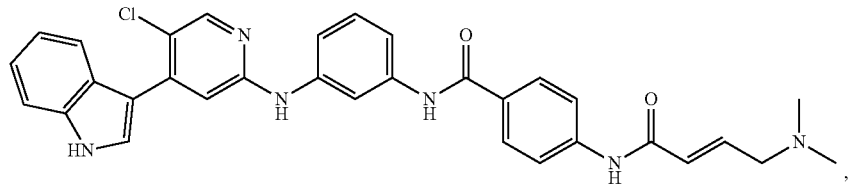
(I-55)
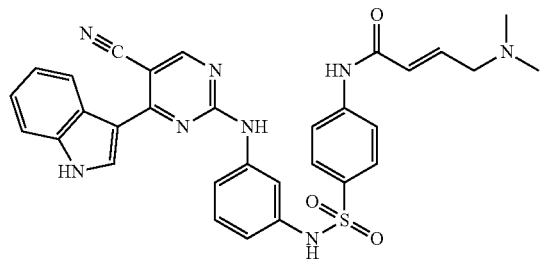
(I-56)
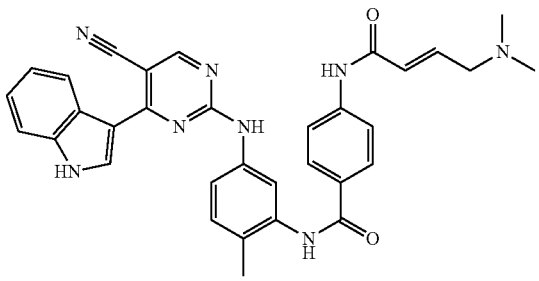
(I-57)
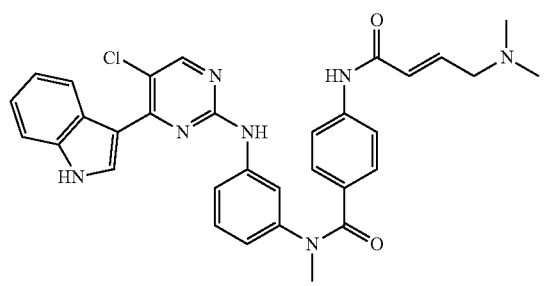
(I-59)
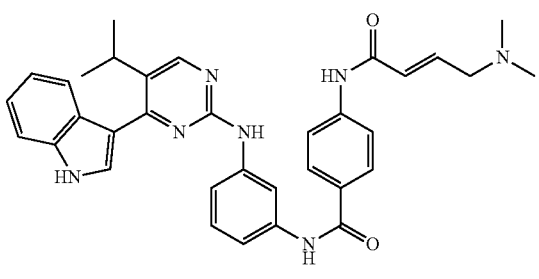
(I-58)
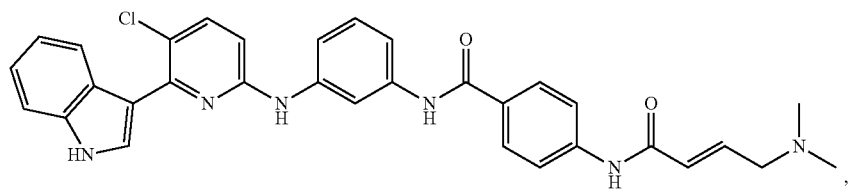
(I-60)
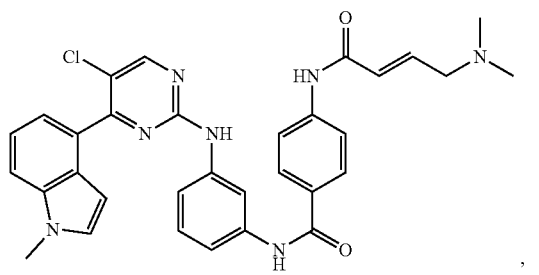
(I-61)
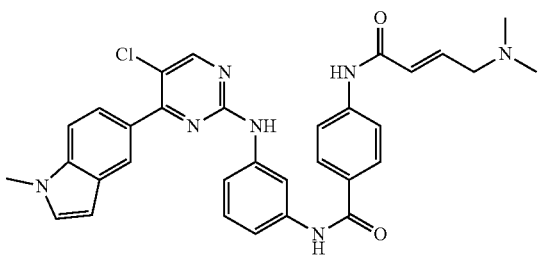

(I-62)
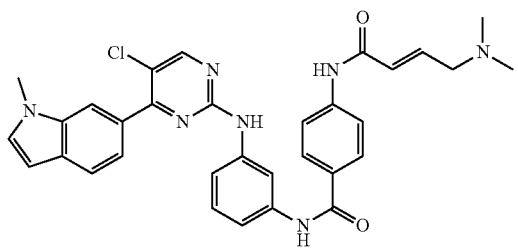
(I-63)
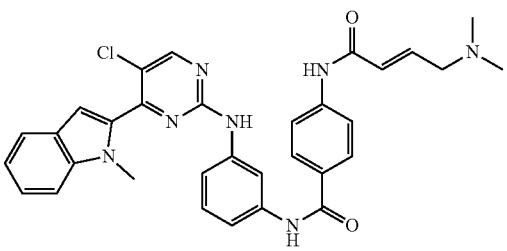
(I-64)
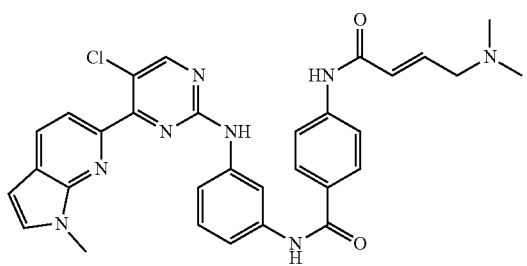
(I-65)
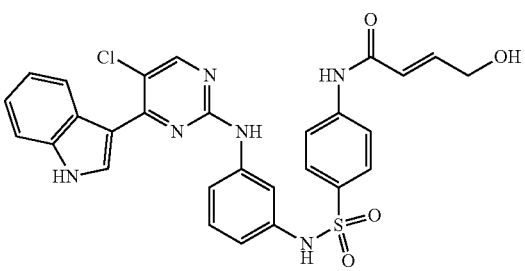
(I-66)
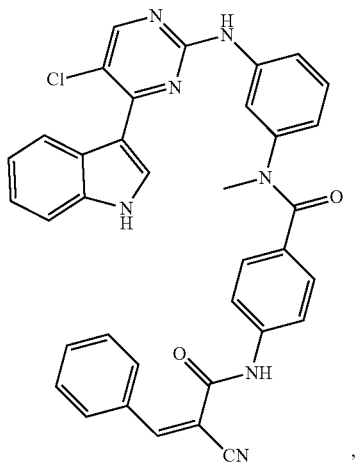
(I-67)
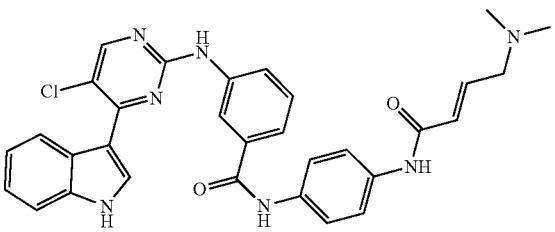
(I-68)
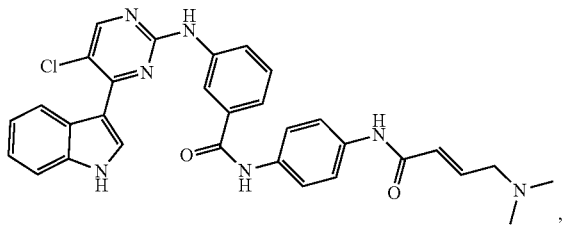
and pharmaceutically acceptable salts, solvates, hydrates, polymorphs, co-crystals, tautomers, stereoisomers, isotopically labeled derivatives, or prodrugs thereof.

In certain embodiments, the compound of Formula (I) is of Formula (I-49):

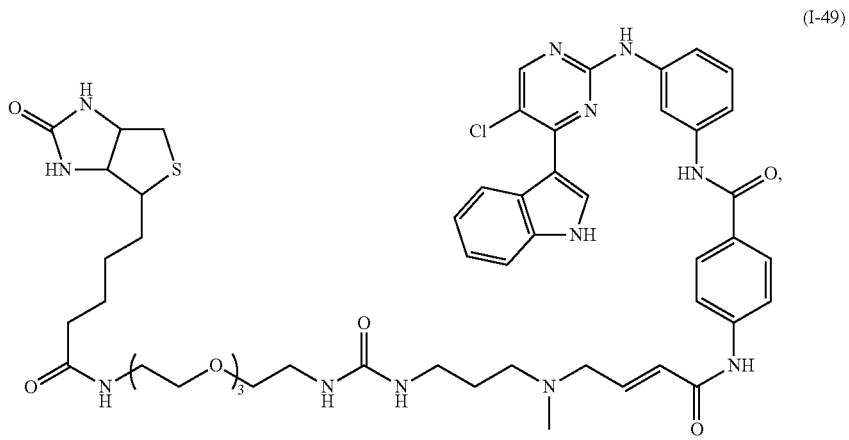

(I-49)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (I-50):

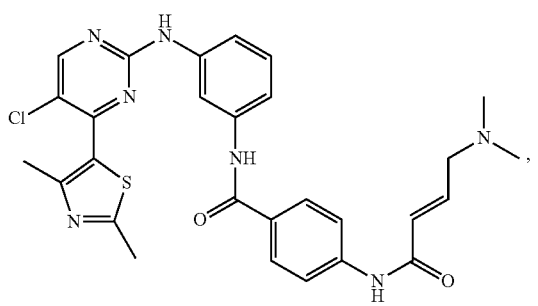

(I-50)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is not of the formula:

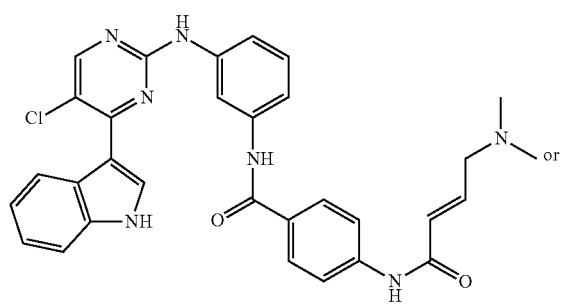

(I-23)

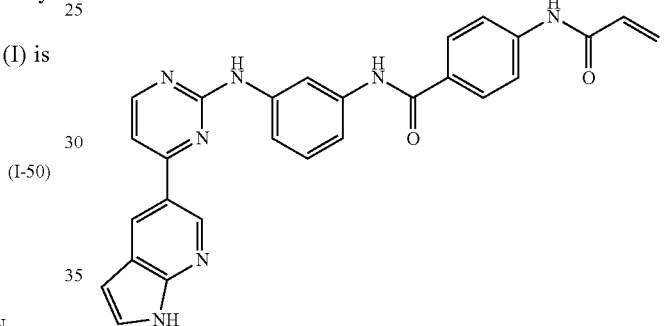

or a pharmaceutically acceptable salt, solvate, hydrate, polymorph, co-crystal, tautomer, stereoisomer, isotopically labeled derivative, or prodrug thereof.

In another aspect, the present invention provides the compound of the formula:

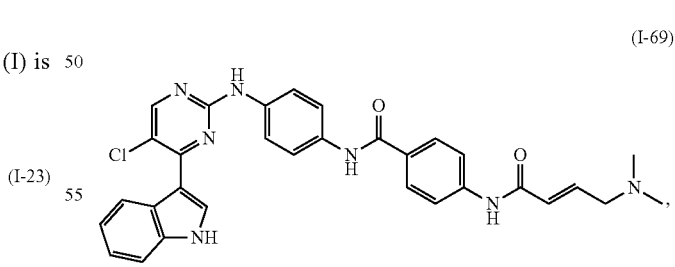

(I-69)

or a pharmaceutically acceptable salt, solvate, hydrate, polymorph, co-crystal, tautomer, stereoisomer, isotopically labeled derivative, or prodrug thereof.

In still another aspect, the present invention provides a compound of the formula:

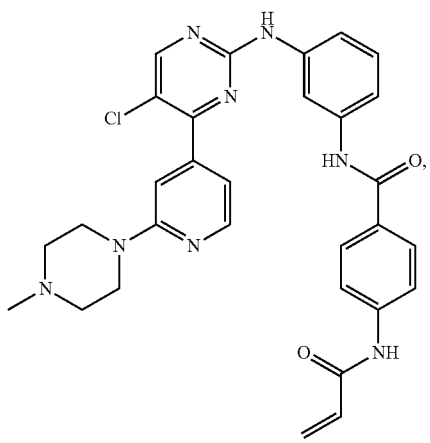
(I-70)

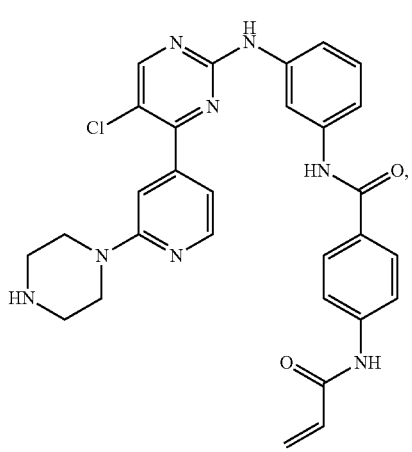
(I-71)

or a pharmaceutically acceptable salt, solvate, hydrate, polymorph, co-crystal, tautomer, stereoisomer, isotopically labeled derivative, or prodrug thereof.

The compounds of the present invention may bear multiple binding motifs for binding to CDK, specifically CDK7. Ring A of the inventive compounds may be accommodated by a hydrophobic pocket in the ATP-binding site of CDK7. Functionalities on Rings A and B may bind to residues of CDK7. For example, Ring A may form a hydrogen bond with Asp155 of CDK7. Functional groups of $R^E$ may form one or more hydrogen bonds with CDK7. Moreover, the Michael acceptor moiety of $R^E$ may react with a cysteine residue (e.g., Cys312) of CDK7 to allow covalent attachment of the compound to CDK7.

In another aspect, the present invention discloses CDK7 inhibitors of Formula

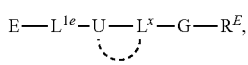
(II)

and pharmaceutically acceptable salts, solvates, hydrates, polymorphs, co-crystals, tautomers, stereoisomers, isotopically labeled derivatives, and prodrugs thereof;

wherein:

G is group of atoms ranging a total length between 20 to 30 Å;

$R^E$ is an electrophile with any one of the Formulae (ii-1)-(ii-17):

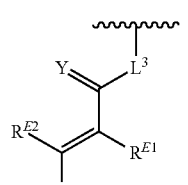
(ii-1)

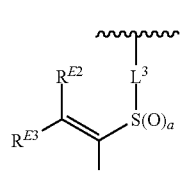
(ii-2)

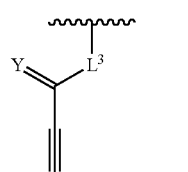
(ii-3)

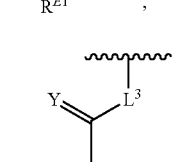
(ii-4)

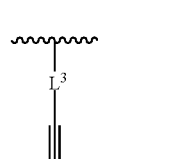
(ii-5)

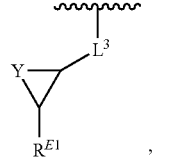
(ii-6)

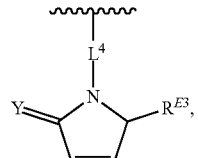
(ii-7)

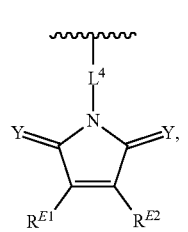
(ii-8)

-continued

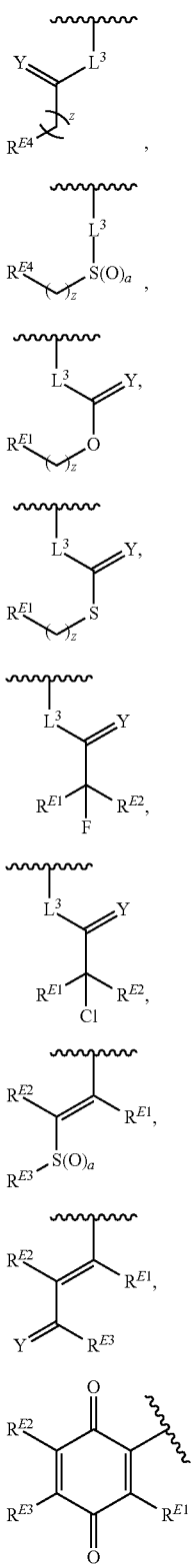

$L^3$ is a bond, —O—, —S—, —NR$^{L3a}$—, or an optionally substituted $C_{1-4}$ hydrocarbon chain, optionally wherein one or more carbon units of the hydrocarbon chain is replaced with —O—, —S—, —NR$^{L3a}$—, —NR$^{L3a}$C(=O)—, —C(=O)NR$^{L3a}$—, —SC(=O)—, —C(=O)S—, —OC (=O)—, —C(=O)O—, —NR$^{L3a}$C(=S)—, —C(=S) NR$^{L3a}$—, trans-CR$^{L3b}$=CR$^{L3b}$—, cis-CR$^{L3b}$=CR$^{L3b}$—, —C≡C—, —S(=O)$_2$O—, —OS(=O)$_2$—, —S(=O)$_2$ NR$^{L3a}$—, or —NR$^{L3a}$S(=O)$_2$—, wherein R$^{L3a}$ is hydrogen, $C_{1-6}$ alkyl, or a nitrogen protecting group, and wherein each occurrence of R$^{L3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

$L^4$ is a bond or an optionally substituted $C_{1-4}$ hydrocarbon chain;

R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E1a}$, —CH$_2$N(R$^{E1a}$)$_2$, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E2a}$, —CH$_2$N(R$^{E2a}$)$_2$, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{E3a}$, —CH$_2$N(R$^{E3a}$)$_2$, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

optionally R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

Y is O, S, or NR$^{E5}$, wherein R$^{E5}$ is hydrogen, $C_{1-6}$ alkyl, or a nitrogen protecting group;

a is 1 or 2; and z is 0, 1 or 2;

$L^{1e}$ is a linker ranging between 0 to 3 atoms in length;

$L^{x}$ is a linker ranging between 0 to 5 atoms in length; and optionally, the $IC_{50}$ for CDK7 is less than approximately 100 nM; and optionally, the compound is selective for CDK7.

In certain embodiments, E is moderately hydrophobic group with a fragment c Log P between 1.0 and 3.0.

In certain embodiments, E contains at least one hydrogen bond donor moiety.

In certain embodiments, E is both a moderately hydrophobic group with a fragment c Log P between 1.0 and 3.0 and contains at least one hydrogen bond donor moiety.

In certain embodiments, E associates with a hydrophobic pocket exposed by the inactive form of CDK7 characterized by a closed conformation of the activation loop (DFG "out").

In certain embodiments, E forms a hydrogen bond to the —$NH_2$ of CDK7 residue lysine-41.

In certain embodiments, U contains at least one hydrogen bond acceptor moiety.

In certain embodiments, U forms a hydrogen bond to the backbone amide —NH— of CDK7 residue methionine-94.

In certain embodiments, $L^x$ contains at least one hydrogen bond donor moiety.

In certain embodiments, $L^x$ forms a hydrogen bond to the backbone amide —CO— group of CDK7 residue methionine-94.

In certain embodiments, $R^E$ forms a covalent bond with a nucleophilic amino acid residue of CDK7. In certain embodiments, $R^E$ forms a covalent bond with the —SH group of a cysteine residue of CDK7. In certain embodiments, $R^E$ forms a covalent bond with the —SH group of cysteine-312 of CDK7.

In certain embodiments, the compound binds to a pocket within CDK7 that is defined by amino acids phenylalanine-93, aspartic acid-92, aspartic acid-97, asparagine-142, and leucine-144.

In certain embodiments, the compound binds to a pocket within CDK7 that is defined by amino acids methionine-94, lysine-41, and phenylalanine-91.

In certain embodiments, the compound binds to the inactive form of CDK7 characterized by a closed conformation of the activation loop (DFG "out").

In certain embodiments, $R^E$ is between 9 to 17 Å from the CDK7 inhibitor binding pocket. In certain embodiments, $R^E$ is between 12 to 14 Å from the CDK7 inhibitor binding pocket.

In certain embodiments, $L^{1e}$ is 0 to 3 atoms in length. In certain embodiments, $L^{1e}$ is 0 to 1 atoms in length.

In certain embodiments, G represents a group of atoms spanning a total length of between 20 to 30 Å. In certain embodiments, G represents two linked, optionally substituted aryl rings of formula (III):

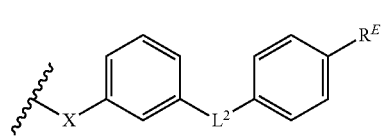

(III)

wherein X and $L^2$ are defined as above.

In certain embodiments, G represents two linked, optionally substituted aryl rings of formula (IIIa):

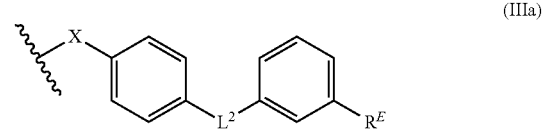

(IIIa)

wherein X and $L^2$ are defined as above.

In another aspect, the present invention discloses a CDK7 inhibitor having molecular dimensions compatible with the shape of a CDK7-active site as defined by the atomic coordinates of phenylalanine-93, aspartic acid-92, aspartic acid-97, asparagine-142, and leucine-144, methionine-94, lysine-41, and phenylalanine-91, wherein a pendent electrophile may reach to and react covalently with cysteine-312 and the compound has a biochemical $IC_{50}$ for CDK7 of less than 100 nM.

In another aspect, the present invention discloses an inhibited Cyclin-dependent kinase comprising an irreversible CDK-7 inhibitor having a covalent bond to the cysteine-312 residue of CDK-7.

In some embodiments, the inhibited cyclin-dependent kinase includes a covalent bond between an electrophilic moiety of the inhibitor and the —SH group of the cysteine-312 residue of CDK-7.

In some embodiments, the inhibited cyclin-dependent kinase forms a covalent bond between a $R^E$ moiety of the inhibitor and the —SH group of the cysteine-312 residue of CDK-7, producing a structure of Formula (IV) when an inhibitor of Formula (II) is used:

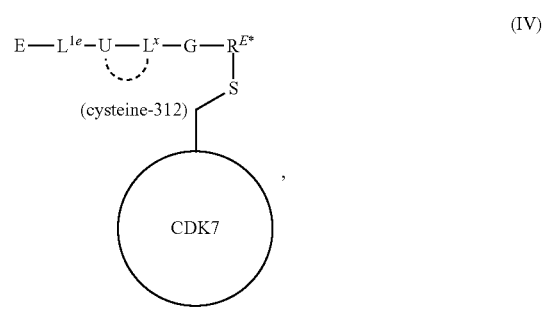

(IV)

wherein $R^{E*}$ is an electrophilic moiety that has reacted with the nucleophilic —SH of cysteine-312, and E, $L^{1e}$, U, $L^x$, and G are defined herein.

In some embodiments, the inhibited cyclin-dependent kinase forms a covalent bond with the $R^E$ moiety of Formula (ii-1), producing a structure of Formula (ii-1*):

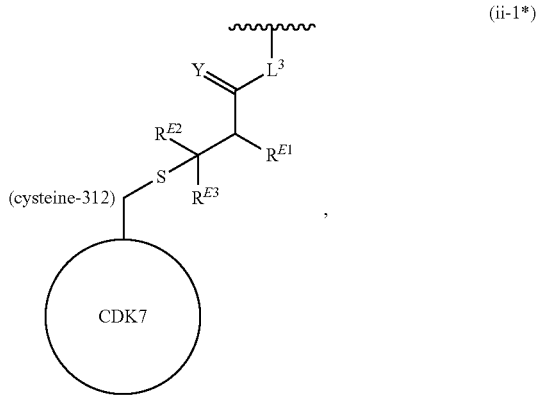

(ii-1*)

wherein $L^3$, Y, $R^{E1}$, $R^{E2}$, and $R^{E3}$ are defined herein.

In some embodiments, the inhibited cyclin-dependent kinase forms a covalent bond with the $R^E$ moiety of Formula (ii-1), wherein $R^{E2}$ is hydrogen. In some embodiments, the inhibited cyclin-dependent kinase forms a covalent bond with the $R^E$ moiety of Formula (ii-1), wherein $R^{E3}$ is hydrogen. In some embodiments, the inhibited cyclin-dependent kinase forms a covalent bond with the $R^E$ moiety of Formula (ii-1), wherein $R^{E2}$ and $R^{E3}$ are each hydrogen. In some embodiments, the inhibited cyclin-dependent kinase forms a covalent bond with the $R^E$ moiety of Formula (ii-1), wherein $R^{E3}$ is —$CH_2N(R^{E3a})$.

In some embodiments, the inhibited cyclin-dependent kinase forms a covalent bond with the $R^E$ moiety of Formula (ii-3), producing a structure of Formula (ii-3*):

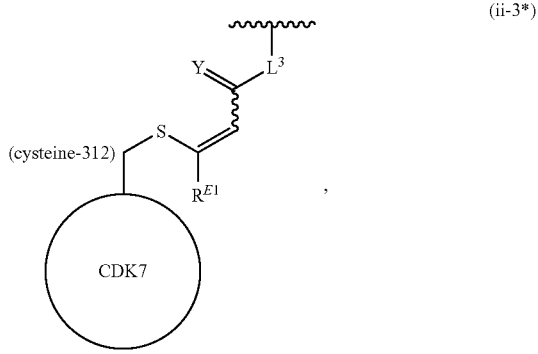

(ii-3*)

wherein $L^3$, Y, and $R^{E1}$ are defined herein.

In some embodiments, the inhibited cyclin-dependent kinase forms a covalent bond with the $R^E$ moiety of Formula (ii-3), wherein Y is O. In some embodiments, the inhibited Cyclin-dependent kinase forms a covalent bond with the $R^E$ moiety of Formula (ii-3), wherein $L^3$ is —$NR^{L3a}$—. In some embodiments, the inhibited cyclin-dependent kinase forms a covalent bond with the $R^E$ moiety of Formula (ii-3), wherein $L^3$ is —NH—. In some embodiments, the inhibited cyclin-dependent kinase forms a covalent bond with the $R^E$ moiety of Formula (ii-3), wherein $L^3$ is —$C(R^{L3b})_2NR^{L3a}$—. In some embodiments, the inhibited cyclin-dependent kinase forms a covalent bond with the $R^E$ moiety of Formula (ii-3), wherein $L^3$ is —$CH_2NH$—. In some embodiments, the inhibited cyclin-dependent kinase forms a covalent bond with the $R^E$ moiety of Formula (ii-3), wherein $R^{E1}$ is hydrogen. In some embodiments, the inhibited cyclin-dependent kinase forms a covalent bond with the $R^E$ moiety of Formula (ii-3), wherein $R^{E1}$ is —$CH_2N(R^{E1a})$.

In another aspect, the present invention discloses an inhibited Cyclin-dependent kinase comprising an irreversible CDK7 inhibitor having a covalent bond to the cysteine-312 residue of CDK7. In certain embodiments, based on an inhibitor of Formula (I) above such a modified CDK7 may have be of Formula (V):

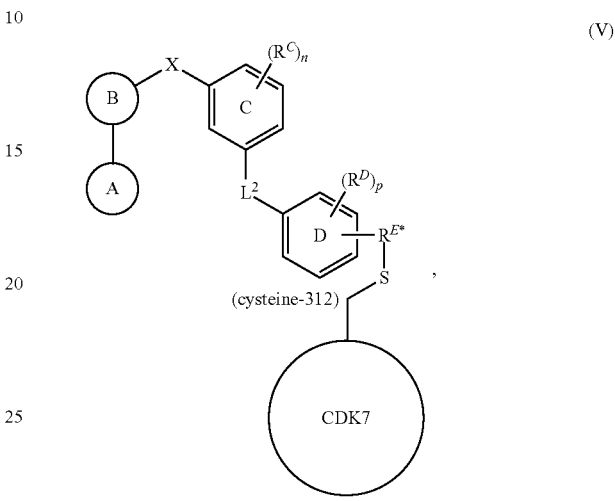

(V)

wherein $R^{E*}$ is an electrophilic moiety that has reacted with the nucleophilic —SH of cysteine-312 and A, B, X, C, D, $L^2$, $R^C$, $R^D$, p, and n are defined herein.

In certain embodiments, the compounds of the present invention are compounds of Formula (I) or (II), and pharmaceutically acceptable salts, solvates, hydrates, polymorphs, co-crystals, tautomers, stereoisomers, isotopically labeled derivatives, and prodrugs thereof. In certain embodiments, the compounds of the present invention are compounds of Formula (I) or (II), and pharmaceutically acceptable salts thereof. In certain embodiments, the compounds of the present invention are compounds of Formula (I), and pharmaceutically acceptable salts, solvates, hydrates, polymorphs, co-crystals, tautomers, stereoisomers, isotopically labeled derivatives, and prodrugs thereof. In certain embodiments, the compounds of the present invention are compounds of Formula (I), and pharmaceutically acceptable salts thereof. In certain embodiments, the compounds of the present invention are compounds of Formula (II), and pharmaceutically acceptable salts, solvates, hydrates, polymorphs, co-crystals, tautomers, stereoisomers, isotopically labeled derivatives, and prodrugs thereof. In certain embodiments, the compounds of the present invention are compounds of Formula (II), and pharmaceutically acceptable salts thereof.

In certain embodiments, the compounds of the present invention are kinase inhibitors. In certain embodiments, the inventive compounds are CDK inhibitors. In certain embodiments, the inventive compounds are CDK7 inhibitors. In certain embodiments, the inventive compounds are selective CDK inhibitors (e.g., being more active in inhibiting a CDK than a non-CDK kinase). In certain embodiments, the inventive compounds are selective CDK7 inhibitors (e.g., being more active in inhibiting CDK7 than a non-CDK7 kinase). In certain embodiments, the inventive compounds are selective CDK12 inhibitors. In certain embodiments, the inventive compounds are selective CDK13 inhibitors.

The selectivity of an inventive compound for a first kinase (e.g., CDK7) over a second kinase (e.g., a non-CDK7 kinase) may be measured by the quotient of the $IC_{50}$ (half maximal inhibitory concentration) value of the inventive compound in inhibiting the activity of the second kinase over the $IC_{50}$ value of the inventive compound in inhibiting the activity of the first kinase. The selectivity of an inventive compound for a first kinase over a second kinase may also be measured by the quotient of the $K_d$ (dissociation constant) value of an adduct (covalent or non-covalent) of the inventive compound and the second kinase over the $K_d$ value of an adduct of the inventive compound and the first kinase. In certain embodiments, the selectivity is at least about 1-fold, at least about 2-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, $IC_{50}$ values are measured by a functional antagonist assay. In certain embodiments, $IC_{50}$ values are measured by a competition binding assay. In certain embodiments, $IC_{50}$ values are measured by a method described herein. In certain embodiments, $K_d$ values are measured by a nuclear magnetic resonance method (e.g., a linearization method and curve fitting method). In certain embodiments, $K_d$ values are measured by a mass spectrometry method (e.g., a one-ligand one-binding-site ESI-MS method).

One skilled in the art will appreciate that there are many tools including computer software for designing the covalent inhibitors of CDK7. These tools may also be used to select a candidate compound for screening as a kinase inhibitor (e.g. CDK7). This design or selection may begin with selection of various moieties which fill binding pockets. There are a number of ways to select moieties to fill individual binding pockets. These include visual inspection of a physical model or computer model of the active site and manual docking of models of selected moieties into various binding pockets. Modeling software that is well known and available in the art may be used. These include Discovery Studio/CHARMm 37b2 (Accelrys, Inc., Burlington, Mass., 2013, see B. R. Brooks, R. E. Bruccoleri, B. D. Olafson, D. J. States, S. Swaminathan, and M. Karplus, J. Comp. Chem. vol. 4, pp. 187-217 (1983)), SYBYL-X (Molecular Modeling Software, Tripos Associates, Inc., St. Louis, Mo., 2010), or AMBER 12 and AmberTools 13 (D. A. Case et al., 2012, for review see R. Salomon-Ferrer, D. A. Case, R. C. Walker, WIREs Comput. Mol. Sci. 3, pp. 198-210 (2013)).

This modeling step may be followed by energy minimization with standard molecular mechanics forcefields such as CHARMm and AMBER 12. In addition, there are a number of more specialized computer programs to assist in the process of selecting the binding moieties of this invention. These include, but are not limited to:

1. GRID (Goodford, P. J. A Computational Procedure for Determining Energetically Favorable Binding Sites on Biologically Important Macromolecules. J. Med. Chem. 1985, 28, 849-857). GRID is available from Oxford University, Oxford, UK.
2. CATALYST or MODELER in Discovery Studio. Discovery Studio is available from Accelrys, Inc., Burlington, Mass.
3. AUTODOCK (Goodsell, D. S.; Olsen, A. J. Automated Docking of Substrates to Proteins by Simulated Annealing. PROTEINS: Structure, Function and Genetics 1990, 8, 195-202). AUTODOCK 4.2.5.1 is available from the Scripps Research Institute, La Jolla, Calif, 2013. DOCK 3.7 (Coleman, R. G.; Carchia, M.; Sterling, T.; Irwin, J. J.; Shoichet, B. K. Ligand Pose and Orientational Sampling in Molecular Docking. PLOS one 2013, 8, e75992). DOCK 3.7 is available from the University of California. San Francisco, Calif, 2013.

Once suitable binding moieties have been selected, they can be assembled into a single compound (e.g. an inhibitor of CDK7). This assembly may be accomplished by connecting the various moieties to a central scaffold. The assembly process may, for example, be done by visual inspection followed by manual model building, again using software as described herein. A number of other programs may also be used to assist in assembly of the compound. These include, but are not limited to:

1. CAVEAT (Bartlett, P. A.; Shea, G. T.; Telfer, S. J.; Waterman, S. CAVET: A Program to Facilitate the Structure-Derived Design of Biologically Active Molecules. In "Molecular Recognition in Chemical and Biological Problems," Special Pub., Royal Chem. Soc. 1989, 78, 182-196). CAVEAT is available from the University of California, Berkeley, Calif.
2. 3D Database systems such as Cambridge Structural Database (Cambridge Crystallographic Data Centre (CCDC), Cambridge, Mass.).
3. QSAR Plus (available from Accelrys. Burlington. Mass.)

In addition to the above computer assisted modeling of inhibitor compounds, the inhibitors of this invention may be constructed de novo using either an empty active site or optionally including some portions of a known inhibitor. Such methods are well known in the art. They include, for example, SYBYL-X (available from Tripos associates. St. Louis. Mo.)

Some examples of these specific applications include: Baldwin, J. J. et al., "Thienothiopyran-2-sulfonamides: Novel Topically Active Carbonic Anhydrase Inhibitors for the Treatment of Glaucoma", J. Med. Chem., 32. pp. 2510-2513 (1989); Appelt, K. et al., "Design of Enzyme Inhibitors Using Iterative Protein Crystallographic Analysis", J. Med. Chem., 34. pp. 1925-1934 (1991); and Ealick, S. E. et al., "Application of Crystallographic and Modeling Methods in the Design of Purine Nucleotide Phosphorylase Inhibitors", Proc. Nat. Acad. Sci. USA, 88, pp. 11540-11544 (1991).

The inventive methods are also useful in the rational design of CDK7 inhibitors and therapeutic and prophylactic agents against CDK7-mediated diseases. Accordingly, the present invention relates to such inhibitors.

A variety of conventional techniques may be used to carry out each of the above evaluations as well as the evaluations necessary in screening a candidate compound for CDK7 inhibitory activity. Generally, these techniques involve determining the location and binding proximity of a given moiety, the occupied space of a bound inhibitor, the deformation energy of binding of a given compound, and electrostatic interaction energies. Examples of conventional techniques useful in the above evaluations include: quantum mechanics, molecular mechanics, molecular dynamics, Monte Carlo sampling, systematic searches and distance geometry methods (G. R. Marshall, Ann. Ref. Pharmacol. Toxicol., 27, p. 193 (1987)). Specific computer software has been developed for use in carrying out these methods. Examples of programs designed for such uses include: Gaussian 09 (M. J. Frisch, Gaussian, Inc., Wallingford, Ct.); AMBER 12 and AmberTools 13 (P. A. Kollman, University of California at San Francisco); Discovery Studio (Accelrys, Inc., Burlington, Mass.). These programs may be implemented on computational hardware systems known to those skilled in the art. Modern versions of these programs or alternatives are known and may be implemented by those skilled in the art.

Different classes of CDK7 inhibitors, according to this invention, may interact in similar ways with the various binding pockets of the CDK7 active site. The spatial arrangement of these important groups is often referred to as a pharmacophore. The concept of the pharmacophore has been well described in the literature (D. Mayer, C. B. Nayloc, I. Motoc, and G. R. Marshall, J. Comp. Aided Molec. Design vol. 1, pp. 3-16 (1987); A. Hopfinger and B. J. Burke, in Concepts and Applications of Molecular Similarity, M. A. Johnson and G. M. Maggiora, ed., Wiley (1990)).

Different classes of CDK7 inhibitors of this invention may also use different scaffolds or core structures, but all of these cores will allow the necessary moieties to be placed in the active site such that the specific interactions necessary for binding may be obtained.

Pharmaceutical Compositions, Kits, and Administration

The present invention provides pharmaceutical compositions comprising a compound of Formula (I), e.g., a compound of Formula (I), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (I), or a pharmaceutically acceptable salt thereof, and optionally a pharmaceutically acceptable excipient. In certain embodiments, the compound of Formula (I), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, lymphoma, melanoma, multiple myeloma, breast cancer, Ewing's sarcoma, osteosarcoma, brain cancer, neuroblastoma, lung cancer), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I) may be associated with overexpression of a kinase, such as cyclin-dependent kinase (CDK). The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins.

Modulation of the expression levels, degradation rates, and activation levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, i.e., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

CDK7, a member of the CDK family, was originally isolated as the catalytic subunit of the trimeric CDK-activating kinase (CAK) complex. This complex, consisting of CDK7, cyclin H, and MAT1, is responsible for activation of the mitotic promoting factor in vitro. The discovery that CDK7 was also a component of the basal transcription repair factor IIH (TFIIH) implicated a dual role for CDK7 in transcription as part of TFIIH and in the control of the cell cycle as the trimeric CAK complex. TFIIH is a multisubunit protein complex identified as a factor required for RNA polymerase II (RNAP II)-catalyzed transcription, and subsequently this complex was found to play a key role in nucleotide excision repair. CDK7 is a component of at least three complexes, i.e., the trimeric CAK complex, the quaternary complex with the XPD (or ERCC2, a protein involved in transcription-coupled nucleotide excision repair), and the nine-subunit TFIIH complex. The two functions of CDK7 in CAK and CTD phosphorylation support critical facets of cellular proliferation, cell cycling, and transcription. Overexpression of CDK7 may inhibit apoptosis, promote transcription and cell proliferation, and/or disrupt DNA repair, and therefore, cause proliferative diseases. In certain embodiments, the proliferative disease to be treated or prevented using the compounds of Formula (I) may be associated with overexpression of CDK7. The compounds of Formula (I), or pharmaceutically acceptable salts, solvates, hydrates, polymorphs, co-crystals, tautomers, stereoisomers, isotopically labeled derivatives, and prodrugs thereof, or pharmaceutical compositions thereof, may downregulate the expression of CDK7.

A proliferative disease may be associated with aberrant activity of CDK7. Aberrant activity of CDK7 may be an elevated and/or an inappropriate activity of CDK7. Deregulation of cell cycle progression is a characteristic of a proliferative disease, and a majority of proliferative diseases have abnormalities in some component of CDK (e.g., CDK7) activity, frequently through elevated and/or inappropriate CDK activation. Inhibition of the catalytic activity of CDK7 would be expected to inhibit cell cycle progression by blocking the phosphorylation of cell cycle CDKs, and would additionally inhibit transcription of effectors of cell division. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of Formula (I), and pharmaceutically acceptable salts, solvates, hydrates, polymorphs, co-crystals, tautomers, stereoisomers, isotopically labeled derivatives, prodrugs, and compositions thereof, may inhibit the activity of CDK7 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Apoptosis is the process of programmed cell death. Inhibition of apoptosis may result in uncontrolled cell proliferation and, therefore, may cause proliferative diseases. The cell cycle CDKs (CDK1, 2, 4, and 6) are activated by phosphorylation by CDK7/cyclin H (also called CAK). Inhibition of CDK7 would therefore result in cell-cycle arrest at multiple points in the cell cycle due to failure to activate the cell cycle CDKs. CDK 7 activates transcription by phosphorylating the CTD of RNAP II. Inhibition of CTD phosphorylation has been shown to inhibit transcription and reduce expression of short lived proteins, including those involved in apoptosis regulation. It is appreciated in the art that stalling of RNA polymerase may activate p53 (also known as protein 53 or tumor protein 53, a tumor suppressor protein that is encoded in humans by the TP53 gene), leading to apoptosis. Thus, inhibition of the activity of CDK7 are expected to cause cytotoxicity by inducing apoptosis. The compounds of Formula (I), and pharmaceutically acceptable salts, solvates, hydrates, polymorphs, co-crystals, tautomers, stereoisomers, isotopically labeled derivatives, prodrugs, and compositions thereof, may induce apoptosis, and therefore, be useful in treating and/or preventing proliferative diseases.

In certain embodiments, the proliferative disease to be treated or prevented using the compounds of Formula (I) is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is breast cancer. In certain embodiments, the proliferative disease is triple-negative breast cancer (TNBC). In certain embodiments, the proliferative disease is Ewing's sarcoma. In certain embodiments, the proliferative disease is a bone cancer. In certain embodiments, the proliferative disease is osteosarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer (NSCLC). In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the infectious disease to be treated or prevented using the compounds of Formula (I) is a viral disease. Such viral infections are described in U.S. Provisional Patent Application, U.S. Ser. No. 61/622,828, filed Apr. 11, 2012, and international PCT application, PCT/US2013/032488, filed Marhc 15, 2013, each of which is incorporated herein in its entirety by reference.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a B-cell. In certain embodiments, the cell is a T-cell. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of a CDK (e.g., CDK7, CDK1, CDK2, CDK5, CDK8, CDK9, CDK12, CDK13) in a biological sample or subject. In another aspect, the present invention provides methods of down-regulating the expression of Jurkat, IRAK1, JNK1, JNK2, or MLK3 in a biological sample or subject.

Another aspect of the invention relates to methods of inhibiting the activity of a kinase in a biological sample or subject. In certain embodiments, the kinase is CDK. In certain embodiments, the kinase is CDK7. In certain embodiments, The activity of the kinase is aberrant activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound of Formula (I) to the kinase.

Also provided in the present invention are methods of inhibiting transcription in a biological sample or subject.

The present invention also provides methods of inhibiting cell growth in a biological sample or subject.

In still another aspect, the present invention provides methods of inducing apoptosis of a cell in a biological sample or a subject. In certain embodiments, the methods described herein include administering to a subject or contacting a biological sample with an effective amount of a compound of Formula (I), or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound of Formula (I), or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of CDK. In certain embodiments, the additional pharmaceutical agent is an inhibitor of CDK7. In certain embodiments, the additional pharmaceutical agent is a selective inhibitor of CDK7. In certain embodiments, the additional pharmaceutical agent is a nonselective inhibitor of CDK7. In certain embodiments, the additional pharmaceutical agent is flavopiridol, triptolide, SNS-032 (BMS-387032), PHA-767491, PHA-793887, BS-181, (S)-CR8, (R)-CR8, or NU6140. In certain embodiments, the additional pharmaceutical agent is an inhibitor of a mitogen-activated protein kinase (MAPK). In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase.

The inventive compounds or compositions may synergistically augment inhibition of CDK7 induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

Another aspect of the invention relates to methods of screening a library of compounds to identify one or more compounds that are useful in the treatment of a proliferative disease, in inhibiting a kinase (e.g., CDK, such as CDK7, CDK12, CDK13), in inhibiting cell growth, in inducing apoptosis of a cell, and/or in inhibiting transcription. In certain embodiments, the library of compounds is a library of compounds of Formula (I). The methods of screening a library include providing at least two different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of Formula (I), or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics associated with the proliferative disease. In certain embodiments, the methods of screening a library include providing at least two different compounds of Formula (I), or pharmaceutically acceptable salts thereof, or pharmaceutical compositions thereof; and performing at least one assay using the different compounds of Formula (I), or pharmaceutically acceptable salts thereof, or pharmaceutical compositions thereof, to detect one or more characteristics associated with the proliferative disease. The characteristic to be detected may be a desired characteristic associated with the proliferative disease. In certain embodiments, the desired characteristic is anti-proliferation. In certain embodiments, the desired characteristic is anti-cancer. In certain embodiments, the desired characteristic is inhibition of a kinase. In certain embodiments, the desired characteristic is inhibition of CDK. In certain embodiments, the desired characteristic is inhibition of CDK7. In certain embodiments, the desired characteristic is down-regulation of a kinase such as CDK (e.g., CDK7). In certain embodiments, the desired characteristic is induction of apoptosis of a cell. In certain embodiments, the desired characteristic is inhibition of transcription. The characteristic to be detected may also be an undesired characteristic associated with the proliferative disease, cell growth, apoptosis of a cell, and/or transcription. In certain embodiments, the undesired characteristic is induction of cell growth. In certain embodiments, the undesired characteristic is inhibition of apoptosis of a cell. In certain embodiments, the undesired characteristic is induction of transcription.

The different compounds of Formula (I) may be provided from natural sources (see, e.g., Sternberg et al., *Proc. Nat. Acad. Sci. USA*, (1995) 92:1609-1613) or generated by synthetic methods such as combinatorial chemistry (see, e.g., Ecker et al., *Bio/Technology*, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a library of compounds involve at least one assay. In certain embodiments, the assay is performed to detect one or more characteristics associated with the proliferative disease described herein. The assay may be an immunoassay, such as a sandwich-type assay, competitive binding assay, one-step direct test, two-step test, or blot assay. The step of performing at least one assay may be performed robotically or manually. In certain embodiments, the activity of a kinase is inhibited. In certain embodiments, the activity of CDK is inhibited. In certain embodiments, the activity of CDK7 is inhibited. In certain embodiments, the expression of a kinase such as CDK (e.g., CDK7) is down-regulated. In certain embodiments, apoptosis of a cell is induced. In certain embodiments, transcription is inhibited.

In yet another aspect, the present invention provides the compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

In another aspect, the present invention discloses a method for the design and/or identification of a potential binding compound for cyclin-dependent kinase 7 (CDK7) comprising the steps of:

(a) generating, on a computer, a three-dimensional representation of CDK7 having the coordinates of the solved X-ray structure, available publically as 1UA2 on PDB.org (b) identifying amino acid residues forming a binding pocket in the three-dimensional structure of CDK7 from step (a), in proximity to cysteine-312;

(c) generating a three-dimensional model of the active site;

(d) designing and/or selecting a compound that potentially binds to the active site using the three-dimensional model of the active site; and (e) synthesizing and/or choosing the potential binding compound.

In certain embodiments, the binding pocket comprises the CDK7 active site.

In certain embodiments, the binding pocket comprises the CDK7 amino acids phenylalanine-93, aspartic acid-92, aspartic acid-97, asparagine-142, and leucine-144, methionine-94, lysine-41, and phenylalanine-91.

In another aspect, the present invention discloses a method of identifying a compound that binds cyclin-dependent kinase 7 (CDK7), the method comprising computationally identifying a compound that binds to CDK7 using the atomic coordinates of cysteine-312, phenylalanine-93, aspartic acid-92, aspartic acid-97, asparagine-142, and leucine-144, methionine-94, lysine-41, and phenylalanine-91.

In another aspect, the present invention discloses a method of identifying a binding compound of cyclin-dependent kinase 7 (CDK7), the method comprising:
(a) providing a set of atomic coordinates for CDK7; and
(b) identifying in silico a binding compound that binds to CDK7 using the coordinates of step (a).

In another aspect, the present invention discloses a method of identifying a drug candidate for the treatment of a disease, the method comprising:
a) using the available atomic coordinates to form a three-dimensional structure of CDK7;
b) selecting a test compound having the best fit with the structure of CDK7; and
c) optionally, assaying the ability of the test compound to modulate CDK7 activity, wherein a test compound that modulates CDK7 activity is considered a drug candidate for treating a disease.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of the Compounds

The compounds provided herein can be prepared from readily available starting materials using the following general methods and procedures. See, e.g., Scheme 1 below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

General processes for preparing the compounds of the invention, such as compounds of Formula (I) (e.g., compounds I-1, I-3, I1-4, I1-5, I1-6, and I-7), are provided as further embodiments of the invention and are illustrated in Scheme 1. Alternatively, the compounds of the invention may be synthesized according to the methods described in U.S. Provisional Patent Application, U.S. Ser. No. 61/561,078, filed Nov. 17, 2011, and international PCT Application, PCT/US2012/065618, filed Nov. 16, 2012, published on May 23, 2013 under Publication No. WO 2013/074986, each of which is incorporated herein in its entirety by reference.

Scheme 1. Exemplary synthesis of compounds of Formula (I)

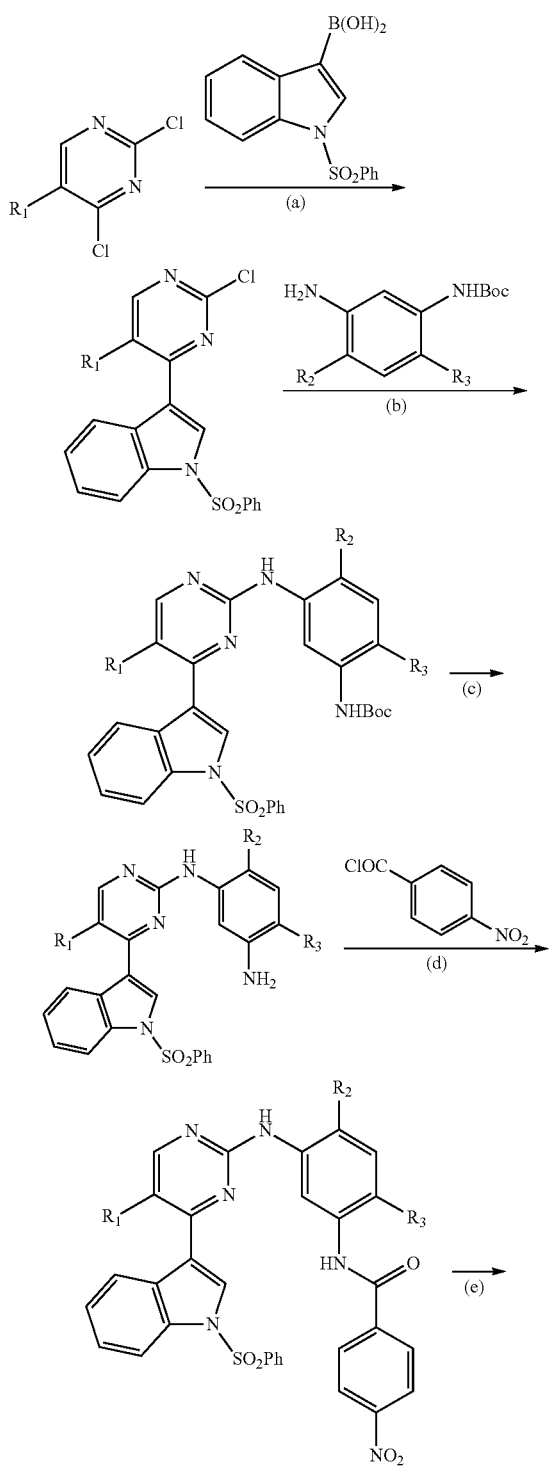

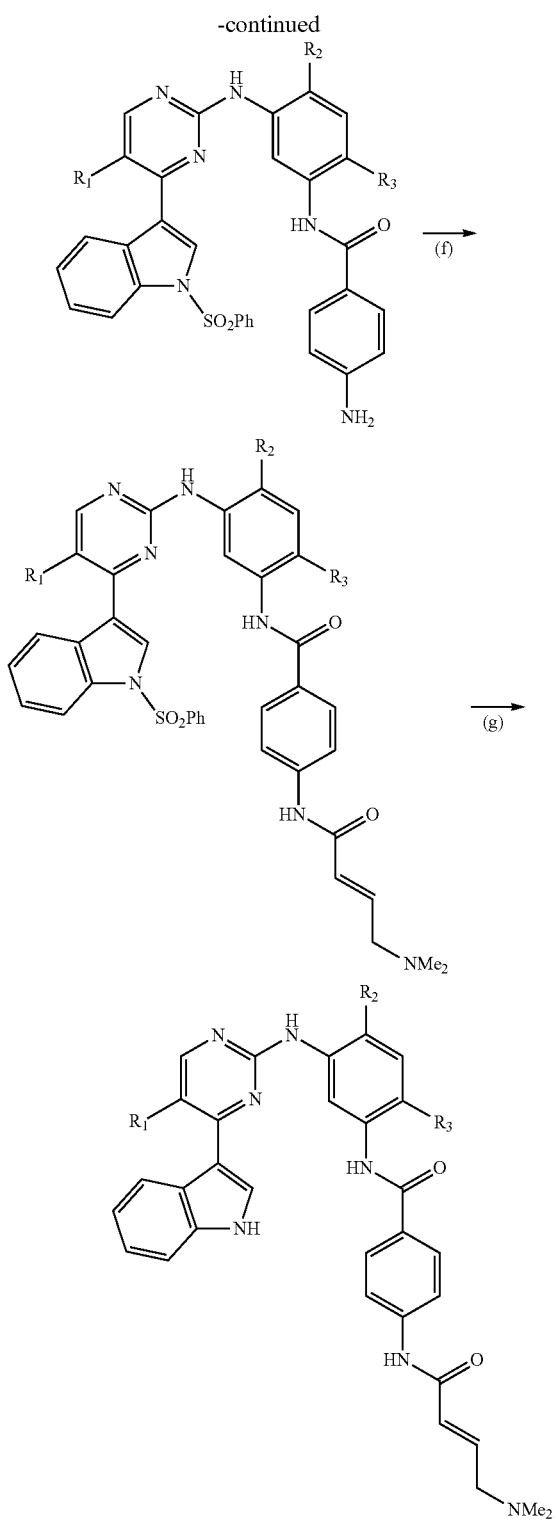

| | $R_1$ | $R_2$ | $R_3$ |
|---|---|---|---|
| I-1 | Cl | H | CH$_3$ |
| I-3 | CH$_3$ | H | H |
| I-4 | CH$_3$ | H | CH$_3$ |
| I-5 | CH$_2$CH$_3$ | H | H |
| I-6 | Cl | CH$_3$ | H |
| I-7 | Cl | H | H |

Reagents and conditions: (a) Pd(PPh$_3$)$_4$, Na$_2$CO$_3$, 1,2-dimethoxylethane, 80° C.; (b) Pd$_2$(dba)$_3$, X-Phos, K$_2$CO$_3$; t-BuOH, 90° C. (R$_1$=CH$_3$ or CH$_2$CH$_3$), or 2-ethoxyl ethanol, 150° C. (R$_1$=C$_1$) (c) TFA, CH$_2$Cl$_2$; (d) pyridine, 90° C.; (e) SnCl$_2$, ethyl acetate and methanol; (f) 4-bromobut-2-enoyl chloride, NHMe$_2$; (g) 1 M NaOH, 1,4-dioxane, 40° C.

Suzuki Coupling

To a solution of 5-substituted-2,4-chloropyrimide in 1,2-dimethoxylmethanol was added 1-(phenylsulfonyl)-1H-indol-3-yl) boronic acid (1.0 equiv.), tetrakis(triphenylphosphine)palladium (0.1 equiv.), and saturated Na$_2$CO$_3$. The reaction mixture was heated for 2 h at 80° C., cooled, and purified using silica gel chromatography.

Buchwald Coupling

To a solution of 5-methyl-4-indol-2-chloropyrimide or 5-ethyl-4-indol-2-chloropyrimide in t-butanol was added t-butyl-3-aminophenylcarbamate (1.0 equiv.), K$_2$CO$_3$ (1.0 equiv.), X-Phos (0.1 equiv.), and Pd$_2$(dba)$_3$. After heating at 90° C. for 6 h, the reaction mixture was diluted with a mixture of chloroform and 2-propanol (4:1). The organic layer was separated, washed with water (3×), dried over MgSO$_4$, filtered, and concentrated under reduced pressure. The resulting crude product was used in the next step without further purification.

For 5-chloro-4-indol-2-chloropyrimidine, the substitution reaction was utilized instead of a Buchwald coupling. 5-chloro-4-indole-2-chloropyrimidine was dissolved in 2-ethoxyethanol, and t-butyl-3-aminophenylcarbamate (1.0 equiv.) was added. The reaction mixture was heated to 150° C. for 2 h. Volatiles were removed, and the residue was purified using silica gel chromatography.

Deprotection of the BOC Protecting Group

The product obtained from Buchwald coupling was dissolved in CH$_2$Cl$_2$, and TFA was added at room temperature (rt or r.t.). The reaction mixture was stirred for 2 h and concentrated under reduced pressure. The resulting free amine crude product was purified using silica gel flash chromatography eluted with CH$_2$Cl$_2$/methanol (10:1).

Preparation of Nitrobenzamide

The free amine crude product was dissolved in pyridine, and nitrobenzoyl chloride (1.2 equiv.) was added. After stirring for 2 h at 80° C., the reaction mixture was concentrated, and the resulting nitrobenzamide crude product was used in the next step without further purification.

Reduction of the Nitrobenzamide

The nitrobenzamide crude product was suspended in ethyl acetate/methanol (5:1) and treated with SnCl$_2$ (2.5 equiv.). After stirring for 2-5 h at 80° C., the reaction mixture was cooled to room temperature and poured into saturated aqueous NaHCO$_3$. The mixture was stirred for 10 min, and the aqueous phase was extracted a few times with a mixture of chloroform and 2-propanol (4:1). The combined organic layers were washed with water and brine, dried over MgSO$_4$, filtered through a pad of Celite®, and concentrated under reduced pressure. The resulting crude product was purified using silica gel flash chromatography eluted with CH$_2$Cl$_2$/methanol (10:1).

Preparation of Acrylamide

To a DMF solution of the product obtained from reducing the nitrobenzamide was added DIPEA (1.2 equiv.). The reaction mixture was cooled to −60° C. and treated with 4-chlorobut-2-enoyl chloride (5.0 equiv.) in CH$_2$Cl$_2$. The reaction mixture was stirred for 10 min at −60° C. and then treated with a solution of dimethylamine in THF. The reaction mixture was then warmed to room temperature, stirred for 1 h, and concentrated under reduced pressure. The resulting acrylamide crude product was purified by preparative HPLC.

Deprotection of the Benzenesulfonyl Group

The acrylamide obtained from the previous step was dissolved in 1,4-dioxane, and a 1 M solution of sodium hydroxide was added. The reaction mixture was stirred at 40° C. for 40 min and neutralized with 1 M hydrochloride. Volatiles were removed under reduced pressure, and the residue was purified by preparative HPLC to give the final product as a salt.

Preparation of Exemplary Compounds

Example 1.1. (E)-N-(4-(N-(3-(5-chloro-4-(1H-indol-3-yl)pyrimidin-2-ylamino)phenyl)sulfamoyl)phenyl)-4-(dimethylamino)but-2-enamide (I-52)

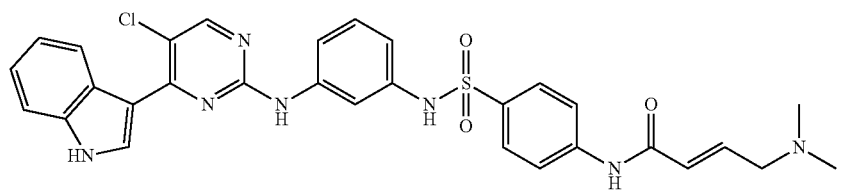 [SMILES: CN(C)C/C=C/C(=O)Nc1ccc(S(=O)(=O)Nc2cccc(Nc3ncc(Cl)c(-c4c[nH]c5ccccc45)n3)c2)cc1]

tert-butyl 3-aminophenylcarbamate

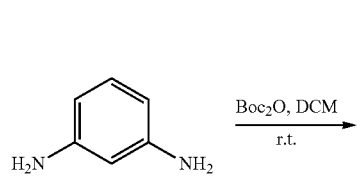

To a suspension of m-phenylenediamine (17.8 g, 0.165 mol) in DCM (94 mL) was added dropwise (over one hour) a solution of di-tert-butyldicarbonate (6.0 g, 27.5 mmol) in DCM (250 mL). The solution was stirred 72 h at room temperature before being evaporated to dryness under reduced pressure. The residual oil was dissolved in EtOAc (100 mL), washed with 1M Na$_2$CO$_3$ (100 mL) and the aqueous layer was extracted with EtOAc (2×100 mL). The combined organic layers were washed with brine (50 mL), dried (MgSO$_4$), filtered, and evaporated under reduce pressure. The residue was purified by SiO$_2$ chromatography (Hex/AcOEt 0 to 50% gradient) to afford the title compound (4.75 g, 0.023 mol, 83%) as a white solid.

tert-butyl 3-(4-nitrophenylsulfonamido)phenylcarbamate

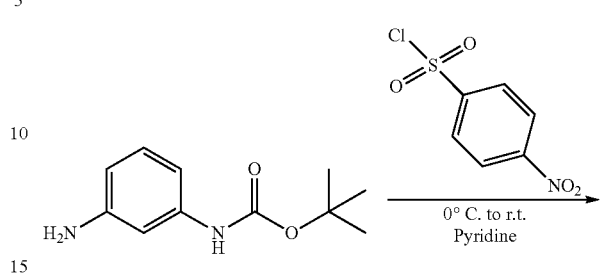

-continued

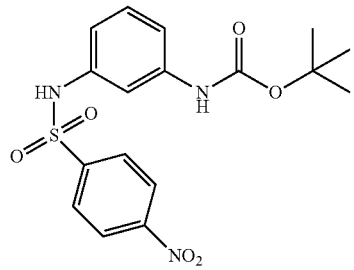

To a solution of tert-butyl 3-aminophenylcarbamate (0.500 g, 2.40 mmol) in pyridine (5 mL) under N$_2$ was added 4-nitrobenzene-1-sulfonyl chloride (0.532 g, 2.40 mmol). The mixture was stirred 21 h at ambient temperature, the solvent was removed under reduced pressure and azeotroped 3 times with toluene. The residue was purified by SiO$_2$ chromatography (Hex/AcOEt 0 to 30%) affording the title compound (937 mg, 2.38 mmol, 99%) as light yellow foam.

N-(3-aminophenyl)-4-nitrobenzenesulfonamide trifluoroacetate

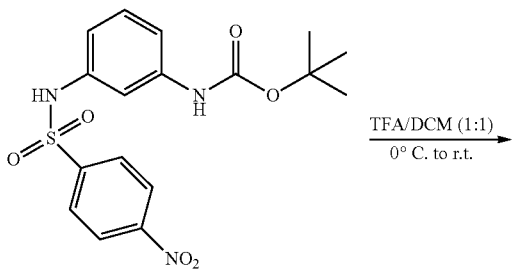

-continued

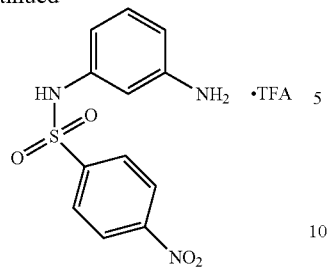

Trifluoroacetic acid (5 mL, 65 mmol) was added to a 0° C. stirring solution of tert-butyl 3-(4-nitrophenylsulfonamido)phenylcarbamate (0.937 g, 2.38 mmol) in DCM (5 mL). The resulting solution was stirred for 1 h at ambient temperature, concentrated under reduced pressure, azeotroped 3x with toluene affording the title compound (887 mg, 2.18 mmol, 92%) as a light yellow solid.

N-(3-(5-chloro-4-(1-(phenylsulfonyl)-1H-indol-3-yl)pyrimidin-2-ylamino)phenyl)-4-nitrobenzenesulfonamide

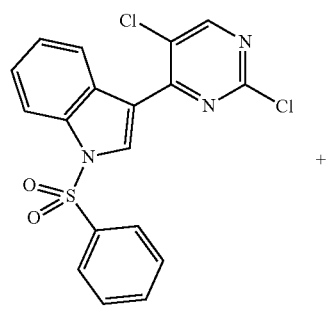

+

-continued

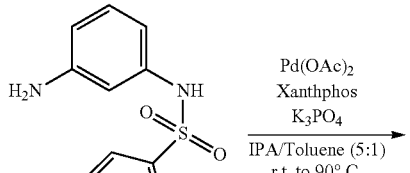

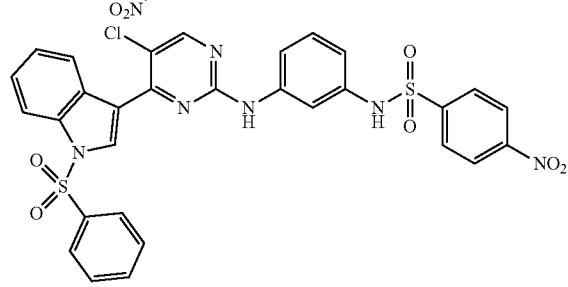

Pd(OAc)$_2$ (15.3 mg, 0.068 mmol), Xanthphos (79 mg, 0.136 mmol) and K$_3$PO$_4$ (1.09 g, 5.12 mmol) were added to a stirring solution of N-(3-aminophenyl)-4-nitrobenzenesulfonamide trifluoroacetate salt (500 mg, 1.71 mmol) and 3-(2,5-dichloropyrimidin-4-yl)-1-(phenylsulfonyl)-1H-indole (759 mg, 1.88 mmol) in degassed 5:1 IPA/toluene (17 mL) and the resulting solution was heated overnight at 90° C. The cooled mixture was diluted with EtOAc (40 mL), filtered through Celite with EtOAc then 9:1 DCM/MeOH. The resulting solution was concentrated under reduced pressure and the mixture was purified on SiO$_2$ chromatography (DCM/EtOAc 0 to 40%), affording the title compound (859 mg, 1.30 mmol, 76%) as light yellow foam.

4-amino-N-(3-(5-chloro-4-(1-(phenylsulfonyl)-1H-indol-3-yl)pyrimidin-2-ylamino)phenyl)benzenesulfonamide

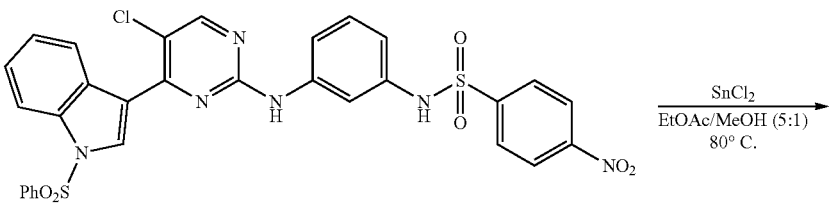

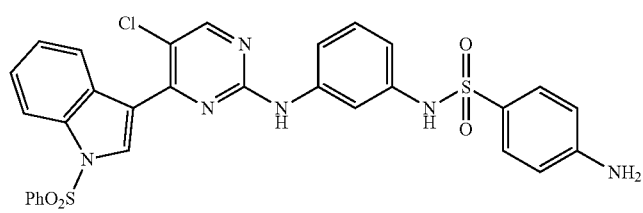

Tin (II) chloride dehydrate (734 mg, 3.25 mmol) was added to a stirring solution of N-(3-(5-chloro-4-(1-(phenylsulfonyl)-1H-indol-3-yl)pyrimidin-2-ylamino)phenyl)-4-nitrobenzenesulfonamide (859 mg, 1.30 mmol) in EtOAc/EtOH (5/1; 10 mL). The resulting solution was heated 2 h at 90° C. in a seal tube. The cooled reaction mixture was diluted with sat. NaHCO₃ (10 mL) and the mixture was stirred 10 min at ambient temperature. The layers were separated and the aqueous phase was extracted with CHCl₃/IPA (4:1, 4×10 mL). The combined organic layers were washed with water (10 mL) and brine (10 mL), dried (MgSO₄), filtered through a pad of Celite, and concentrated under reduced pressure. The residue was purified by SiO₂ chromatography (Hex/EtOAc 0 to 60% gradient), affording the title compound (529 mg, 0.838 mmol, 65%) as bright yellow-orange solid.

(E)-N-(4-(N-(3-(5-chloro-4-(1-(phenylsulfonyl)-1H-indol-3-yl)pyrimidin-2-ylamino)phenyl)sulfamoyl)phenyl)-4-(dimethylamino)but-2-enamide

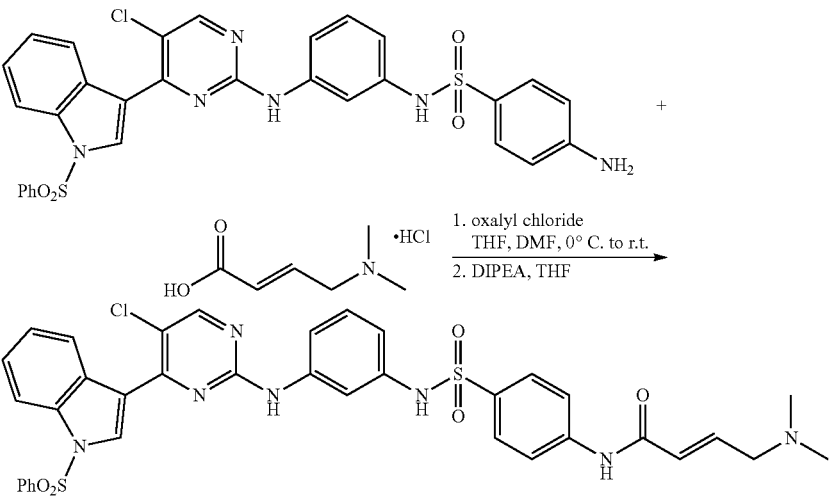

Oxalyl chloride (41 μL, 0.475 mmol) was added to a stirring solution of carboxylic acid (29.0 mg, 0.174 mmol) in THF (2 mL) and DMF (2 μL). After 3 h at ambient temperature, the mixture was concentrated under reduced pressure and re-suspended with THF (1 mL). A solution of DIPEA (248 μL, 1.43 mmol) and 4-amino-N-(3-(5-chloro-4-(1-(phenylsulfonyl)-1H-indol-3-yl)pyrimidin-2-ylamino)phenyl)benzenesulfonamide (100 mg, 0.158 mmol) in THF (1 mL) was then added to the previous suspension and the resulting mixture was stirred 2 h at ambient temperature. The mixture was concentrated under pressure affording the title compound (117 mg, 0.158 mmol, 100%) as bright brown foam which was used in the next step without further purification.

(E)-N-(4-(N-(3-(5-chloro-4-(1H-indol-3-yl)pyrimidin-2-ylamino)phenyl)sulfamoyl)phenyl)-4-(dimethylamino)but-2-enamide (I-52)

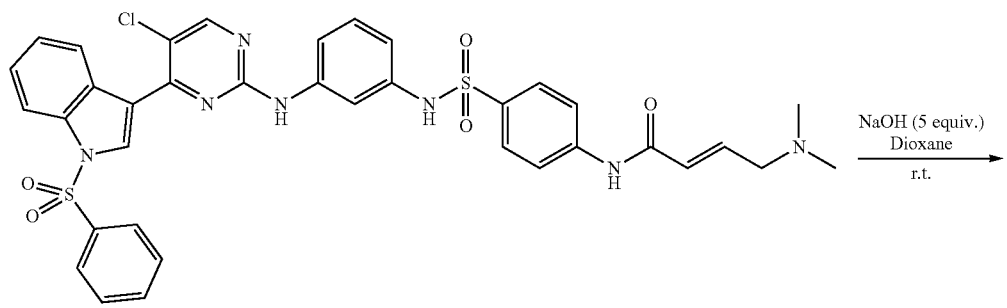

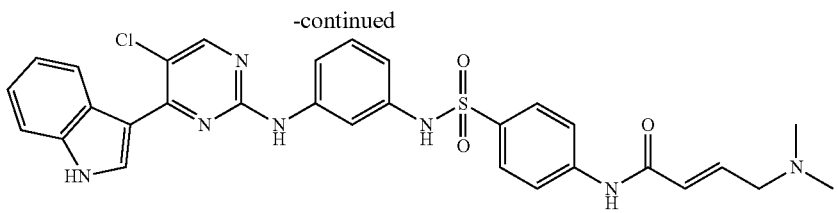

A solution of (E)-N-(4-(N-(3-(5-chloro-4-(1-(phenylsulfonyl)-1H-indol-3-yl)pyrimidin-2-ylamino)phenyl)sulfamoyl)phenyl)-4-(dimethylamino)but-2-enamide (117 mg, 0.158 mmol) and NaOH 5M (0.16 mL, 0.793 mmol) in dioxane (5 mL) was heated overnight at 50° C. The cooled mixture was diluted with CHCl₃/IPA 5/1 (10 mL), washed with water (5 mL), dried (MgSO₄), filtered, and concentrated under reduced pressure. The residue was purified by reverse phase chromatography (C18, water/ACN 20 to 70%, gradient), affording the title compound (7.1 mg, 0.012 mmol, 7%) as white solid after lyophilisation.

$^1$H NMR (500 MHz, DMSO-d6) δ 11.92 (s, 1H), 10.57 (s, 1H), 10.15 (s, 1H), 9.63 (s, 1H), 8.60 (d, J=7.7 Hz, 1H), 8.50 (d, J=3.1 Hz, 1H), 8.42 (s, 1H), 7.80-7.76 (m, 3H), 7.54 (s, 1H), 7.49 (d, J=8.1 Hz, 2H), 7.30 (d, J=7.9 Hz, 1H), 7.22 (t, J=7.5 Hz, 1H), 7.13 (d, J=7.1 Hz, 1H), 7.10 (t, J=8.1 Hz, 1H), 6.76 (ddd, J=15.0, 6.6, 6.6 Hz, 1H), 6.68 (d, J=8.0 Hz, 1H), 6.37 (d, J=14.7 Hz, 1H), 2.65 (s, 2H), 2.50 (s, 6H); MS (m/z): 604.59 [M+1]⁺.

Example 1.2. (E)-N-(3-(5-cyano-4-(1H-indol-3-yl)pyrimidin-2-ylamino)phenyl)-4-(4-(dimethylamino)but-2-enamido)benzamide (I-53)

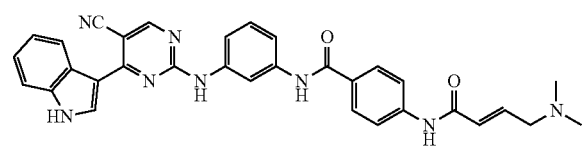 [SMILES: CN(C)C/C=C/C(=O)Nc1ccc(C(=O)Nc2cccc(Nc3ncc(C#N)c(-c4c[nH]c5ccccc45)n3)c2)cc1]

tert-butyl 4-(3-(2-oxo-2-phenylethylideneamino)phenylcarbamoyl)phenylcarbamate

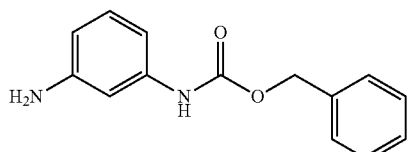

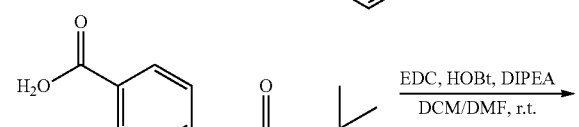

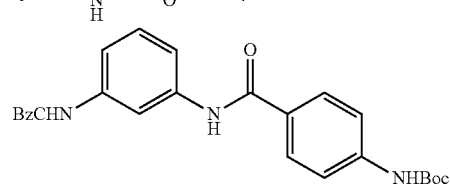

To a solution of 4-(tert-butoxycarbonylamino)benzoic acid (9.79 g, 41.28 mmol) in DCM (206 mL) and DMF (206 mL) was added EDC (8.7 g, 41.28 mmol), HOBt (6.95 g, 45.4 mmol) and diisopropylethylamine (28.76 mL, 165.11 mmol). The mixture was stirred for 30 min at ambient temperature before addition of benzyl 3-aminophenylcarbamate (10 g, 41.28 mmol) was added. The reaction mixture was stirred overnight at ambient temperature, diluted with EtOAc (500 mL), washed with sat. NaHCO₃ (100 mL), brine (100 mL), dried (Na₂SO₄), concentrated, affording the title compound (13.15 g, 28.5 mmol, 69%) as colorless glue.

tert-butyl 4-(3-aminophenylcarbamoyl)phenylcarbamate

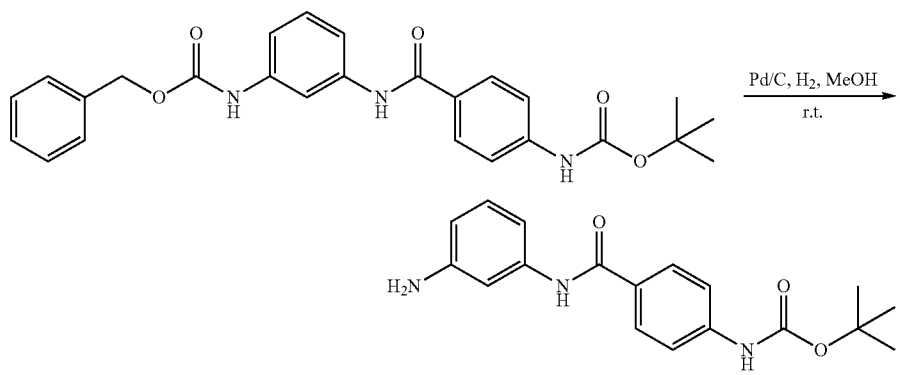

To a degassed solution of tert-butyl 4-(3-(2-oxo-2-phenylethylideneamino)phenylcarbamoyl)phenylcarbamate (13.15 g, 28.5 mmol) in MeOH (570 mL) was added 10% Pd/C (1.52 g, 1.42 mmol) and the mixture was stirred 96 h under H$_2$ (1 Atm.). The mixture was filtrated over Celite (MeOH), concentrated under reduced pressure; the residue was purified by SiO$_2$ chromatography (Hex/EtOAc 25 to 40%) to afford the title compound (9.31 g, 28.5 mmol, 100%) as a brownish solid.

4-amino-N-(3-(5-chloro-4-(1-(phenylsulfonyl)-1H-indol-3-yl)pyrimidin-2-ylamino)phenyl)benzamide

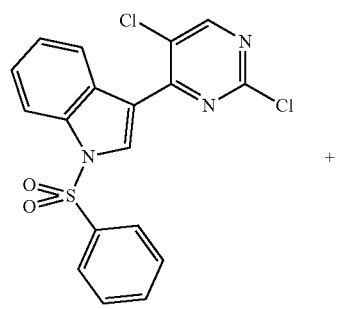

+

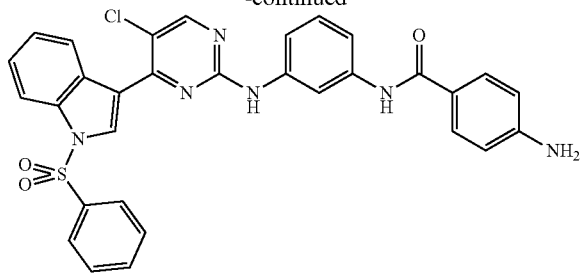

A solution of 3-(2,5-dichloropyrimidin-4-yl)-1-(phenylsulfonyl)-1H-indole (350 mg, 0.87 mmol) and tert-butyl 4-(3-aminophenylcarbamoyl)phenylcarbamate (283 mg, 0.87 mmol) in NMP (2.3 mL, 0.25M) was heated 30 min at 175° C. (μW). The cooled mixture was diluted with EtOAc (20 mL), washed with water (3×5 mL), brine (5 mL), dried (MgSO$_4$), filtered, and concentrated under reduced pressure. The residue was purified by SiO$_2$ chromatography (DCM/EtOAc 0 to 30% gradient), affording the title compound (180 mg, 0.303 mmol, 35%) as white solid.

4-amino-N-(3-(5-cyano-4-(1-(phenylsulfonyl)-1H-indol-3-yl)pyrimidin-2-ylamino)phenyl)benzamide

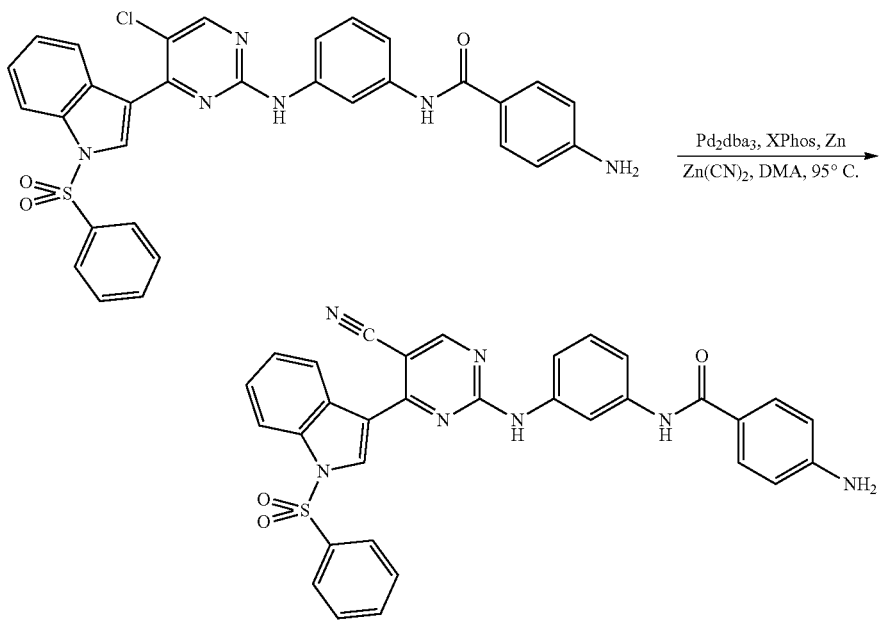

-continued

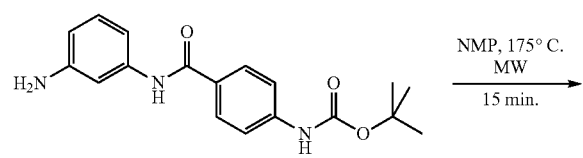

NMP, 175° C.
MW
15 min.

A degassed solution of 4-amino-N-(3-(5-chloro-4-(1-(phenylsulfonyl)-1H-indol-3-yl)pyrimidin-2-ylamino)phenyl)benzamide (181 mg, 0.3 mmol), zinc dust (2 mg, 0.03 mmol), Pd$_2$dba$_3$ (27.9 mg, 0.03 mmol), Xphos (29.0 mg, 0.06 mmol) and zinc cyanide (2.2 mg, 0.18 mmol) in DMA (4.1 mL) was heated 2 h at 95° C. The cooled mixture was diluted with EtOAc (20 mL), washed with water (5 mL), brine (5 mL), dried (MgSO$_4$), filtered, and concentrated under reduced pressure. The residue was purified by SiO$_2$ chromatography (DCM/EtOAc 0 to 30% gradient), affording the title compound (96 mg, 0.164 mmol, 54%) as a yellowish glue.

4-amino-N-(3-(5-cyano-4-(1H-indol-3-yl)pyrimidin-2-ylamino)phenyl)benzamide

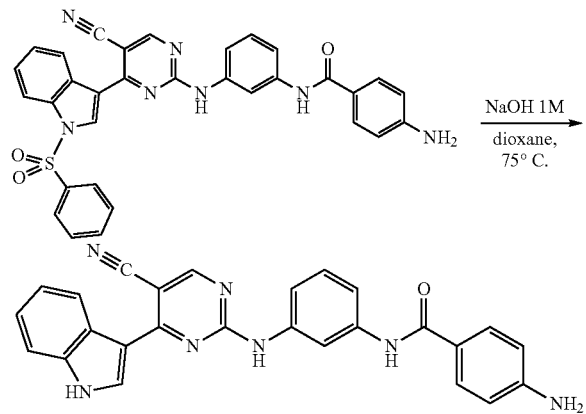

A solution of 4-amino-N-(3-(5-cyano-4-(1-(phenylsulfonyl)-1H-indol-3-yl)pyrimidin-2-ylamino)phenyl)benzamide (15 mg, 0.03 mmol) in 1,4-dioxane (0.17 mL) and 5M NaOH (0.05 mL, 0.26 mmol) was heated 2 h at 75° C. The cooled mixture was concentrated under reduced pressure. The residue was purified by reverse phase chromatography (C18, water/ACN 5 to 100% gradient), affording the title compound (4.4 mg, 0.010 mmol, 39%).

(E)-N-(3-(5-cyano-4-(1-(phenylsulfonyl)-1H-indol-3-yl)pyrimidin-2-ylamino)phenyl)-4-(4-(dimethylamino)but-2-enamido)benzamide

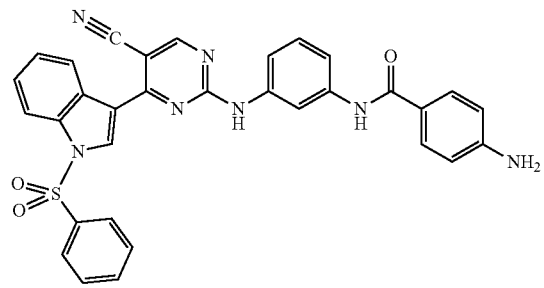

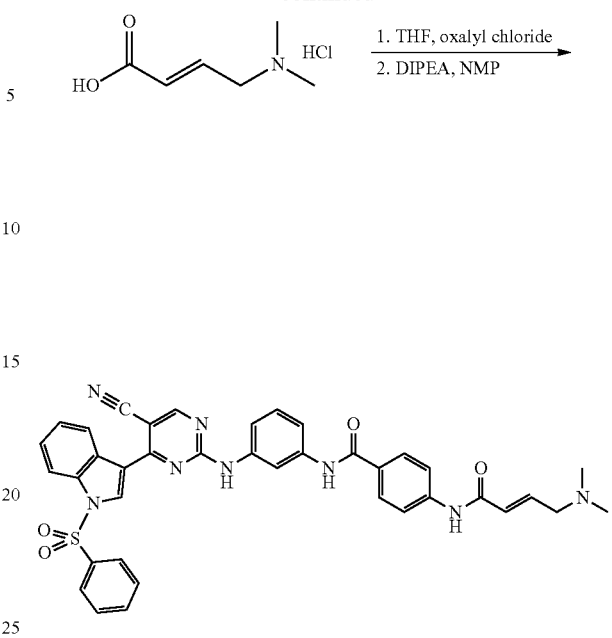

To a cooled (0° C.) solution of (E)-4-(dimethylamino)-2-butenoic acid hydrochloride (22.1 mg, 0.13 mmol) in THF (1.33 mL) and a catalytic amount of DMF was added oxalyl chloride (57 μL, 0.67 mmol). The mixture was stirred 2 h at ambient temperature and the resulting suspension was concentrated under reduced pressure and co-evaporated 3 times with THF. The residue was re-dissolved in THF (1.5 mL), cooled to 0° C., and a solution of 4-amino-N-(3-(5-cyano-4-(1H-indol-3-yl)pyrimidin-2-ylamino)phenyl)benzamide (39 mg, 0.07 mmol) in THF (1 mL) was added dropwise. The mixture was stirred 3 h at ambient temperature and diluted with 1:10 CHCl$_3$/IPA (10 mL) and water (5 mL). The aqueous layer was extracted with 1:10 CHCl$_3$/IPA (3*5 mL), the combined organic layers were washed with brine (5 mL), dried (MgSO$_4$), filtered, and concentrated under reduced pressure to afford the title compound (61 mg, 0.088 mmol, 67%) as a yellowish oil which was used in the next step without purification.

(E)-N-(3-(5-cyano-4-(1H-indol-3-yl)pyrimidin-2-ylamino)phenyl)-4-(4-(dimethylamino)but-2-enamido)benzamide (I-53)

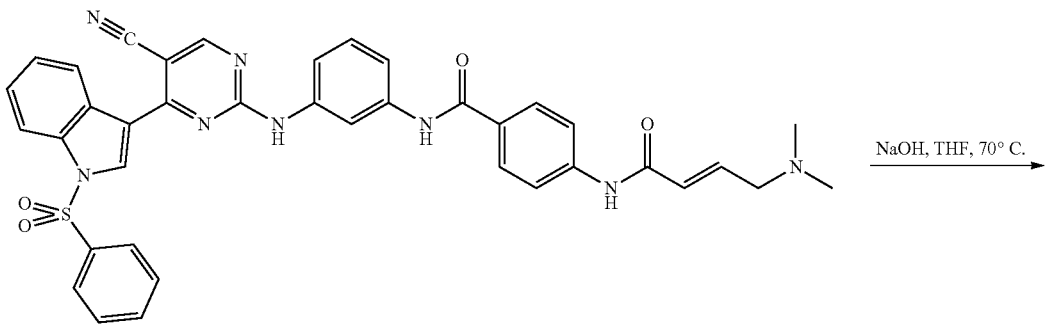

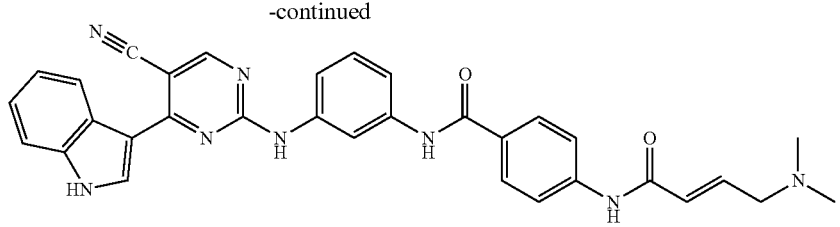

A solution of (E)-N-(3-(5-cyano-4-(1-(phenylsulfonyl)-H-indol-3-yl)pyrimidin-2-ylamino)phenyl)-4-(4-(dimethylamino)but-2-enamido)benzamide (61 mg, 0.088 mmol) and 1M NaOH (0.66 mL, 0.66 mmol) in THF (1.32 mL) was heated 3 h at 70° C. The cooled mixture was treated with 1M HCl (0.66 mL, 0.66 mmol) and directly injected on preparative reverse phase LC-MS (0.1% $(NH_4)_2CO_3$ Water/ACN $NH_4HCO_3$), affording the title compound (1.2 mg, 0.002 mmol, 3.2%) as a white solid after lyophilisation.

$^1$H NMR (500 MHz, DMSO) δ 11.99 (s, 1H), 10.27 (s, 1H), 10.18 (s, 1H), 10.10 (s, 1H), 8.73 (s, 1H), 8.49 (s, 1H), 8.13 (s, 1H), 7.86 (d, J=8.4 Hz, 2H), 7.71 (d, J=8.8 Hz, 2H), 7.51-7.36 (m, 3H), 7.26 (t, J=8.1 Hz, 1H), 7.18-6.97 (m, 3H), 6.72 (dt, J=15.3, 5.8 Hz, 1H), 6.24 (dt, J=15.3, 1.4 Hz, 1H), 3.01 (dd, J=5.9, 1.4 Hz, 2H), 2.50 (s, 3H), 2.12 (s, 3H); MS (m/z): 557.65 [M+I]$^+$.

Example 1.3. (E)-N-(3-(5-chloro-4-(1H-indol-3-yl)pyridin-2-ylamino)phenyl)-4-(4-(dimethylamino)but-2-enamido)benzamide (I-54)

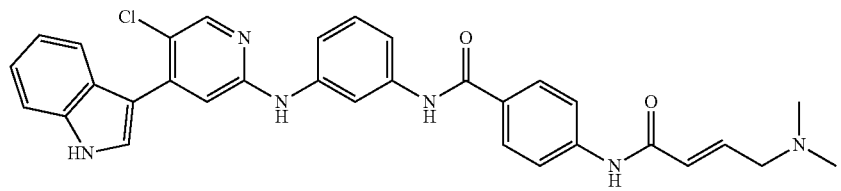 [SMILES: CN(C)C/C=C/C(=O)Nc1ccc(C(=O)Nc2cccc(Nc3cc(-c4c[nH]c5ccccc45)c(Cl)cn3)c2)cc1]

3-(2-bromo-5-chloropyridin-4-yl)-1-(phenylsulfonyl)-1H-indole

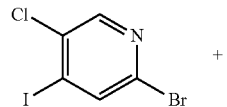

+

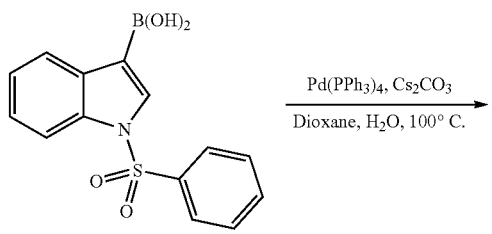

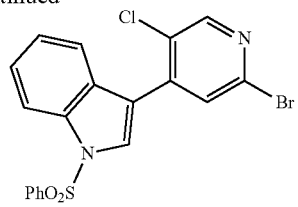

A degassed solution of 2-bromo-5-chloro-4-iodopyridine (0.5 g, 1.57 mmol), 1-(phenylsulfonyl)-1H-indol-3-ylboronic acid (0.497 g, 1.65 mmol) Pd(PPh$_3$)$_4$ (181 mg, 0.16 mmol) and cesium carbonate (1.023 g, 3.14 mmol) in 2:1 dioxane/water (52 mL) was heated 3 h at 100° C. The cooled mixture was diluted with EtOAc (50 mL) and sat. NaHCO$_3$ (20 mL). The aqueous layer was extracted with EtOAc (3×20 mL), the combined organics layers were dried (MgSO$_4$), filtered, and concentrated under reduced pressure. The residue was purified by SiO$_2$ chromatography (Hex/EtOAc 5 to 70% gradient), affording the title compound (373 mg, 0.833 mmol, 53%) as white solid.

benzyl 3-aminophenylcarbamate

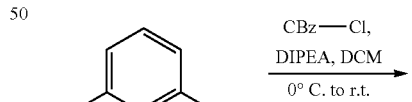

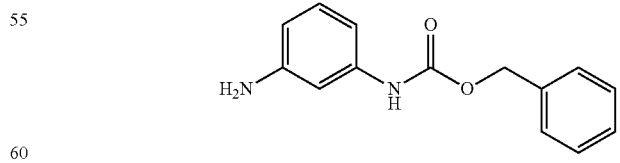

To a stirred solution of m-phenylenediamine (20.0 g, 0.185 mol) and N,N-diisopropylethylamine (32.2 mL, 0.185 mol) in DCM (616 mL) at 0° C. was slowly added benzyl chloroformate (26.0 mL, 0.185 mol). The mixture was stirred at 0° C. for 2 h and then warmed to ambient temperature for 2 h. The mixture was washed with sat.

NaHCO$_3$ (100 mL), brine (50 mL), dried (Na$_2$SO$_4$), and concentrated under reduced pressure. The residue was purified by SiO$_2$ chromatography (Hex/EtOAc 10 to 50% gradient), affording the title compound (20.96 g, 0.087 mol, 47%) as colorless syrup.

tert-butyl 4-(3-(5-chloro-4-(1-(phenylsulfonyl)-1H-indol-3-yl)pyridin-2-ylamino)phenylcarbamoyl)phenylcarbamate

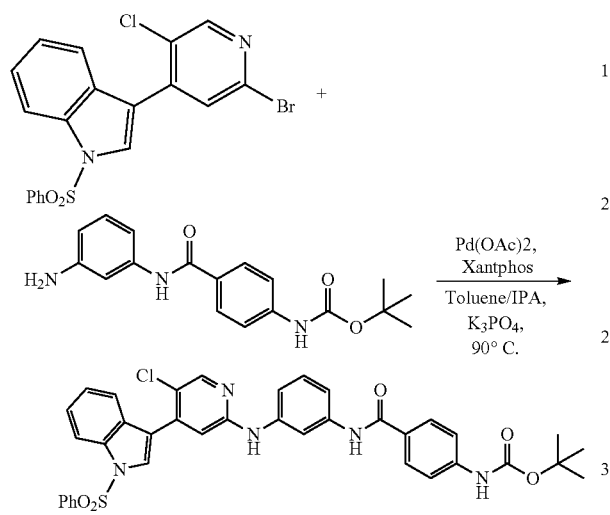

A degassed solution of 2-bromo-5-chloro-pyridine (0.1 g, 0.22 mmol), tert-butyl 4-(3-aminophenylcarbamoyl)phenylcarbamate (0.084 g, 0.2 mmol), K$_3$PO$_4$ (95 mg, 0.45 mmol), Pd(OAc)$_2$ (4 mg, 0.02 mmol) and Xantphos (31 mg, 0.05 mmol) in 5:1 IPA/toluene (2.3 mL) was heated 3 h at 90° C. The cooled mixture was filtered through Celite with EtOAc and the filtrate was concentrated under reduce pressure. The residue was purified by SiO$_2$ chromatography (Hex/EtOAc 0 to 55% gradient), affording the title compound (121 mg, 0.174 mmol, 78%) as a white solid.

4-amino-N-(3-(5-chloro-4-(1H-indol-3-yl)pyridin-2-ylamino)phenyl)benzamide

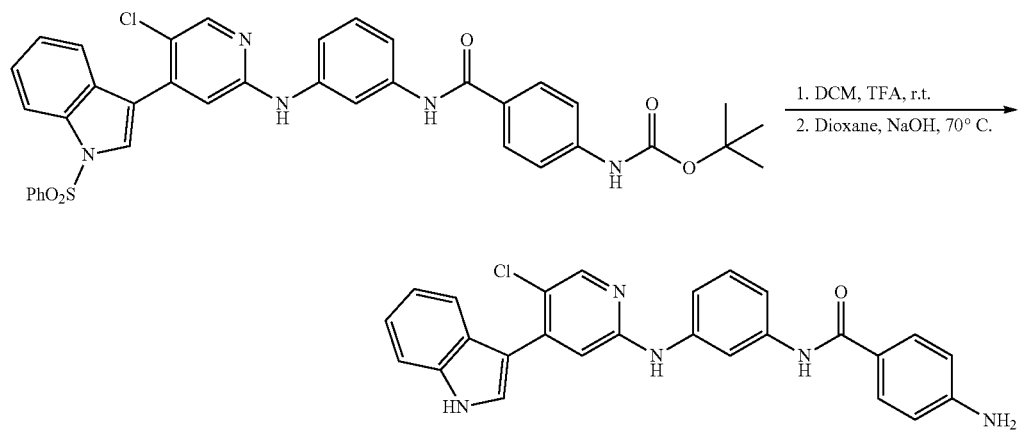

A solution of tert-butyl 4-(3-(5-chloro-4-(1-(phenylsulfonyl)-1H-indol-3-yl)pyridin-2-ylamino)phenylcarbamoyl) phenylcarbamate (121 mg, 0.17 mmol) in DCM (1.2 mL) was treated with TFA (0.13 mL, 1.74 mmol). The mixture was stirred overnight at ambient temperature, concentrated under reduced pressure, and co-evaporated with 1,4-dioxane (2×2 mL). The residue was dissolved in 1,4-dioxane (3.5 mL), a 5M NaOH solution (0.52 mL, 2.6 mmol) was added, and the mixture was heated for 3 h at 70° C. The cooled mixture was treated with HCl 1M (2.6 mL, 2.6 mmol) and concentrated under reduce pressure. The residue was purified by SiO$_2$ chromatography (DCM/EtOAc 0 to 40% gradient), affording the title compound (52 mg, 0.115 mmol, 66%) as a yellowish solid.

(E)-N-(3-(5-chloro-4-(1H-indol-3-yl)pyridin-2-ylamino)phenyl)-4-(4-(dimethylamino)but-2-enamido)benzamide (I-54)

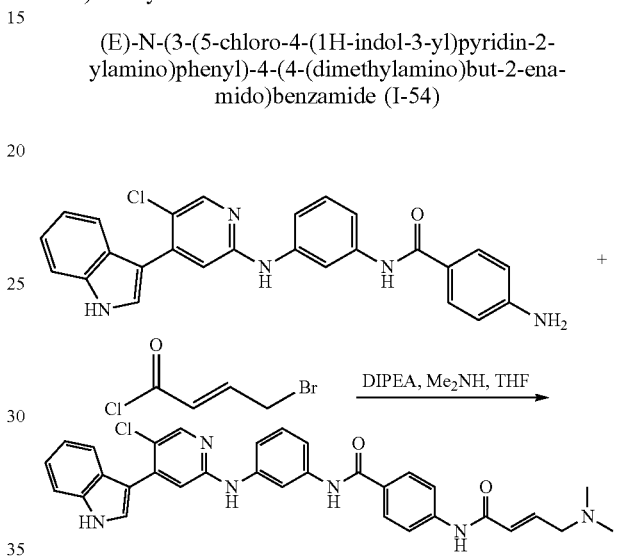

To a cooled (−60° C.) solution of 4-amino-N-(3-(5-chloro-4-(1H-indol-3-yl)pyridin-2-ylamino)phenyl)benzamide (48 mg, 0.11 mmol) in THF (1.3 mL) and DIPEA (57 µL, 0.33 mmol) was added a 55.6 mg/mL solution of (E)-4-bromobut-2-enoyl chloride in THF (545 µL, 0.11 mmol). The mixture was stirred 1.5 h at −60° C. before addition of a 2M solution of dimethylamine in THF (159 µL, 0.32 mmol). The mixture was stirred 14 h at ambient temperature and diluted with 15:1 CHCl$_3$/IPA (10 mL) and sat. NaHCO$_3$ (5 mL). The aqueous layer was extracted with 15:1 CHCl₃/IPA (3×5 mL), washed with brine (10 ml), dried (MgSO₄), filtered, and concentrated under reduced pressure. The residue was purified by reverse phase chromatography (C18, water/ACN 5 to 100% gradient), affording the title compound (6.4 mg, 0.011 mmol, 11%) as white solid after lyophilisation.

¹H NMR (500 MHz, DMSO) δ 11.66 (d, J=2.3 Hz, 1H), 10.33 (s, 1H), 10.09 (s, 1H), 9.26 (s, 1H), 8.26 (s, 1H), 8.11 (t, J=1.8 Hz, 1H), 7.96 (d, J=8.8 Hz, 2H), 7.85 (d, J=2.7 Hz, 1H), 7.79 (d, J=8.8 Hz, 2H), 7.75 (d, J=8.0 Hz, 1H), 7.55-7.45 (m, 2H), 7.31-7.16 (m, 4H), 7.13 (ddd, J=8.0, 7.0, 1.0 Hz, 1H), 6.79 (dt, J=15.4, 5.8 Hz, 1H), 6.31 (dt, J=15.4, 1.6 Hz, 1H), 3.08 (dd, J=5.8, 1.4 Hz, 2H), 2.19 (s, 6H); MS (m/z): 565.4 [M+1]⁺.

Example 1.4. (E)-N-(4-(N-(3-(5-cyano-4-(1H-indol-3-yl)pyrimidin-2-ylamino)phenyl)sulfamoyl)phenyl)-4-(dimethylamino)but-2-enamide (I-55)

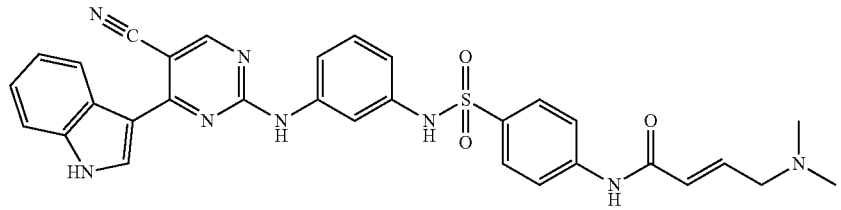 [SMILES: CN(C)C/C=C/C(=O)Nc1ccc(S(=O)(=O)Nc2cccc(Nc3ncc(C#N)c(-c4c[nH]c5ccccc45)n3)c2)cc1]

4-amino-N-(3-(5-cyano-4-(1-(phenylsulfonyl)-1H-indol-3-yl)pyrimidin-2-ylamino)phenyl)benzenesulfonamide

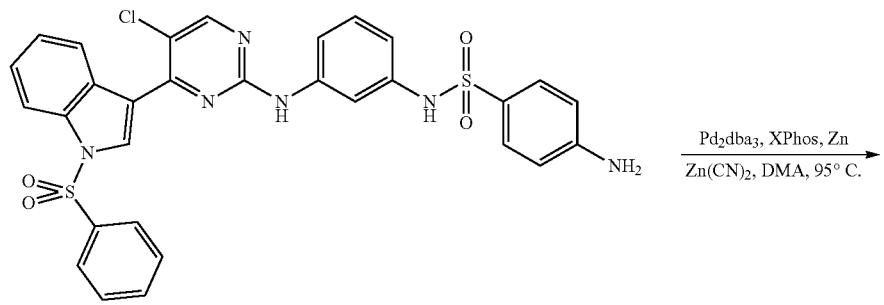

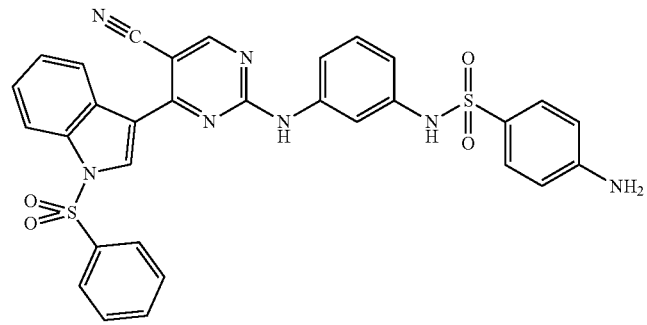

A degassed solution of 4-amino-N-(3-(5-chloro-4-(1-(phenylsulfonyl)-1H-indol-3-yl)pyrimidin-2-ylamino)phenyl)benzenesulfonamide (197 mg, 0.312 mmol), zinc dust (2.0 mg, 0.03 mmol), Pd₂dba₃ (28.6 mg, 0.03 mmol), Xphos (29.8 mg, 0.06 mmol) and zinc cyanide (22.0 mg, 0.19 mmol) in DMA (6 mL) was heated 75 min at 95° C. The cooled mixture was diluted with EtOAc (15 mL), washed with water (3×5 mL), brine (5 mL), dried (MgSO₄), filtered, and concentrated, affording the title compound (194 mg, 0.312 mmol, 100%) as a white solid which was used in the next step without further purification.

(E)-N-(4-(N-(3-(5-cyano-4-(1H-indol-3-yl)pyrimidin-2-ylamino)phenyl)sulfamoyl)phenyl)-4-(dimethylamino)but-2-enamide (I-55)

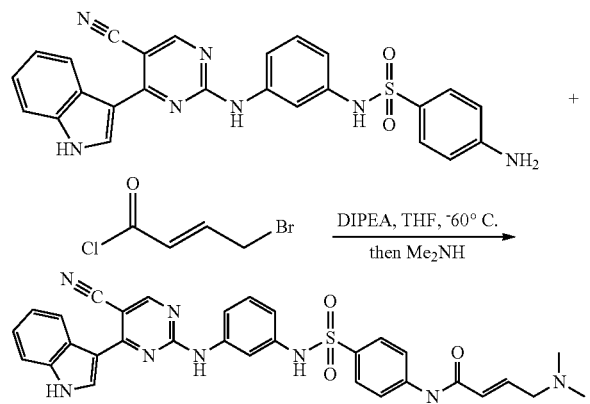

To a −60° C. solution of 4-amino-N-(3-(5-cyano-4-(1-(phenylsulfonyl)-1H-indol-3-yl)pyrimidin-2-ylamino)phenyl)benzenesulfonamide (73 mg, 0.1516 mmol) and DIPEA (79 µl, 0.4548 mmol) in THF (5.1 mL) was slowly added a 56 mg/mL solution of (E)-4-bromobut-2-enoyl chloride in THF (0.49 mL, 0.1516 mmol). After 1.25 h at −60° C. a 2M solution of dimethylamine in THF (0.30 mL, 0.5986 mmol) was added and the mixture was stirred 2 h at ambient temperature. The mixture was concentrated under reduced pressure. The residue was purified by reverse phase chromatography (C18, water/ACN 0 to 100% gradient), affording the title compound (22.1 mg, 0.037 mmol, 25%) as a white solid after lyophilisation.

$^1$H NMR (500 MHz, DMSO-d6) δ 12.06 (s, 1H), 10.66 (s, 1H), 10.26 (s, 1H), 10.17 (s, 1H), 8.76 (s, 1H), 8.53 (d, J=3.1 Hz, 1H), 7.86-7.73 (m, 3H), 7.53 (br s, 1H), 7.52 (d, J=8.2 Hz, 1H), 7.47 (d, J=8.1 Hz, 2H), 7.25 (t, J=7.3 Hz, 1H), 7.18 (t, J=8.1 Hz, 2H), 7.16 (br s, 1H), 6.80 (d, J=6.0 Hz, 1H), 6.77 (dt, J=14.4, 6.5 Hz, 1H), 6.43 (d, J=15.3 Hz, 1H), 3.88 (d, J=5.0 Hz, 2H), 2.74 (s, 6H); MS (m/z): 593.64 [M+1]$^+$.

Example 1.5. (E)-N-(5-(5-cyano-4-(1H-indol-3-yl)pyrimidin-2-ylamino)-2-methylphenyl)-4-(4-(dimethylamino)but-2-enamido)benzamide (I-56)

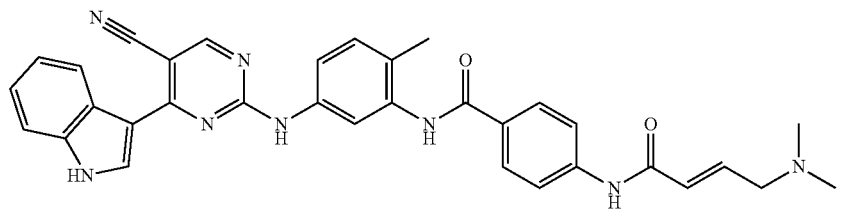 [SMILES: Cc1ccc(Nc2ncc(C#N)c(-c3c[nH]c4ccccc34)n2)cc1NC(=O)c1ccc(NC(=O)/C=C/CN(C)C)cc1]

4-amino-N-(5-(5-cyano-4-(1-(phenylsulfonyl)-1H-indol-3-yl)pyrimidin-2-ylamino)-2-methylphenyl)benzamide

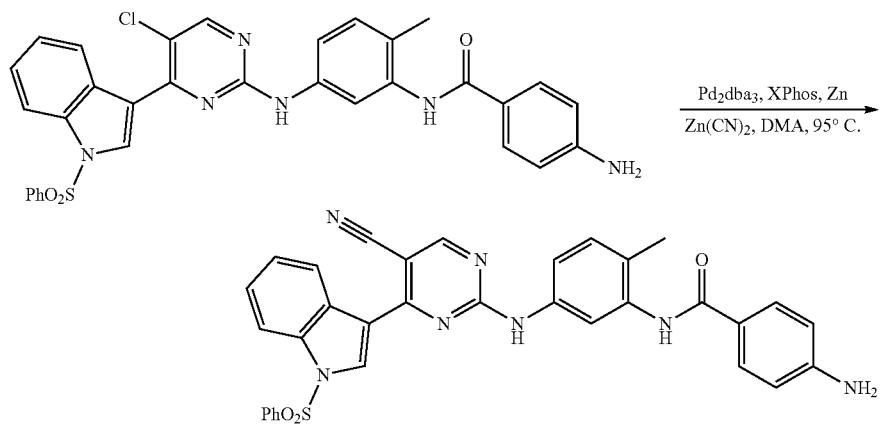

A degassed solution of 4-amino-N-(5-(5-chloro-4-(1-(phenylsulfonyl)-1H-indol-3-yl)pyrimidin-2-ylamino)-2-methylphenyl)benzamide (89 mg, 0.196 mmol), zinc dust (2 mg, 0.03 mmol), Pd$_2$dba$_3$ (27.9 mg, 0.03 mmol), Xphos (29.0 mg, 0.06 mmol) and zinc cyanide (2.2 mg, 0.18 mmol) in DMA (4.1 mL) was heated 2 h at 95° C. The cooled mixture was diluted with EtOAc (15 mL) was washed with water (3×5 mL), brine (5 mL), dried (MgSO$_4$), filtered, and concentrated under reduced pressure. The residue was purified by SiO$_2$ chromatography (Hex/EtOAc 20 to 100 gradient), affording the title compound (90 mg, 0.150 mmol, 77%) as a white solid.

4-amino-N-(5-(5-cyano-4-(1H-indol-3-yl)pyrimidin-2-ylamino)-2-methylphenyl)benzamide

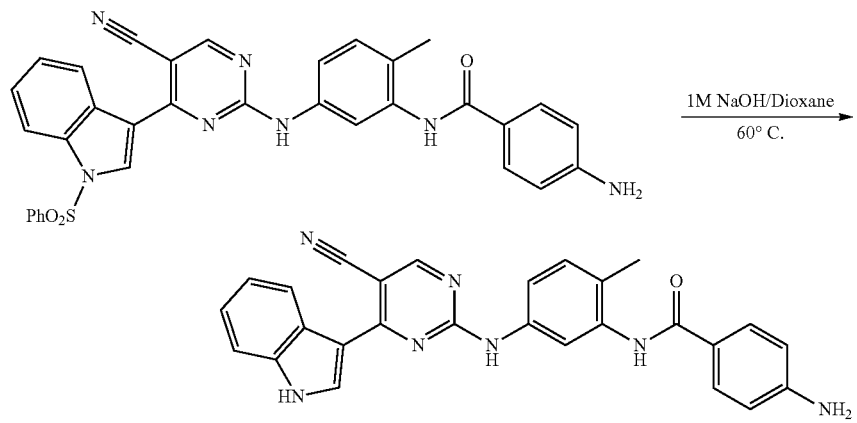

A solution of 4-amino-N-(5-(5-cyano-4-(1-(phenylsulfonyl)-1H-indol-3-yl)pyrimidin-2-ylamino)-2-methylphenyl)benzamide (75 mg, 0.125 mmol) and 1M NaOH (2 mL, 2 mmol) in dioxane (2 mL) was heated for 3 h at 60° C. The cooled mixture was diluted with DCM (15 mL), washed with water (5 mL), then dried (MgSO₄), filtered, and concentrated under reduced pressure to afford the title compound (57 mg, 0.123 mmol, 99%) as a yellow solid.

(E)-N-(5-(5-cyano-4-(1H-indol-3-yl)pyrimidin-2-ylamino)-2-methylphenyl)-4-(4-(dimethylamino)but-2-enamido)benzamide (I-56)

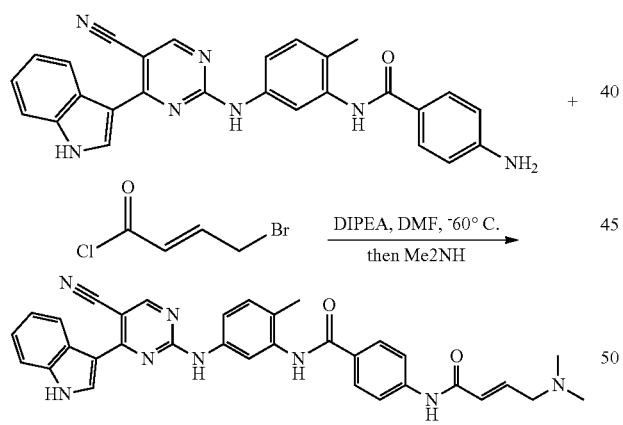

To a −30° C. solution of 4-amino-N-(5-(5-cyano-4-(1H-indol-3-yl)pyrimidin-2-ylamino)-2-methylphenyl)benzamide (57 mg, 0.123 mmol) and DIPEA (66 ul, 0.38 mmol) in DMF (1 mL) and THF (1 mL) was slowly added a 55 mg/mL solution of (E)-4-bromobut-2-enoyl chloride in THF (418 μL, 0.123 mmol). After 30 min at −30° C., a 2M solution of dimethylamine (400 μL, 0.8 mmol) was added and the resulting mixture was stirred for 1 h at ambient temperature. The mixture was concentrated under reduced pressure, the residue was purified by reverse phase chromatography (water/ACN+0.1% (NH₄)₂CO₃ 20 to 70% gradient), affording the title compound (14.1 mg, 0.031 mmol, 25%) as a white solid after lyophilisation.

$^1$H NMR (500 MHz, DMSO) δ 12.08 (s, 1H), 10.38 (s, 1H), 10.25 (s, 1H), 9.85 (s, 1H), 8.81 (s, 1H), 8.55 (s, 1H), 8.03-7.84 (m, 2H), 7.80 (d, J=8.7 Hz, 1H), 7.63-7.47 (m, 2H), 7.29-7.20 (m, 1H), 7.25-7.09 (m, 1H), 6.81 (dt, J=15.4, 5.8 Hz, 1H), 6.33 (d, J=15.4 Hz, 1H), 3.14-3.04 (m, 2H), 2.21 (s, 3H); MS (m/z): 571.64 [M+1]⁺.

Example 1.6. (E)-N-(3-(5-chloro-4-(1H-indol-3-yl)pyrimidin-2-ylamino)phenyl)-4-(4-(dimethylamino)but-2-enamido)-N-methylbenzamide (I-57)

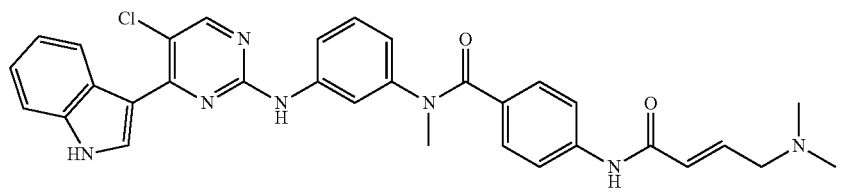 [SMILES: CN(C)C/C=C/C(=O)Nc1ccc(C(=O)N(C)c2cccc(Nc3ncc(Cl)c(-c4c[nH]c5ccccc45)n3)c2)cc1]

185 benzyl 3-(2,2,2-trifluoroacetamido)phenylcarbamate

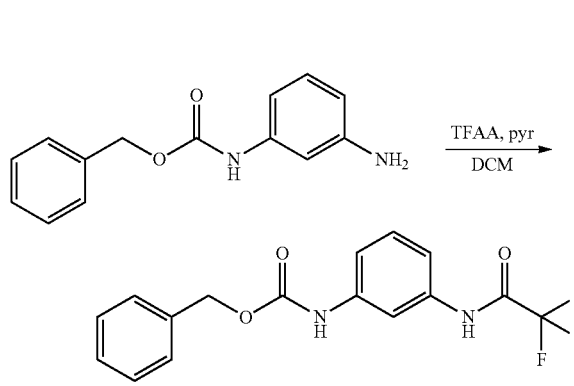

To a stirred solution of benzyl 3-aminophenylcarbamate (1.5 g, 6.19 mmol) and pyridine (1.25 mL, 15.5 mmol) in DCM (31 mL) was added TFAA (990 μL, 7.12 mmol). The mixture was stirred overnight at ambient temperature, diluted with DCM (50 mL), washed with 20% citric acid (30 mL), sat. NaHCO$_3$ (20 mL), dried (phase cartridge separator) and concentrated under reduced pressure. The residue was purified by SiO$_2$ chromatography (Hex/EtOAc 20 to 100% gradient), affording the title compound (1.97 g, 5.83 mmol, 94%) as an orange solid.

benzyl 3-(2,2,2-trifluoro-N-methylacetamido)phenylcarbamate

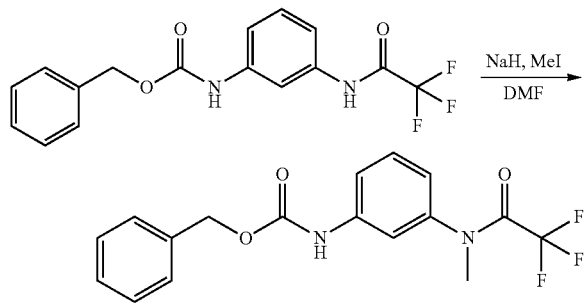

To a cooled (0° C.) solution of benzyl 3-(2,2,2-trifluoroacetamido)phenylcarbamate (1.97 g, 5.82 mmol) in DMF (15 mL) was added 60% NaH in oil (256 mg, 6.41 mmol). The mixture was stirred 15 min at ambient temperature before addition of iodomethane (381 μL, 0.868 mmol). The resulting mixture was stirred 4 h at ambient temperature, diluted with EtOAc (100 mL), washed with water (20 mL), brine (2×20 mL), dried (MgSO$_4$), filtered, and concentrated. The residue was purified by SiO$_2$ chromatography (Hex/EtOAc 5 to 60% gradient), affording the title compound (1.65 g, 4.69 mmol, 80%) as a colorless oil.

benzyl 3-(methylamino)phenylcarbamate

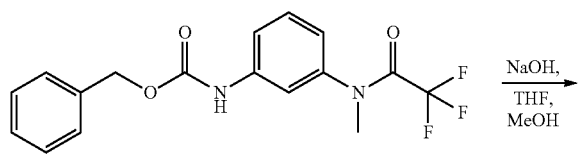

186

-continued

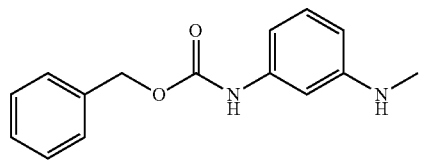

A solution of benzyl 3-(2,2,2-trifluoro-N-methylacetamido)phenylcarbamate (1.65 g, 4.68 mmol) and 5M NaOH solution (2.81 mL, 14.0 mmol) in 2:1 THF/MeOH (30 mL) was stirred 4 h at ambient temperature. The mixture was diluted with DCM (100 mL), washed with sat. NH$_4$Cl (20 mL), dried (phase cartridge separator), and concentrated under reduce pressure. The residue was purified by SiO$_2$ chromatography (Hex/EtOAc 10 to 100% gradient), affording the title compound (782 mg, 3.05 mmol, 65%) as a colorless oil. tert-butyl-4-(3-benzyloxycarbonylaminophenylmethylcarbamoyl)phenyl)carbamate

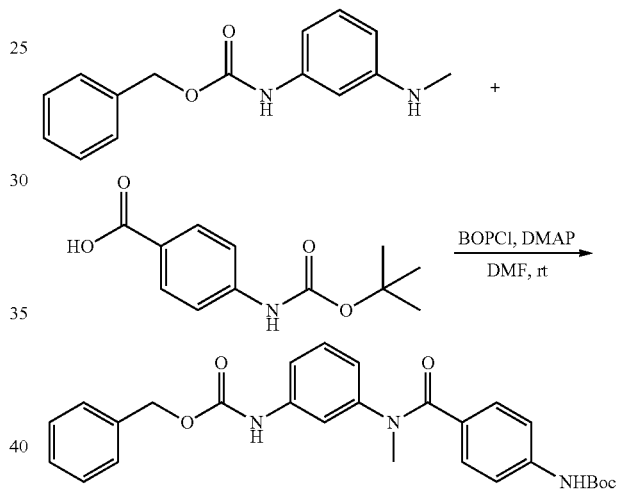

A solution of benzyl 3-(methylamino)phenylcarbamate (765 mg, 2.99 mmol), BOPCl (1.45 g, 3.28 mmol), dimethylaminopyridine (401 mg, 3.28 mmol), and 4-(tert-butoxycarbonylamino)benzoic acid (708 mg, 2.99 mmol) in 2:1 DCM/DMF (45 mL) was stirred overnight at ambient temperature. The mixture was diluted with DCM (50 mL), washed with sat. NaHCO$_3$ (20 mL), brine (20 mL), dried (MgSO$_4$), and concentrated under reduced pressure. The residue was purified by SiO$_2$ chromatography (Hex/EtOAc 5 to 100% gradient), affording the title compound (910 mg, 1.91 mmol, 64%) as a yellow solid.

tert-butyl 4-((3-aminophenyl)(methyl)carbamoyl)phenylcarbamate

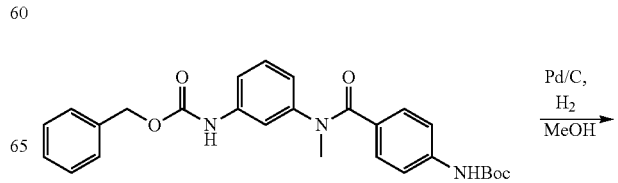

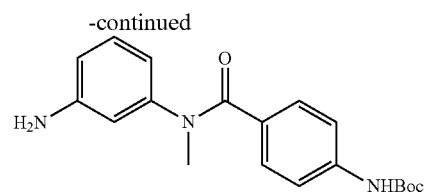

To a degassed solution of tert-butyl-4-(3-benzyloxycarbonylaminophenyl methylcarbamoyl)phenyl)carbamate (910 mg, 1.91 mmol) in 5:1 MeOH/EtOAc (24 mL) was added 10% Pd/C (50 mg). The mixture was stirred 4 h under $H_2$ (1 Atm.), filtered over Celite with MeOH, and concentrated under reduced pressure. The residue was purified by $SiO_2$ chromatography (DCM/EtOAc 0 to 60% gradient), to afford the title compound (550 mg, 1.61 mmol, 84%) as a white solid.

tert-butyl 4-((3-(5-chloro-4-(1-(phenylsulfonyl)-1H-indol-3-yl)pyrimidin-2-ylamino)phenyl)(methyl)carbamoyl)phenylcarbamate

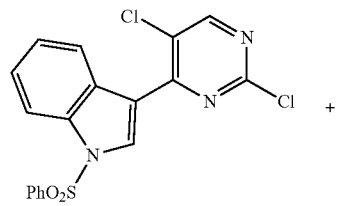

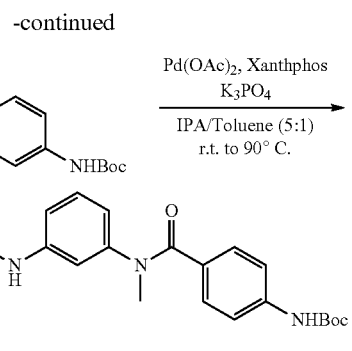

A degassed solution of tert-butyl 4-((3-aminophenyl)(methyl)carbamoyl)phenylcarbamate (300 mg, 0.879 mmol), 3-(2,5-dichloropyrimidin-4-yl)-1-(phenylsulfonyl)-1H-indole (533 mg, 1.318 mmol), $Pd(OAc)_2$ (7.9 mg, 0.035 mmol), Xanthphos (41 mg, 0.070 mmol) and $K_3PO_4$ (560 mg, 2.64 mmol) in 5:1 IPA/toluene (5 mL) was heated 72 h at 90° C. The cooled mixture was diluted with 5:1 $CHCl_3$/IPA (10 mL), filtered over a pad of Celite, and concentrated under reduce pressure. The residue was purified by $SiO_2$ chromatography (DCM/EtOAc 0 to 40% gradient), affording the title compound (190 mg, 0.268 mmol, 31%) as a white solid.

4-amino-N-(3-(5-chloro-4-(1-(phenylsulfonyl)-1H-indol-3-yl)pyrimidin-2-ylamino)phenyl)-N-methyl-benzamide

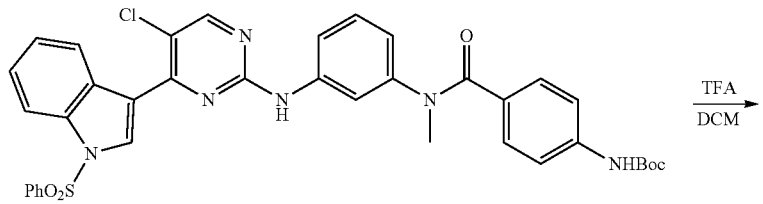

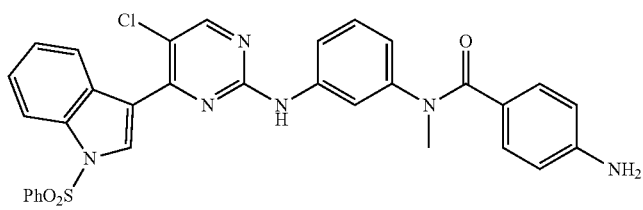

A solution of tert-butyl 4-((3-(5-chloro-4-(1-(phenylsulfonyl)-1H-indol-3-yl)pyrimidin-2-ylamino)phenyl)(methyl)carbamoyl)phenylcarbamate (167 mg, 0.237 mmol) in DCM (2.4 mL) was treated with TFA (364 μL, 4.7 mmol). The mixture was stirred for 2 h at ambient temperature, diluted with DCM (20 mL), washed with sat. $NaHCO_3$ (5 mL), dried (phase cartridge separator), and concentrated to afford the title compound (145 mg, 0.237 mmol, 100%) as a white solid which was used in the next step without further purification.

4-amino-N-(3-(5-chloro-4-(1H-indol-3-yl)pyrimidin-2-ylamino)phenyl)-N-methylbenzamide

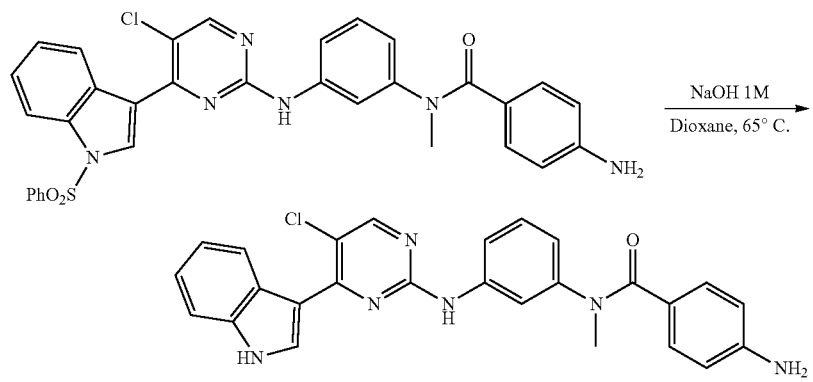

A solution of 4-amino-N-(3-(5-chloro-4-(1-(phenylsulfonyl)-1H-indol-3-yl)pyrimidin-2-ylamino)phenyl)-N-methylbenzamide (144 mg, 0.236 mmol) and NaOH 1M (2.4 mL, 2.36 mmol) in dioxane (4 mL) was heated for 3 h at 65° C. The cooled mixture was diluted with EtOAc (20 mL), sat. NH₄Cl (5 ml) and water (5 mL). The aqueous layer was extracted with EtOAc (3×10 mL), the combined organic layers were washed with brine (10 mL), dried (MgSO₄), filtered, and concentrated to afford the title compound (111 mg, 0.236 mmol, 100%) as a beige solid.

(E)-N-(3-(5-chloro-4-(1H-indol-3-yl)pyrimidin-2-ylamino)phenyl)-4-(4-(dimethylamino)but-2-enamido)-N-methylbenzamide (I-57)

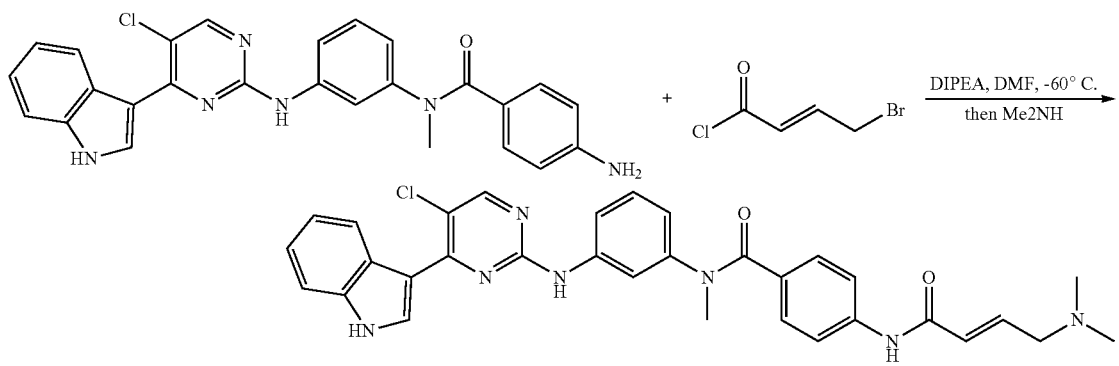

To a −60° C. solution of 4-amino-N-(3-(5-chloro-4-(1H-indol-3-yl)pyrimidin-2-ylamino)phenyl)-N-methylbenzamide (100 mg, 0.213 mmol) and DIPEA (112 µL, 0.640 mmol) in THF (4 mL) was slowly added a 56 mg/mL solution of (E)-4-bromobut-2-enoyl chloride in THF (0.698 mL, 0.213 mmol). The mixture was stirred for 1.5 h at −60° C. before addition of a 2M solution of dimethylamine in THF (426 µL, 0.640 mmol). The mixture was stirred overnight at ambient temperature and concentrated under reduced pressure. The residue was purified by reverse phase chromatography (C18, water/ACN 15 to 100% gradient), affording the title compound (47 mg, 0.081 mmol, 38%) as a white solid after lyophilisation.

$^1$H NMR (500 MHz, DMSO) δ 11.92 (s, 1H), 10.18 (s, 1H), 9.67 (s, 1H), 8.55 (d, J=8.0 Hz, 1H), 8.50-8.44 (m, 2H), 7.75 (t, J=2.0 Hz, 1H), 7.56 (dd, J=8.3, 1.2 Hz, 1H), 7.49 (dd, J=15.0, 8.4 Hz, 2H), 7.22 (ddd, J=11.2, 6.5, 2.4 Hz, 2H), 7.18-7.08 (m, 2H), 6.73-6.64 (m, 2H), 6.26 (d, J=15.3 Hz, 1H), 3.37 (s, 3H), 3.30 (s, 2H), 2.49 (s, 3H), 2.34 (s, 3H); MS (m/z): 580.65 [M+1]⁺.

Example 1.7. (E)-N-(3-(5-chloro-6-(1H-indol-3-yl)pyridin-2-ylamino)phenyl)-4-(4-(dimethylamino)but-2-enamido)benzamide (I-58)

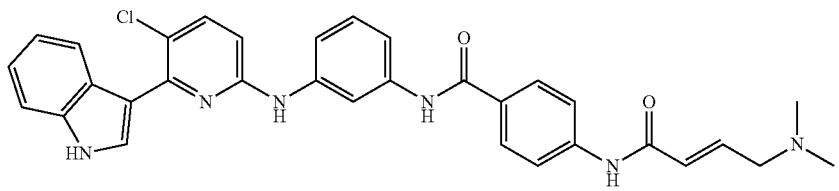 [SMILES: CN(C)C/C=C/C(=O)Nc1ccc(C(=O)Nc2cccc(Nc3ccc(Cl)c(-c4c[nH]c5ccccc45)n3)c2)cc1]

tert-butyl 4-(3-bromophenylcarbamoyl)phenylcarbamate

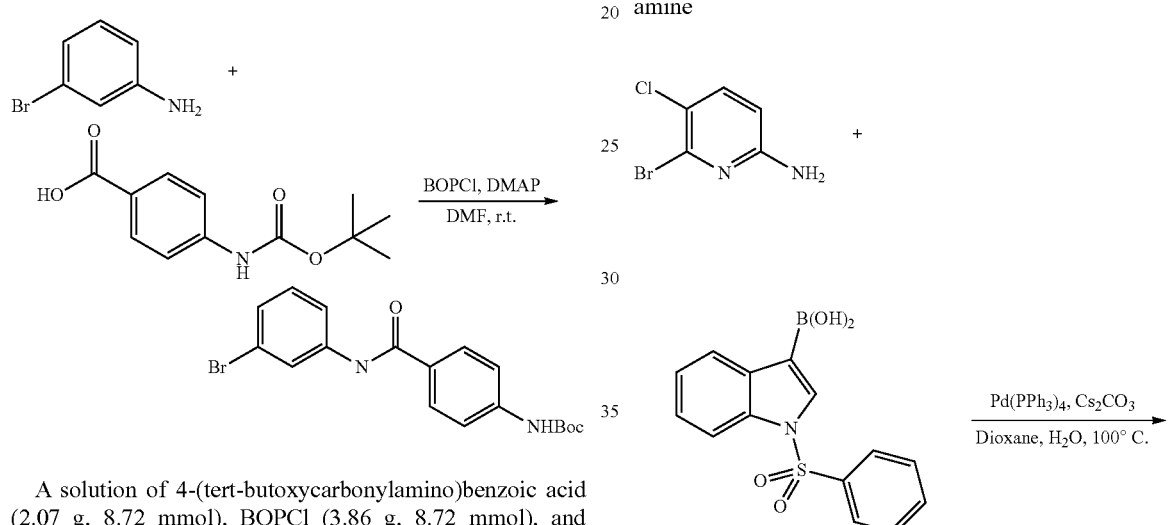

A solution of 4-(tert-butoxycarbonylamino)benzoic acid (2.07 g, 8.72 mmol), BOPCl (3.86 g, 8.72 mmol), and dimethylaminopyridine (1.07 g, 8.72 mmol) in DCM (70 mL) and DMF (17 mL) was stirred 30 min at ambient temperature before addition of 3-bromoaniline (1500 mg, 8.72 mmol). The reaction mixture was stirred overnight at ambient temperature, diluted with DCM (70 mL), washed with sat. NaHCO$_3$ (20 mL), brine (30 mL), dried (Na$_2$SO$_4$), and concentrated under reduced pressure. The residue was purified by filtration over a pad of SiO$_2$ with EtOAc to afford the title compound (2.319 g, 5.93 mmol, 68%) as a white solid.

6-bromo-5-chloropyridin-2-amine

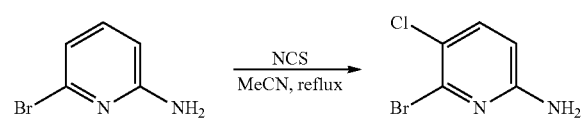 [SMILES: Nc1cccc(Br)n1 ; "NCS" ; Nc1ccc(Cl)c(Br)n1]

A solution of 2-amino-6-bromopyridine (1000 mg, 5.78 mmol) and N-chlorosuccinimide (771 mg, 5.78 mmol) in ACN (23 mL) was heated for 18 h at 80° C. The cooled mixture was diluted with EtOAc (70 mL) and sat. NaHCO$_3$ (30 mL). The aqueous layer was extracted with EtOAc (3×30 mL), the combined organic layers were washed with brine (20 mL), dried (MgSO$_4$), and concentrated under reduce pressure. The residue was purified by SiO$_2$ chroamatography (Hex/EtOAc 0 to 50% gradient), affording the title compound (890 mg, 4.29 mmol, 74%) as a white solid.

5-chloro-6-(1-(phenylsulfonyl)-1H-indol-3-yl)pyridin-2-amine

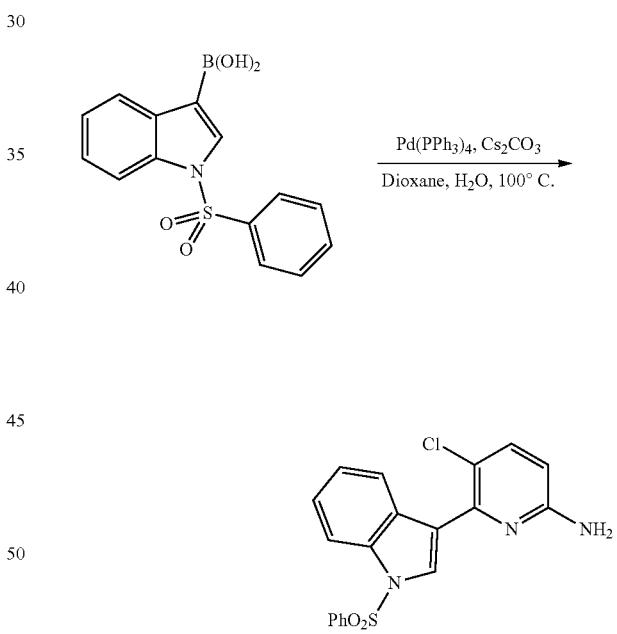

A degassed solution of 2-amino-5-chloro-6-bromopyridine (300 mg, 1.45 mmol) and 1-(phenylsulfonyl)-1H-indol-3-ylboronic acid (457 mg, 1.52 mmol), Cs$_2$CO$_3$ (942 mg, 2.89 mmol), Pd(PPh$_3$)$_4$ (167 mg, 0.14 mmol) in 2:1 dioxane/water (15 mL) was heated for 3 h at 100° C. The cooled mixture was diluted with EtOAc (50 mL) and sat. NaHCO$_3$ (20 mL). The aqueous layer was extracted with EtOAc (3×30 mL), the combined organic layers were washed with brine (20 mL), dried (MgSO$_4$), and concentrated under reduced pressure. The residue was purified by SiO$_2$ chromatography (Hex/EtOAc 10 to 60% gradient), affording the title compound (523 mg, 1.36 mmol, 94%) as a white solid.

193 tert-butyl 4-(3-(5-chloro-6-(1-(phenylsulfonyl)-1H-indol-3-yl)pyridin-2-ylamino)phenylcarbamoyl)phenylcarbamate

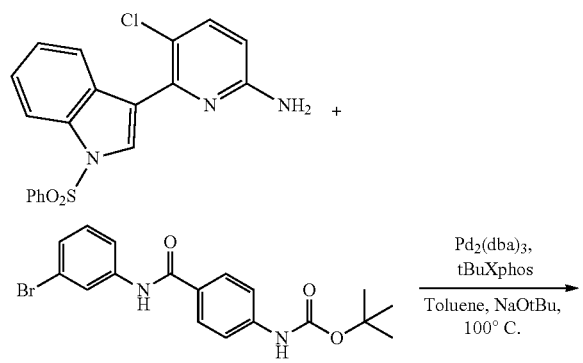

194

-continued

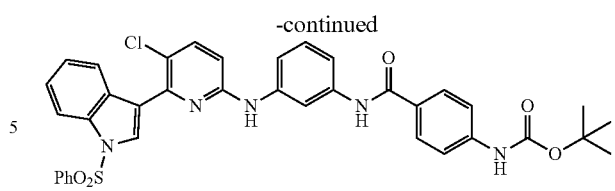

A degassed solution of 5-chloro-6-(1-(phenylsulfonyl)-1H-indol-3-yl)pyridin-2-amine (0.150 g, 0.39 mmol), tert-butyl 4-(3-bromophenylcarbamoyl)phenylcarbamate (0.153 g, 0.39 mmol), Pd(OAc)$_2$ (7 mg, 0.03 mmol), Xantphos (54 mg, 0.09 mmol), and K$_3$PO$_4$ (166 mg, 0.78 mmol) in 5:1 IPA/Tol (4 mL) was heated for 6 h at 100° C. The cooled mixture was filtrated through Celite with EtOAc and concentrated under reduced pressure. The residue was purified by SiO$_2$ chromatography (Hex/EtOAc 0 to 50% gradient), affording the title compound (102 mg, 0.147 mmol, 56%) as a white solid.

4-amino-N-(3-(5-chloro-6-(1-(phenylsulfonyl)-1H-indol-3-yl)pyridin-2-ylamino)phenyl)benzamide

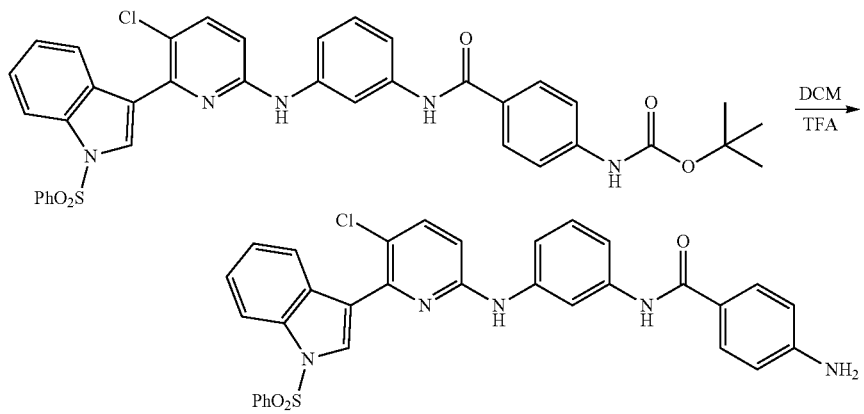

A solution of tert-butyl 4-(3-(5-chloro-6-(1-(phenylsulfonyl)-1H-indol-3-yl)pyridin-2-ylamino)phenylcarbamoyl)phenylcarbamate (102 mg, 0.15 mmol) in DCM (1 mL) was treated with TFA (0.11 mL, 1.47 mmol). The mixture was stirred overnight at ambient temperature, concentrated under reduced pressure, diluted with EtOAc (15 mL), washed with sat. NaHCO$_3$ (5 mL), brine (5 mL), dried (MgSO$_4$), filtered, and concentrated under reduced pressure. The residue was purified by SiO$_2$ chromatography (DCM/EtOAc 20 to 60% gradient), affording the title compound (57.4 mg, 0.097 mmol, 66%) as a beige solid.

4-amino-N-(3-(5-chloro-6-(1H-indol-3-yl)pyridin-2-ylamino)phenyl)benzamide

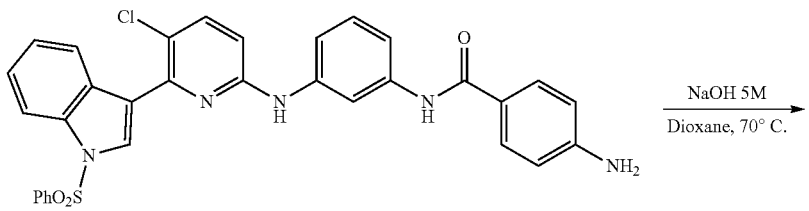

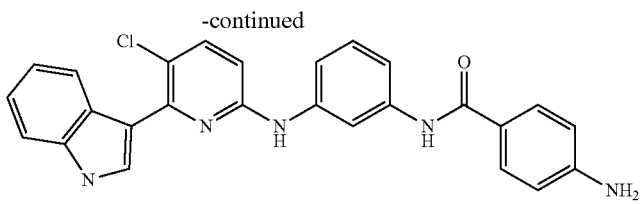

A solution of 4-amino-N-(3-(5-chloro-6-(1-(phenylsulfonyl)-1H-indol-3-yl)pyridin-2-ylamino)phenyl)benzamide (57.4 mg, 0.097 mmol) and 5M NaOH (0.10 mL, 0.48 mmol) in 1,4-dioxane (1.93 mL) was heated for 24 h at 80° C. The cooled mixture was concentrated under reduce pressure and the residue was purified by $SiO_2$ chromatography (DCM/EtOAc 0 to 40% gradient) to afford the title compound (32 mg, 0.071 mmol, 73%) as a white solid.

(E)-N-(3-(5-chloro-6-(1H-indol-3-yl)pyridin-2-ylamino)phenyl)-4-(4-(dimethylamino)but-2-enamido)benzamide (I-58)

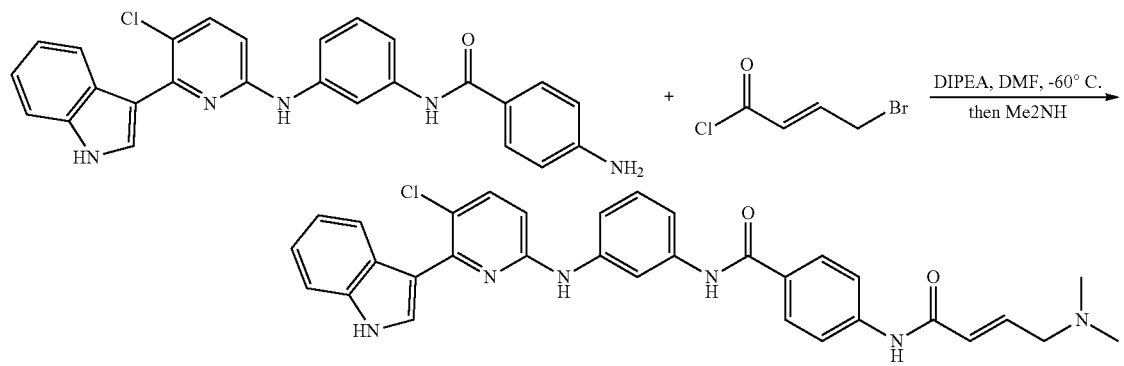

To a solution of 4-amino-N-(3-(5-chloro-6-(1H-indol-3-yl)pyridin-2-ylamino)phenyl)benzamide (32 mg, 0.07 mmol) and DIPEA (49 µL, 0.28 mmol) in THF (0.88 mL) was added a 55.6 mg/mL solution of (E)-4-bromobut-2-enoyl chloride in THF (245 µL, 0.07 mmol) at −60° C. The resulting mixture was stirred for 4.5 h at −60° C. before addition of a 2M solution of dimethylamine in THF (106 µL, 0.21 mmol). The mixture was stirred 14 h at ambient temperature and concentrated under reduced pressure. The residue was purified by reverse phase preparative LC-MS (water/ACN+0.1% $NH_4HCO_3$, 40 to 65% gradient), affording the title compound (5.8 mg, 0.010 mmol, 15%) as a white solid after lyophilization.

$^1$H NMR (500 MHz, DMSO) δ 11.52 (s, 1H), 10.33 (s, 1H), 9.97 (s, 1H), 9.18 (s, 1H), 8.20 (d, J=8.1 Hz, 1H), 8.09 (d, J=2.7 Hz, 1H), 8.00 (s, 1H), 7.88 (d, J=8.7 Hz, 2H), 7.77 (d, J=8.7 Hz, 2H), 7.69 (d, J=8.7 Hz, 1H), 7.59 (d, J=8.1 Hz, 1H), 7.43 (d, J=8.2 Hz, 1H), 7.26 (d, J=8.2 Hz, 1H), 7.16 (t, J=8.0 Hz, 1H), 7.08 (t, J=7.6 Hz, 1H), 6.97 (t, J=7.6 Hz, 1H), 6.78 (dt, J=15.2, 5.6 Hz, 1H), 6.76 (d, J=8.8 Hz, 1H), 6.31 (d, J=15.4 Hz, 1H), 3.07 (d, J=4.8 Hz, 2H), 2.50 (s, 3H), 2.19 (s, 3H); MS (m/z): 565.56 $[M+1]^+$.

Characterization data of additional exemplary compounds of the invention are shown below.

Compound I-17.
LC-MS: m/z (M+H) 580; $^1$H NMR (600 MHz, DMSO-$d_6$) 11.98 (s, 1H), 10.67 (s, 1H), 9.85 (s, 1H), 9.69 (s, 1H), 8.67 (d, J=7.8 Hz, 1H), 8.55 (d, J=3.0 Hz, 1H), 8.51 (s, 1H), 8.01 (d, J=9.0 Hz, 2H), 7.90 (d, J=1.8 Hz, 1H), 7.87 (d, J=9.0 Hz, 2H), 7.65 (dd, J=2.4, 8.4 Hz, 1H), 7.53 (d, J=8.4 Hz, 1H), 7.24 (d, J=8.4 Hz, 1 H), 7.19 (t, J=7.8 Hz, 2H), 6.86 (m, 1H), 6.58 (d, J=16.2 Hz, 1H), 3.86 (s, 2H), 2.75 (s, 6H), 2.25 (s, 3H).

Compound I-18.
LC-MS: m/z (M+H) 566; $^1$H NMR (400 MHz, DMSO-$d_6$) 11.90 (s, 1H), 10.52 (s, 1H), 10.22 (s, 1H), 9.66 (s, 1H), 8.63 (d, J=8.0 Hz, 1H), 8.50 (d, J=3.2 Hz, 1H), 8.42 (s, 1H), 8.13 (d, J=8.0 Hz, 2H), 7.91 (dd, J=1.2, 8.0 Hz, 1H), 7.65 (d, J=8.0 Hz, 1H), 7.51 (dd, J=2.0, 8.0 Hz, 1H), 7.45 (m, 2H), 7.35 (d, J=7.2 Hz, 1H), 7.25 (t, J=8.0 Hz, 1H), 7.15 (t, J=8.0 Hz, 1H), 7.06 (t, J=8.0 Hz, 1H), 6.76 (m, 1H), 6.45 (d, J=15.6 Hz, 1H), 3.95 (d, J=6.0 Hz, 2H), 2.79 (s, 6H).

Compound I-19.
LC-MS: m/z (M+H) 546; $^1$H NMR (600 MHz, DMSO-$d_6$) 11.90 (s, 1H), 10.60 (s, 1H), 10.10 (s, 1H), 9.64 (s, 1H), 8.54 (d, J=7.8 Hz, 1H), 8.25 (s, 1H), 8.12 (m, 2H), 7.94 (d, J=8.4 Hz, 2H), 7.77 (d, J=8.4 Hz, 1H), 7.50 (d, J=8.0 Hz, 1 H), 7.45 (d, J=7.8 Hz, 1H), 7.39 (d, J=8.4 Hz, 1H), 7.25 (t, J=8.4 Hz, 1H), 7.13 (t, J=8.4 Hz, 1H), 7.03 (t, J=8.4 Hz, 1H), 6.78 (m, 1H), 6.49 (d, J=15.0 Hz, 1H), 3.95 (d, J=6.0 Hz, 2H), 2.79 (s, 6H), 2.39 (s, 3H).

Compound I-20.
LC-MS: m/z (M+H) 560; $^1$H NMR (600 MHz, DMSO-$d_6$) 11.85 (s, 1H), 10.60 (s, 1H), 9.76 (s, 1H), 9.53 (s, 1H), 8.53 (br, 1H), 8.52 (d, J=7.8 Hz, 1 H), 8.24 (s, 1H), 8.06 (d, J=2.4 Hz, 1H), 7.94 (d, J=8.4 Hz, 2H), 7.82 (d, J=1.8 Hz, 1 H), 7.79 (d, J=8.4 Hz, 2H), 7.56 (dd, J=1.8, 7.8 Hz, 1H), 7.43 (d, J=7.8 Hz, 1H), 7.15 (d, J=7.8 Hz, 1H), 7.10 (t, J=7.2 Hz, 1H), 7.06 (t, J=7.2 Hz, 1H), 6.78 (m, 1H), 6.49 (d, J=15.0 Hz, 1H), 3.95 (d, J=6.0 Hz, 2H), 2.79 (s, 6H), 2.37 (s, 3H), 2.17 (s, 3H).

Compound I-21.
LC-MS: m/z (M+H) 560; $^1$H NMR (600 MHz, DMSO-$d_6$) 11.85 (s, 1H), 10.60 (s, 1H), 10.09 (s, 1H), 9.67 (s, 1H), 8.52 (d, J=7.8 Hz, 1H), 8.27 (s, 1H), 8.12 (m, 1H), 8.02 (d, J=3.0 Hz, 1H), 7.92 (d, J=8.4 Hz, 2H), 7.77 (d, J=8.4 Hz, 2 H), 7.51 (dd, J=1.8, 8.4 Hz, 1H), 7.45 (d, J=8.4 Hz, 1H), 7.39 (d, J=8.4 Hz, 1H), 7.23 (t, J=7.8 Hz, 1H), 7.12 (t, J=7.8 Hz, 1H), 7.02 (t, J=7.8 Hz, 1H), 6.78 (m, 1H), 6.47 (d, J=15.0 Hz, 1H), 3.95 (d, J=6.0 Hz, 2H), 2.83 (q, J=7.8 Hz, 2H), 2.79 (s, 6H), 1.21 (t, J=7.8 Hz, 3H).

Compound I-22.

LC-MS: m/z (M+H) 580; $^1$H NMR (400 MHz, DMSO-$d_6$) 11.89 (s, 1H), 10.60 (s, 1H), 9.77 (s, 1H), 9.61 (s, 1H), 8.59 (d, J=7.2 Hz, 1H), 8.47 (d, J=3.2 Hz, 1H), 8.42 (s, 1H), 7.95 (d, J=8.4 Hz, 2H), 7.81 (d, J=2.0 Hz, 1H), 7.67 (d, J=8.4 Hz, 2H), 7.56 (dd, J=1.6, 8.4 Hz, 1H), 7.45 (dd, J=3.0, 8.4 Hz, 1H), 7.15 (d, J=8.4 Hz, 1H), 7.11 (t, J=8.4 Hz, 1H), 6.78 (m, 1H), 6.47 (d, J=15.2 Hz, 1H), 3.95 (d, J=6.0 Hz, 2H), 2.79 (s, 6H), 2.16 (s, 3H).

Compound I-23.

LC-MS: m/z (M+H) 566; $^1$H NMR (600 MHz, DMSO-$d_6$) 11.91 (s, 1H), 10.59 (s, 1H), 10.09 (s, 1H), 9.65 (s, 1H), 8.62 (d, J=7.8 Hz, 1H), 8.51 (d, J=3.6 Hz, 1H), 8.44 (s, 1H), 8.14 (s, 1H), 7.94 (d, J=8.4 Hz, 2H), 7.77 (d, J=8.4 Hz, 2 H), 7.50 (d, J=7.8 Hz, 1H), 7.47 (d, J=7.8 Hz, 1H), 7.37 (d, J=7.8 Hz, 1H), 7.26 (t, J=7.8 Hz, 1H), 7.15 (t, J=7.8 Hz, 1H), 7.07 (t, J=7.8 Hz, 1H), 6.77 (m, 1H), 6.49 (d, J=15.0 Hz, 1H), 3.95 (d, J=6.0 Hz, 2H), 2.79 (s, 6H).

Compound I-24.

LC-MS: m/z (M+H) 509; $^1$H NMR (600 MHz, DMSO-$d_6$) 11.99 (s, 1H), 10.51 (s, 1H), 10.16 (s, 1H), 9.72 (s, 1H), 8.70 (d, J=8.4 Hz, 1H), 8.59 (d, J=3.0 Hz, 1H), 8.52 (s, 1H), 8.20 (s, 1H), 7.98 (d, J=8.4 Hz, 2H), 7.86 (d, J=8.4 Hz, 2 H), 7.58 (d, J=7.8 Hz, 1H), 7.54 (d, J=7.8 Hz, 1H), 7.44 (d, J=7.8 Hz, 1H), 7.31 (t, J=7.8 Hz, 1H), 7.20 (t, J=7.8 Hz, 1H), 7.14 (t, J=7.8 Hz, 1H), 6.57 (m, 1H), 6.38 (d, J=16.8 Hz, 1H), 5.88 (d, J=16.8 Hz, 1H)

Compound I-25.

LC-MS: m/z (M+H) 600; $^1$H NMR (600 MHz, DMSO-$d_6$) 12.00 (s, 1H), 10.70 (s, 1H), 9.99 (s, 1H), 9.94 (s, 1H), 8.57 (d, J=8.4 Hz, 1H), 8.56 (s, 1 H), 8.18 (d, J=8.4 Hz, 1H), 8.03 (d, J=8.4 Hz, 2H), 7.88 (d, J=7.8 Hz, 2H), 7.80 (d, J=8.4 Hz, 1H), 7.78 (d, J=8.4 Hz, 1H), 7.54 (m, 1H), 7.51 (d, J=8.4 Hz, 1H), 7.22 (m, 2 H), 6.86 (m, 1H), 6.58 (d, J=16.8 Hz, 1H), 3.95 (d, J=6.0 Hz, 2H), 2.79 (s, 6H).

Compound I-26.

LC-MS: m/z (M+H) 572; $^1$H NMR (600 MHz, DMSO-$d_6$) 11.95 (s, 1H), 10.59 (s, 1H), 10.12 (s, 1H), 9.77 (br, 1H), 8.57 (d, J=7.2 Hz, 1H), 8.50 (d, J=3.0 Hz, 1H), 8.16 (s, 1H), 8.11 (s, 1H), 7.93 (d, J=8.4 Hz, 2H), 7.77 (d, J=8.4 Hz, 2 H), 7.45 (d, J=8.4 Hz, 2H), 7.42 (d, J=7.8 Hz, 1H), 7.29 (t, J=8.4 Hz, 1H), 7.15 (t, J=8.4 Hz, 1H), 7.05 (t, J=8.4 Hz, 1H), 6.76 (m, 1H), 6.45 (d, J=15.6 Hz, 1H), 3.95 (d, J=6.0 Hz, 2H), 2.79 (s, 6H), 2.03 (m, 1H), 1.02 (m, 2H), 0.67 (m, 2H).

Compound I-27.

LC-MS: m/z (M+H) 567; $^1$H NMR (600 MHz, DMSO-$d_6$) 10.33 (s, 1H), 10.17 (s, 1H), 10.09 (s, 1H), 8.80 (s, 2H), 8.14 (m, 1H), 7.91 (d, J=8.4 Hz, 2H), 7.86 (d, J=8.4 Hz 1H), 7.77 (m, 3H), 7.42 (d, J=8.4 Hz, 1H), 7.34 (d, J=8.4 Hz, 1 H), 7.29 (m, 2H), 7.24 (t, J=7.8 Hz, 1H), 6.76 (m, 1H), 6.45 (d, J=15.6 Hz, 1H), 3.05 (d, J=6.0 Hz, 2H), 2.17 (s, 6H).

Compound I-28.

LC-MS: m/z (M+H) 580; $^1$H NMR (600 MHz, DMSO-$d_6$) 10.67 (s, 1H), 10.17 (s, 1H), 9.98 (br, 1H), 9.72 (s, 1H), 8.72 (d, J=8.4 Hz, 1H), 8.64 (s, 1 H), 8.51 (s, 1H), 8.23 (m, 1H), 8.01 (d, J=8.4 Hz, 2H), 7.86 (d, J=8.4 Hz, 2H), 7.59 (d, J=8.4 Hz, 1H), 7.55 (d, J=8.4 Hz, 1H), 7.45 (d, J=8.4 Hz, 1H), 7.31 (m, 2H), 7.20 (t, J=8.4 Hz, 1H), 6.86 (m, 1H), 6.47 (d, J=15.6 Hz, 1H), 4.03 (d, J=6.0 Hz, 2H), 3.98 (s, 3 H), 2.87 (s, 6H).

Compound I-29.

LC-MS: m/z (M+H) 567; $^1$H NMR (600 MHz, DMSO-$d_6$) 11.87 (s, 1H), 10.57 (s, 1H), 10.08 (s, 1H), 9.88 (s, 2H), 8.68 (d, J=8.4 Hz, 1H), 8.54 (s, 1H), 8.48 (s, 1H), 8.23 (s, 1H), 7.93 (d, J=8.4 Hz, 2H), 7.76 (d, J=8.4 Hz 2H), 7.50 (t, J=3.0 Hz, 1H), 7.40 (d, J=8.4 Hz, 1H), 7.25 (d, J=8.4 Hz, 1H), 7.19 (t, J=8.4 Hz, 1H), 6.73 (m, 1H), 6.48 (m, 1H), 6.43 (d, J=15.0 Hz, 1H), 3.90 (d, J=6.0 Hz, 2H), 2.75 (s, 6 H).

Compound I-30.

LC-MS: m/z (M+H) 566; $^1$H NMR (600 MHz, DMSO-$d_6$) 11.30 (s, 1H), 10.61 (s, 1H), 10.09 (s, 1H), 9.88 (s, 1H), 8.61 (s, 1H), 8.06 (m, 1H), 7.95 (d, J=8.0 Hz, 2H), 7.77 (d, J=8.0 Hz, 2H), 7.59 (m, 1H), 7.53 (m, 3H), 7.38 (t, J=3.0 Hz, 1H), 7.29 (m, 2H), 7.19 (m, 2H), 6.77 (m, 1H), 6.48 (d, J=15.0 Hz, 1H), 6.42 (m, 1 H), 3.95 (d, J=6.0 Hz, 2H), 2.79 (s, 6H).

Compound I-31.

LC-MS: m/z (M+H) 566; $^1$H NMR (600 MHz, DMSO-$d_6$) 11.30 (s, 1H), 10.35 (s, 1H), 10.09 (s, 1H), 9.83 (s, 1H), 8.54 (s, 1H), 8.27 (s, 1H), 8.18 (s, 1H), 7.95 (d, J=8.0 Hz, 2H), 7.79 (d, J=8.0 Hz, 2H), 7.67 (dd, J=1.8, 8.0 Hz, 1H), 7.47 (d, J=8.0 Hz, 1H), 7.44 (d, J=8.0 Hz, 1H), 7.40 (t, J=3.0 Hz, 1H), 7.30 (d, J=8.0 Hz, 1 H), 7.23 (t, J=8.0 Hz, 1H), 6.77 (m, 1H), 6.51 (m, 1H), 6.32 (d, J=15.0 Hz, 1H), 3.11 (d, J=6.0 Hz, 2H), 2.22 (s, 6H).

Compound I-32.

LC-MS: m/z (M+H) 566; $^1$H NMR (600 MHz, DMSO-$d_6$) 11.38 (s, 1H), 10.61 (s, 1H), 10.12 (s, 1H), 9.88 (s, 1H), 8.54 (s, 1H), 8.16 (m, 1H), 8.00 (s, 1H), 7.95 (d, J=8.0 Hz, 2H), 7.78 (d, J=8.0 Hz, 2H), 7.62 (d, J=8.0 Hz, 1H), 7.57 (dd, J=1.2, 8.0 Hz, 1H), 7.52 (d, J=8.0 Hz, 1H), 7.50 (t, J=3.0 Hz, 1H), 7.30 (d, J=8.0 Hz, 1H), 7.23 (t, J=8.0 Hz, 1H), 6.77 (m, 1H), 6.49 (m, 1H), 6.48 (d, J=15.0 Hz, 1H), 3.95 (d, J=6.0 Hz, 2H), 2.79 (s, 6H).

Compound I-33.

LC-MS: m/z (M+H) 582; $^1$H NMR (600 MHz, DMSO-$d_6$) 12.15 (s, 1H), 10.62 (s, 1H), 10.20 (s, 1H), 9.96 (br, 1H), 8.35 (m, 4H), 7.96 (d, J=7.2 Hz, 2H) 7.84 (t, J=7.2 Hz, 1H), 7.79 (d, J=8.4 Hz, 2H), 7.73 (d, J=7.8 Hz, 1H), 7.61 (d, J=1.8 Hz, 1H), 7.51 (d, J=, 8.0 Hz, 1H), 7.46 (d, J=7.8 Hz, 1H), 7.43 (t, J=7.8 Hz, 1 H), 7.33 (t, J=7.8 Hz, 1H), 7.20 (t, J=7.8 Hz, 1H), 7.12 (t, J=7.8 Hz, 1H), 6.77 (m, 1H), 6.48 (d, J=15.0 Hz, 1H), 3.95 (d, J=6.0 Hz, 2H), 2.79 (s, 6H).

Compound I-34.

LC-MS: m/z (M+H) 566; $^1$H NMR (600 MHz, DMSO-$d_6$) 11.29 (s, 1H), 10.71 (s, 1H), 10.38 (s, 1H), 9.91 (s, 1H), 9.01 (s, 1H), 8.59 (m, 1H), 8.05 (d, J=8.0 Hz, 2H), 7.86 (d, J=8.0 Hz, 2H), 7.73 (d, J=1.8 Hz, 1H), 7.69 (d, J=8.0 Hz, 1 H), 7.65 (d, J=8.0 Hz, 1H), 7.26 (t, J=8.4 Hz, 1H), 7.19 (m, 2H), 7.15 (m, 1H), 7.06 (t, J=7.8 Hz, 1H), 6.81 (m, 1H), 6.51 (d, J=15.0 Hz, 1H), 3.95 (d, J=6.0 Hz, 2H), 2.79 (s, 6 H).

Compound I-35.

LC-MS: m/z (M+H) 510; $^1$H NMR (600 MHz, DMSO-$d_6$) 11.91 (s, 1H), 10.41 (s, 1H), 10.12 (s, 1H), 9.91 (s, 2H), 8.73 (s, 1H), 8.60 (s, 1H), 8.54 (s, 1H), 8.27 (s, 1H), 7.96 (d, J=8.4 Hz, 2H), 7.80 (d, J=8.4 Hz, 2H), 7.54 (m, 1H), 7.44 (d, J=8.4 Hz, 1H), 7.31 (d, J=8.0 Hz, 1H), 7.25 (t, J=7.8 Hz, 1H), 6.53 (m, 1H), 6.45 (m, 1H), 6.28 (dd, J=1.8, 15.6 Hz, 1H), 5.78 (dd, J=1.8, 15.6 Hz, 1H).

Compound I-37.

LC-MS: m/z (M+H) 571; $^1$H NMR (600 MHz, DMSO-$d_6$) 11.88 (s, 1H), 9.75 (s, 1H), 9.58 (s, 1H), 8.61 (d, J=8.4 Hz, 1H), 8.50 (d, J=3.0 Hz, 1H), 8.42 (s, 1H), 8.07 (m, 1H), 7.75 (d, J=7.2 Hz, 2H) 7.45 (m, 2H), 7.33 (d, J=8.4 Hz, 1H), 7.22 (t, J=7.8 Hz, 1H), 7.14 (t, J=7.8 Hz, 1H), 7.06 (t, J=7.8 Hz, 1H), 6.60 (d, J=8.0 Hz, 2H), 3.37 (t, J=6.6 Hz, 2H), 2.84 (m, 4H), 1.14 (t, J=7.2 Hz, 3H).

Compound I-38.

LC-MS: m/z (M+H) 643; $^1$H NMR (600 MHz, DMSO-d$_6$) 10.38 (s, 1H), 10.03 (s, 1H), 9.88 (s, 1H), 8.83 (d, J=7.8 Hz, 1H), 8.55 (s, 1H), 7.99 (m, 2H), 7.91 (d, J=8.4 Hz, 2H), 7.76 (d, J=8.4 Hz, 2H), 7.68 (d, J=8.0 Hz, 1H), 7.54 (d, J=8.4 Hz, 2H), 7.38 (m, 3H), 7.30 (m, 2H), 7.10 (t, J=7.8 Hz, 1H), 7.03 (t, J=7.2 Hz, 1H), 6.77 (m, 1H), 6.43 (d, J=15.0 Hz, 1H), 3.25 (s, 2H), 2.30 (s, 6H).

Compound I-39.

LC-MS: m/z (M+H) 560; $^1$H NMR (600 MHz, DMSO-d$_6$) 11.67 (s, 1H), 10.39 (s, 1H), 10.03 (s, 1H), 9.30 (s, 1H), 8.25 (m, 2H), 7.97 (d, J=8.4 Hz, 2H), 7.91 (d, J=3.0 Hz, 1H), 7.85 (d, J=8.4 Hz, 2H), 7.66 (d, J=8.4 Hz, 1H), 7.51 (d, J=8.4 Hz, 1H), 7.31 (d, J=8.4 Hz, 1H), 7.22 (t, J=8.4 Hz, 1H), 7.17 (d, J=8.4 Hz, 1H), 7.07 t, J=8.4 Hz, 1H), 6.84 (m, 1H), 6.39 (d, J=15.0 Hz, 1H), 3.15 (d, J=6.0 Hz, 2H), 2.52 (s, 3H), 2.39 (s, 3H), 2.25 (s, 6H).

Compound I-40.

LC-MS: m/z (M+H) 546; $^1$H NMR (600 MHz, DMSO-d$_6$) 11.61 (s, 1H), 10.32 (s, 1H), 10.01 (s, 1H), 9.44 (s, 1H), 8.37 (d, J=5.4 Hz, 1H), 8.18 (t, J=2.4 Hz, 1H), 7.92 (d, J=8.4 Hz, 2H), 7.80 (d, J=3.0 Hz, 1H), 7.76 (d, J=8.4 Hz, 2H), 7.54 (d, J=8.4 Hz, 1H), 7.27 (t, J=8.4 Hz, 2H), 7.18 (t, J=8.0 Hz, 1H), 7.04 (t, J=8.0 Hz, 1H), 7.01 (d, J=8.4 Hz, 1H), 6.84 (m, J=8.4 Hz, 1H), 6.76 (m, 1H), 6.47 (d, J=15.0 Hz, 1H), 3.05 (d, J=6.0 Hz, 2H), 2.54 (s, 3H), 2.17 (s, 6H).

Compound I-41.

LC-MS: m/z (M+H) 560; $^1$H NMR (600 MHz, DMSO-d$_6$) 11.42 (s, 1H), 10.31 (s, 1H), 10.02 (s, 1H), 9.42 (s, 1H), 8.32 (s, 1H), 8.05 (m, 1H), 7.91 (d, J=8.4 Hz, 2H), 7.76 (d, J=8.4 Hz, 2H), 7.55 (m, 2H), 7.26 (d, J=8.4 Hz, 1H), 7.23 (d, J=8.4 Hz, 1H), 7.16 (t, J=8.4 Hz, 1H), 7.02 (t, J=8.4 Hz, 1H), 6.77 (d, J=8.0 Hz, 1H), 6.75 (m, 1H), 6.29 (d, J=15.0 Hz, 1H), 3.05 (d, J=6.0 Hz, 2H), 2.21 (s, 3H), 2.15 (s, 6H), 2.11 (s, 3H).

Compound I-42.

LC-MS: m/z (M+H) 600; $^1$H NMR (600 MHz, DMSO-d$_6$) 11.85 (s, 1H), 10.61 (s, 1H), 10.11 (s, 1H), 10.08 (s, 1H), 8.72 (s, 1H), 8.33 (br, 1H), 8.14 (s, 1H), 7.93 (d, J=8.4 Hz, 2H), 7.88 (d, J=3.0 Hz, 1H), 7.78 (d, J=8.4 Hz, 2H), 7.52 (d, J=8.4 Hz, 1H), 7.45 (d, J=8.4 Hz, 1H), 7.41 (d, J=8.4 Hz, 1H), 7.26 (t, J=8.4 Hz, 1H), 7.12 (t, J=8.0 Hz, 1H), 7.04 (m, 1H), 6.79 (m, 1H), 6.47 (d, J=15.0 Hz, 1H), 3.95 (d, J=6.0 Hz, 2H), 2.79 (s, 6H).

Compound I-43.

LC-MS: m/z (M+H) 580; $^1$H NMR (600 MHz, DMSO-d$_6$) 11.92 (s, 1H), 10.13 (s, 1H), 9.64 (s, 1H), 8.61 (d, J=7.2 Hz, 1H), 8.59 (t, J=6.0 Hz, 1H), 8.51 (d, J=8.4 Hz, 1H), 8.44 (s, 1H), 8.13 (s, 1H), 7.87 (d, J=8.4 Hz, 2H), 7.50 (d, J=8.4 Hz, 1H), 7.45 (d, J=8.4 Hz, 1H), 7.35 (d, J=8.4 Hz, 3H), 7.24 (t, J=8.4 Hz, 1H), 7.15 (t, J=8.4 Hz, 1H), 7.07 (t, J=8.0 Hz, 1H), 6.60 (m, 1H), 6.10 (d, J=15.0 Hz, 1H), 4.39 (d, J=7.2 Hz, 2H), 3.01 (d, J=6.0 Hz, 2H), 2.15 (s, 6H).

Compound I-44.

LC-MS: m/z (M+H) 532; $^1$H NMR (600 MHz, DMSO-d$_6$) 11.97 (s, 1H), 10.59 (s, 1H), 10.17 (s, 1H), 9.92 (br, 1H), 9.80 (br, 1H), 8.51 (d, J=8.4 Hz, 1H), 8.48 (d, J=1.8 Hz, 1H), 8.30 (d, J=8.4 Hz, 1H), 8.25 (s, 1H), 7.91 (d, J=8.0 Hz, 2H), 7.78 (d, J=8.0 Hz, 2H), 7.43 (d, J=8.0 Hz, 2H), 7.40 (d, J=8.4 Hz, 1H), 7.33 (d, J=8.4 Hz, 1H), 7.29 (t, J=8.4 Hz, 1H), 7.13 (t, J=8.4 Hz, 1H), 7.06 (t, J=8.0 Hz, 1H), 6.77 (m, 1H), 6.46 (d, J=15.0 Hz, 1H), 3.95 (d, J=6.0 Hz, 2H), 2.79 (s, 6H).

Compound I-49.

LC-MS: m/z (M+H) 1053, $^1$H NMR (600 MHz, DMSO-d$_6$) 11.93 (s, 1H), 10.67 (s, 1H), 10.17 (s, 1H), 9.90 (br, 1H), 9.73 (s, 1H), 8.70 (s, 1H), 8.55 (d, J=3.0 Hz, 1H), 8.52 (s, 1H), 8.21 (m, 1H), 8.02 (d, J=8.0 Hz, 2H), 7.89 (t, J=6.0 Hz, 1H), 7.85 (d, J=8.0 Hz, 2H), 7.57 (d, J=8.4 Hz, 1H), 7.54 (d, J=8.4 Hz, 1H), 7.46 (t, J=7.8 Hz, 1H), 7.32 (t, J=8.4 Hz, 1H), 7.22 (t, J=8.4 Hz, 1H), 7.15 (t, J=8.4 Hz, 1H), 6.87 (m, 1H), 6.58 (d, J=16.2 Hz, 1H), 6.48 (br, 1H), 6.27 (br, 1H), 6.15 (br, 1H), 4.35 (m, 2H), 4.17 (m, 2H), 4.10-2.55 (m, 26H) 2.12 (t, J=7.2 Hz, 2H), 1.82 (m, 2H), 1.65 (m, 1H), 1.56 (m, 3H), 1.34 (m, 2H).

Compound I-50.

LC-MS: m/z (M+H) 562; $^1$H NMR (600 MHz, DMSO-d$_6$) 10.60 (s, 1H), 10.13 (s, 1H), 9.94 (s, 2H), 8.60 (s, 1H), 8.05 (s, 1H), 7.96 (d, J=8.4 Hz, 2H), 7.77 (d, J=8.4 Hz, 2H), 7.47 (d, J=8.4 Hz, 1H), 7.31 (d, J=8.0 Hz, 1H), 7.24 (t, J=8.0 Hz, 1H), 6.77 (m, 1H), 6.46 (d, J=15.0 Hz, 1H), 3.95 (d, J=6.0 Hz, 2H), 2.79 (s, 6 H), 2.64 (s, 3H), 2.41 (s, 3H).

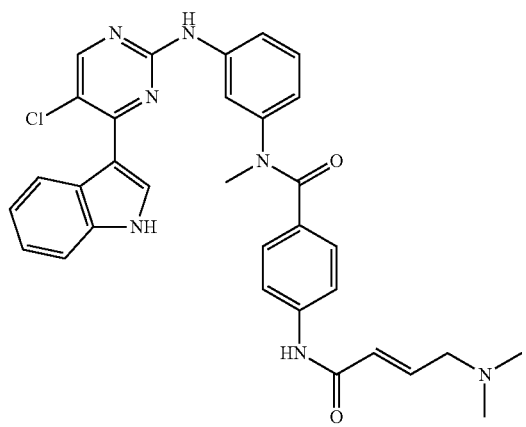 [SMILES: CN(C)C/C=C/C(=O)Nc1ccc(C(=O)N(C)c2cccc(Nc3ncc(Cl)c(-c4c[nH]c5ccccc45)n3)c2)cc1]

LC-MS: (M+H) 580. $^1$H NMR (600 MHz, DMSO-d$_6$) δ 11.91 (s, 1H), 10.34 (s, 1H), 10.09 (s, 1H), 9.66 (s, 1H), 8.55 (d, J=7.8 Hz, 1H), 8.46 (d, J=3.6 Hz, 1H), 8.45 (s, 1H), 7.73 (m, 1H), 7.57 (d, J=8.4 Hz, 1H), 7.50 (m, 3H), 7.27 (d, J=8.4 Hz, 2H), 7.15 (m, 3H), 6.77 (m, 1H), 6.49 (d, J=15.0 Hz, 1H), 3.95 (d, J=6.0 Hz, 2H), 3.29 (s, 3H), 2.79 (s, 6H) ppm.

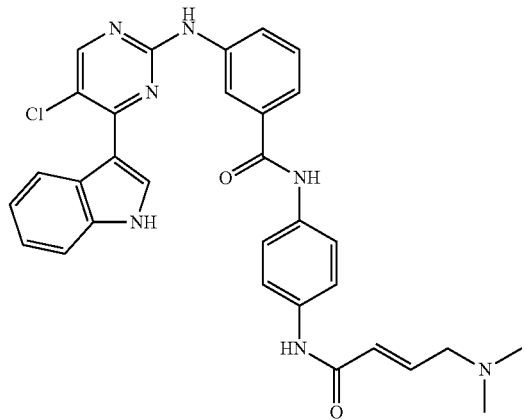 [SMILES: CN(C)C/C=C/C(=O)Nc1ccc(NC(=O)c2cccc(Nc3ncc(Cl)c(-c4c[nH]c5ccccc45)n3)c2)cc1]

LC-MS: (M+H) 566. $^1$H NMR (600 MHz, DMSO-d$_6$) δ 11.91 (s, 1H), 10.34 (s, 1H), 10.20 (s, 1H), 9.81 (s, 1H), 8.61 (d, J=7.8 Hz, 1H), 8.52 (d, J=3.6 Hz, 1H), 8.48 (s, 1H), 8.23 (m, 1H), 8.00 (d, J=8.4 Hz, 1H), 7.70 (d, J=8.4 Hz, 2H), 7.62 (d, J=8.4 Hz, 2H), 7.54 (d, J=7.8 Hz, 1H), 7.46 (d, J=7.8 Hz, 1H), 7.43 (t, J=7.8 Hz, 1H), 7.16 (t, J=7.8 Hz, 1H), 7.08 (t, J=7.8 Hz, 1H), 6.76 (m, 1H), 6.44 (d, J=16.8 Hz, 1H), 3.95 (d, J=6.0 Hz, 2H), 2.79 (s, 6H) ppm.

(I-69)

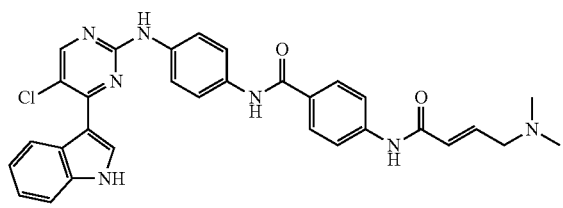

LC-MS: (M+H) 566. $^1$H NMR (600 MHz, DMSO-d$_6$) δ 11.99 (s, 1H), 10.67 (s, 1H), 10.16 (s, 1H), 9.67 (s, 1H), 8.64 (d, J=8.4 Hz, 1H), 8.54 (d, J=3.0 Hz, 1H), 8.52 (s, 1H), 8.05 (d, J=8.4 Hz, 2H), 7.86 (d, J=8.4 Hz, 2H), 7.80 (d, J=7.8 Hz, 2H), 7.74 (d, J=7.8 Hz, 2H), 7.57 (d, J=7.8 Hz, 1H), 7.28 (t, J=7.8 Hz, 1H), 7.20 (t, J=7.8 Hz, 1H), 6.82 (m, 1H), 6.54 (d, J=16.8 Hz, 1H), 4.00 (d, J=6.0 Hz, 2H), 2.87 (s, 6H) ppm.

(I-70)

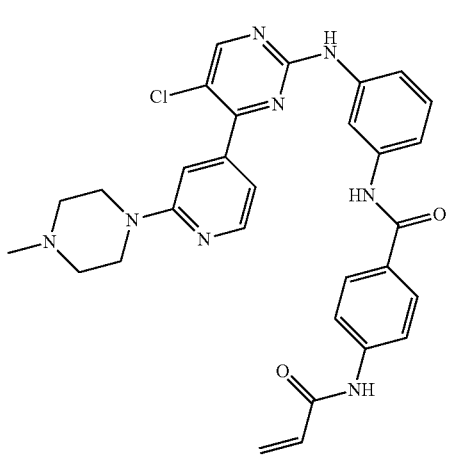

LC-MS: (M+H) 569. $^1$H NMR (600 MHz, DMSO-d$_6$) δ 10.45 (s, 1H), 10.12 (s, 1H), 10.00 (s, 1H), 8.66 (s, 1H), 8.30 (d, J=8.4 Hz, 1H), 8.19 (s, 1H), 7.97 (d, J=8.4 Hz, 2H), 7.80 (d, J=7.8 Hz, 2H), 7.45 (d, J=8.4 Hz, 1H), 7.30 (d, J=8.4 Hz, 1H), 7.24 (m, 2H), 7.10 (d, J=8.4 Hz, 1H), 6.44 (m, 1H), 6.27 (d, J=18.0 Hz, 1H), 5.58 (d, J=18.0 Hz, 1H), 4.43 (m, 2H), 3.44 (m, 2H), 3.17 (m, 2H), 3.00 (m, 2H), 2.79 (s, 3H) ppm.

(I-71)

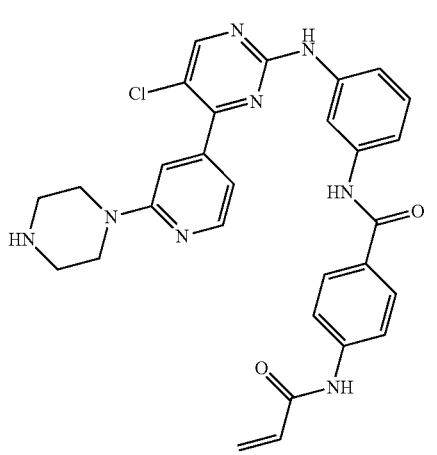

LC-MS: (M+H) 554. $^1$H NMR (600 MHz, DMSO-d$_6$) δ 10.71 (s, 1H), 10.21 (s, 1H), 10.09 (s, 1H), 8.95 (br, 2H), 8.73 (s, 1H), 8.37 (d, J=8.4 Hz, 1H), 8.24 (m, 1H), 8.04 (d, J=8.4 Hz, 2H), 7.88 (d, J=7.8 Hz, 2H), 7.55 (d, J=8.4 Hz, 1H), 7.37 (d, J=8.4 Hz, 1H), 7.31 (m, 2H), 7.17 (d, J=8.4 Hz, 1H), 6.82 (m, 1H), 6.55 (d, J=18.0 Hz, 1H), 4.43 (m, 2H), 3.44 (m, 2H), 3.17 (m, 2H), 3.00 (m, 2H), 2.79 (s, 3H) ppm.

Example 2. Biological Assays of the Compounds

The present invention relates, in one aspect, to the discovery of compounds of Formula (I) (e.g., compound I-23) as the first irreversible inhibitors of CDK7, which represent the first covalent inhibitors of any CDK. While all reported covalent kinase inhibitors to-date target a cysteine located near the ATP-binding site in primary sequence, the compounds of Formula (I) (e.g., compound I-23) have the unprecedented mechanism of targeting a cysteine residue situated completely outside of the canonical kinase fold. Molecular modeling based on the X-ray structure of CDK7, demonstrates that Cys312 is situated on a loop outside of the kinase domain that passes in front of the ATP-binding site thereby providing a fortuitous covalent attachment point for the compounds of Formula (I) (e.g., compound I-23). Sequence alignments suggest that this cysteine is largely unique amongst the CDKs and other kinases and affords an unanticipated opportunity to generate selective CDK7 inhibitors. Treatment of cells with the compounds of Formula (I) (e.g., compound I-23) leads to prolonged cessation of CTD phosphorylation; decreased transcription elongation processivity; decreased active transcription at genes critically required for the cancer cell state, including MCL-1 and MYC genes; and induction of apoptosis. Moreover, these effects are observed with short compound administration followed by washout; therefore, this mode of inhibition affords the potential for increased cellular and in vivo specificity by reducing the likelihood that free compound can engage in off-target interactions. The therapeutic potential of the CDK7 inhibitors of the invention was examined, and it was found that the compounds of Formula (I) (e.g., compound I-23) display strong anti-cancer potential against a broad range of cancer types, in particular against multiple myeloma and leukemia cell lines and against primary patient-derived chronic lymphocytic leukemia isolates. Therefore, it is demonstrated that irreversible inhibition of CDK7 is a viable strategy for gaining intra-CDK selectivity and, as a result, CDK7 inhibitor can be a valuable tool for dissecting CDK7's role in maintenance of gene expression and the cancer cell state.

Materials and Methods

Reagents and Antibodies.

Compounds 1-23, I-23R, and 1-49 were synthesized using the protocols described herein. The following antibodies were used for immunoblots: RNAP II CTD Ser-2 (04-1571), Ser-5 (04-1572), and Ser-7 (04-1570) phospho-antibodies (Millipore); Total RNAP II (Covance, MMS-126R); CDK7 (Bethyl, A300-405A); CDK1 (Bethyl, A303-664A), CDK2 (Bethyl, A301-812A); CDK4 (Cell Signaling, 2906); CDK6 (Cell Signaling, 3136); cyclin K (Bethyl, A301-939A); MCL-1 (Millipore, MAB4602); BCL-XL (Bethyl, A300-284A); PARP (Cell Signaling, 9542); and t-Tubulin DM1A (Sigma, T9026). For chromatin immunoprecipitation studies, total RNAP II (Santa Cruz, sc-899) and CDK7 (Bethyl, A300-405A) antibodies were used.

Cell Culture.

Loucy and Jurkat cells were grown in RPMI-1640 with 1% glutamine. HCT116 cells expressing FLAG-tagged CDK7 proteins were grown in DMEM medium supplemented with 2 µg/mL puromycin. All cell lines were supplemented with 10% FBS (Sigma) and 100 U·mL$^{-1}$ penicillin, 100 µg·mL$^{-1}$ streptomycin (Invitrogen) and cultured at 37° C. in a humidified chamber in the presence of 5% $CO_2$, unless otherwise noted.

Inhibitor Washout Experiments.

Cells were treated with compound I-23, compound I-23R, or DMSO for 4 hours. Following the treatment, the cells were washed 2-fold with PBS. Fresh medium containing no inhibitors were added back to the cells. The cells were lysed at indicated time points, and the lysates were probed for RNAP II CTD phosphorylation.

Pull Down/Immunoprecipitation Experiments.

Cells were treated with compound I-23, compound I-23R, or DMSO for 4 hours. Following the treatment, the cells were washed 2-fold with cold PBS and then lysed in the following lysis buffer: 50 mM TrisHCl pH 8.0, 150 mM NaCl, 1% NP-40, 5 mM EDTA, 1 mM DTT, and protease/phosphatase cocktails. Following clearance, the lysates were treated with compound I-49 for pulldown (or CDK7 antibody for IP) overnight at 4° C. The lysates were then incubated with streptavidin agarose for pulldown (or Protein G Agarose for IP) for an additional 2-3 hours at 4° C. Agarose beads were washed 5 times with a lysis buffer and then boiled in 2X SDS for 10 minutes at 95° C.

In Vitro Kinase Assays.

In vitro kinase assays with immunoprecipitated proteins (or recombinant CAK complexes) were performed as follows. Kinase reactions were performed in 25 µL of final volume of reaction buffer (50 mM Hepes, pH 7.5, 150 mM NaCl, 10 mM $MgCl_2$, 5% glycerol, 25 µM ATP, and 10 µCi of [γ-32P]ATP). Each reaction contained 1 µg of RNAP II. Incubation was at 30° C. for 30-45 min. Reactions were terminated by addition of 5 µL of 5×SDS-PAGE sample buffer and incubated at 95° C. for 5 min. Reactions were analyzed by SDS-PAGE, and the dried gel was exposed to film or PhosphorImager plate.

Chromatin Immunoprecipitation Coupled to High Throughput Sequences (ChIP-seq).

ChIP was carried out as described in Rahl et. al., Cell (2010) 141:432-45. In summary, Jurkat cells were treated with DMSO alone or compound I-23 (250 nM for 6 hours or 500 nM for 12 hours), compound I-23R (250 nM for 6 hours) or flavopiridol (250 nM for 6 hours). After the indicated treatment time, cells were crosslinked for 10 minutes at room temperature by the addition of one-tenth of the volume of 11% formaldehyde solution (11% formaldehyde, 50 mM Hepes (pH 7.3), 100 mM NaCl, 1 mM EDTA (pH 8.0), 0.5 mM EGTA (pH 8.0)) to the growth media followed by two washes with PBS. Following the final PBS wash, supernatant was aspirated, and the cell pellet was flash frozen in liquid nitrogen. Frozen crosslinked cells were stored at −80° C.

50 µl of Dynal magnetic beads (Sigma) were blocked with 0.5% BSA (w/v) in PBS. Magnetic beads were bound with 5 µg of the indicated antibody. Antibodies used are as follows: Total RNAP II (Rpb1 N-terminus): Santa Cruz sc-899; CDK7: Bethyl A300-405A. Crosslinked cells were lysed with lysis buffer 1 (50 mM Hepes (pH 7.3), 140 mM NaCl, 1 mM EDTA, 10% glycerol, 0.5% NP-40, and 0.25% Triton X-100) and washed with lysis buffer 2 (10 mM Tris-HCl (pH 8.0), 200 mM NaCl, 1 mM EDTA (pH 8.0) and 0.5 mM EGTA (pH 8.0)). The cells were resuspended and sonicated in sonication buffer (50 mM Tris-HCl (pH 7.5), 140 mM NaCl, 1 mM EDTA, 1 mM EGTA, 1% Triton X-100, 0.1% Na-deoxycholate, 0.1% SDS) for 9 cycles at 30 seconds each on ice (18-21 watts) with 60 seconds on ice between cycles. Sonicated lysates were cleared and incubated overnight at 4° C. with magnetic beads bound with antibody to enrich for DNA fragments bound by the indicated factor. Beads were washed three times with sonication buffer, one time with sonication buffer with 500 mM NaCl, one time with LiCl wash buffer (20 mM Tris (pH 8.0), 1 mM EDTA, 250 mM LiCl, 0.5% NP-40, 0.5% Na-deoxycholate), and one time with TE. DNA was eluted in elution buffer. Cross-links were reversed overnight. The RNA and protein were digested using RNAse A and Proteinase K, respectively, and the DNA was purified with phenol chloroform extraction and ethanol precipitation.

Illumina sequencing libraries were generated, and data were processed according to Lin et al., Cell (2012) 151:56-67. In brief, libraries were generated for ChIP samples following the Illumina TruSeq™ DNA Sample Preparation v2 kit protocol with minor changes. All ChIP-Seq datasets were aligned using Bowtie (version 0.12.2) (Langmead et al., Genome Biology (2009), 10:R25) to build version NCBI36/HG18 of the human genome. Alignments were performed using the following criteria: -n2, -e70, -m1, -k1, -best. These criteria preserved only reads that mapped uniquely to the genome with 1 or fewer mismatches. ChIP binding density was visualized on the UCSC genome browser (genome.ucsc.edu). Replicate experiments were performed for RNAP II ChIPs in cells treated with 250 nM of compound I-23 for 6 hours. The phenotype observed on RNAP II occupancy as a result of 250 nM of compound I-23 was consistent for both replicates, and therefore, the reads from the two replicate samples were merged for the figure displays for simplicity.

Proliferation Assays.

Proliferation assays were conducted over a 48-72 hour time period (as noted). Cell titer glo was used to assess the anti-proliferative effects of the compounds as described in the product manual. Cancer cell line profiling was performed over a 72 time period using Alamar Blue reagent.

Apoptosis Assays.

PBMCs freshly isolated from peripheral blood are seeded in 24 well plates at a volume of 0.5 ml and a concentration of $2\times10^6$ cells/ml. Compounds and controls are added to respective wells in a total volume of 2.5 µl. Plates are mixed gently and incubated approximately 24 hours at 37° C., 5% $CO_2$. Apoptosis was measured in all cells from each well using the Annexin V: FITC Apoptosis Detection Kit I (BD Biosciences). Normalized % death was calculated as follows:

[(% Dead Drug−% Dead DMSO)/(100%−% Dead DMSO)]×100

NanoLC/MS.

Recombinant CAK complex was incubated with CDK7-IN-1 or DMSO for 4 hours at 37° C., and the reactions were resolved by SDS-PAGE. Bands corresponding to CDK7 were excised, and digested in gel with trypsin according to standard protocols. Extracted peptides were loaded via autosampler injection (NanoAcquity Sample Manager, Waters, Milford, Mass.) onto a precolumn (4 cm POROS 10R2, Applied Biosystems, Framingham, Mass.) and eluted with an HPLC gradient (NanoAcquity Binary Sample Manager, Waters; 0-35% B in 60 minutes; A=0.1 M acetic acid in water, B=0.1 M acetic acid in acetonitrile). Peptides were resolved on a self-packed analytical column (12 cm Monitor Cis, Column Engineering, Ontario, Calif.) and introduced to the mass spectrometer (LTQ Orbitrap XL or LTQ Orbitrap Velos) at a flow rate of about 30 nL/min (ESI spray voltage=2.2 kV). The Orbitrap XL was operated in data dependent mode such that the 15 most abundant precursors were subjected to MS/MS (CAD with electron multiplier detection, NCE=35%). To facilitate detection of peptides labeled with the inhibitor, acetonitrile was added to the peptides (final concentration 25%) prior to injection. In addition, the peptides were eluted using a modified HPLC gradient (10-70% B in 24 minutes) and analyzed on the Orbitrap Velos. Here, the mass spectrometer performed alternating CAD (EM detection, NCE=35%) and HCD MS/MS (NCE=35%, image current detection, resolution 7500 at m/z 400) scans on the top seven most abundant precursors and included additional targeted scans for various charge states predicted for the inhibitor labeled C312 peptide.

MS Data Analysis.

Files were searched using Mascot version 2.2.1 against a database of CDK7. Precursor and product ion tolerances were 10 ppm and 0.6 Da, respectively. Search parameters included trypsin specificity, up to 2 missed cleavages, fixed carbamidomethylation (C, +57 Da), variable deamidation (NQ, −1 Da), oxidation (M, +16 Da), and inhibitor modification (CK, +565 Da). The doubly carbamidomethylated C312 containing peptide was quantified from MS scans using peak heights corresponding to triply and quadruply charged peptide precursors using 2 unlabeled CDK7 peptides for normalization.

Kinome Profiling and Compound-Based Affinity Chromatography Identified Phenylamino-Pyrimidine Scaffold as a Potential CDK7 Scaffold The phenylamino-pyrimidine (PAP) core scaffold is a "privileged" ATP-site directed pharmacophore with the most famous example being imatinib, a Bcr-Abl inhibitor approved to treat several cancers including Chronic Myelogenous Leukemia. Numerous PAP derivatives have been reported as potent inhibitors of various CDKs; however, efforts to achieve greater selectivity amongst the CDK family members have been hindered by the high sequence and structural similarity of CDKs. All CDK inhibitors reported to date are non-covalent but sequence and structural analysis reveals that a number of CDKs possess cysteine residues that might form the basis for the development of potent and selective covalent inhibitors. In an effort to explore broadly which CDKs might be targetable by a covalent inhibitor, a library of acrylamide-modified PAPs was built, and the library was subject to cell proliferation as well broad kinase selectivity profiling using the Kinativ chemical proteomics approach. A compound to emerge from the screen was compound I-23 (FIG. 1A), which had lost its ability to inhibit JNK but gained potent antiproliferative activity against a number of cell lines. Comparison of compound I-23 to an analog lacking the electrophilic acrylamide (α,β-unsaturated carbonyl) moiety (compound I-23R, FIG. 1A), which is required to form covalent bonds with cysteine residues, revealed compound I-23 to be roughly 10-fold more potent as an anti-proliferative agent, suggesting that compound I-23 was likely acting through a putatively irreversible binding mechanism (FIG. 1B). A combination of unbiased kinase profiling, candidate-based screening of kinases with appropriately positioned nucleophilic amino acids, and compound-based affinity chromatography, leveraging the perceived covalent nature of compound I-23, were used to find possible targets of compound I-23. To corroborate this finding using an independent approach, a biotinylated derivative of compound I-23 was synthesized (compound I-49, FIG. 1A) which was capable of specifically binding to CDK7 as monitored by western-blot (FIG. 1C).

Consistent with the PAP scaffold being capable of targeting a variety of kinases, the KiNativ profiling identified several other kinases as potential targets of compound I-23. However, with the exception of CDK7 and PIP4K2C both compounds I-23 and I-23R engaged all other targets with comparable potency suggesting that most of these kinases are reversible targets of compound I-23. In order to discriminate between reversible and irreversible kinase binding, in vitro binding and enzymatic assays were performed which demonstrated that compound I-23 displayed covalent binding to CDK7.

Compound I-23 Irreversibly Inhibits RNAP II CTD Phosphorylation

CDK7 exerts its regulatory control of transcription largely by phosphorylating RNAP II CTD, which promotes active transcription. To investigate whether compound I-23 treatment recapitulates cellular phenotypes consistent with those previously reported for disruption of CDK7, Loucy cells were treated with compound I-23 or I-23R, in a dose-response format and immunoblotted for RNAP II CTD Ser-2, Ser-5, and Ser-7 phosphoepitopes (FIG. 2A). Compound I-23 caused a dose-dependent decrease in the phosphorylation of all RNAP II CTD sites, with Ser-7 and Ser-2 being the most dramatically affected. Reduction of Ser-5 phosphorylation was seen only at higher concentrations. The cellular $IC_{50}$s of compound I-23 for Ser-7 and Ser-2 were approximately 4 nM and 20 nM, respectively. Conversely, compound I-23R showed significantly higher $IC_{50}$ values for phosphorylation of these phosphoepitopes.

Figure 2B:
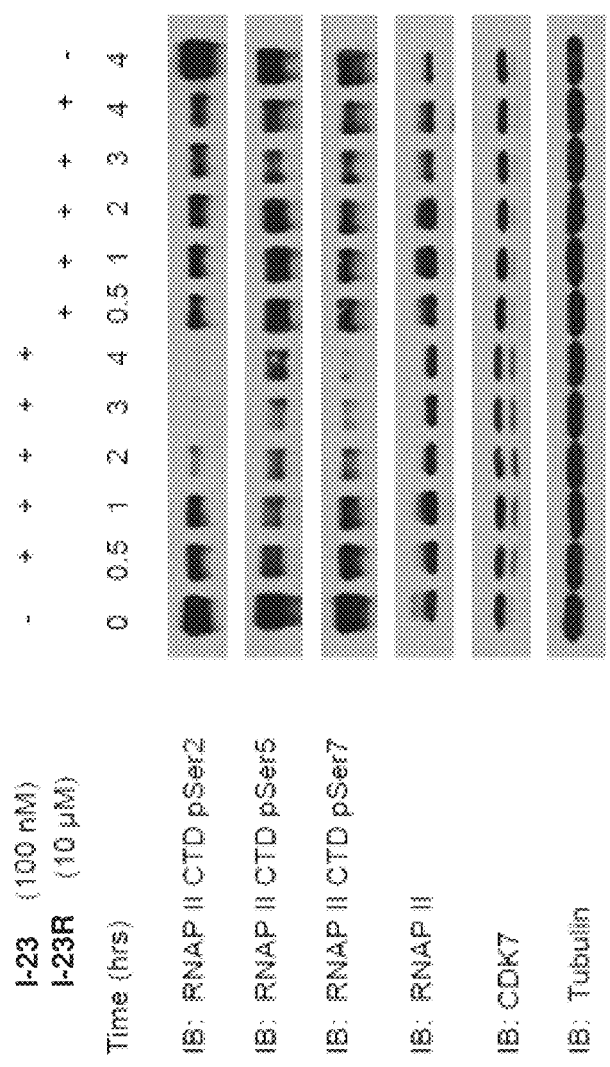
Figure 2C:
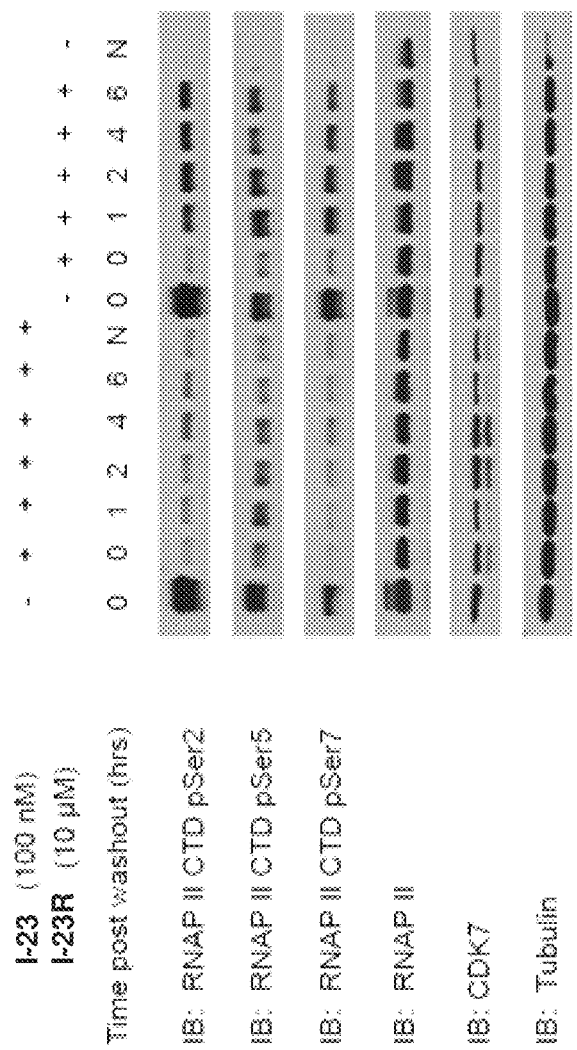
Figure 2D:
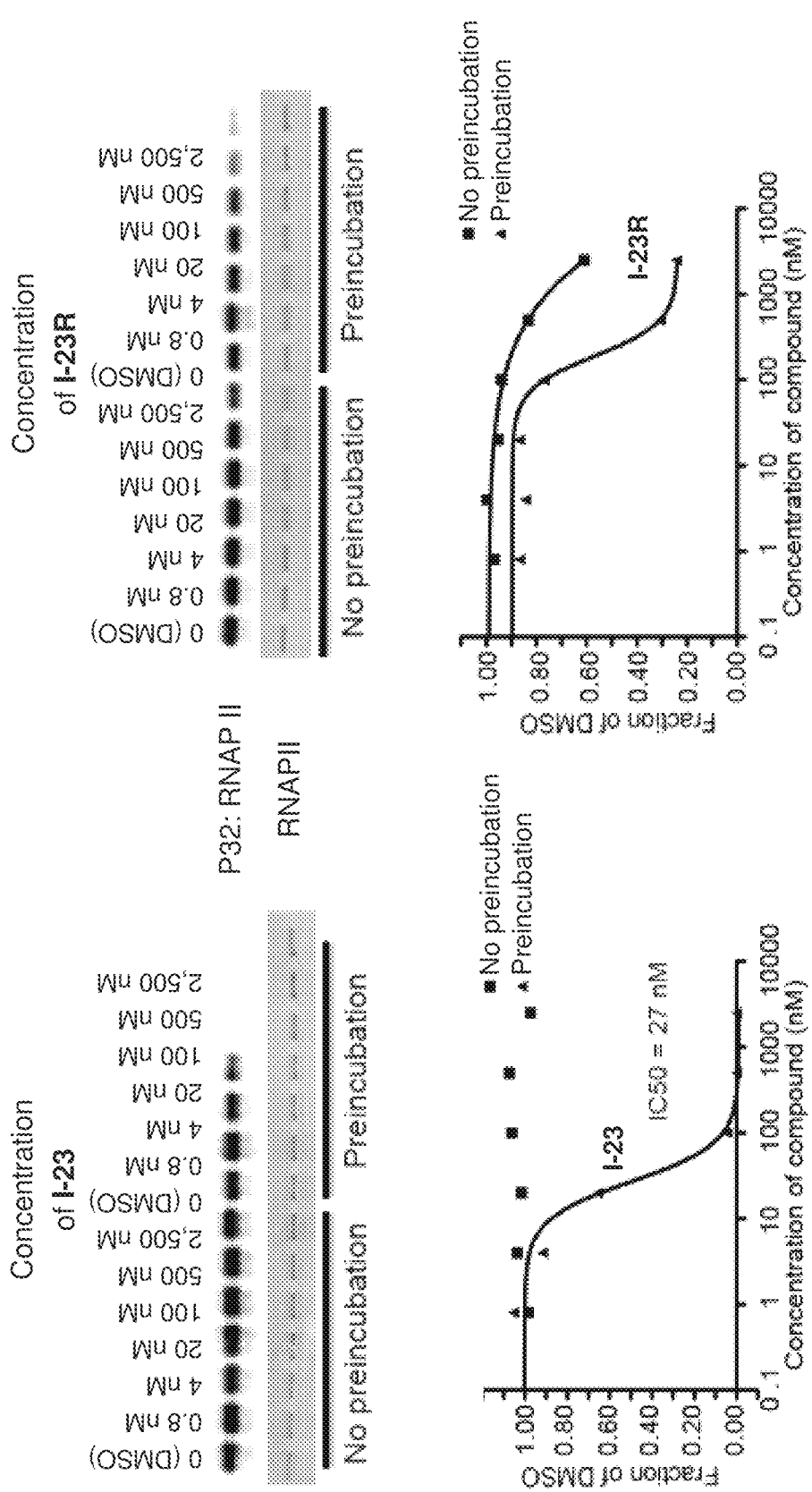

Covalent kinase inhibitors have several characteristics that functionally differentiate themselves from their reversible counterparts. Generally, (1) covalent kinase inhibitors have electrophilic substituents that react covalently with nucleophilic centers on their target kinase; (2) covalent kinase inhibitors exhibit two-step inhibitory kinetics marked by a fast reversible binding event, followed by a slow covalent (irreversible) binding event, which causes the overall kinetics of target inactivation to be slow relative to noncovalent inhibitors; and (3) once covalently bound, covalent kinase inhibitors are impervious to washout of the inhibitors and are no longer ATP-competitive. To determine if compound I-23 displays slow kinetics of target inactivation, Loucy cells were treated with compound I-23 or I-23R for varying times, and lysates were harvested to probe for RNAP II CTD phosphorylation. Compound I-23 exhibited slow inactivation of CDK7, with complete inhibition of target coming only after 3-4 hours (FIG. 2B). In comparison, compound I-23R exhibited rapid inactivation of the target, indicative of a reversible inhibitor. To assess if compound I-23 shows irreversible inhibition of CDK7 kinase activity, it was investigated whether CDK7 kinase activity returns following removal of compound I-23. Washout of compound I-23R, following a 4-hour administration led to the recovery of RNAP II CTD phosphorylation within 1 hour (FIG. 2C). Conversely, washout of compound I-23 did not restore normal CTD phosphorylation levels over the time course of this experiment. This phenomenon was also visible using in vitro kinase reactions comparing pre-incubation of compound I-23 with compound I-23 introduced concurrently with ATP. Here, when compound I-23 was pre-incubated with recombinant CAK complex (prior to the addition of ATP), I-23 led to a dramatic increase in CDK7 inhibitory activity (FIG. 2D). These results further suggest that compound I-23 is working through a covalent mechanism to inhibit CDK7.

Affinity Chromatography Demonstrates Compound I-23 Binds Irreversibly to CDK7

While the previous results suggest that compound I-23 operates by an irreversible inhibitory mechanism, direct evidence of covalent modification was sought. A recombinantly-expressed CAK complex was incubated with compound I-49 for 4 hours at 37° C., and the proteins were resolved on a SDS-page gel. Immunoblot with streptavidin-HRP indicated that CDK7 was labeled with compound I-49 (FIG. 3A). Because this labeling is detected after denaturation of the protein, it was established that this interaction is likely covalent in nature. Likewise, it was made possible to detect direct labeling of endogenous CDK7 with compound I-49, further suggesting that compound I-23 was operating via covalent modification of CDK7 (FIG. 3B). A reciprocal affinity chromatography experiment corroborated this covalent CDK7 engagement. Here, a competition-based experiment was employed, whereby intact cells were pre-treated with compound I-23 or I-23R, lysed, and probed with compound I-49 (FIG. 3C). If pre-treated cells undergo a covalent interaction, the covalent interaction would have the effect of protecting CDK7 from binding to compound I-49. Indeed, cells pre-treated with compound I-23, but not with compound I-23R, successfully blocked compound I-49 from binding CDK7 in a dose-dependent manner (FIG. 3D). These results again support the notion that compound I-23 interacts with CDK7 in a covalent and irreversible manner.

Figure 4A:
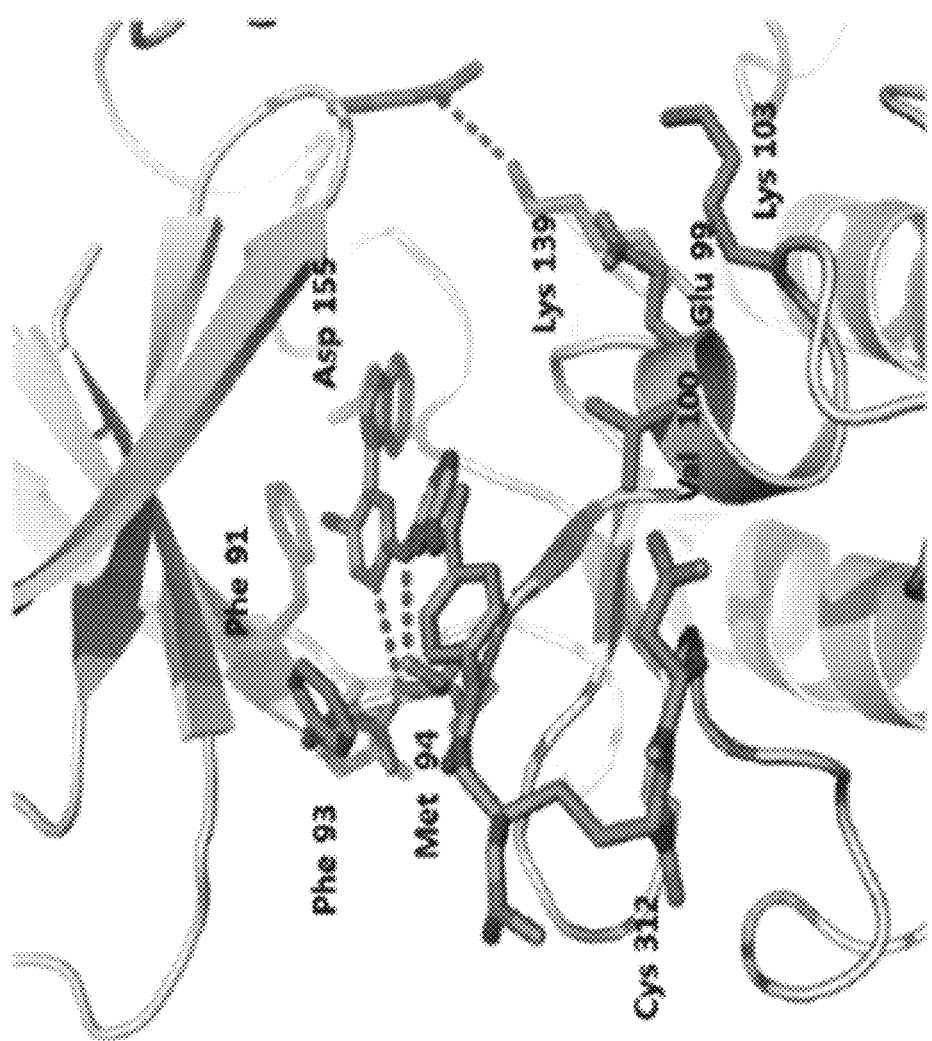
Figure 4C:
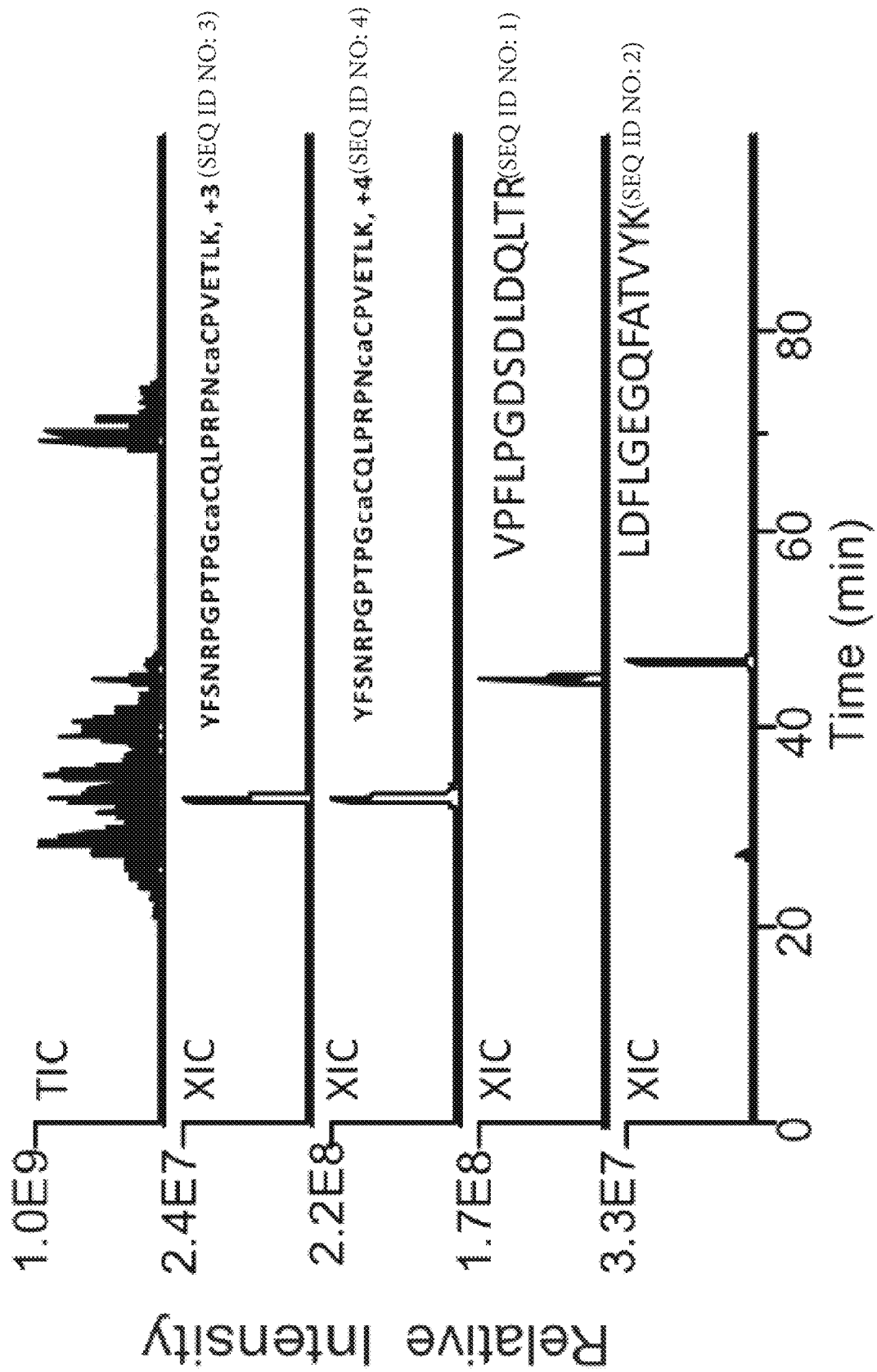
Figure 4D:
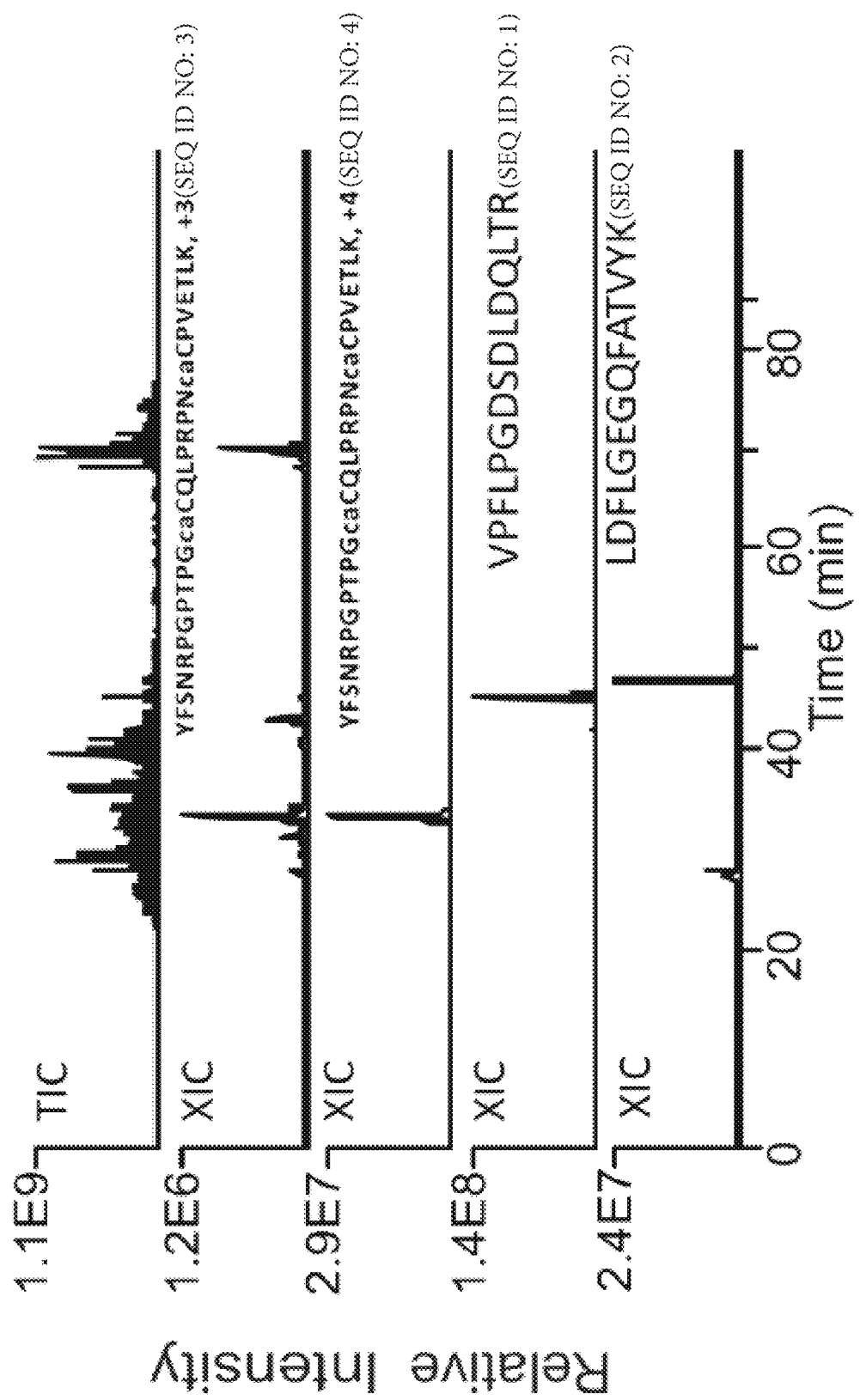
Figure 4E:
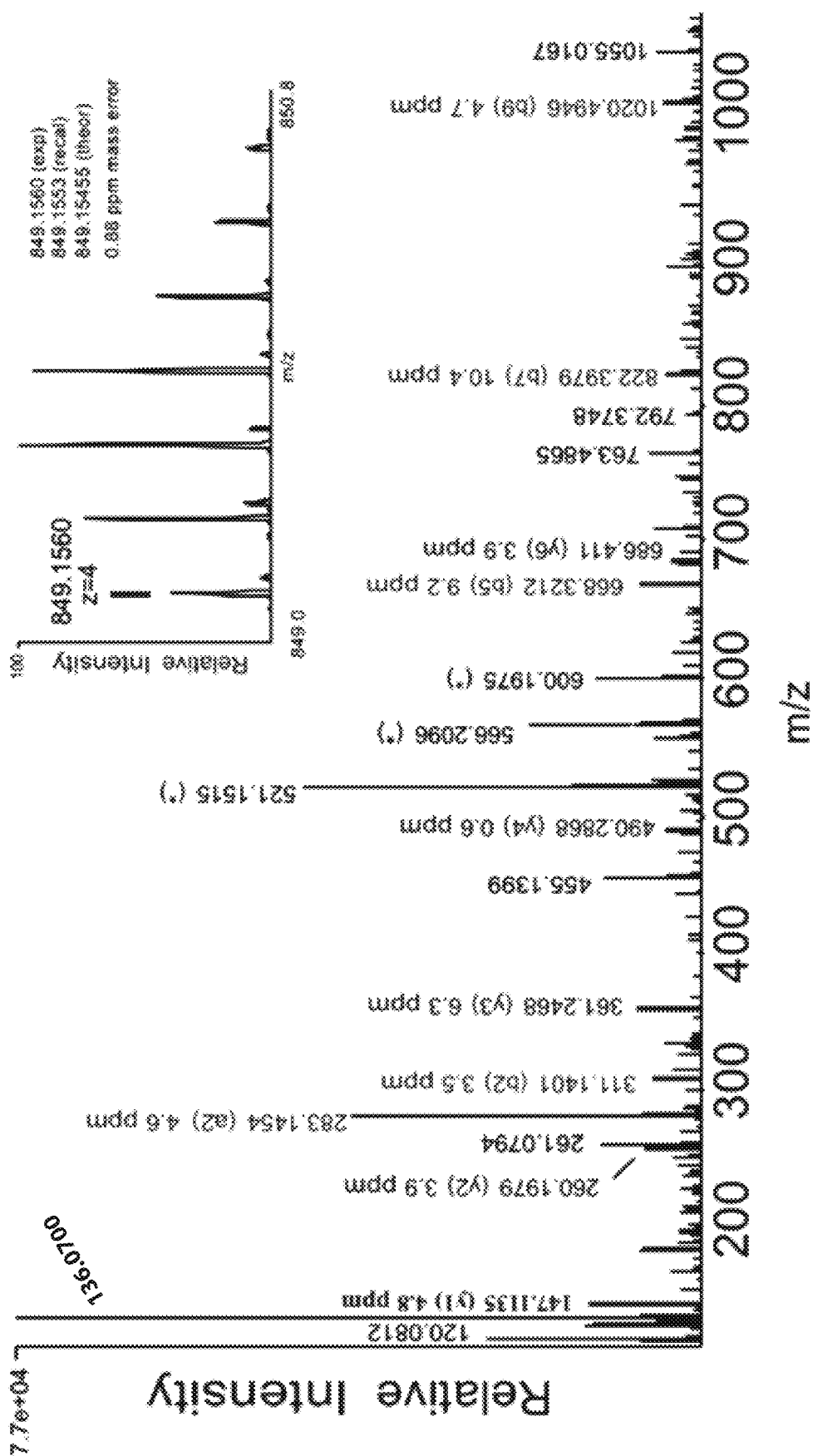

CDK7 Covalently Binds a Unique Cysteine in a Distal C-Terminal Region Located Outside the Kinase Domain The data described above establish that compound I-23 operates via an irreversible inhibitory mechanism. Next, the site of covalent modification on CDK7 was identified. Initial comparison of the binding mode of this compound class (see, U.S. Patent Application U.S. Ser. No. 61/561,078, which is incorporated in its entirety by reference) with the X-ray structure of CDK7 (Endicott) suggested that there was no cysteine (typical nucleophile) in position to react with the electrophilic center of compound I-23. Closer inspection of the X-ray structure of CDK7, which terminates at the C-terminus with residue N311, showed that the next residue is a cysteine (C312). Insertion of this residue into a model of compound I-23 in the ATP-binding pocket of CDK7 revealed that this cysteine approaches the β-carbon of the electrophilic center and could form a covalent bond with compound I-23 (FIG. 4A). Alignment of CDK7 with other CDK family members indicated that this cysteine was highly unique among CDKs (FIG. 4B). To determine if compound I-23 indeed binds C312 of CDK7, a recombinant CAK complex was incubated with DMSO or compound I-23 for 4 hours at 37° C., and the reactions were resolved by SDS-PAGE. Bands corresponding to CDK7 were excised, and tryptic peptides were analyzed by nanoLC/MS. CDK7 treated with compound I-23 showed a significant decrease in signal (~85%) for the doubly carbamidomethylated C312 containing a tryptic peptide relative to the untreated control, indicating this peptide was modified by the inhibitor (see the "Materials and Methods" subsection and FIGS. 4C to 4D), while peptides spanning C241 were detected at similar levels in both samples (not shown; C201 and C281 were not observed presumably due to the large size of the corresponding tryptic peptides). Unfortunately, the inhibitor-labeled peptide was not detected in the treated sample, possibly due to the precipitation under the aqueous conditions used to inject and analyze standard tryptic peptides. To facilitate detection of the modified analog, CDK7 peptides were injected in a solution containing 10% acetonitrile and eluted using a modified LC gradient. In this experiment, the C312-labeled peptide was identified in MS scans, and FT-MS2 spectra allowed localization of the modification site to C312 (FIG. 4E). Importantly, no other peptides that were modified with compound I-23 were detected, suggesting that this is a specific interaction.

Mutation of C312 Restores Wild-Type (WT) Kinase Function

Figure 4F:
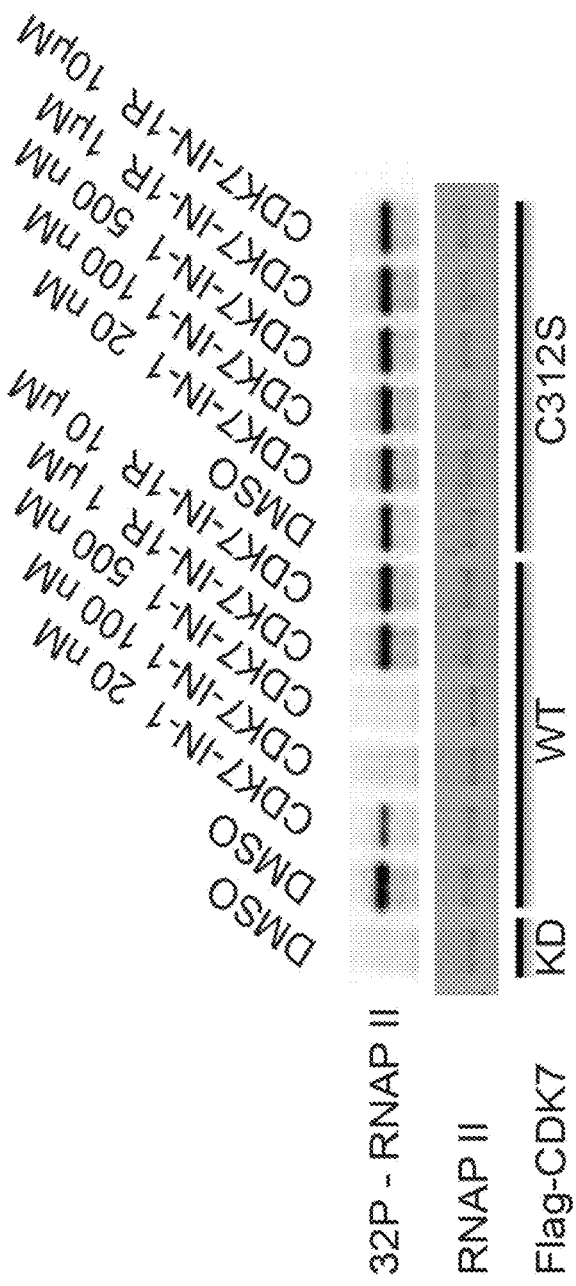

To determine if covalent attachment at C312 is critical to the activity of compound I-23, C312 was mutated to a serine (C312S), which will not react with the acrylamide of the inhibitor. HCT116 cells were generated stably expressing FLAG-CDK7 WT and C312S. Each HCT116 population was treated with compound I-23 or I-23R in a dose-response format. CDK7 was then immunoprecipitated (IP) from each combination treatment using a FLAG antibody, and washed IPs were subjected to in vitro kinase assays (FIG. 4F). Compound I-23, but not compound I-23R, inhibited FLAG-CDK7 WT in a dose-dependent fashion. In contrast, FLAG-CDK7 C312S was impervious to both compounds. Using this experimental format, whereby inhibitors are added directly to cells, the site of covalent modification was proven by demonstrating that the C312S mutation protects CDK7 from irreversible inhibition by compound I-23. Additionally, pre-treatment with compound I-23 allows target engagement of CDK7 directly in cells; therefore, despite the fact that the reaction occurs in a test tube, it acts as surrogate readout for intracellular inhibition. The inhibition of CDK7 in the kinase reaction at 2-digit nanomolar concentrations of compound I-23 is consistent with those seen to affect intracellular RNAP II CTD phosphorylation (FIG. 2A).

Compound I-23 Decreases RNAP II Processivity by Disruption of CDK7 Kinase Activity CDK7 inhibition results in decreased RNAP II CTD phosphorylation, which suggests altered transcriptional control. To investigate how decreased CDK7 kinase activity alters global transcription, RNAP II genome-wide occupancy was investigated in Jurkat cells following compound I-23 treatment using chromatin immunoprecipitation coupled to high-throughput sequencing (ChIP-seq). These studies revealed a striking defect in RNAP II occupancy across the genome following compound I-23 treatment.

Figure 5A:
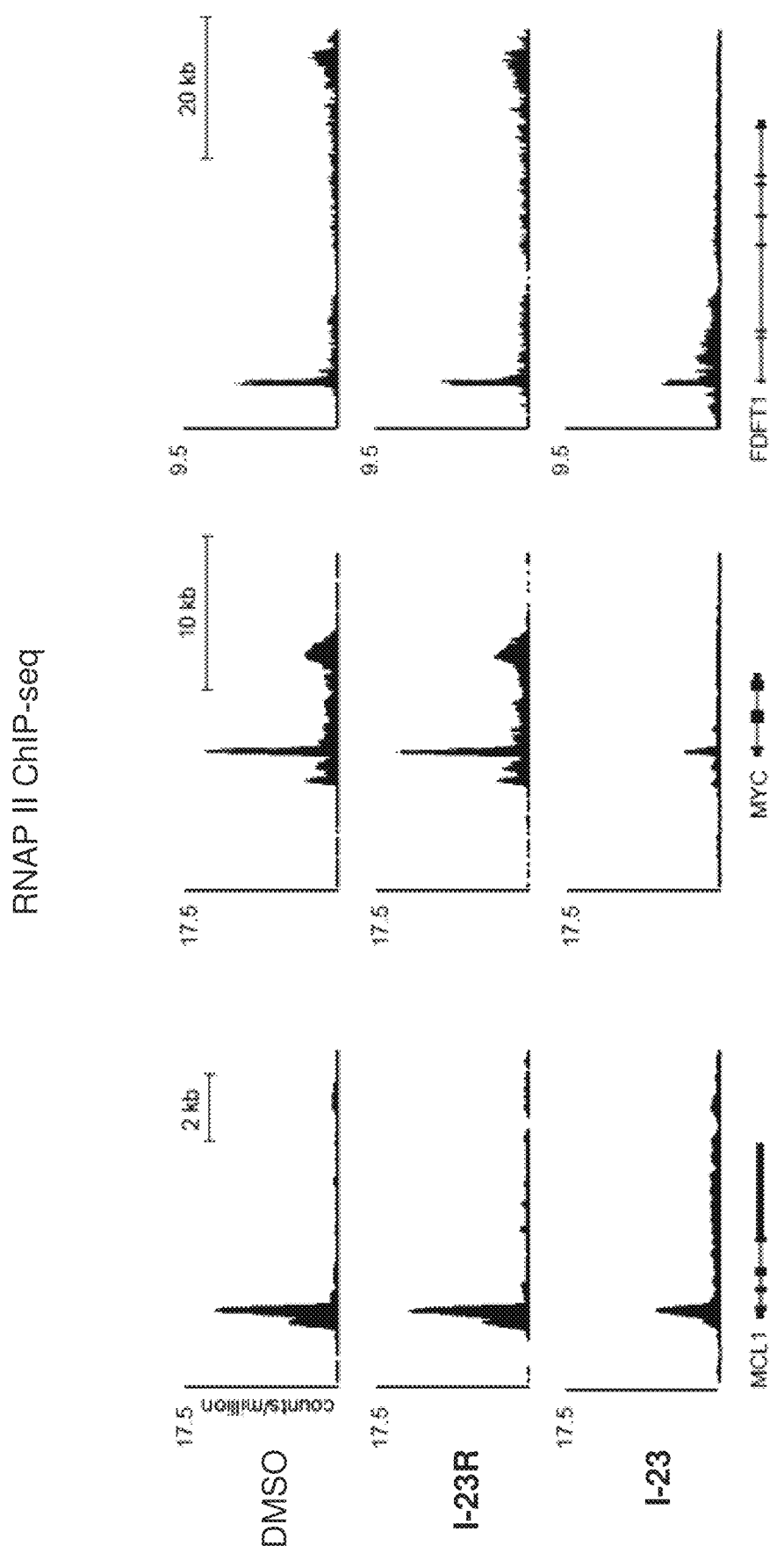
Figure 8:
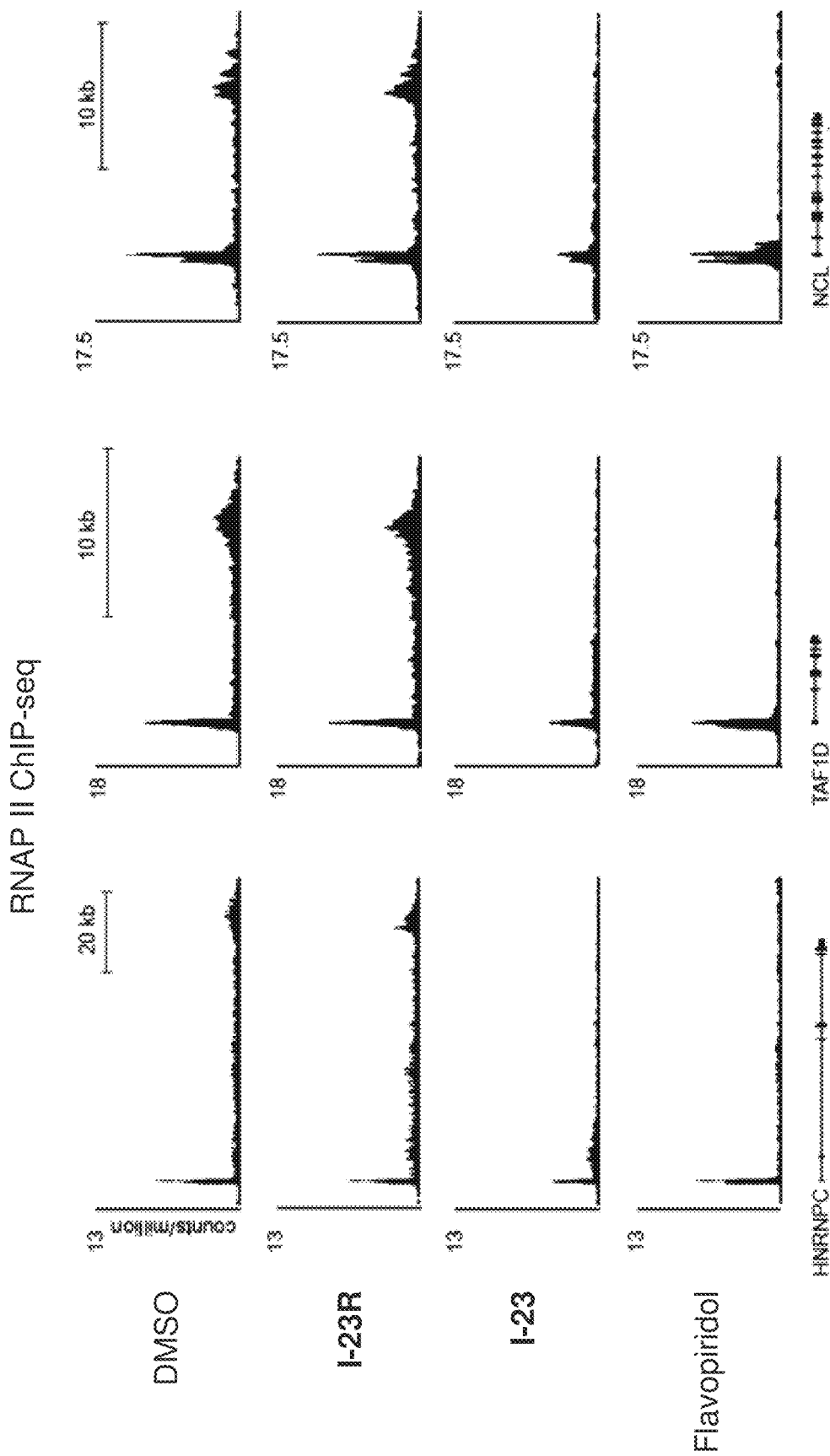
FIG. 8 shows that compound I-23 induces a differential phenotype, as compared to flavopiridol, on RNAP II occupancy at housekeeping genes.
Figure 9:
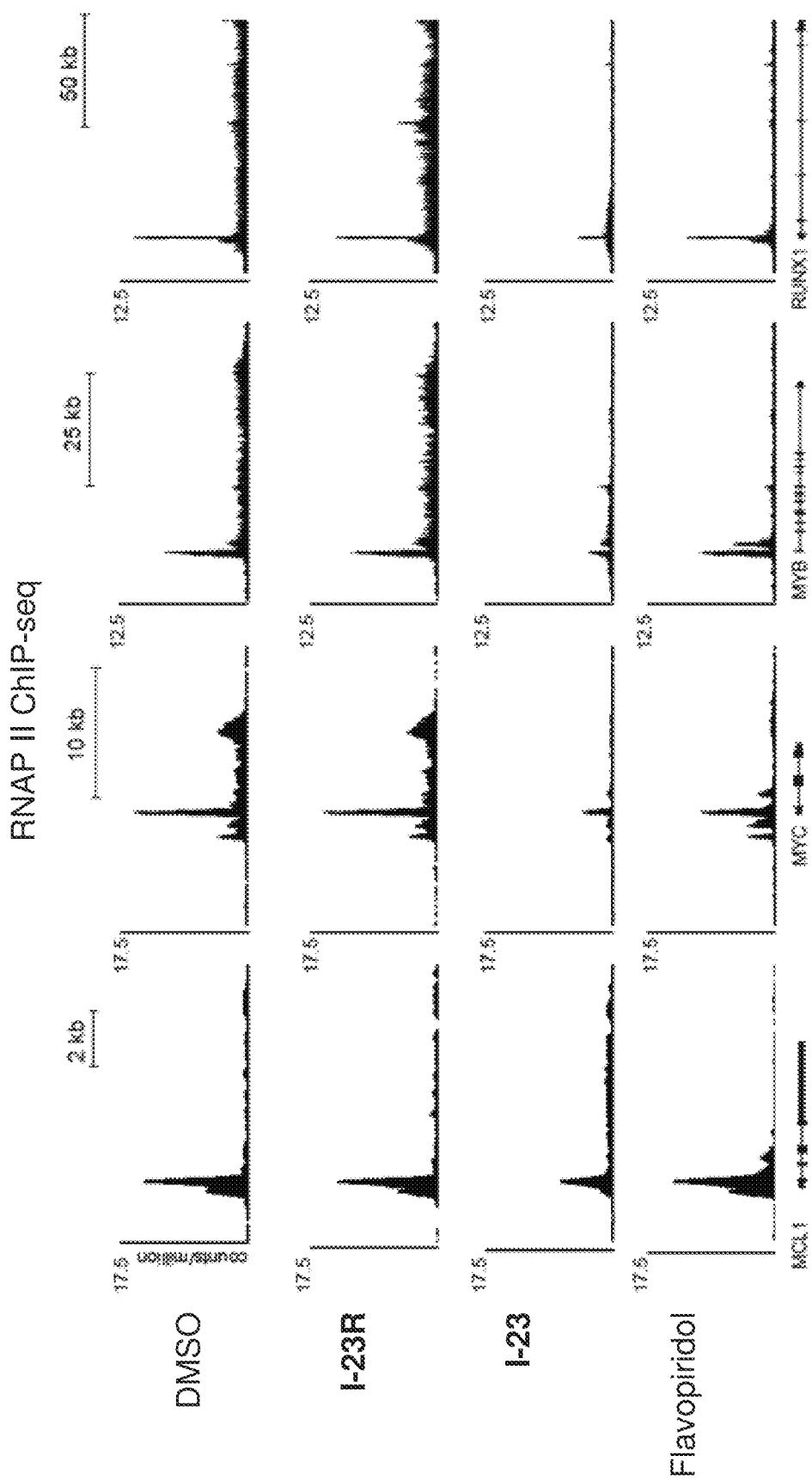
FIG. 9 shows that compound I-23 induces a differential phenotype, as compared to flavopiridol, on RNAP II occupancy at genes important for Jurkat cancer cell state.

Two major regulated steps in transcription occur at the level of RNAP II initiation and pause release where RNAP II occupancy is indicative of these regulatory mechanisms (Fuda et al., Nature (2009) 461:186-92). RNAP II displayed the typical distribution in Jurkat cells treated with DMSO or compound I-23R (250 nM) for 6 hours where a large fraction is detected at the promoter proximal pause site, elongating RNAP II is detected in the gene body of actively transcribed genes, and a fraction is detected downstream of the 3'-end of genes (FIGS. 5A and 8 to 10). Treatment with 250 nM of compound I-23 for 6 hours dramatically altered the RNAP II occupancy where the RNAP II at the promoter proximal pause site is drastically diminished (FIGS. 5A to 5B). Interestingly, RNAP II is largely depleted from the 3'-end of genes but detected with increased density downstream of the promoter proximal pause site (FIGS. 5A to 5B and 8 to 9). The RNAP II occupancy defect following the treatment with compound I-23 is strikingly different than flavopiridol treatment, where paused RNAP II occupancy is unaffected by the CDK inhibitor flavopiridol, but the transition into elongation is inhibited (FIGS. 8 to 9). These results provide insights into how CDK7 kinase inhibition leads to changes in CTD phosphorylation patterns where there is a global decrease in RNAP II detected at pause sites with defects in elongating RNAP II.

Figure 10A:
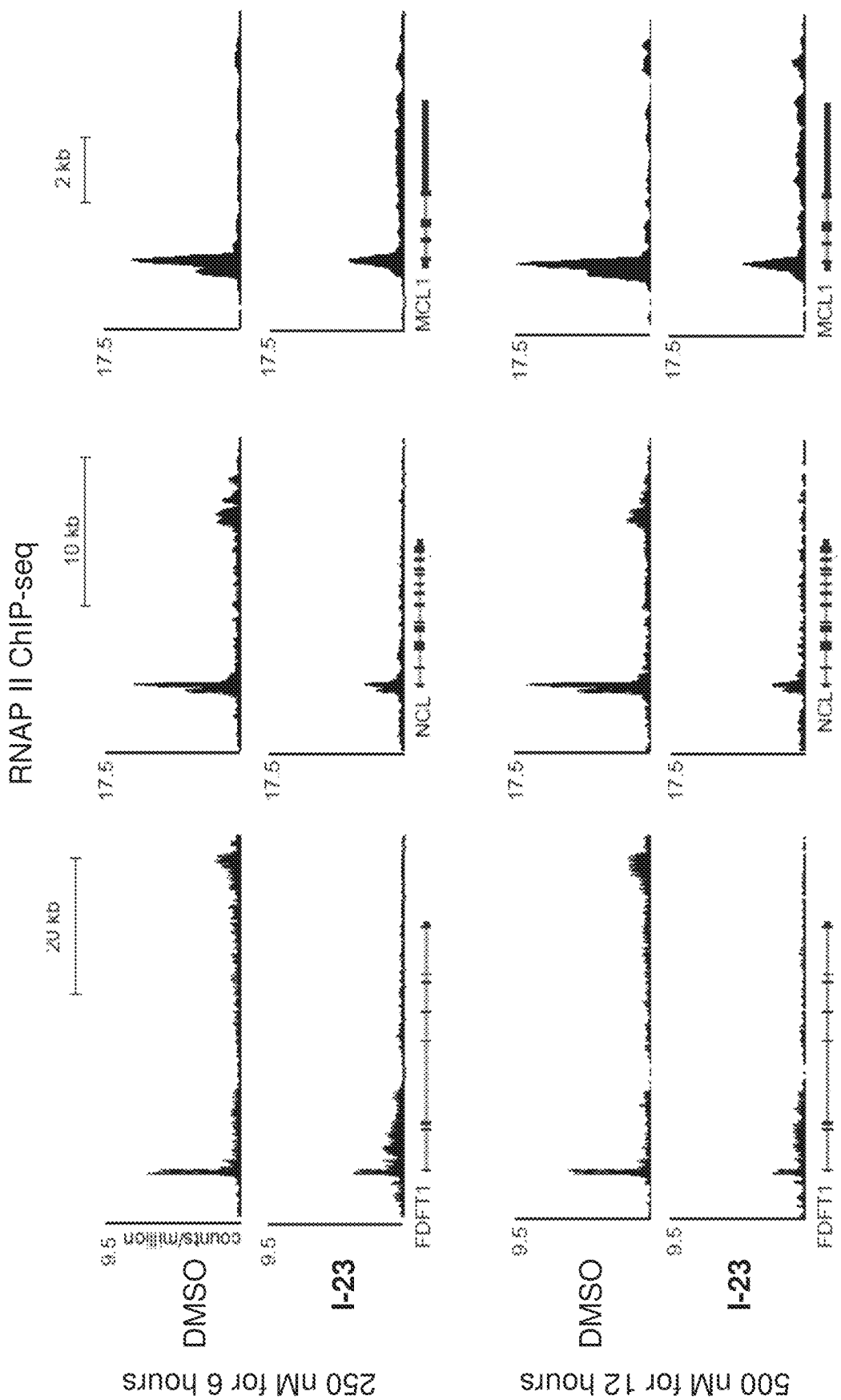
FIGS. 10A to 10B show that RNAP II occupancy defect is similar after 6 or 12 hours of a treatment with compound I-23.
Figure 10B:
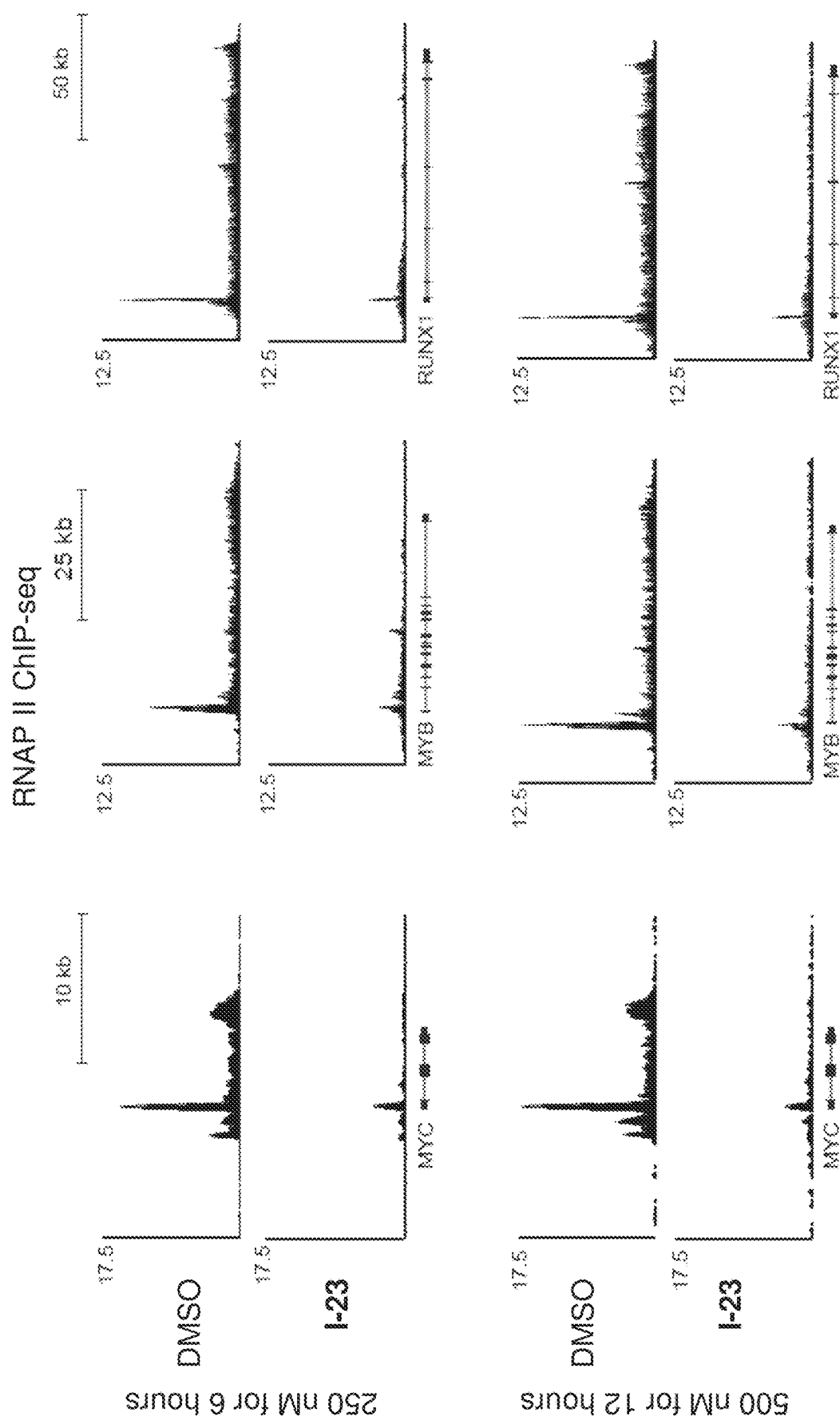

CDK7 covalent inhibition is required to alter RNAP II occupancy and transcriptional control across the genome (FIGS. 5A to 5B). Kinetic analysis described above indicated that complete enzymatic activity is achieved following 3-4 hours of treatment (FIG. 2B). To investigate if prolonged treatment with compound I-23 leads to greater defects in RNAP II occupancy, Jurkat cells were treated for 6 hours (roughly at $IC_{95}$, 250 nM) or 12 hours (greater than $IC_{95}$, 500 nM), and RNAP II ChIP-seq analysis was performed. Consistent with the kinetic analysis, the RNAP II occupancy defect is vastly similar following 6- and 12-hour treatments, suggesting that RNAP II occupancy is altered rapidly across the genome (FIG. 10).

It was next asked whether the changes in RNAP II occupancy resulted strictly from loss of catalytic activity or whether compound I-23 compromised the targeting of TFIIH to promoters. CDK7 ChIP-seq analysis was used to investigate if CDK7 inhibition affects its association with chromatin. It was indicated that compound I-23 treatment did not disrupt CDK7 occupancy (FIGS. 5C to 5D).

Figure 6A:
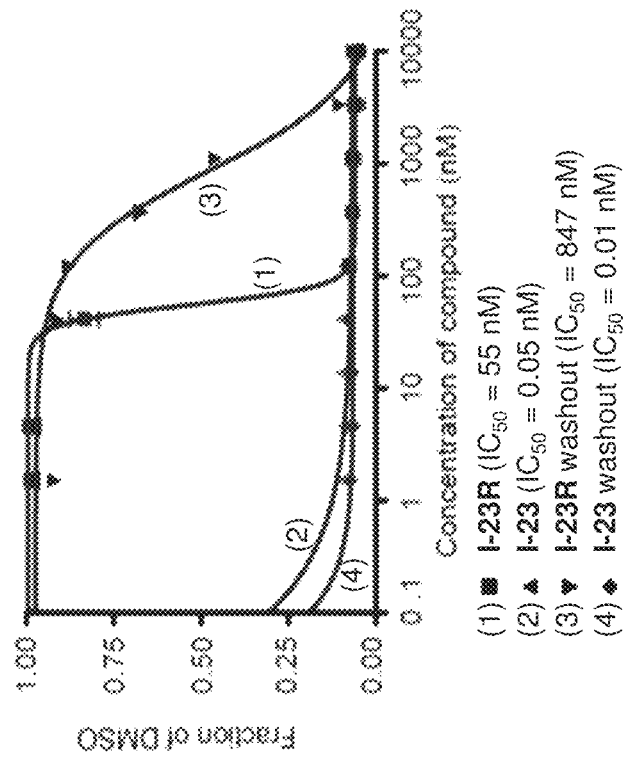
Figure 6B:
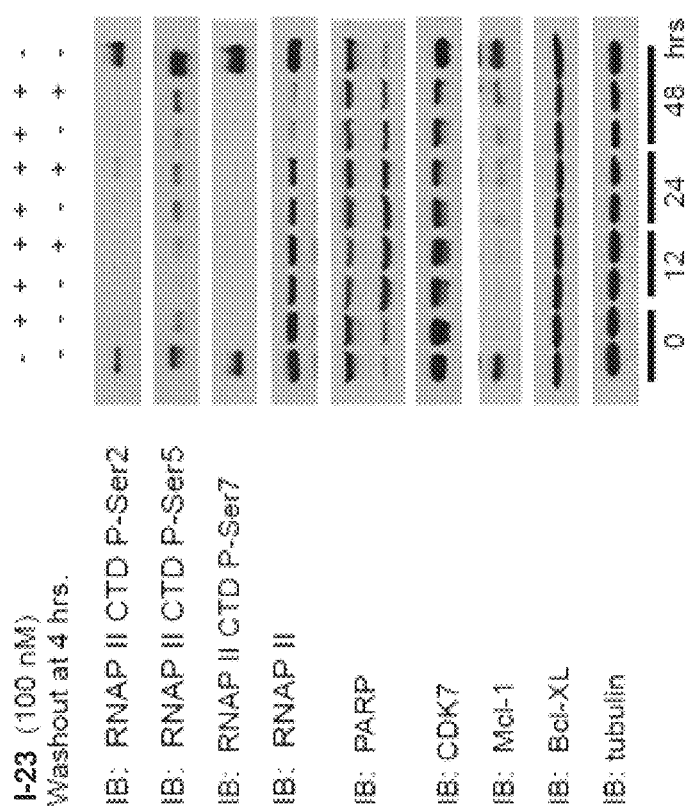
Figure 7:
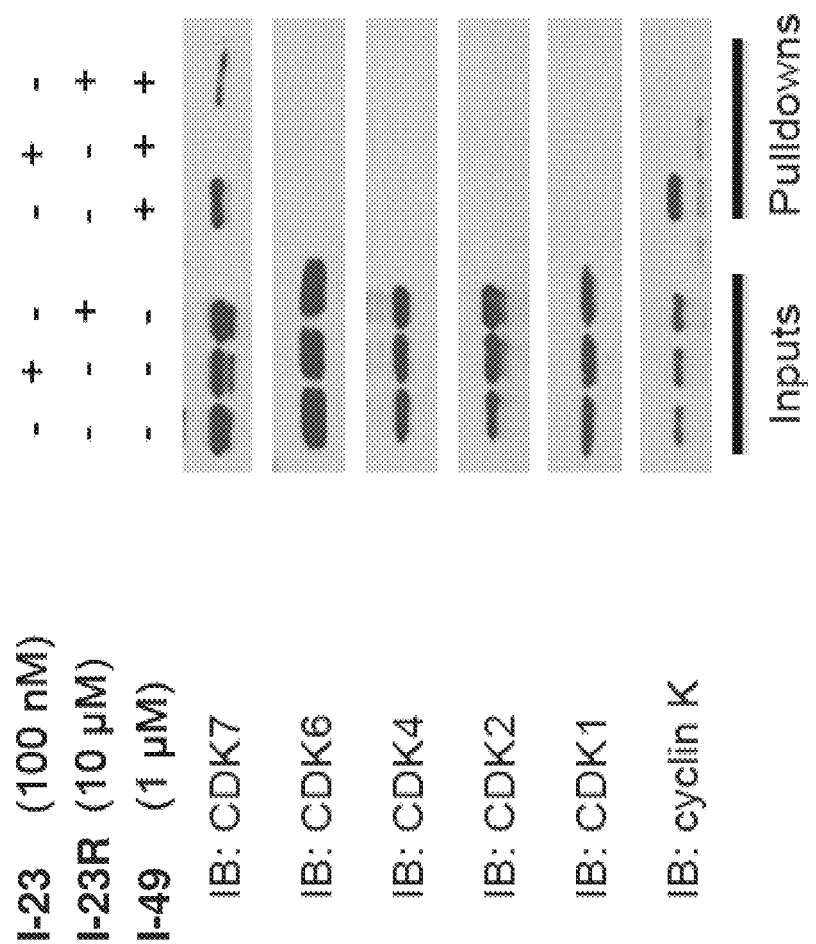
FIG. 7 shows that certain CDKs tested (e.g., CDK1, CDK2, CDK4, and CDK6) do not interact with I-49. However, cyclin K, which is known to bind to CDK12/13, did interact with I-49. Loucy cells were treated with I-23, I-23R, or vehicle for 4 hours. Lysates were then probed with I-49. Precipitated proteins were washed and probed with antibodies as shown.

Compound I-23 Induces Apoptosis and Downregulates Anti-Apoptotic BCL-2 Family Members Previous studies have indicated that chemical inhibition of CDK7 leads to reduced expression of anti-apoptotic BCL-2 family members. To investigate if compound I-23 causes a similar downregulation of BCL-2 family members, Loucy cells were treated with increasing amounts of compound I-23 over a time course of 12 to 48 hours (FIG. 6A). Treatment with as little as 100 nM of compound I-23 was sufficient to elicit a reduction in MCL-1 protein levels after 12 hours. Reductions in other BCL-2 family members, such as BCL-XL, were not reduced even at higher concentrations. Consistent with its covalent inhibitory mechanism, similar results were seen over the same time span following washout (FIGS. 6A to 6B). These data indicate that inhibition of CDK7 is an effective method for tipping the balance between cell death and survival signals in favor of cell death by apoptosis.

Compound I-23 Exhibits Strong Antiproliferative Activity Against a Wide-Range of Cancer Cell Lines.

CDK7 inhibitors display strong antiproflierative effects in leukemia and lymphoma cancer cells. However, a better definition of the breadth of their therapeutic potential in other cell types has not been reported. To address this deficiency, compound I-23 was screened in a dose-response format against a panel of >300 diverse cancer cell lines to identify new cancer cell lines that are uniquely sensitive or uniquely resistant to CDK7 inhibition. The rationale for examining such a large panel of human cancer cell lines is based on the fact that there is substantial genetic heterogeneity among human tumor cells, even with the same histological origins. In general, the data reveal a bimodal distribution with cell lines displaying exquisite sensitivity or apparent complete insensitivity to the compound. Of the cancer cell types tested, compound I-23 showed $IC_{50}$ values less than 200 nM in 70% of cell lines and showed $IC_{50}$ values greater than 2.5 µM in 24% of cell lines (FIGS. 6C to 6D). Consistent with previous results, all (48/48) lymphoma cell lines and 94% (132/140) of leukemia cell lines tested were sensitive to compound I-23 exhibiting $IC_{50}$s below 150 nM and 200 nM, respectively. In contrast, untransformed retinal pigment epithelial (RPE1) cells were largely resistant to I-23 (FIG. 6E).

Figure 11A:
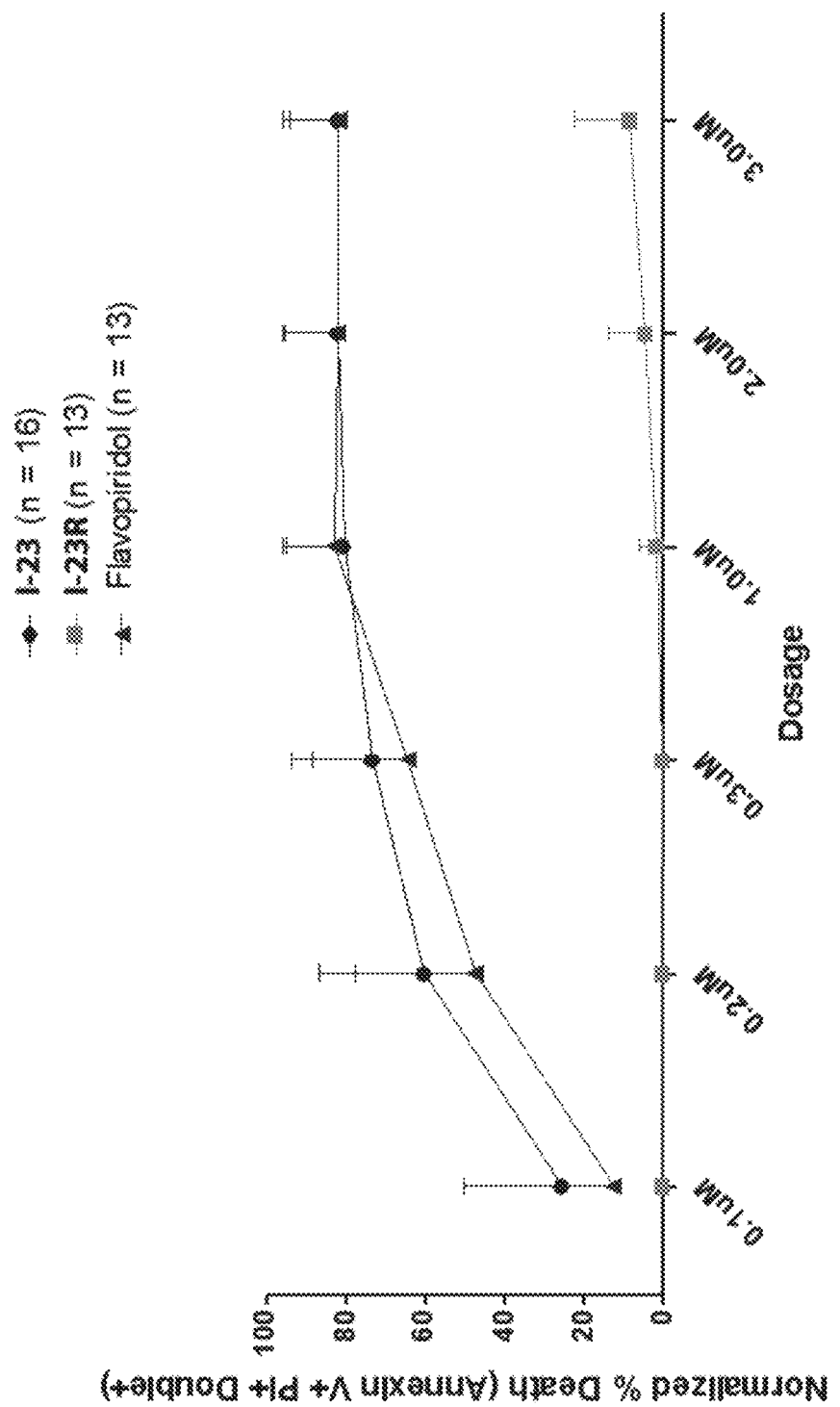
Figure 11B:
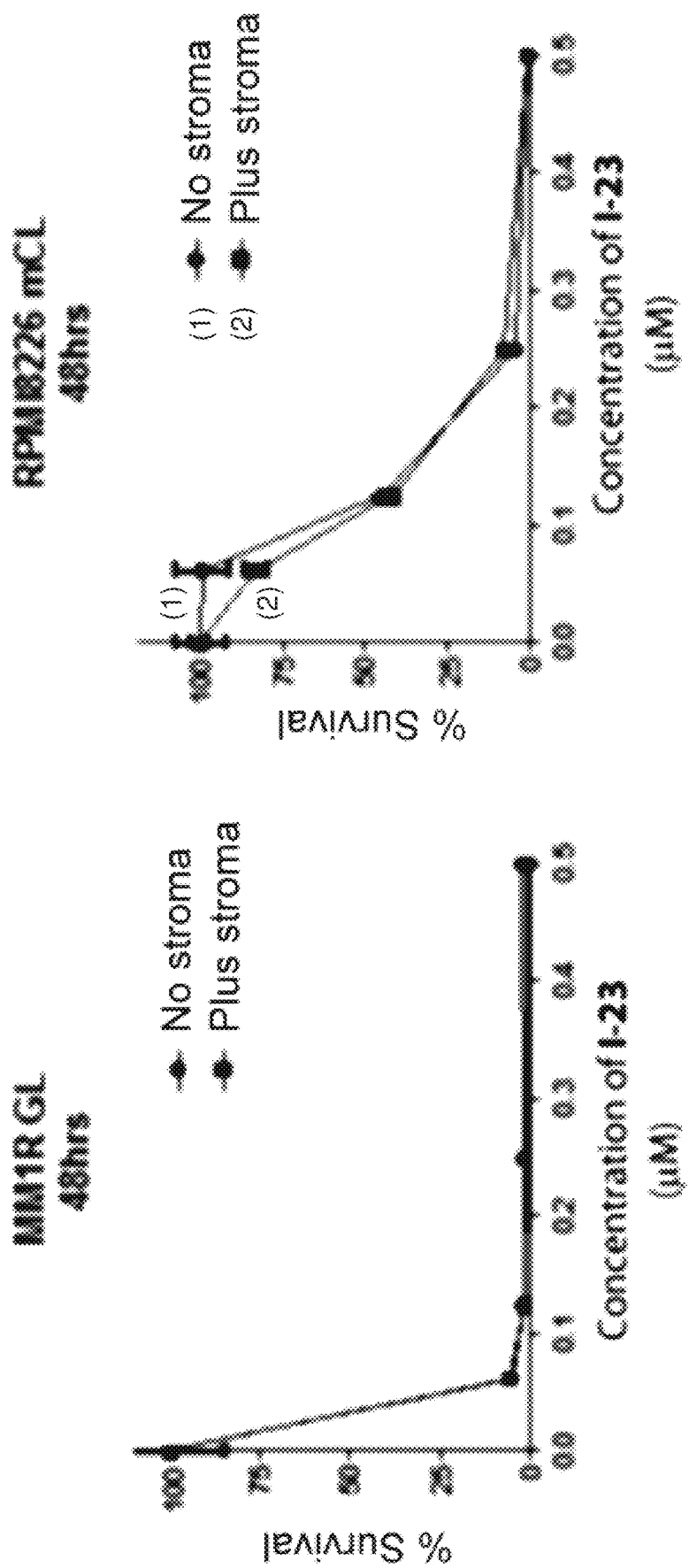
Figure 11E:
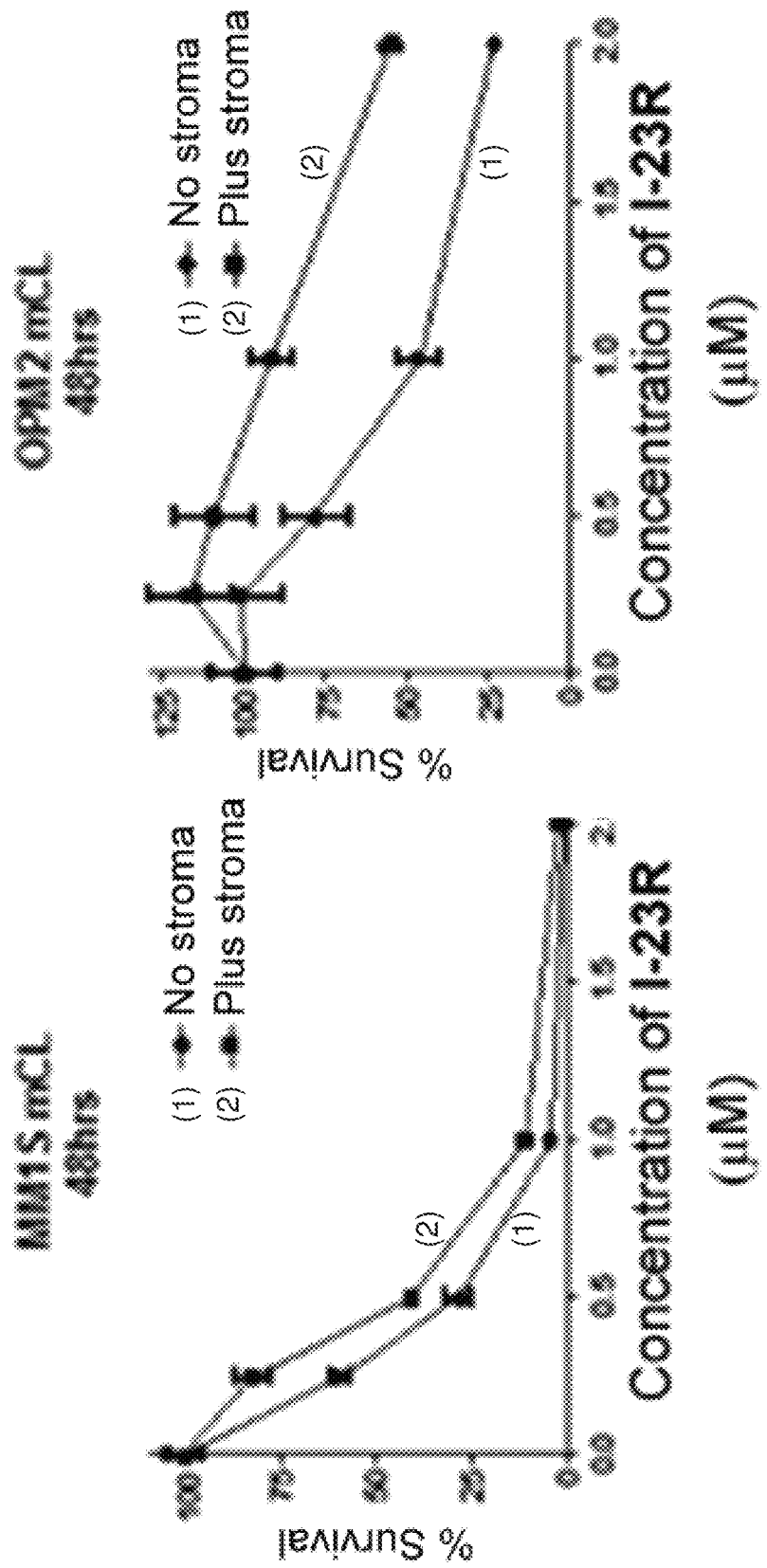
Figure 11F:
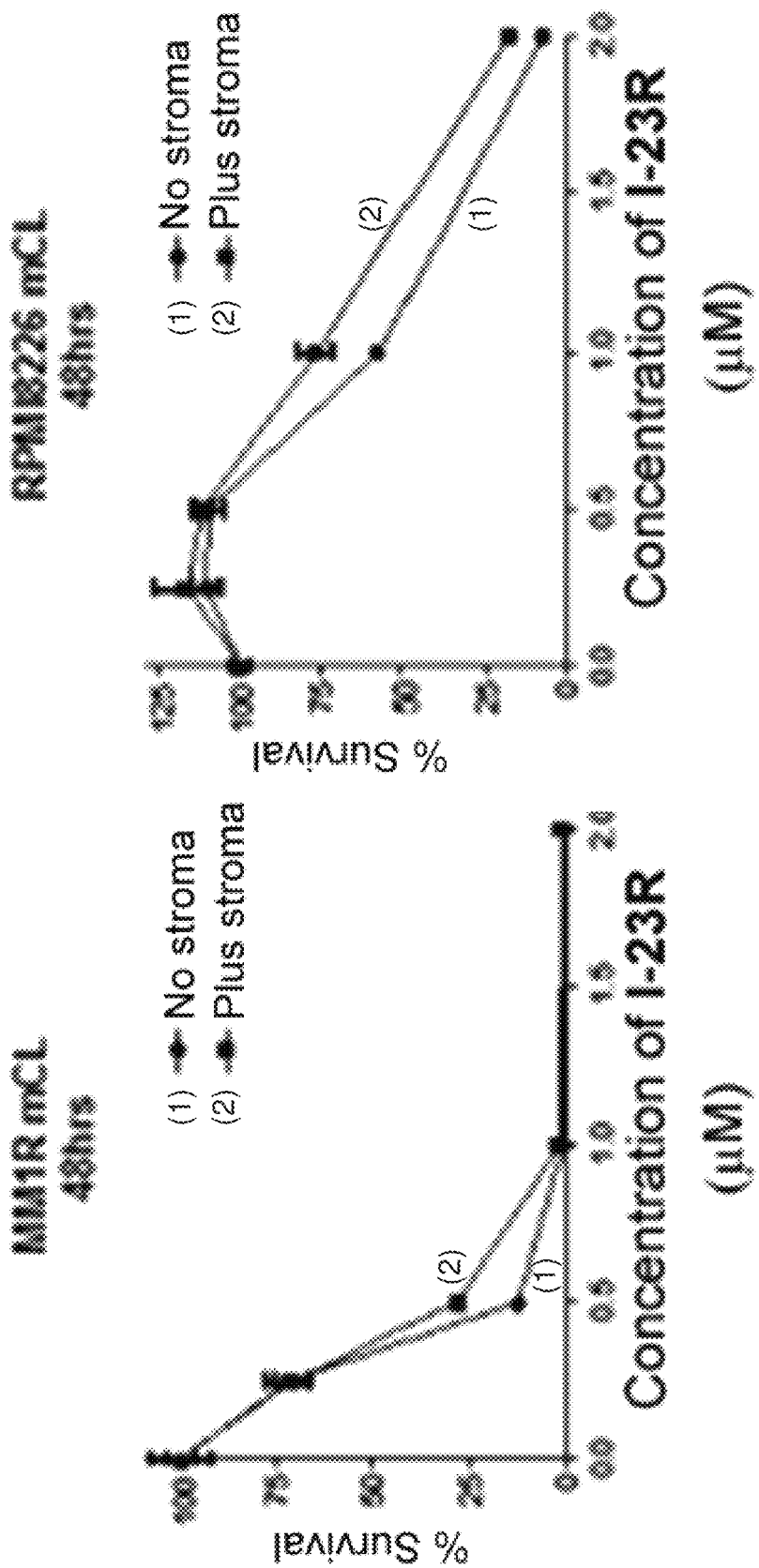
Figure 11G:
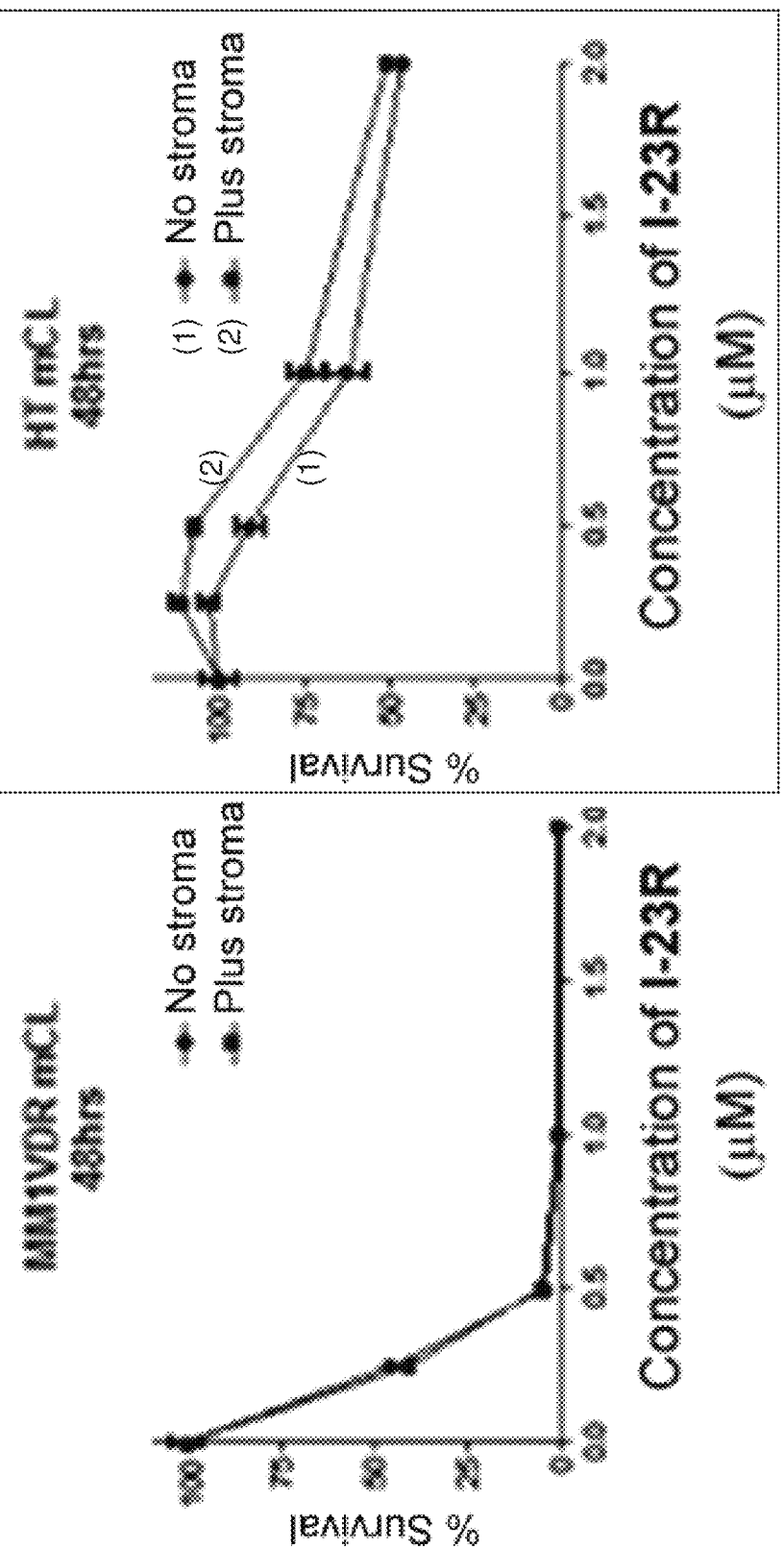
Figure 11H:
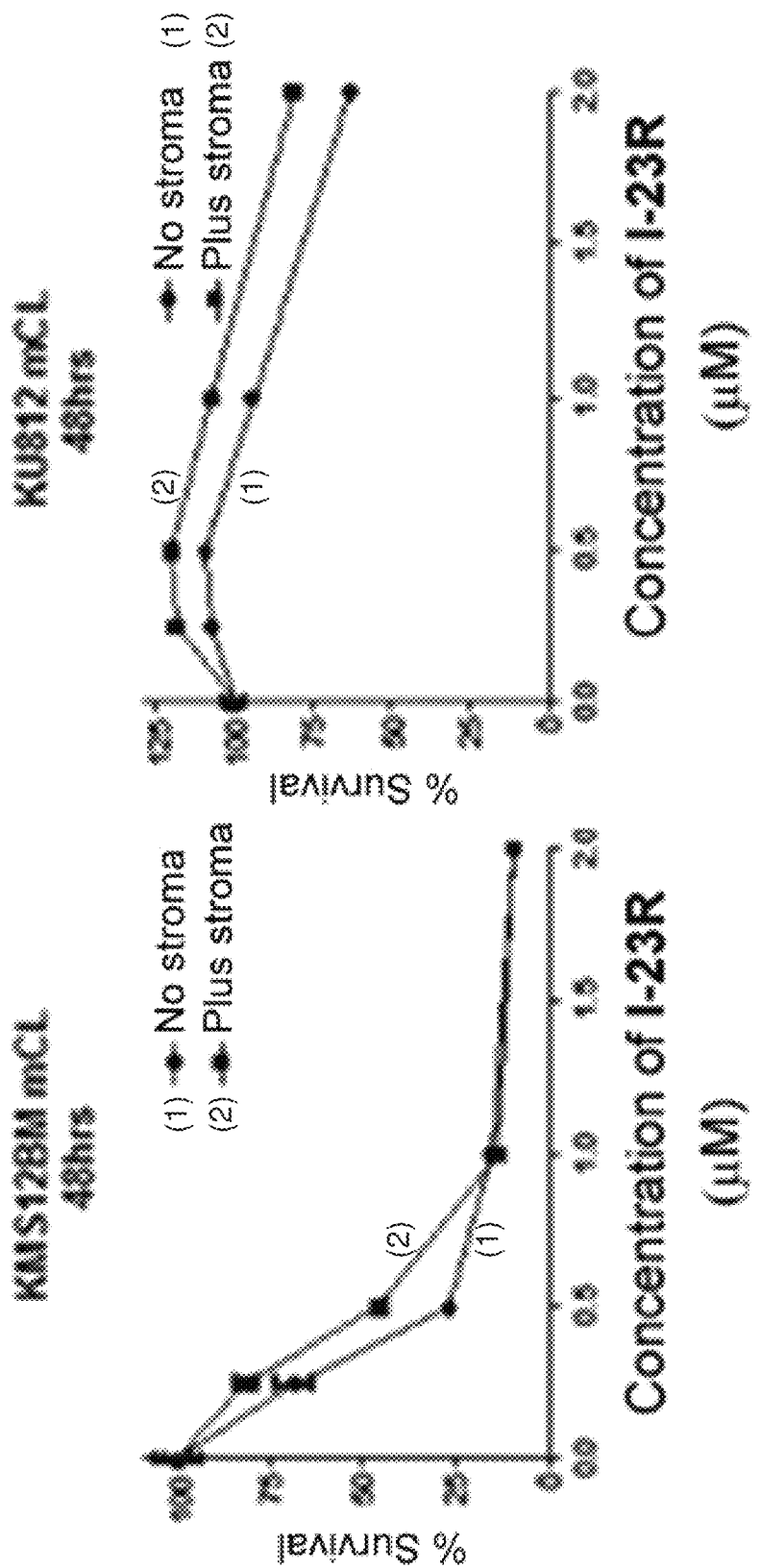

Compound I-23 Strongly Reduces Cell Viability of Multiple Myeloma and Chronic Lymphocytic Leukemia Cells To better evaluate the utility of compound I-23 in the treatment of blood cancers, the effects of compound I-23 on chronic lymphocytic leukemia (CLL) and multiple myeloma (MM) cells were investigated. To determine if compound I-23 shows efficacy in primary leukemia cancer cells, patient-derived CLL isolates were treated with compound I-23, compound I-23R, or flavopiridol (a pan-CDK inhibitor). Compound I-23 and flavopiridol displayed strong pro-death signaling with average $EC_{50}$ values less than 200 nM (FIG. 11A). Consistent with our previous results, compound I-23R was largely inactive in these assays. Similarly, in MM cell lines compound I-23 displayed highly effective antiproliferative activity. Compound I-23's mode of action was largely impervious to the presence of underlying stroma with the compound exhibiting similar $IC_{50}$ in the absence or presence of stromal cells (FIGS. 11B to 11D). Crosstalk between stromal and cancer cells provides a protective effect for the tumor and has been shown to lead to resistance to therapies. Therefore, studying compound I-23's antiproliferative effects in this context provides a more accurate depiction of the compound's therapeutic utility in these tumor cell types. Again, compound I-23R was largely inactive in these assays (FIGS. 11A and 11C to 11H).

Here, the discovery and characterization of compounds of Formula (I) (e.g., compound I-23) as the first covalent inhibitors of CDK7 are reported. A comprehensive strategy was employed utilizing protein- and lysate-based kinase profiling to identify CDK7 as a primary target of the compounds of Formula (I) (e.g., compound I-23). The in vitro $IC_{50}$ values of exemplary compounds of Formula (I) in inhibiting CDK7 are shown in Table 1. Additionally, leveraging the covalent nature of the compounds, compound I-49 was developed as an affinity reagent that allowed capturing CDK7 from cellular lysates. Thus, using orthogonal approaches, CDK7 was independently corroborated as a primary target of the compounds of Formula (I) (e.g., compound I-23). Consistent with an irreversible mechanism of action, compound I-23R, an analog lacking a reactive electrophilic center, showed markedly decreased activity against intracellular CDK7 and a 10-fold decrease in antiproliferative activity. Characteristic of covalent inhibitors, the inhibitory activity of the compounds of Formula (I) (e.g., compound I-23) against CDK7 was both time-dependent and resistant to inhibitor washout. The compounds of Formula (I) (e.g., compound I-23) were shown to recapitulate previous findings obtained with other small molecule inhibitors of CDK7. Cells treated with the compounds of Formula (I) (e.g., compound I-23) displayed significant impairment in RNAP II CTD phosphorylation at residues Ser-7 and Ser-2 and, to a lesser extent, Ser-5. These results agree with previous accounts suggesting that CDK7 is the major Ser-7 kinase and possibly coordinates with other kinases to phosphorylate Ser-5. The strong reduction in Ser-2 CTD phospho-epitope suggests that this phosphorylation event likely requires upstream Ser-5/7 phosphorylation. These results are consistent with the ChIP-seq data, which indicates that a treatment with the compounds of Formula (I) (e.g., compound I-23) reduces RNAP II occupancy at the 3' ends of genes where the majority of Ser-2 phosphorylation occurs.

TABLE 1

In vitro inhibitory activities of exemplary compounds of Formula (I) against CDK7

| Compound | $IC_{50}$ (nM) |
| --- | --- |
| I-17 | 11.3 |
| I-18 | 13.9 |
| I-19 | 15.7 |
| I-20 | 20.9 |

TABLE 1-continued

In vitro inhibitory activities of exemplary compounds of Formula (I) against CDK7

| Compound | IC$_{50}$ (nM) |
|---|---|
| I-21 | 22.7 |
| I-22 | 32.6 |
| I-23 | 33.5 |
| I-24 | 40 |
| I-25 | 87.8 |
| I-26 | 184 |
| I-27 | 201 |
| I-28 | 238 |
| I-29 | 288 |
| I-30 | 347 |
| I-31 | 416 |
| I-32 | 1,180 |
| I-33 | 1,420 |
| I-34 | 4,750 |
| I-37 | 557 |
| I-38 | 3,010 |
| I-39 | 1,350 |
| I-40 | 3,470 |
| I-41 | 809 |
| I-42 | 35.7 |
| I-43 | 36.2 |
| I-44 | 391 |
| I-50 | 92.3 |

The compounds of Formula (I) (e.g., compound I-23) show the unprecedented ability to target C312 of CDK7, which is located outside of the canonical kinase fold. Though distantly separated from the kinase domain in primary sequence, the C-terminus of CDK7 containing C312 traverses closely to the ATP-binding site affording the opportunity to be targeted by an ATP-competitive ligand. Molecular modeling of compounds of Formula (I) (e.g., compound I-23) with the X-ray structure of CDK7 demonstrates that the inhibitor can bridge the ATP-binding site with the C-terminus of CDK7 containing C312 (FIG. 4A). Mass spectrometry was used to unequivocally verify that C312 is the site of covalent modification. Furthermore, a conserved C312S mutation demonstrated that this nucleophilic cysteine C312 was essential for the irreversible inhibitory activity of compound I-23.

Inhibitory Activity of Exemplary Compounds Against Exemplary Kinases

Compounds of the invention were assayed for activity against a variety of different kinases at Life Technologies™ (Grand Island, N.Y.) using their commercially available Adapta® (for CDK7, CDK9/cyclin Ti, and IRAK1 kinases), Z'-Lyte® (for CDK1, CDK2, CDK5/p25, CDK5/p35, JNK1 and JNK2 kinases), and LanthaScreen Eu® (for CDK8, CDK9/cyclin K and MLK3) kinase assay services. Test compounds were tested at 100 nM and 1 µM final concentrations in 1% DMSO against all kinases except CDK7. For CDK7, test compounds were tested at concentrations ranging from 10 µM down to 0.514 nM in a series of 3-fold serial dilutions. Detailed protocols of these assays, including substrates used for each kinase, are known in the art, such as on the Life Technologies web site (www.lifetechnologies.com/us/en/home/life-science/drug-discovery/target-and-lead-identification-and-validation/kinasebiology/kinase-activity-assays.html). Exemplary results are presented as calculated IC$_{50}$ values (Tables 2A to 2C) or as percent inhibitions of activity (Tables 3A to 3C). In Tables 2A to 2C, "A" represents a calculated IC$_{50}$ value of less than 100 nM; "B" represents a calculated IC$_{50}$ value of greater than or equal to 100 nM and less than 1 µM; and "C" represents a calculated IC$_{50}$ value of 1 µM or greater. In Tables 3A to 3C, "A" represents greater than 70% inhibition of a kinase by the test compound, "B" represents between 50% and 70% inhibition, inclusive; and "C" represents less than 50% inhibition. The co-factors used for each kinase in the assays were as follows: CDK1: cyclin B; CDK2: cyclin A; CDK5: p25 or p35 as indicated; CDK7: cyclin H and MNAT1; CDK8: cyclin C; CDK9: cyclin K or cyclin T1 as indicated; IRAK1: Histone H3 (1-20) peptide; JNK1: none required; JNK2: none required; MLK3: none required.

TABLE 2A

Calculated IC$_{50}$ values of exemplary compounds of the invention against CDK7

| Compound | CDK7 |
|---|---|
| I-17 | A |
| I-18 | A |
| I-19 | A |
| I-20 | A |
| I-21 | A |
| I-22 | A |
| I-23 | A |
| I-24 | A |
| I-25 | A |
| I-27 | B |
| I-28 | B |
| I-31 | C |
| I-37 | B |
| I-38 | C |
| I-39 | C |
| I-42 | A |
| I-43 | A |
| I-44 | B |
| I-49 | A |
| I-50 | A |
| I-52 | A |
| I-53 | A |
| I-55 | A |
| I-56 | A |
| I-57 | A |
| I-59 | B |
| I-60 | B |
| I-61 | B |
| I-62 | C |
| I-63 | C |
| I-64 | B |
| I-64 | B |
| I-65 | A |
| I-68 | A |
| I-69 | B |
| I-70 | A |
| I-71 | B |

TABLE 2B

Calculated IC$_{50}$ values of exemplary compounds of the invention against exemplary kinases

| Compound | Jurkat | CDK1/ cyclin B | CDK2/ cyclin A | CDK5/ p25 | CDK8/ cyclin C |
|---|---|---|---|---|---|
| I-17 | B | | C | C | |
| I-23 | A | B | B | B | C |
| I-52 | B | | | | |
| I-53 | A | | | B | |
| I-55 | B | | | | |
| I-56 | A | | | | |
| I-57 | C | | | | |
| I-65 | | | | B | |

TABLE 2C

Calculated IC$_{50}$ values of exemplary compounds of the invention against exemplary kinases

| Compound | CDK9/ cyclin T1 | IRAK1 | JNK1 (MAPK8) | JNK2 (MAPK9) | MLK3 |
|---|---|---|---|---|---|
| I-17 | B | | | | B |
| I-20 | | | | | A |
| I-23 | C | A | B | B | A |
| I-53 | | | | | A |
| I-65 | | | | | B |

TABLE 3A

Percent inhibition of various kinases by exemplary compounds of the invention

| Compound | CDK1$^{a, g}$ | CDK1$^{b, g}$ | CDK2$^{a, h}$ | CBK2$^{b, h}$ | CDK5$^{a, c}$ | CDK5$^{b, c}$ |
|---|---|---|---|---|---|---|
| I-20 | A | A | A | A | A | A |
| I-23 | A | B | A | A | A | B |
| I-56 | A | A | A | A | A | A |
| I-57 | A | A | A | A | A | A |

TABLE 3B

Percent inhibition of various kinases by exemplary compounds of the invention

| Compound | CDK5$^{a, d}$ | CDK5$^{b, d}$ | CDK8$^{a, i}$ | CDK8$^{b, i}$ | CDK9$^{a, e}$ | CDK9$^{b, e}$ |
|---|---|---|---|---|---|---|
| I-20 | A | A | A | A | A | A |
| I-23 | A | B | | | | |
| I-56 | A | A | A | A | A | A |
| I-57 | A | A | A | A | A | B |

TABLE 3C

Percent inhibition of various kinases by exemplary compounds of the invention

| Compound | IRAK1$^{a}$ | IRAK1$^{b}$ | JNK1$^{a}$ | JNK1$^{b}$ | JNK2$^{a}$ | JNK2$^{b}$ | MLK3$^{a}$ | MLK3$^{b}$ |
|---|---|---|---|---|---|---|---|---|
| I-20 | B | C | A | A | A | A | B | C |
| I-23 | | | A | A | A | C | | |
| I-56 | A | C | A | A | A | A | B | C |
| I-57 | A | C | A | A | A | A | A | C |

Inhibitory Activity of Exemplary Compounds Against the Proliferation of Exemplary Cell Lines The representative compounds of the invention were tested at different concentrations (from 10 μM to 316 μM; 0.5 log serial dilutions) for their ability to inhibit the proliferation of various cancer cell lines. Known CDK inhibitors flavopiridol and triptolide were used as positive controls. Cells were grown in the indicated media below. All cell lines were supplemented with FBS (Life Technologies) and 100 U·mL-1 penicillin, 100 μg·mL-1 streptomycin (Invitrogen) and cultured at 37° C. in a humidified chamber in the presence of 5% CO$_2$. Proliferation assays were conducted over a 72 hour time period. CellTiter-Glo® (Promega Corporation, Madison, Wis. USA) was used to assess the anti-proliferative effects of the compounds following manufacturer's directions and utilizing the reagents supplied with the CellTiter-Glo® kit.

The following cancer cell lines were tested with the media conditions indicated:

Blood Cancer Cell Lines
  Jurkat—RPMI 1640+10% FBS+1% Glutamax
  HL60: RPMI 1640+10% FBS+1% Glutamax
  THP-1: RPMI 1640+10% FBS+1% Glutamax+0.05 mM 2-Mercaptoethanol
  MV4-11: RPMI 1640+10% FBS+1% Glutamax
  RS4-11: RPMI 1640+10% FBS+1% Glutamax;
Breast Cancer Cell Lines
  hTERT-HME1: Mammary Epithelial Cell Basal Medium (500 mL; Lonza CC-3151)+2 mL BPE+0.5 mL hEGF+0.5 mL Hydrocortisone+0.5 mL GA-1000+0.5 mL insulin (Lonza CC-4136)+100 ng/mL cholera toxin
  MDA-MB231: Leibovitz's L-15 Medium+10% FBS+1% Glutamax
  MCF7: RPMI 1640+10% FBS+1% Glutamax
  MCF10A: Mammary Epithelial Cell Basal Medium (500 mL; Lonza CC-3151)+2 mL BPE+0.5 mL hEGF+0.5 mL Hydrocortisone+0.5 mL GA-1000+0.5 mL insulin (Lonza CC-4136)+100 ng/mL cholera toxin
  T47D: RPMI 1640+10% FBS+1% Glutamax+0.2 Units/ml bovine insulin;
  SKBR3: McCoy's 5a Medium Modified+10% FBS
Ewing's Sarcoma Cell Lines
  A673: DMEM (4 mM L-Glut, 4.5 g/L Glucose, 1 mM pyruvate, 1.5 g/l bicarb)+10% FBS
  Hs822T: DMEM (4 mM L-Glut, 4.5 g/L Glucose, 1 mM pyruvate, 1.5 g/l bicarb)+10% FBS
  Hs863T: DMEM (4 mM L-Glut, 4.5 g/L Glucose, 1 mM pyruvate, 1.5 g/l bicarb)+10% FBS
  RD-ES: RPMI 1640+15% FBS
  SK-ES: McCoy's 5a Medium Modified (modified—1.5 mM L-glut, 2.2 g/L bicarb)+15% FBS Osteosarcoma Cell Lines
  SAOS: McCoy's 5a Medium Modified+10% FBS+2 mM L-Glut
  MNNG-HOS Cl#5: EMEM+10% FBS
  143B: EMEM+10% FBS+15 ug/ml Bromo-deoxy Uridine (BUdR)+2 mM Glutamine+1% Non Essential Amino Acids (NEAA)
  MG-63: EMEM+10% FBS.

Exemplary results of these assays are set forth in Tables 4A to 4D, where "A" represents an $IC_{50}$ value of less than 500 nM; "B" represents an $IC_{50}$ value of between 500 nM and 5 µM, inclusive; and "C" represents an $IC_{50}$ value of greater than 5 PM.

TABLE 4A

Inhibition of proliferation of various blood cancer cell lines by exemplary compounds of the invention

| Compound | HL60 | THP-1 | MV4-11 | RS4-11 |
|---|---|---|---|---|
| I-17 | A | A | A | A |
| I-20 | A | A | A | A |
| I-23 | A | A | A | A |
| Flavopiridol | A | A | A | A |
| Triptolide | A | A | A | A |

TABLE 4B

Inhibition of proliferation of various breast cancer cell lines by exemplary compounds of the invention

| Compound | hTERT-HME1 | MDA-MB231 | MCF7 | MCF10A | T47D | SKBR3 |
|---|---|---|---|---|---|---|
| I-17 | A | A | A | A | B | B |
| I-20 | A | A | A | A | B | B |
| I-23 | A | A | A | A | C | B |
| Flavopiridol | A | A | B | A | C | A |
| Triptolide | A | A | A | A | C | A |

TABLE 4C

Inhibition of proliferation of various Ewing's sarcoma cell lines by exemplary compounds of the invention

| Compound | A673 | Hs822T | Hs863T | RD-ES | SK-ES |
|---|---|---|---|---|---|
| I-17 | A | A | B | A | A |
| I-20 | A | A | A | A | A |
| I-23 | A | A | B | A | A |
| Flavopiridol | A | C | C | A | A |
| Triptolide | A | B | C | A | A |

TABLE 4D

Inhibition of proliferation of various osteosarcoma cell lines by exemplary compounds of the invention

| Compound | SAOS | MNNG-HOS Cl#5 | 143B |
|---|---|---|---|
| I-17 | A | B | B |
| I-20 | A | B | C |
| I-23 | A | B | C |
| Flavopiridol | A | B | B |
| Triptolide | A | A | A |

Multiple sequence alignment demonstrates that this cysteine C312 is unique, and therefore provides an unanticipated way to achieve selectivity within the CDK family, where high sequence and shape homology has posed a formidable challenge to achieving selectivity with ATP-competitive inhibitors. Therefore, employing an inhibitor washout strategy, which leverages the irreversible inhibitory activity of the compounds of Formula (I) (e.g., compound I-23) against a non-conserved cysteine, one can further mitigate off-target effects. Thus, the compounds of Formula (I) (e.g., compound I-23) offer a unique mechanism, which combines ATP-site and allosteric covalent binding, to deliver potent and selective inhibition of CDK7.

Characteristics of the compounds of Formula (I) (e.g., compound I-23) were exploited to investigate the effects of acute pharmacological inhibition of CDK7 on control of the global gene expression program and its involvement in maintenance of the cancer state. ChIP-seq in Jurkat cells demonstrated a genome-wide decrease in RNAP II gene occupancy, reflecting a large downregulation of active transcription. Untreated Jurkat cells displayed prominent RNAP II occupancy at both MYC and MCL-1; however treatment with the compounds of Formula (I) (e.g., compound I-23) led to a disproportionate decrease in RNAP II occupancy at these promoters. It is known that many cancer cell lines, particularly those of white blood cell origin, exhibit high levels of transcription at these promoters; thus, it is expected that decrease of RNAP II occupancy at these sites may contribute to these compounds' anti-proliferative capacity. Illustrative of this point, leukemia and lymphoma cell lines demonstrate high dependence on the constant expression of MCL-1 to maintain cell viability. It was found that the growth in the vast majority of leukemias and lymphomas screened was potently suppressed by the compounds of Formula (I) (e.g., compound I-23). Likewise, the viability of clinical CLL isolates as well as the proliferation of clinically relevant MM variants were also potently suppressed by the compounds of Formula (I) (e.g., compound I-23). These results further support the notion that targeting the BCL-2 family and MYC proteins either through direct or, in this case, indirect means, can be an effective therapeutic strategy.

Therapeutically, irreversible inhibition of CDK7 comprises both advantages and disadvantages. First, targeting site-specific cysteine residues, specifically in CDK7, offers the possibility of making CDK7-specific inhibitors. This approach could then be applied to other tCDKs by leveraging unique cysteines in their kinase domains. Second, treatment with the compounds of Formula (I) (e.g., compound I-23) is resistant to washout of inhibitor in solution. As a consequence, a short compound administration, which is sufficient to give elicit an apoptotic response, may limit reversible off-target interactions and circumvent sub-optimal pharmacokinetic properties. Third, covalent modification results in termination of CDK7 activity until CDK7 protein turnover may occur, resulting in long-lasting inhibition. However, idiosyncratic toxicities have been described for irreversible inhibitors, and it is currently unknown whether the compounds of Formula (I) (e.g., compound I-23) would suffer from this problem. Furthermore, it is currently unclear to what extent that irreversible inhibition of CDK7 can be tolerated within the normal cell population.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a cancer in a subject in need thereof, the method comprising:

administering to the subject in need thereof a therapeutically effective amount of a compound of Formula (I), a pharmaceutically acceptable salt of a compound of Formula (I), or a pharmaceutical composition comprising a compound of Formula (I) or a pharmaceutically acceptable salt thereof, wherein Formula (I) is:

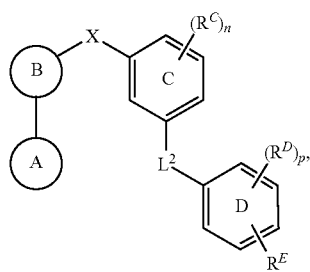

(I)

wherein:
Ring A is

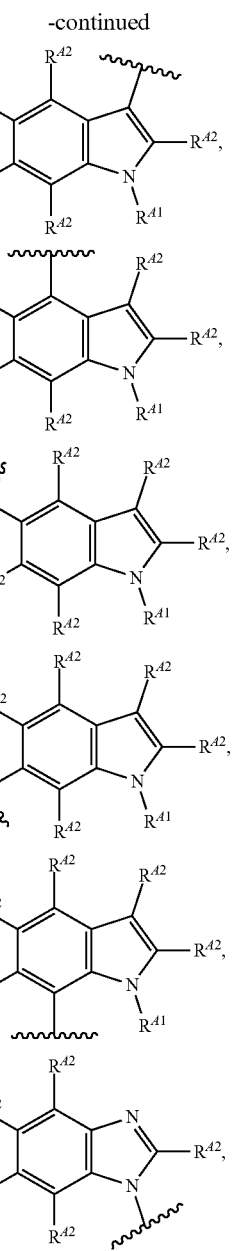

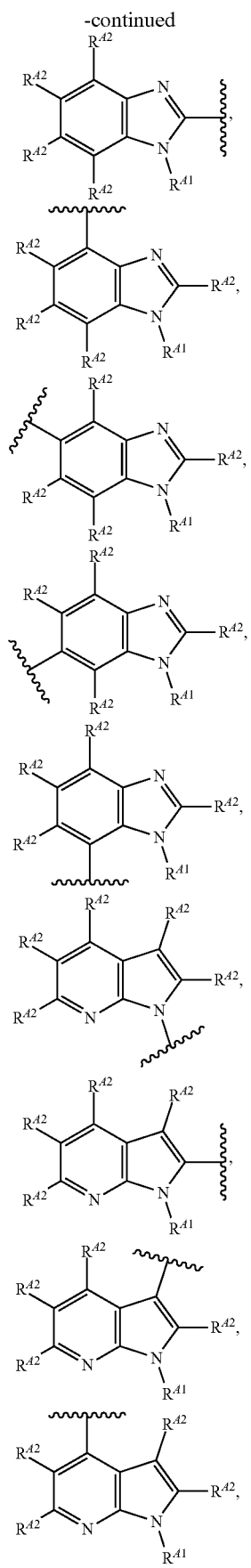
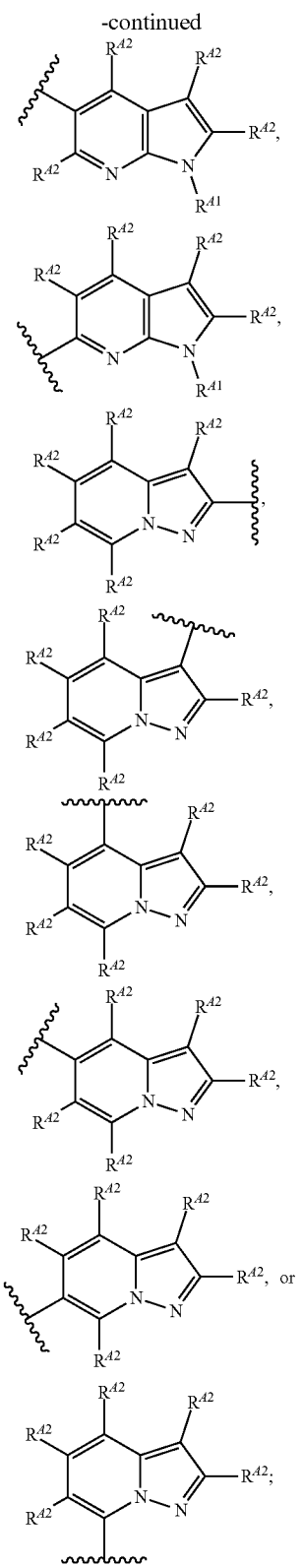
each instance of $R^{A1}$ is independently selected from the group consisting of hydrogen and alkyl;
each instance of $R^{A2}$ is independently selected from the group consisting of hydrogen, halogen, alkyl, aryl, and heteroaryl;

Ring B is of the formula:

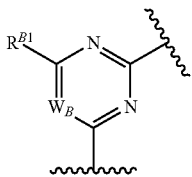
;

$R^{B1}$ is selected from the group consisting of hydrogen and alkyl, $W_B$ is $CR^{B2}$, wherein $R^{B2}$ is selected from the group consisting of hydrogen, cyano, halogen, optionally substituted alkyl, carbocyclyl, and —$OR^{B2a}$, wherein $R^{B2a}$ is selected from the group consisting of hydrogen and alkyl;

or $R^{B1}$ and $R^{B2}$ are joined to form a carbocyclyl or aryl ring;

X is —$NR^X$—, wherein $R^X$ is hydrogen or $C_{1-6}$ alkyl;

$L^2$ is —$NR^{L2a}C(=O)$— or —$NR^{L2a}S(=O)_2$—, wherein $R^{L2a}$ is hydrogen or $C_{1-6}$ alkyl;

each instance of $R^C$ is independently selected from the group consisting of hydrogen, halogen, and alkyl;

n is 0, 1, 2, 3, or 4;

each instance of $R^D$ is independently selected from the group consisting of hydrogen, halogen, alkyl, and —$N(R^{D1})_2$, wherein each occurrence of $R^{D1}$ is independently selected from the group consisting of hydrogen and alkyl;

p is 0, 1, 2, 3, or 4;

$R^E$ is

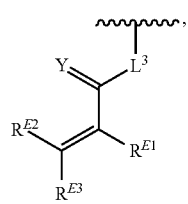
(ii-1)

$R^E$ and $L^2$ are para or meta to each other;

$L^3$ is —$NR^{L3a}$— or an optionally substituted $C_{1-4}$ hydrocarbon chain, wherein $R^{L3a}$ is hydrogen;

$R^{E1}$ is selected from the group consisting of hydrogen and alkyl;

$R^{E2}$ is hydrogen or alkyl;

$R^{E3}$ is selected from the group consisting of hydrogen, alkyl, —$CH_2OR^{E3a}$, and —$CH_2N(R^{E3a})_2$, wherein each occurrence of $R^{E3a}$ is independently selected from the group consisting of hydrogen, alkyl,

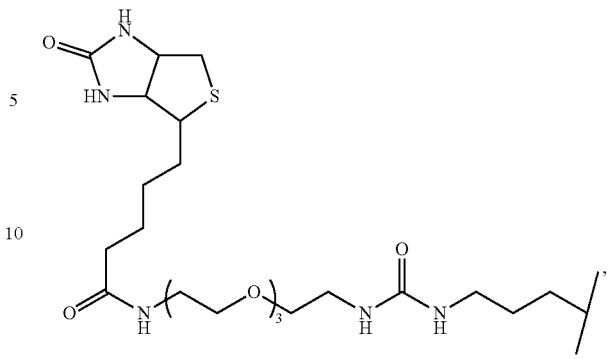

and alkynyl; and

Y is O;

wherein "substituted" within each of $R^{B2}$ and $L^3$ refers independently to halogen, cyano, —$NO_2$, —OH, —$OR^{aa}$, —$N(R^{bb})_2$, —SH, —$SR^{aa}$, —$C(=O)R^{aa}$, —$CO_2H$, —CHO, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})N(R^{bb})_2$, or —$NR^{bb}C(=NR^{bb})N(R^{bb})_2$;

each of $R^{aa}$ is independently alkyl; and each of $R^{bb}$ is independently hydrogen or alkyl.

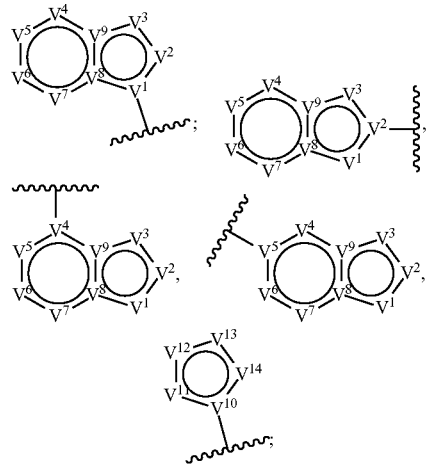

2. The method of claim 1, wherein Ring A is:

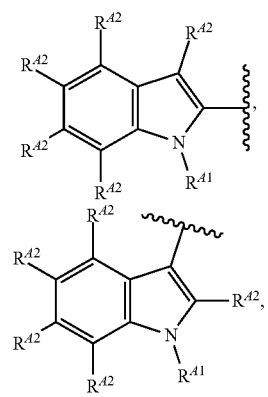

-continued

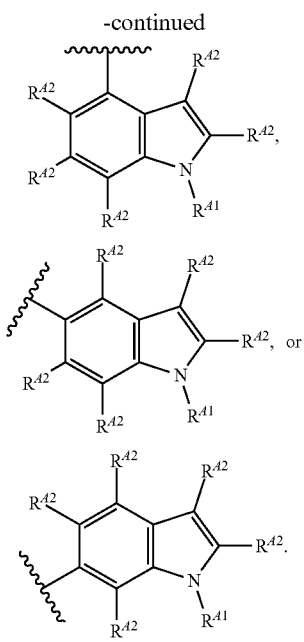

3. The method of claim 1, wherein Ring A is:

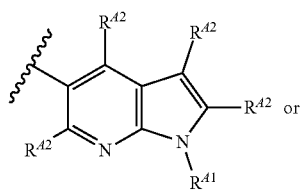

4. The method of claim 1, wherein Ring A is:

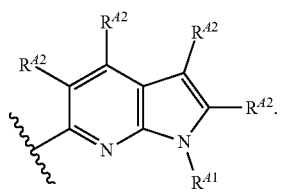

5. The method of claim 1, wherein $R^{B1}$ is hydrogen or methyl.

6. The method of claim 1, wherein $L^2$ is —NH—C(O)—, —N(CH$_3$)—C(O)—, or —NH—S(O)$_2$—.

7. The method of claim 1, wherein $R^E$ is of Formula (ii-1):

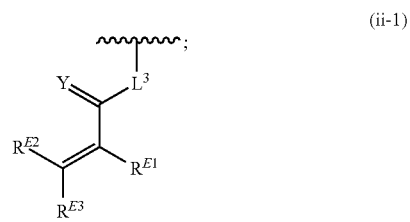
(ii-1)

wherein Y is O;

$L^3$ is —NH— or ⟨—CH$_2$—NH—;

$R^{E1}$ and $R^{E2}$ are each hydrogen; and $R^{E3}$ is selected from hydrogen, —CH$_2$N(CH$_3$)C≡CH, —CH$_2$N(CH$_3$)$_2$, and —CH$_2$OH.

8. The method of claim 1, wherein the compound is of Formula (I-3):

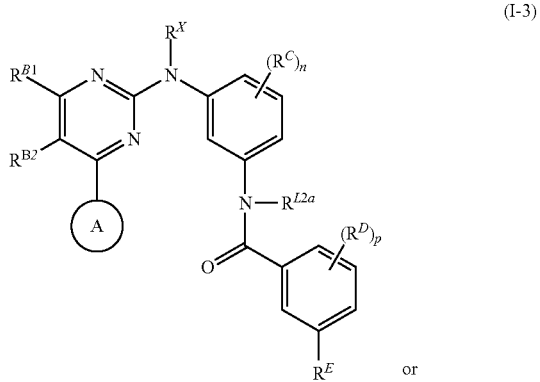
(I-3)

or

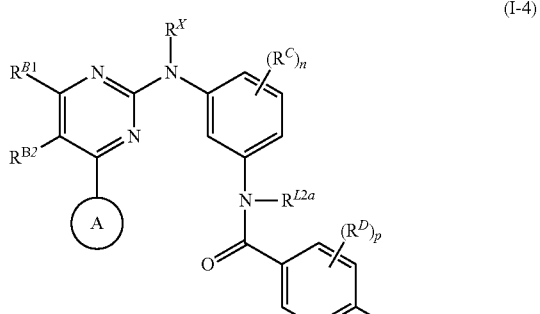
(I-4)

or a pharmaceutically acceptable salt thereof.

9. The method of claim 1, wherein the compound is of Formula (I-5):
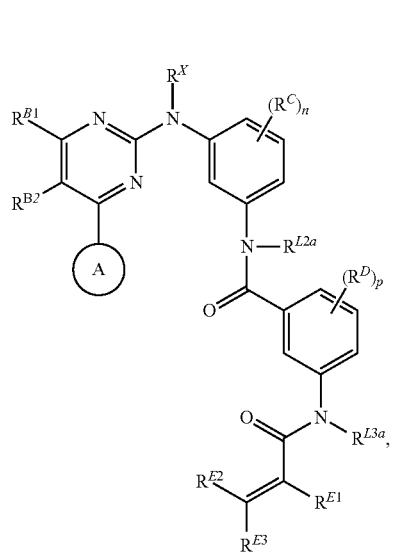
(I-5)
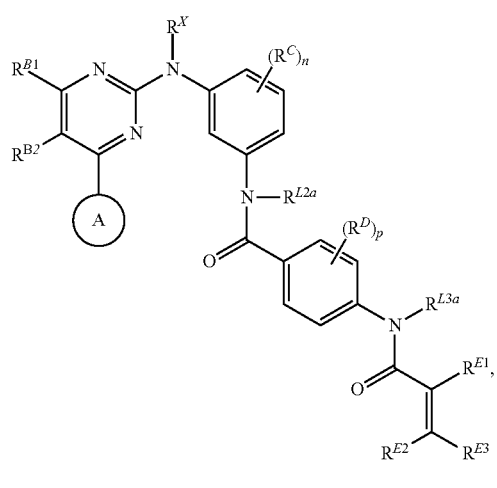
(I-6)
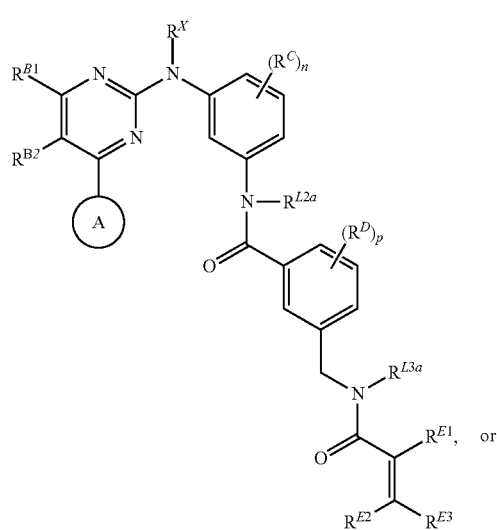
(I-7), or
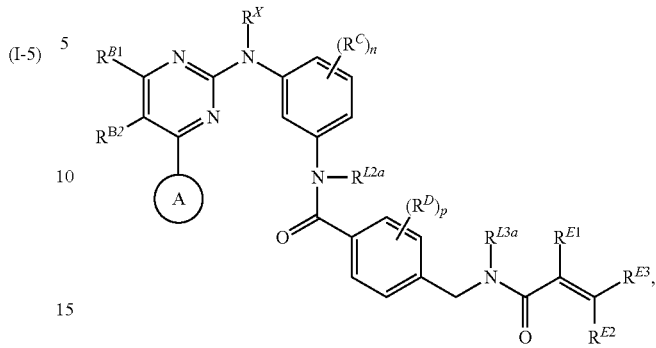
(I-8)
or a pharmaceutically acceptable salt thereof.
10. The method of claim 1, wherein the compound is of Formula (I-7):
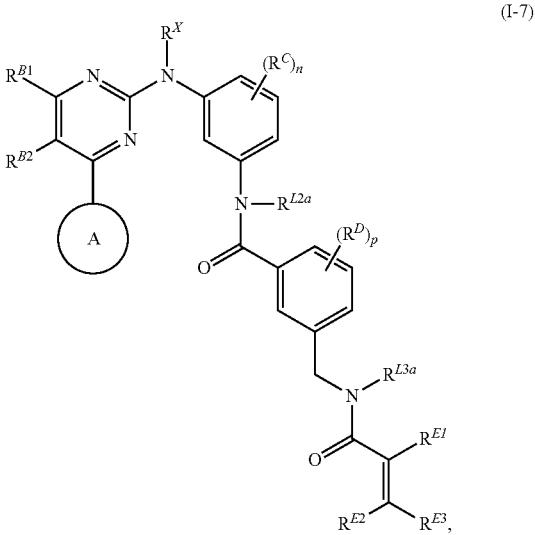
(I-7)
or a pharmaceutically acceptable salt thereof.

11. The method of claim 1, wherein the compound is selected from the group consisting of:
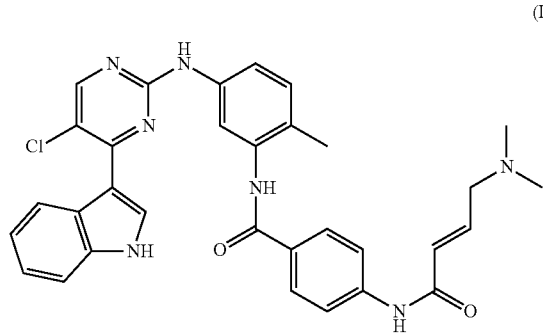
(I-17)
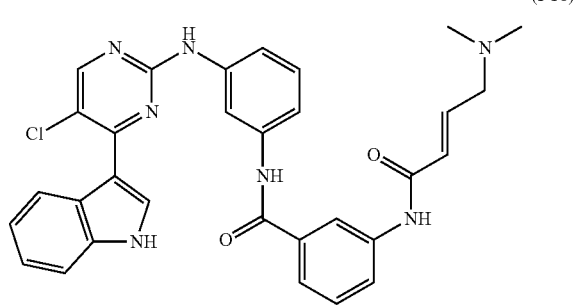
(I-18)
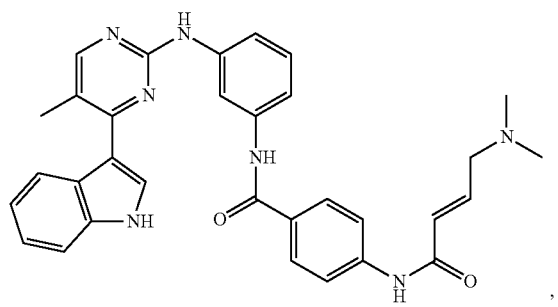
(I-19)
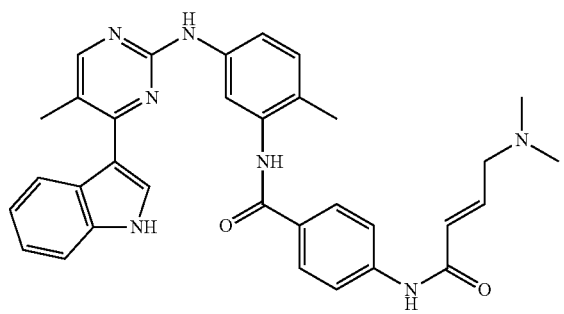
(I-20)
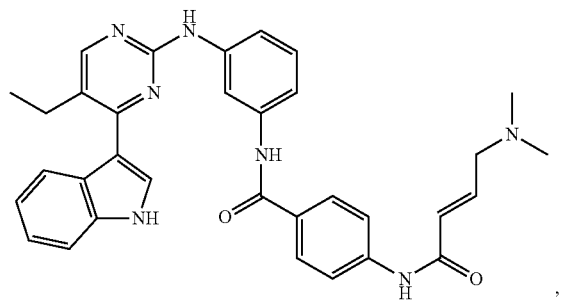
(I-21)
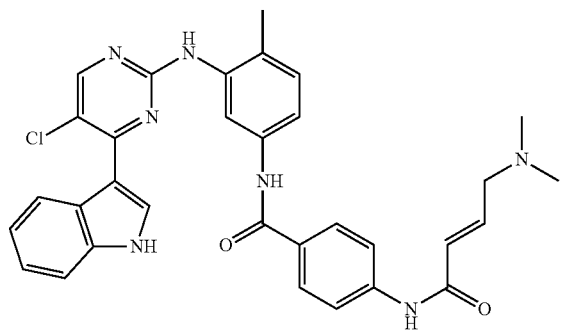
(I-22)
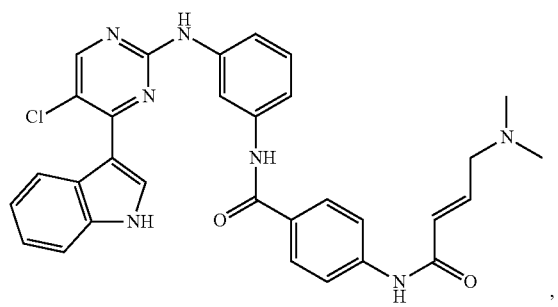
(I-23)
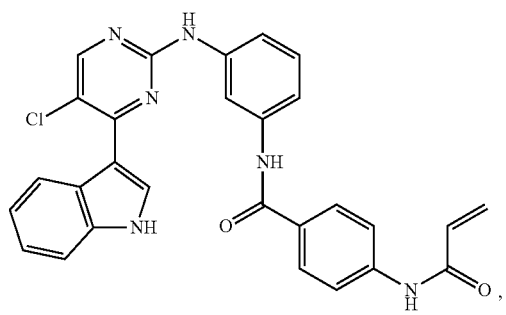
(I-24)

(I-25)
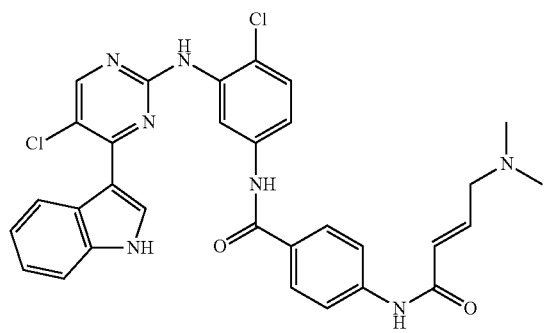
(I-26)
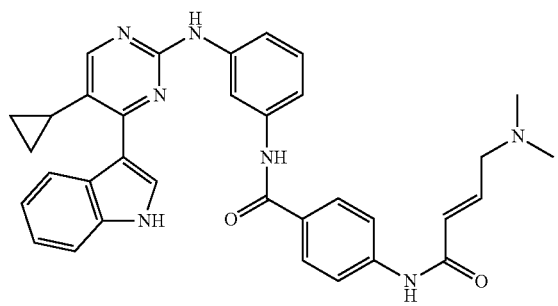
(I-27)
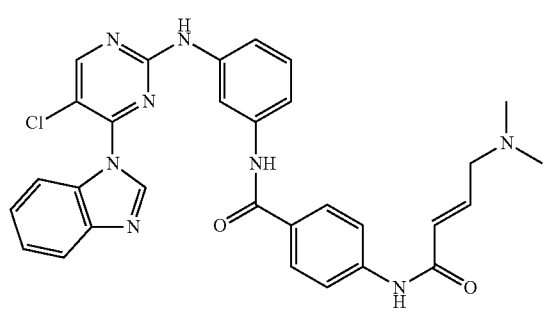
(I-28)
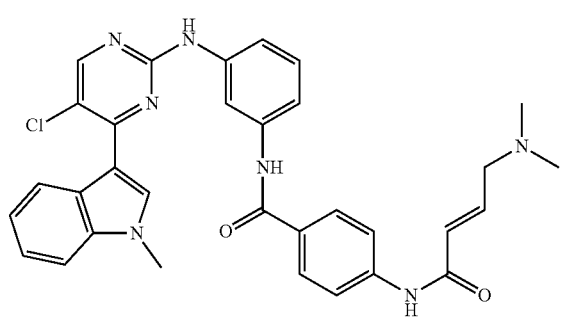
(I-29)
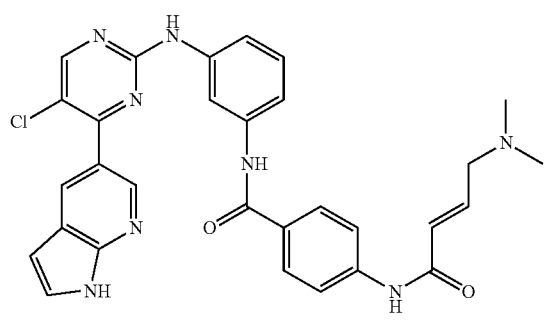
(I-30)
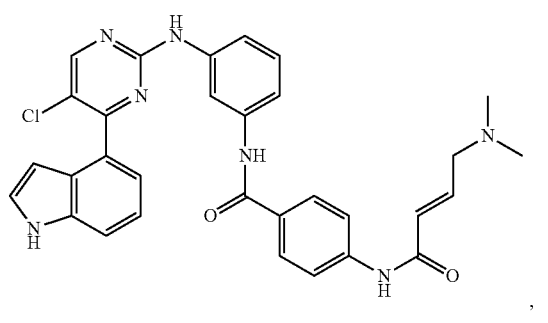
(I-31)
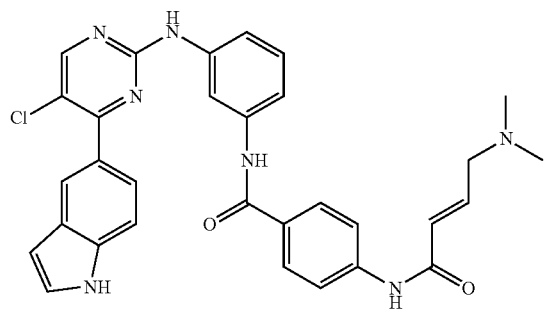
(I-32)
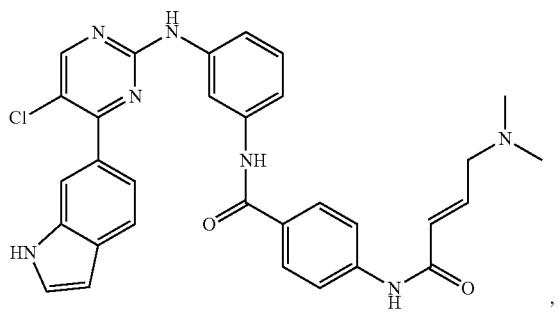

-continued
(I-33)
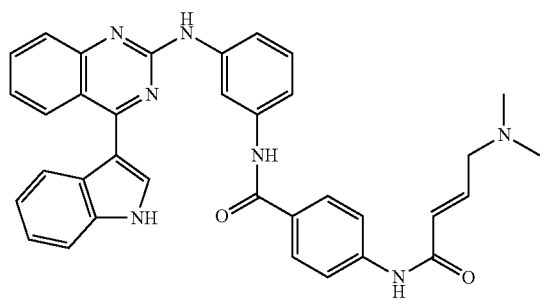
(I-34)
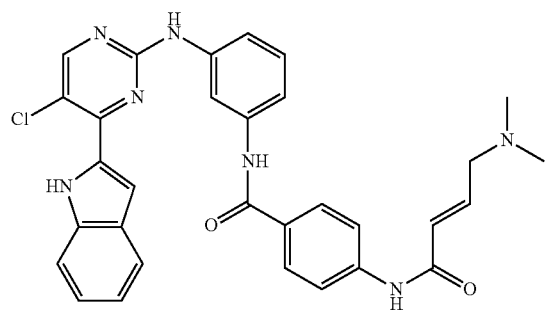
(I-35)
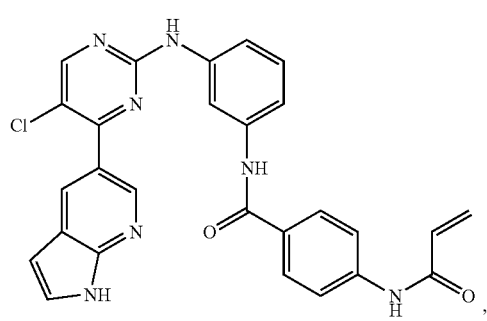
(I-36)
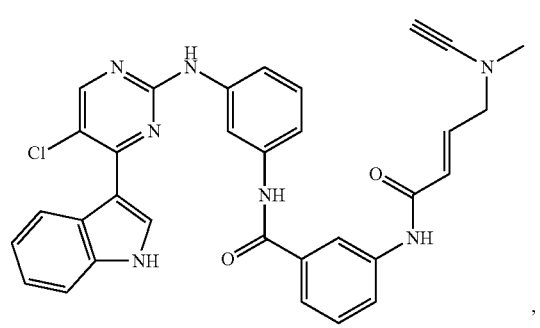
(I-37)
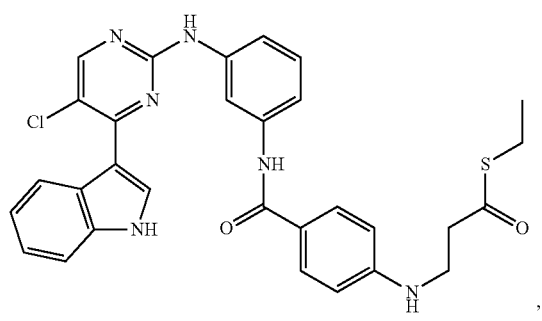
(I-38)
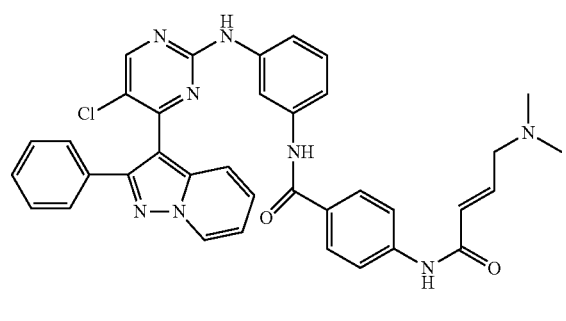
(I-39)
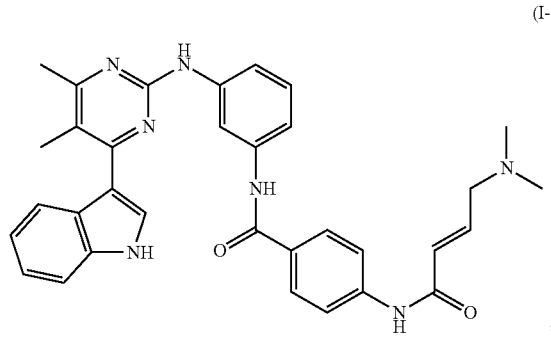
(I-40)
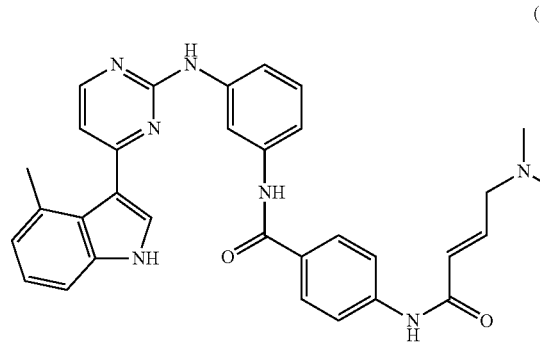

-continued
(I-41)
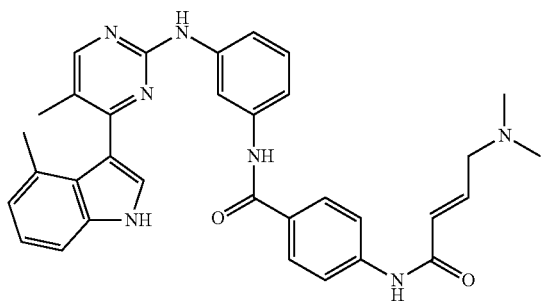
(I-42)
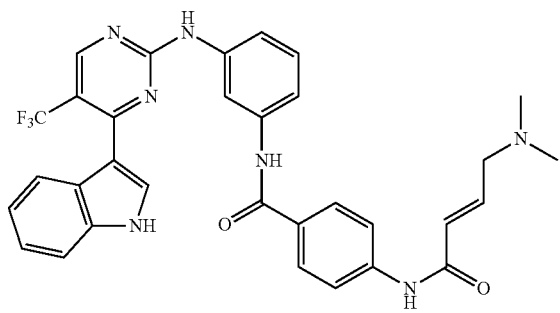
(I-43)
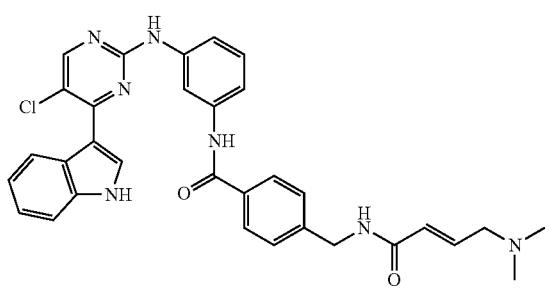
(I-44)
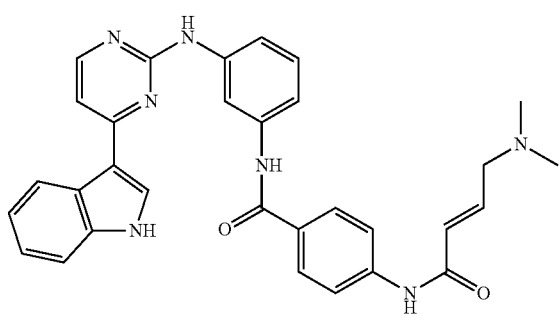
(I-45)
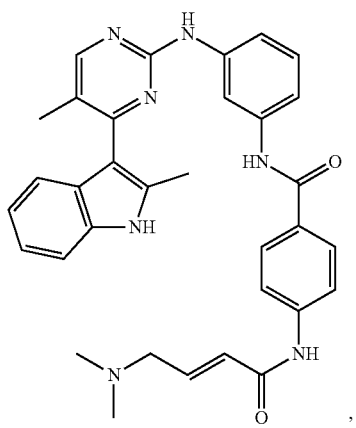
(I-46)
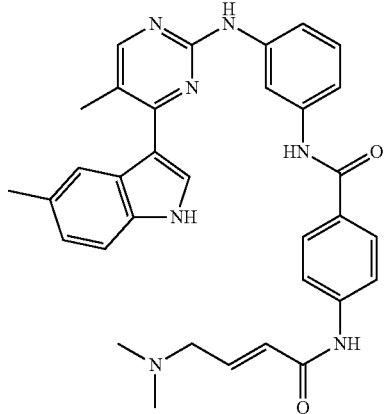
(I-47)
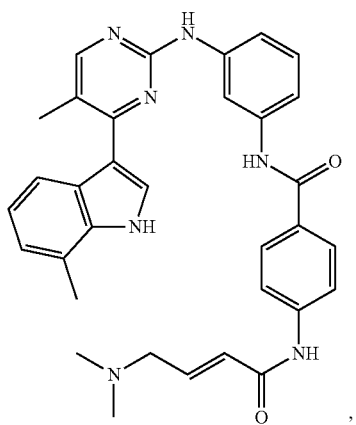
(I-48)
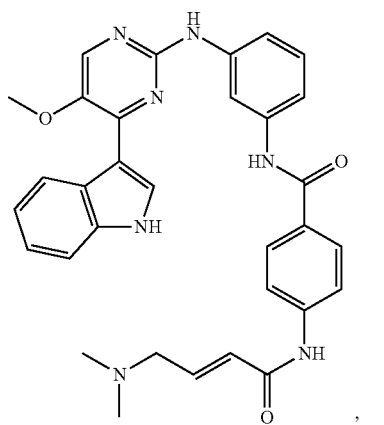

-continued

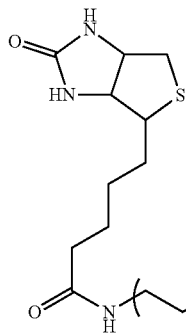 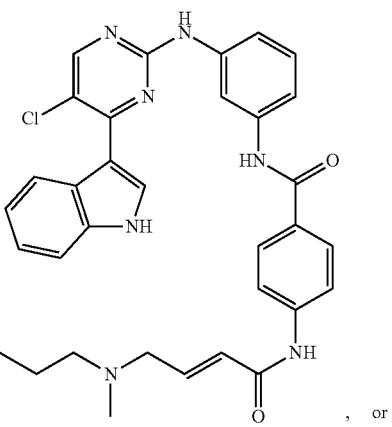

(I-49)

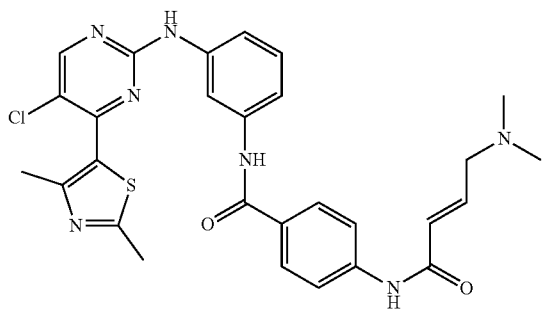

, or

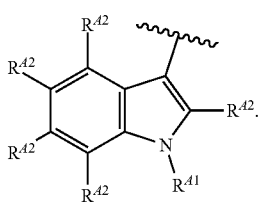

(I-50)

and pharmaceutically acceptable salts thereof.

12. The method of claim 11, wherein the cancer is leukemia, lymphoma, multiple myeloma, breast cancer, Ewing's sarcoma, osteosarcoma, colorectal cancer, ovarian cancer, pancreatic cancer, gall bladder cancer, neuroblastoma, melanoma, or lung cancer.

13. The method of claim 1, wherein $R^{B2}$ is selected from hydrogen, methyl, ethyl, chloro, —$CF_3$, cyclopropyl, —$OCH_3$, cyano, and isopropyl.

14. The method of claim 1, wherein Ring A

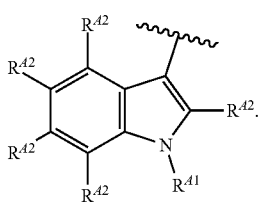

15. The method of claim 1, wherein $L^2$ is —$NR^{L2a}C(=O)$—.

16. The method of claim 1, wherein the compound is of the formula:

(I-23)

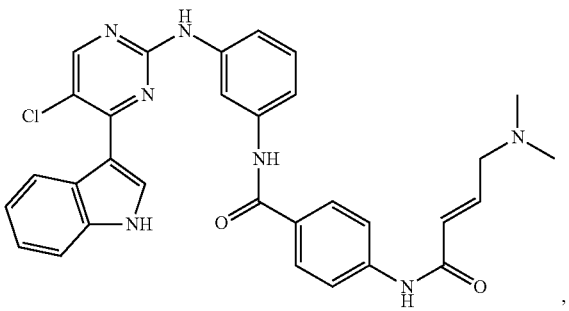

or a pharmaceutically acceptable salt thereof.

17. The method of claim 16, wherein the cancer is leukemia, lymphoma, multiple myeloma, breast cancer, Ewing's sarcoma, osteosarcoma, colorectal cancer, ovarian cancer, pancreatic cancer, gall bladder cancer, neuroblastoma, melanoma, or lung cancer.

18. The method of claim 1, wherein the compound is of the formula:

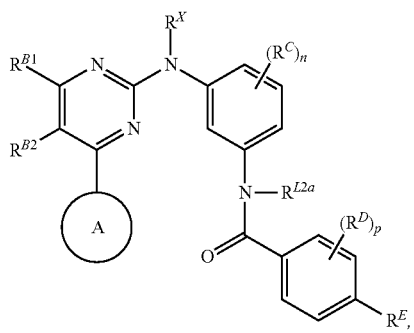
(I-4)

or a pharmaceutically acceptable salt thereof.

19. The method of claim 1, wherein the compound is of the formula:

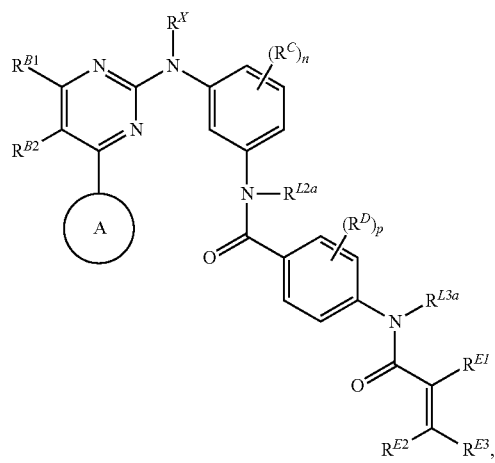
(I-6)

or a pharmaceutically acceptable salt thereof.

20. The method of claim 1, wherein the compound is of the formula:

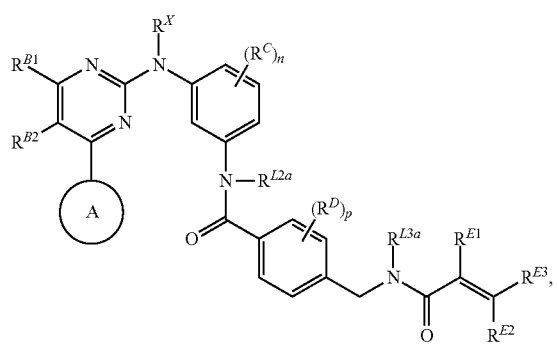
(I-8)

or a pharmaceutically acceptable salt thereof.

21. The method of claim 1, wherein the compound is of the formula:

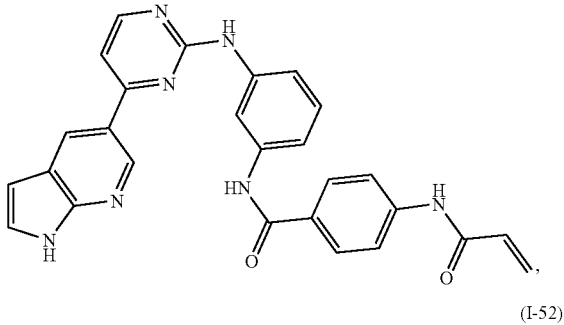
(I-51)

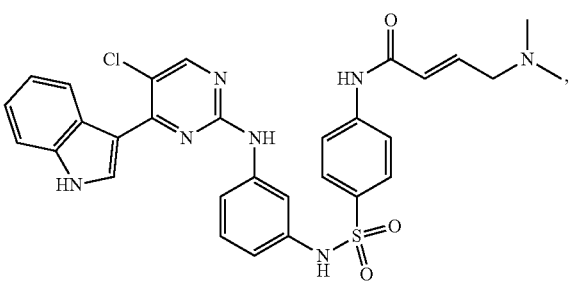
(I-52)

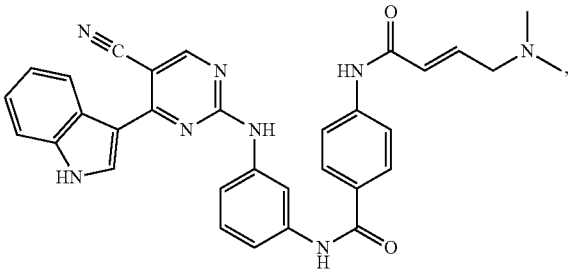
(I-53)

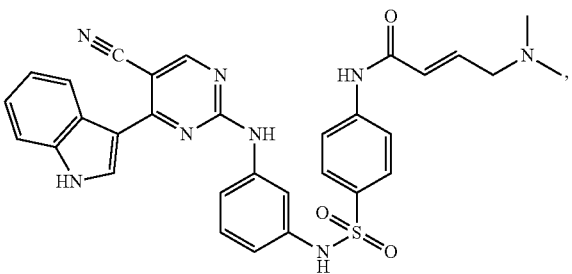
(I-55)

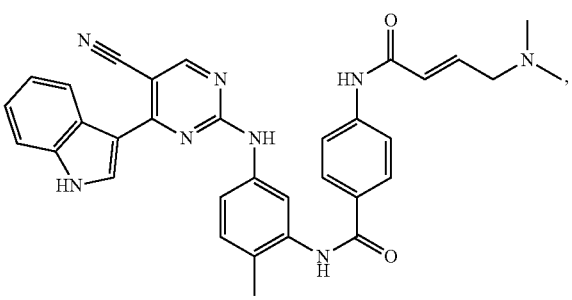
(I-56)

(I-57)
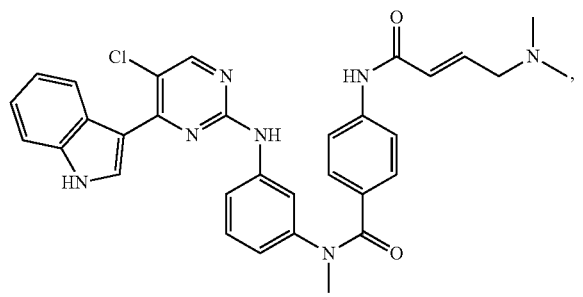
(I-59)
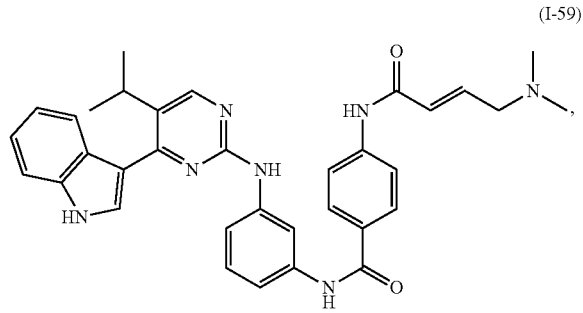
(I-60)
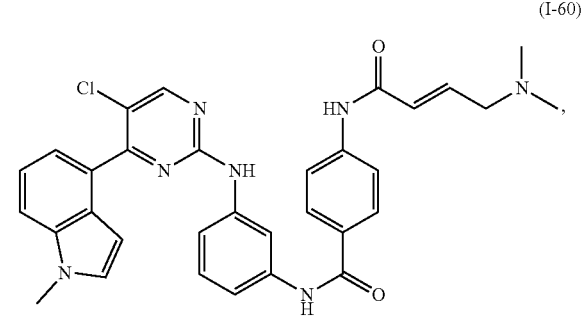
(I-61)
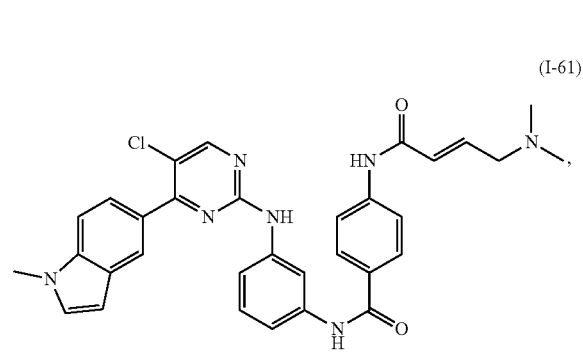
(I-62)
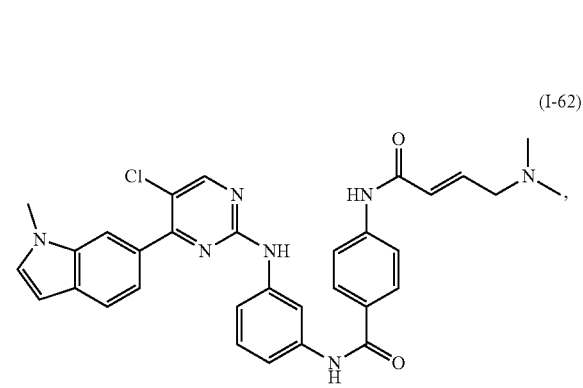
(I-63)
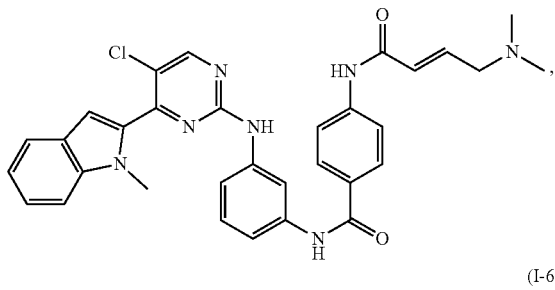
(I-64)
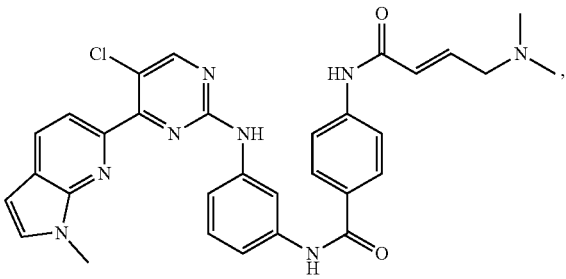
(I-65)
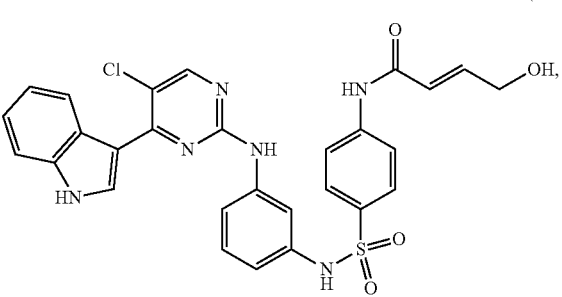
(I-67)
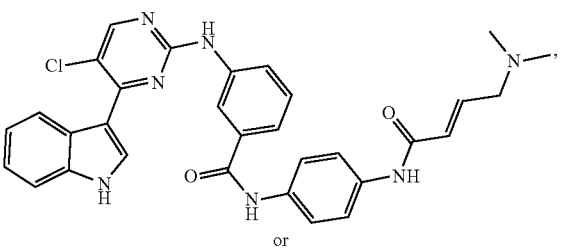
or
(I-68)
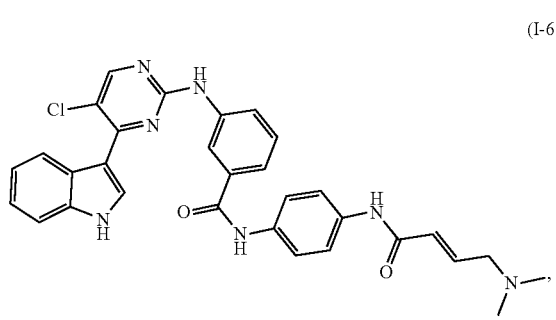
or a pharmaceutically acceptable salt thereof.
22. The method of claim 21, wherein the cancer is leukemia, lymphoma, multiple myeloma, breast cancer, Ewing's sarcoma, osteosarcoma, colorectal cancer, ovarian cancer, pancreatic cancer, gall bladder cancer, neuroblastoma, melanoma, or lung cancer.

23. The method of claim 1, wherein the cancer is a hematopoietic cancer.

24. The method of claim 1, wherein the cancer is a leukemia.

25. The method of claim 1, wherein the cancer is lymphoma.

26. The method of claim 1, wherein the cancer is multiple myeloma.

27. The method of claim 1, wherein the cancer is breast cancer.

28. The method of claim 1, wherein the cancer is Ewing's sarcoma.

29. The method of claim 1, wherein the cancer is osteosarcoma.

30. The method of claim 1, wherein the cancer is colorectal cancer.

31. The method of claim 1, wherein the cancer is ovarian cancer.

32. The method of claim 1, wherein the cancer is pancreatic cancer.

33. The method of claim 1, wherein the cancer is gall bladder cancer.

34. The method of claim 1, wherein the cancer is neuroblastoma.

35. The method of claim 1, wherein the cancer is melanoma.

36. The method of claim 1, wherein the cancer is lung cancer.

37. The method of claim 1, wherein the subject is a human.

* * * * *

UNITED STATES PATENT AND TRADEMARK OFFICE
CERTIFICATE OF CORRECTION

PATENT NO. : 10,787,436 B2  Page 1 of 3
APPLICATION NO. : 16/130975
DATED : September 29, 2020
INVENTOR(S) : Nathanael S. Gray et al.

It is certified that error appears in the above-identified patent and that said Letters Patent is hereby corrected as shown below:

In the Claims

In Claim 1, at Column 219, Lines 44-45, the text: "wherein:" should be replaced with the text:
--wherein: the cancer is associated with overexpression or aberrant activity of cyclin-dependent kinase 7, cyclin-dependent kinase 12, or cyclin-dependent kinase 13;--.

Between Claim 1 and Claim 2, at Column 224, Lines 30-49, formulae:

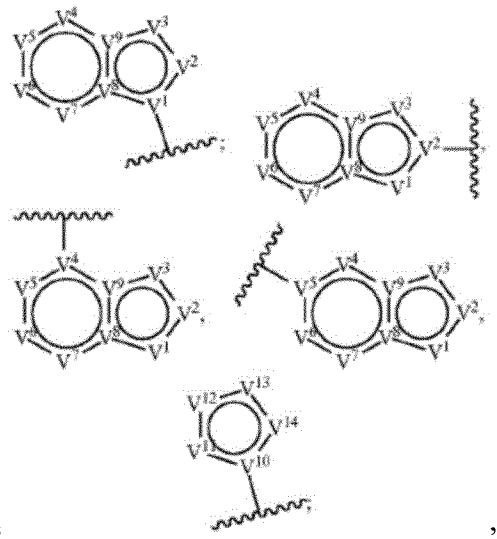

" should be removed.

In Claim 7, Column 226, Lines 16-18, the text "$L^3$ is —NH— or $\xi$—CH$_2$—NH—;" should be replaced with the text: --$L^3$ is –NH– or $\xi$—CH$_2$—NH—;--.

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,787,436 B2

In Claim 8, at Column 226, Lines 50-64, the formula:

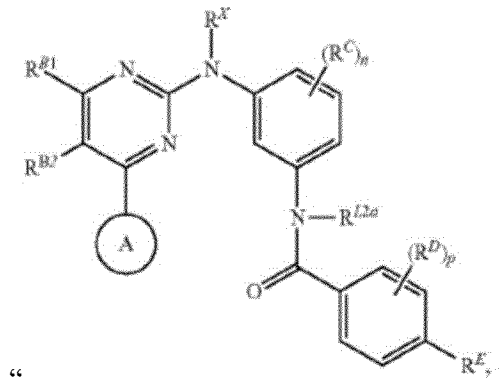

" should be removed.

In Claim 9, at Column 227, Line 25 to Column 228, Line 20, the text:

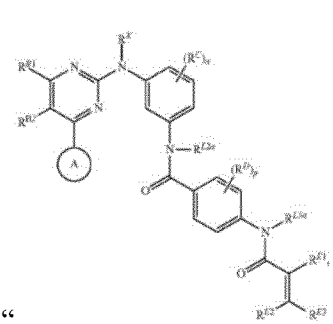 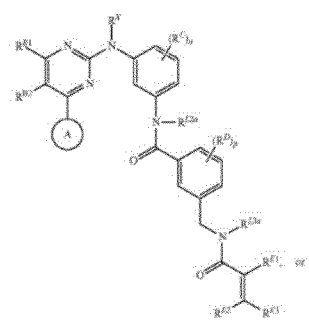 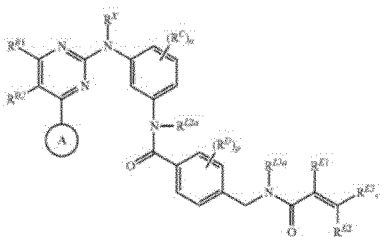

" should be removed.

In Claim 11, at Column 233, the formula:

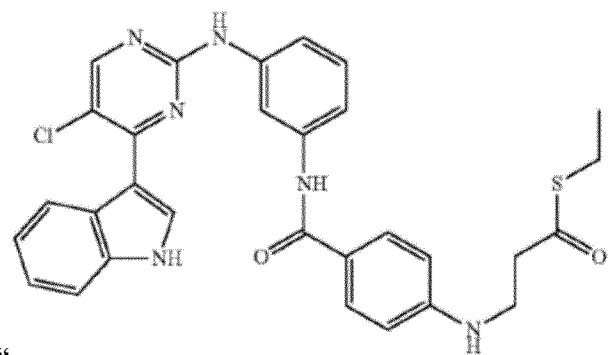

" should be removed.

CERTIFICATE OF CORRECTION (continued) Page 3 of 3
U.S. Pat. No. 10,787,436 B2

In Claim 11, at Column 237, Lines 24-40, the text:

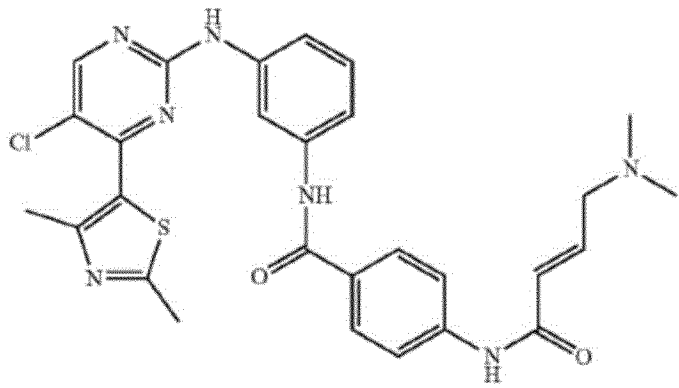

"or                                                          " should be removed.

In Claim 14, at Column 237, Lines 54-65, the text: "wherein Ring A 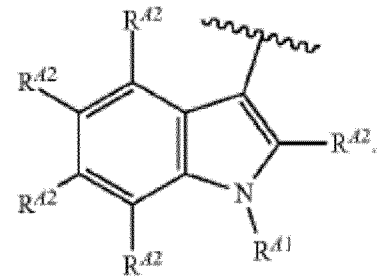"

should be replaced with the text: --wherein Ring A is 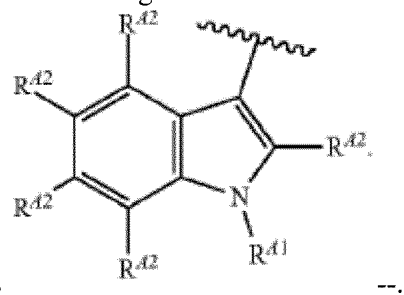 --.